(12) United States Patent
Chen et al.

(10) Patent No.: US 6,229,011 B1
(45) Date of Patent: May 8, 2001

(54) N-AROYLPHENYLALANINE DERIVATIVE VCAM-1 INHIBITORS

(75) Inventors: Li Chen, Westfield; Robert William Guthrie, Saddle Brook, both of NJ (US); Tai-Nang Huang, Lexington, MA (US); Achyutharao Sidduri, Livingston; Jefferson Wright Tilley, North Caldwell, both of NJ (US); Kenneth Gregory Hull, Cambridge, MA (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/137,798

(22) Filed: Aug. 21, 1998

Related U.S. Application Data

(60) Provisional application No. 60/094,592, filed on Jul. 29, 1998, and provisional application No. 60/056,718, filed on Aug. 22, 1997.

(51) Int. Cl.⁷ ............ C07C 311/47; C07D 239/14; C07D 233/88; C07D 230/30; C07D 223/04
(52) U.S. Cl. ............ 544/171; 548/324.5; 548/323.5; 548/200; 548/215; 548/254; 548/261; 548/512; 562/443; 562/446; 562/447; 562/448; 562/449; 562/455; 562/457; 562/430; 560/34; 560/41; 544/171; 544/263; 544/325; 544/400; 546/116; 546/121; 546/175; 546/199; 546/215; 546/316
(58) Field of Search ............... 548/323.5, 215, 548/261, 324.1, 254, 200, 510; 562/443, 455, 457, 446, 447, 448, 449, 430; 544/171, 263, 335, 400; 560/34, 41; 546/116, 121, 175, 199, 215, 316

(56) References Cited

U.S. PATENT DOCUMENTS

| | | | |
|---|---|---|---|
| 3,023,235 | * | 2/1962 | Leonard ............... 562/445 |
| 3,527,793 | * | 9/1970 | Holdrege ............ 562/450 X |
| 5,463,116 | * | 10/1995 | Sumikawa et al. ....... 562/450 |
| 5,804,595 | * | 9/1998 | Portoghese et al. ........ 514/428 |

FOREIGN PATENT DOCUMENTS

| | | | |
|---|---|---|---|
| 2004127 | * | 6/1990 | (CA) . |
| 19548709 | | 7/1997 | (DK) . |
| 19654483 | | 1/1998 | (DK) . |
| 0207681 | * | 1/1987 | (EP) . |
| WO 95/35296 | | 12/1995 | (WO) . |
| WO 96/22966 | | 8/1996 | (WO) . |
| WO 97/36859 | | 10/1997 | (WO) . |
| WO 97/36862 | | 10/1997 | (WO) . |

OTHER PUBLICATIONS

Patani, et al. Chem. Reviews vol. 96, No. 8, 1996 pp. 3147–3176.
Abstract corresponding to DE19654483.
Abstract corresponding to DE 19548709 (B1) 1997.
Patent Abstracts of Japan vol. 013, No. 029 (C–562), Jan. 23, 1989—JP 63233963 A, Showa Denko.
Abstract corresponding to JP63233963 (1998).

* cited by examiner

Primary Examiner—Floyd D. Higel
(74) Attorney, Agent, or Firm—George W. Johnston; Dennis P. Tramaloni

(57) ABSTRACT

Compounds of the formula:

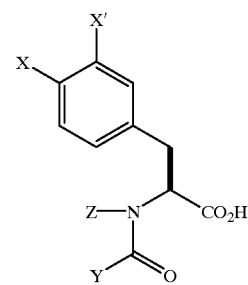

are disclosed which have activity as inhibitors of binding between VCAM-1 and cells expressing VLA-4. Such compounds are useful for treating diseases whose symptoms and/or damage are related to the binding of VCAM-1 to cells expressing VLA-4.

308 Claims, No Drawings

N-AROYLPHENYLALANINE DERIVATIVE VCAM-1 INHIBITORS

This application claims the benefit of U.S. Provisional Application Nos. 60/056,718, filed Aug. 22, 1997 and 60/094,592, filed Jul. 29, 1998.

BACKGROUND OF THE INVENTION

Vascular cell adhesion molecule-1 (VCAM-1), a member of the immunoglobulin (Ig) supergene family, is expressed on activated, but not resting, endothelium. The integrin VLA-4 ($a_4b_1$), which is expressed on many cell types including circulating lymphocytes, eosinophils, basophils, and monocytes, but not neutrophils, is the principal receptor for VCAM-1. Antibodies to VCAM-1 or VLA-4 can block the adhesion of these mononuclear leukocytes, as well as melanoma cells, to activated endothelium in vitro. Antibodies to either protein have been effective at inhibiting leukocyte infiltration and preventing tissue damage in several animal models of inflammation. Anti-VLA-4 monoclonal antibodies have been shown to block T-cell emigration in adjuvant-induced arthritis, prevent eosinophil accumulation and bronchoconstriction in models of asthma, and reduce paralysis and inhibit monocyte and lymphocyte infiltration in experimental autoimmune encephalitis (EAE). Anti-VCAM-1 monoclonal antibodies have been shown to prolong the surival time of cardiac allografts. Recent studies have demonstrated that anti-VLA-4 mAbs can prevent insulitis and diabetes in non-obese diabetic mice, and significantly attenuate inflammation in the cotton-top tamarin model of colitis.

Thus, compounds which inhibit the interaction between $\alpha_4$-containing integrins and VCAM-1 will be useful as therapeutic agents for the treatment of chronic inflammatory diseases such as RA, multiple sclerosis (MS), asthma, and inflammatory bowel disease (IBD).

SUMMARY OF THE INVENTION

It has been discovered that compounds of the formula:

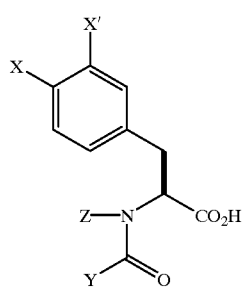

1 and the pharmaceutically acceptable salts and esters thereof wherein X, X', Y and Z are as defined below, inhibit the binding of VCAM-1 to VLA-4 and so would be useful in treating inflammatory diseases in which such binding contributes to the disease process.

DETAILED DESCRIPTION OF THE INVENTION

As used in this specification, the term "lower alkyl", alone or in combination, means a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. Lower alkyl groups may be unsubstituted or substituted by one or more groups selected independently from cycloalkyl, nitro, aryloxy, aryl, hydroxy, halogen, cyano, lower alkoxy, lower alkanoyl, lower alkylthio, lower alkyl sulfinyl, lower alkyl sulfonyl, and substituted amino. Examples of substituted lower alkyl groups include 2-hydroxylethyl, 3-oxobutyl, cyanomethyl, and 2-nitropropyl.

The term "cycloalkyl" means an unsubstituted or substituted 3- to 7-membered carbacyclic ring. Substitutents useful in accordance with the present invention are hydroxy, halogen, cyano, lower alkoxy, lower allcanoyl, lower alkyl, aroyl, lower alkylthio, lower alkyl sulfinyl, lower alkyl sulfonyl, aryl, heteroaryl and substituted amino.

The term "lower alkoxy" means a straight-chain or branched-chain alkoxy group containing a maximum of six carbon atoms, such as methoxy, ethoxy, n-propoxy, isopropoxy, n-butoxy, tert-butoxy and the like.

The term "lower alkylthio" means a lower alkyl group bonded through a divalent sulfur atom, for example, a methyl mercapto or a isopropyl mercapto group.

The term "aryl" means a mono- or bicylic aromatic group, such as phenyl or naphthyl, which is unsubstituted or substituted by conventional substituent groups. Preferred substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoroalkyl, alkanoyl, aroyl, aryl alkynyl, lower alkynyl and lower alkanoylamino. The especially preferred substituents are lower alkyl, lower alkoxy, hydroxy, halogen, cyano and perfluoro lower alkyl. Examples of aryl groups that may be used in accordance with this invention are phenyl, p-tolyl, p-methoxyphenyl, p-chlorophenyl, m-hydroxy phenyl, m-methylthiophenyl, 2-methyl-5-nitrophenyl, 2,6-dichlorophenyl, 1-naphthyl and the like.

The term "arylalkyl" means a lower alkyl group as hereinbefore defined in which one or more hydrogen atoms is/are replaced by an aryl or heteroaryl group as herein defined. Any conventional aralkyl may be used in accordance with this invention, such as benzyl and the like.

The term "heteroaryl" means an unsubstituted or substituted 5- or 6-membered monocyclic hetereoaromatic ring or a 9- or 10-membered bicyclic hetereoaromatic ring containing 1, 2, 3 or 4 hetereoatoms which are independently N, S or O. Examples of hetereoaryl rings are pyridine, benzimidazole, indole, imidazole, thiophene, isoquinoline, quinzoline and the like. Substitutents as defined above for "aryl" are included in the definition of heteroaryl.

The term "lower alkoxycarbonyl" means a lower alkoxy group bonded via a carbonyl group. Examples of alkoxy-carbonyl groups are ethoxycarbonyl and the like.

The term "lower alkylcarbonyloxy" means lower alkyl-carbonyloxy groups bonded via an oxygen atom, for example an acetoxy group.

The term "lower alkanoyl" means lower alkyl groups bonded via a carbonyl group and embraces in the sense of the foregoing definition groups such as acetyl, propionyl and the like.

The term "lower alkylcarbonylamino" means lower alkylcarbonyl groups bonded via a nitrogen atom, such as acetylamino.

The term "aroyl" means an mono- or bicyclic aryl or heteroaryl group bonded via a carbonyl group. Examples of aroyl groups are benzoyl, 3-cyanobenzoyl, 2-naphthtyl and the like.

The term "aryloxy" means an aryl group, as hereinbefore defined, which is bonded via an oxygen atom. The preferred aryloxy group is phenoxy.

The present invention comprises a compound of the formula:

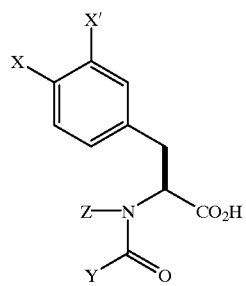

and the pharmaceutically acceptable salts and esters thereof.

In accordance with the invention, Z is hydrogen or lower alkyl (preferably hydrogen), one of X and X' is hydrogen, halogen, or lower alkyl (X' is preferably hydrogen), and the other (preferably X) is a group X-6, X-7 or X-10 as described below. Y is a group Y-1 or Y-2 as described below.

The group X-6 is of the formula:

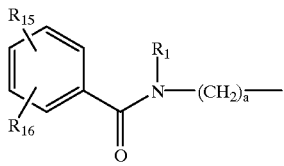

wherein:
$R_1$ is hydrogen or lower alkyl,
$R_{15}$ is halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, alkylthio lower alkyl, alkylsulfinyl lower alkyl, alkylsufonyl lower alkyl, lower alkylsulfinyl, lower alkanoyl, aroyl, aryl, aryloxy or a group of the formula $R_{17}$—C≡C—,
$R_{16}$ is H, halogen, nitro, cyano, lower alkyl, OH, perfluorolower alkyl, or lower alkylthio,
$R_{17}$ is H, aryl, heteroaryl, or lower alkyl which is unsubstituted or substituted by OH, aryl, or heteroaryl, and
a is 0 or 1.

The groups $R_{15}$ and $R_{16}$ are preferably independently hydrogen, lower alkyl, nitro, halogen (especially chloro or fluoro), perfluoromethyl, cyano or phenoxy. $R_1$ is preferably hydrogen and a is preferably 0.

X-7 is a group of the formula:

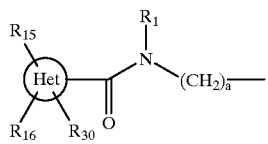

wherein
Het is a 5- or 6-membered heteroaromatic ring containing 1, 2 or 3 heteroatoms selected from N, O, and S, or
Het is a 9- or 10-membered bicyclic heteroaromatic ring containing 1, 2, 3 or 4 heteroatoms selected from O, S, and N;

a, $R_1$, $R_{15}$ and $R_{16}$ are as above, and
$R_{30}$ is absent or is hydrogen or lower alkyl.

Het is preferably a 5- or 6-membered monocyclic heteroaromatic ring containing 1, 2 or 3 nitrogens, or a nitrogen and a sulfur, or a nitrogen and an oxygen. When Het is a bicyclic heteroaromatic ring, it preferably contains from 1 to 3 nitrogens as the heteroatoms. $R_{15}$ is preferably, nitro, lower alkyl sulfonyl, cyano, lower alkyl, lower alkoxy, perfluorolower alkyl, lower alkylthio, lower alkanoyl, or aryl (especially unsubstituted phenyl); $R_{16}$ is preferably halogen, nitro, cyano, lower alkyl, perfluoro lower alkyl; and $R_{30}$, when present, is preferably hydrogen or lower alkyl.

The group X-10 is of the formula:

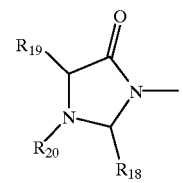

wherein:

$R_{18}$ is hydrogen, substituted or unsubstituted lower alkyl, aryl, heteroaryl, arylalkyl, heteroaryl alkyl, $R_{19}$ is substituted or unsubstituted lower alkyl, aryl, heteroaryl, arylaklyl, heteroaryl alkyl, and $R_{20}$ is substituted or unsubstituted lower alkyl, substituted or unsubstituted lower alkanoyl, carboxyl lower alkanoyl, aroyl, aryloxylower alkanoyl.

$R_{18}$ is preferably 1) lower alkyl, especially t-butyl, 2) phenyl wherein the phenyl ring is unsubstituted or mono-substituted by lower alkoxy or halogen, or 3) phenyl lower alkyl. $R_{19}$ is preferably lower alkyl, which is unsubstituted or substituted by pyridyl or phenyl wherein the phenyl ring is unsubstituted or monosubstituted by lower alkoxy or halogen. $R_{20}$ is preferably lower alkanoyl.

The compounds of the invention include the pharmaceutically acceptable salts and esters thereof. Certain preferred esters of the invention were discovered which are useful to improve bioavailability of compounds of this invention. These preferred esters are of the formula:

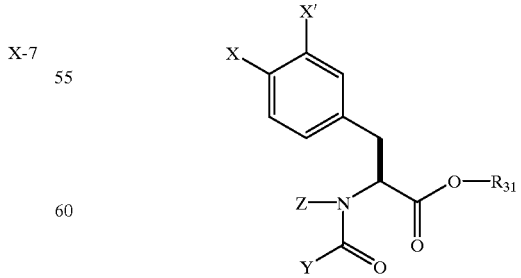

wherein X, X', Z and Y are as described above, and $R_{31}$ is lower alkyl, or $R_{31}$ is a group of formula P-1:

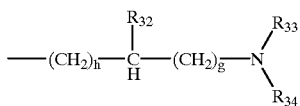

P-1 wherein
R$_{32}$ is hydrogen or lower alkyl,
R$_{33}$ is hydrogen, lower alkyl, aryl,
R$_{34}$ is hydrogen or lower alkyl,
h is an integer from 0 to 2,
g is an integer from 0 to 2,
the sum of h and g is 1 to 3; or
R$_{31}$ is a group of formula P-2:

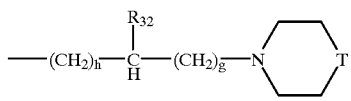

P-2 wherein
R$_{32}$, g, and h are as previously defined,
T is O, S, —(CH$_2$)$_j$—, a bond (when j=0) or a group of the formula N—R$_{35}$,
R$_{35}$ is hydrogen, lower alkyl, lower alkanoyl, lower alkoxycarbonyl, and
j is 0, 1 or 2.
R$_{31}$ is preferably methyl, ethyl or 2-(4-morpholinyl)ethyl.
Y-1 is a group of the formula:

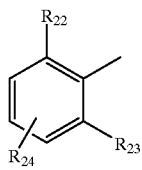

Y-1 wherein:
R$_{22}$ and R$_{23}$ are independently hydrogen, lower alkyl, lower alkoxy, lower cycloalkyl, lower alkoxylalkyl, lower alkylamino, aryl, arylalkyl, nitro, cyano, lower alkylthio, lower alkylsulfinyl, lower alkyl sulfonyl, lower alkanoyl, halogen, or perfluorolower alkyl and at least one of R$_{22}$ and R$_{23}$ is other than hydrogen, and
R$_{24}$ is hydrogen, hydroxy, lower alkyl, lower alkoxy, aryl, nitro, cyano, lower alkyl sulfonyl, halogen, or is a group of the formula:

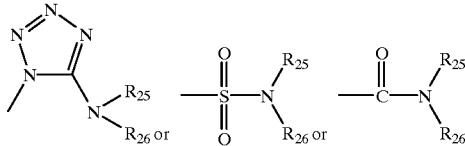

wherein R$_{25}$ is hydrogen, lower alkyl, aminolower alkyl, aryl, aryl lower alkyl, alkoxy lower alkyl and
R$_{26}$ is hydrogen or lower alkyl, or
R$_{22}$ and R$_{24}$ taken together are a fused benzene ring.
Y-2 is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atom is adjacent to the carbon atom bonded to the amide carbonyl.

Y is preferably the group Y-1 whereby the invention comprises a compound of the formula:

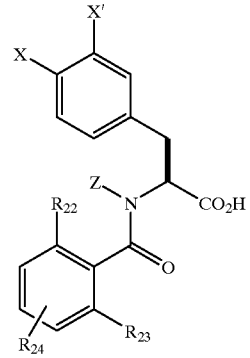

wherein X, X', Z, R$_{22}$, R$_{23}$ and R$_{24}$ are as above.

In the group Y-1, R$_{23}$ is preferably hydrogen (when R$_{22}$ is other than hydrogen), lower alkyl, halogen, nitro, perfluoro loweralkyl, loweralkoxy, lower alkylthio, lower alkylsulfinyl or lower alkyl sulfonyl; R$_{22}$ is preferably hydrogen (when R$_{23}$ is other than hydrogen), lower alkyl, halogen, or, taken together with R$_{24}$, a fused phenyl ring; and R$_{24}$ is preferably hydrogen, lower alkyl, hydroxy, amino, nitro, halogen, lower alkoxy, lower alkyl sulfonyl, or, taken together with R$_{22}$, a fused phenyl ring, or a group of the formula:

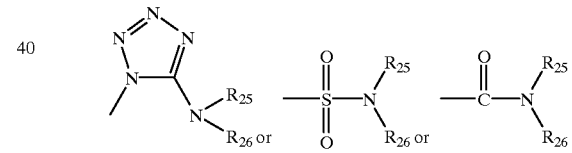

wherein R$_{25}$ is aryl lower alkyl, especially unsubstituted or hydroxy-substituted phenyl lower alkyl, and R$_{26}$ is hydrogen.

Among the groups Y-1, when R$_{23}$ is lower-alkyl, Y-1 is preferably:

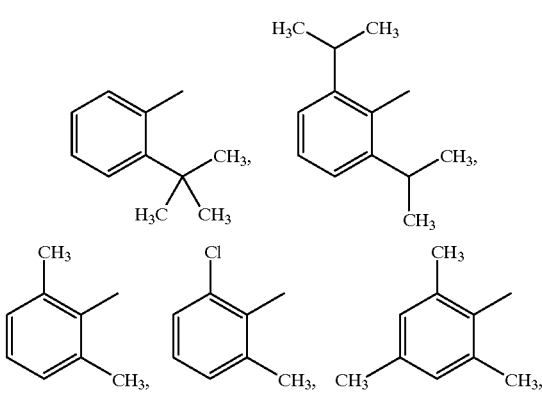

-continued
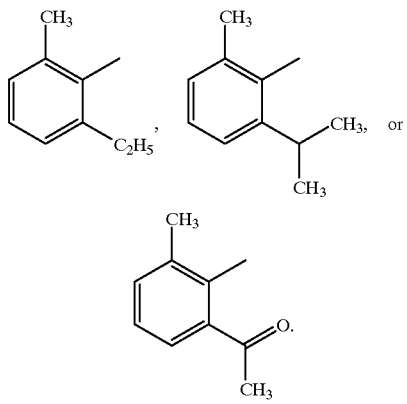
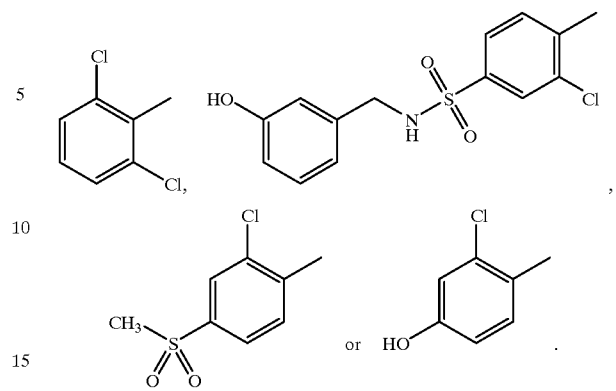
When R₂₃ is lower alkanoyl, Y-1 is preferably:
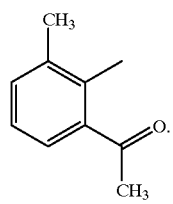
When R₂₃ is perfluoroalkyl, Y-1 is preferably:
When R₂₃ is chloro, Y-1 is preferably:
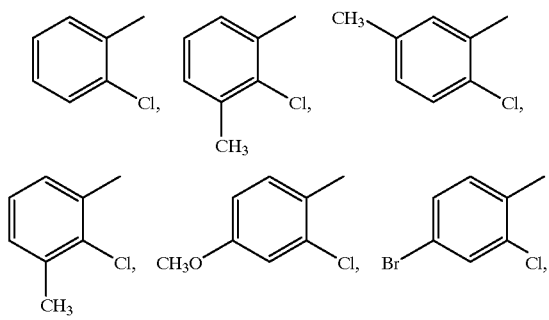
When R₂₃ is bromo, Y-1 is preferably:
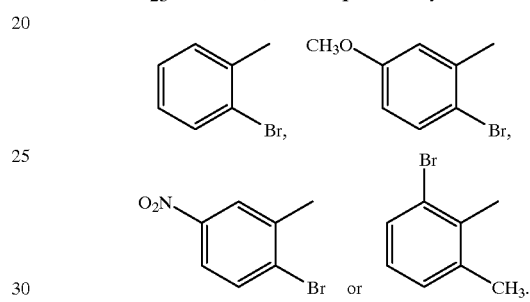
When R₂₃ is fluoro, Y-1 is preferably:
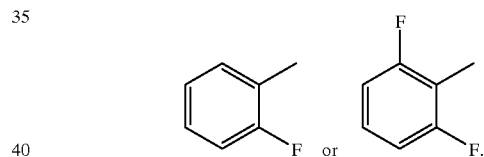
When R₂₃ is nitro, Y-1 is preferably:
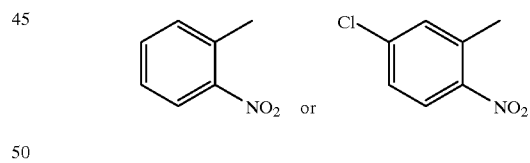
When R₂₃ is lower alkylthio, lower alkylsulfinyl or lower alkyl sulfonyl, Y-1 is preferably:
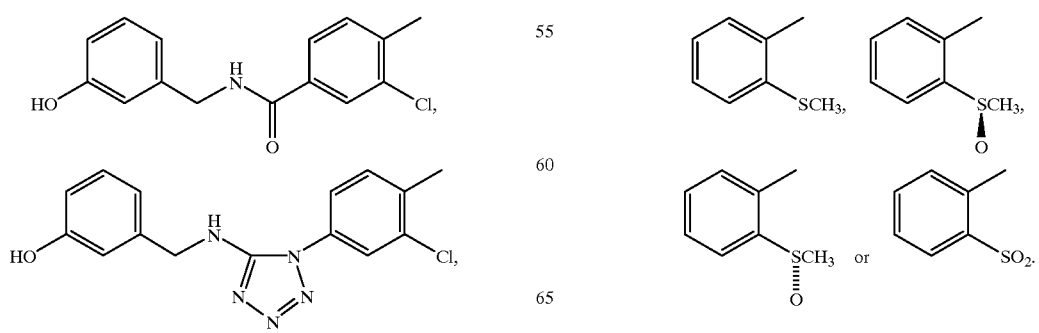

When $R_{23}$ is lower alkylamino, Y-1 is preferably:
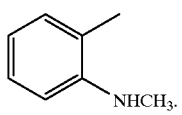
When $R_{23}$ is lower alkoxy, Y-1 is preferably:
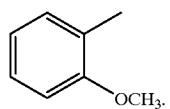
When Y is a group Y-2, Y is preferably:
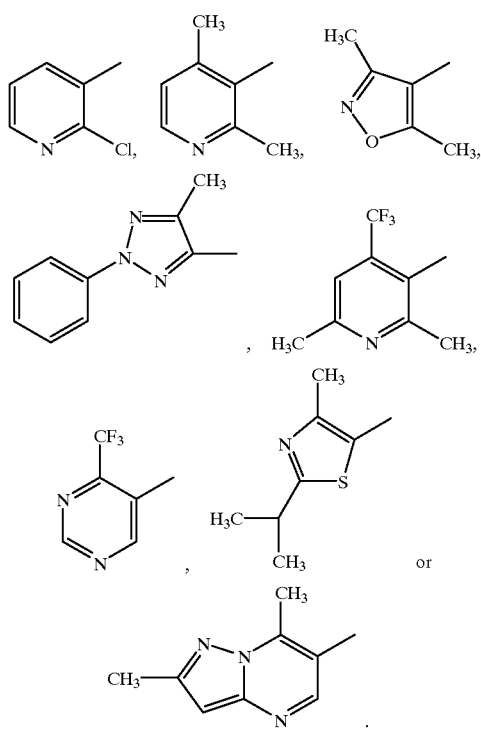
X' and Z are preferably hydrogen.
In all groups X-6 and X-7, $R_1$ is preferably hydrogen and a is preferably zero.
The especially preferred groups X-6 are of the formula:
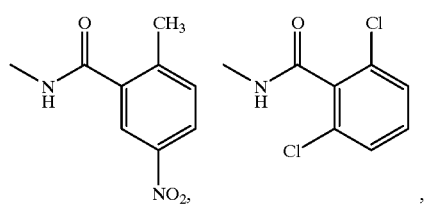
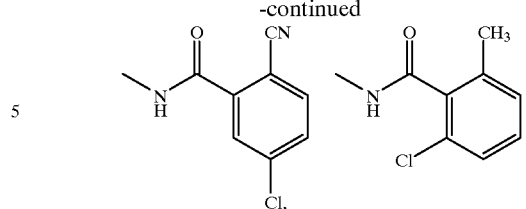
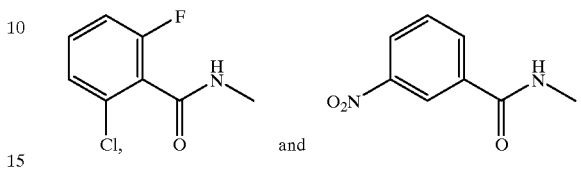
The especially preferred groups X-7 are of the formula:
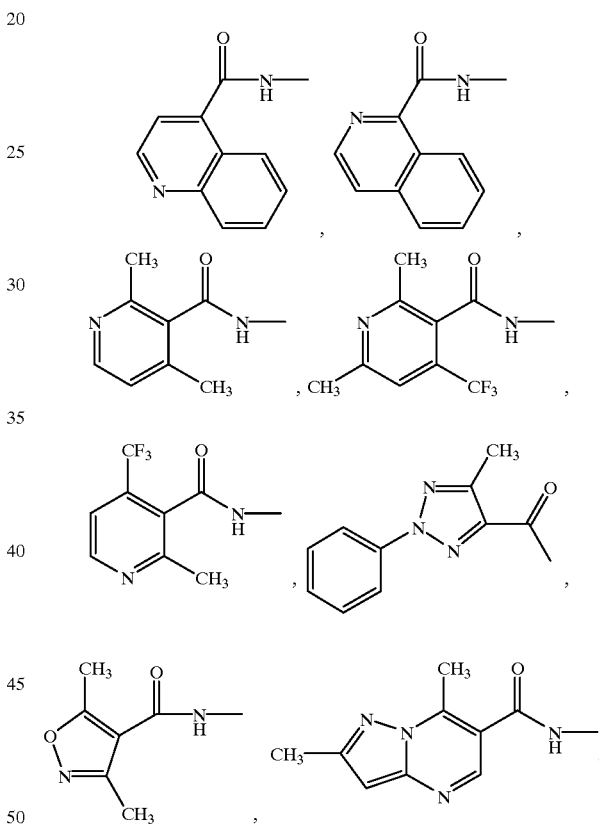
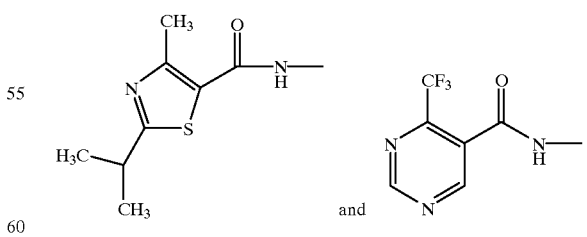

The especially preferred groups X-10 are of the formula:

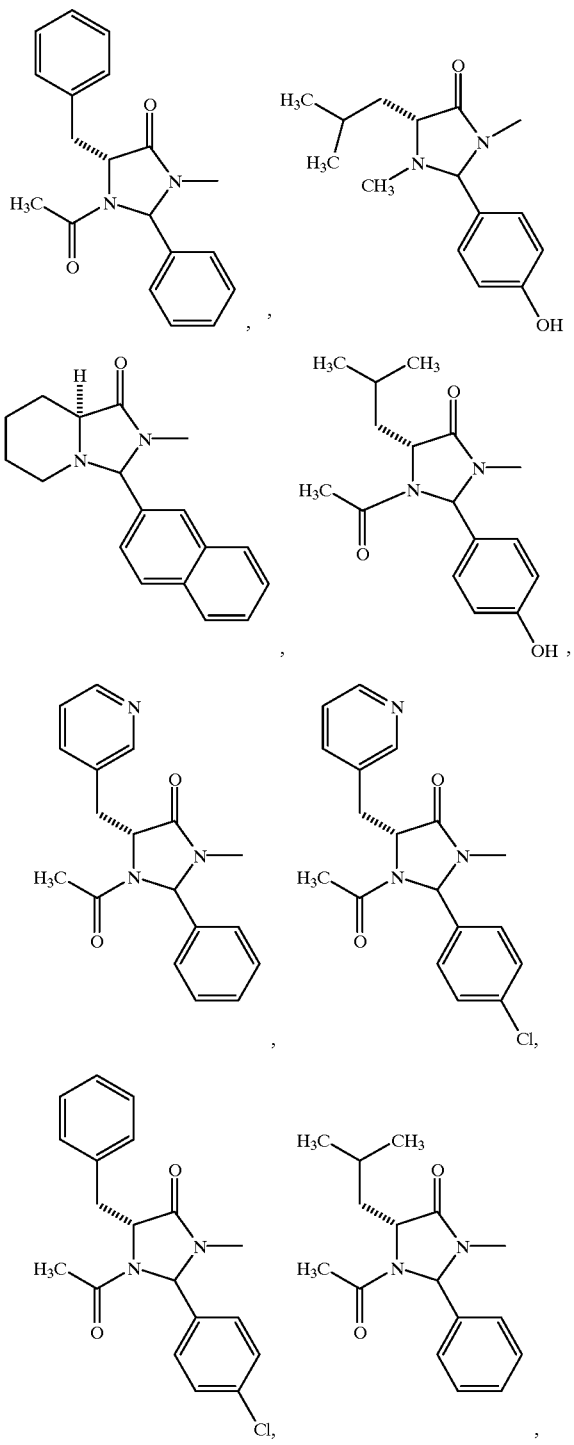

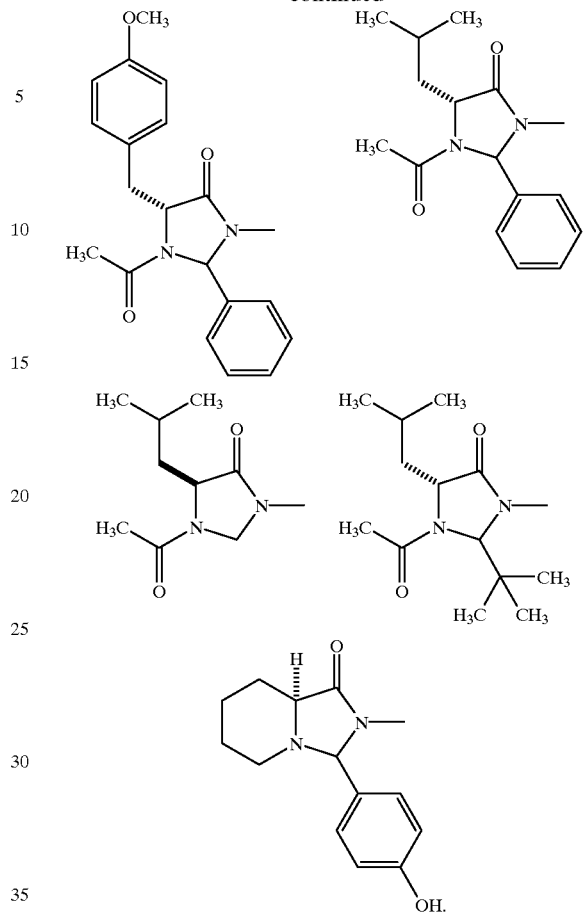

The compounds of the invention can exist as stereoisomers and diastereomers, all of which are encompassed within the scope of the present invention.

The compounds of the invention inhibit the binding of VCAM-1 and fibronectin to VLA-4 on circulating lymphocytes, eosinophils, basophils, and monocytes ("VLA-4-expressing cells"). The binding of VCAM-1 and fibronectin to VLA-4 on such cells is known to be implicated in certain disease states, such as rheumatoid arthritis, multiple sclerosis, inflammatory bowel disease, and particularly in the binding of eosinophils to pulmonary endothelium which contributes to the cause of the pulmonary inflammation which occurs in asthma. Thus, the compounds of the present invention would be useful for the treatment of asthma.

On the basis of their capability of inhibiting binding of VCAM-1 and fibronectin to VLA-4 on circulating lymphocytes, eosinophils, basophils, and monocytes, the compounds of the invention can be used as medicament for the treatment of disorders which are known to be associated with such binding. Examples of such disorders are rheumatoid arthritis, multiple sclerosis, asthma, and inflammatory bowel disease. The compounds of the invention are preferably used in the treatment of diseases which involve pulmonary inflammation, such as asthma. The pulmonary inflammation which occurs in asthma is related to eosinophil infiltration into the lungs wherein the eosinophils bind to endothelium which has been activated by some asthma-triggering event or substance.

Furthermore, compounds of the invention also inhibit the binding of VCAM-1 and MadCAM to the cellular receptor alpha4-beta7, also known as LPAM, which is expressed on lymphocytes, eosinophiles and T-cells. While the precise role of alpha4-beta7 interaction with various ligands in inflammatory conditions such as asthma is not completely understood, compounds of the invention which inhibit both alpha4-beta1 and alpha4-beta7 receptor binding are particularly effective in animal models of asthma. Furthermore work with monoclonal antibodies to alpha4-beta7 indicate that compounds which inhibit alpha4-beta7 binding to MadCAM or VCAM are useful for the treatment of inflammatory bowel disease. They would also be useful in the treatment of other diseases in which such binding is implicated as a cause of disease damage or symptoms.

The compounds of the invention can be administered orally, rectally, or parentally. e.g., intravenously, intramuscularly, subcutaneously, intrathecally or transdermally; or sublingually, or as opthalmalogical preparations, or as an aerosol in the case of pulmonary inflammation. Capsules, tablets, suspensions or solutions for oral administration, suppositories, injection solutions, eye drops, salves or spray solutions are examples of administration forms.

Intravenous, intramuscular, oral or inhalation administration is a preferred form of use. The dosages in which the compounds of the invention are administered in effective amounts depending on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which VCAM-1 of fibronectin binding to VLA-4-expressing cells is a causative factor in the disease symptoms or damage by administering an amount of a compound of the invention sufficient to inhibit VCAM-1 or fibronectin binding to VLA-4-expressing cells so that said symptoms or said damage is reduced. In general, dosages of about 0.1–100 mg/kg body weight per day are preferred, with dosages of 1–25 mg/kg per day being particularly preferred, and dosages of 1–10 mg/kg body weight per day being especially preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 25 mg to 1000 mg of a compound of the invention.

The compounds of the present invention may be prepared by any conventional means. In reaction Scheme 1, a compound of formula 1 in which $R_1$ is H or lower alkyl, and which is a known compound or can be prepared by standard methodology, is treated with a reducing agent capable of selectively reducing a nitro group in the presence of a benzylic alcohol. This procedure is advantageously carried out in the presence of a derivatizing agent of the formula $R_2$—OCOX wherein X is a leaving group and $R_2$ is tert-alkyl, benzyl or the like so as to form a readily cleavable protecting group, thus leading directly to a compound of formula 2. For example, this procedure can be conveniently carried out by catalytic hydrogenation of 1 over Pd© in ethyl acetate in the presence of di-tert-butyl dicarbonate to give a derivative of 2 in which $R_2$ is tert-butyl.

Conversion to an aldehyde of formula 3 can be carried out using any one of a variety of oxidizing agents capable of oxidizing a benzylic alcohol to the corresponding aldehyde, for example activated manganese dioxide in a suitable solvent, for example dichloromethane. Reaction of 3 to give a dehydroamino acid of formula 5 can be effected by treatment with a Wittig reagent of formula 4 in which $R_3$ is lower alkyl and $R_4$ is an alkoxy group, for example benzyloxy- or tert-butoxy- or represents a portion of one of the acyl groups of the compounds of the invention, for example substituted lower aryl. For example treatment of 3 with (±)-N-(benzyloxycarbonyl)-α-phosphonoglycine trimethyl ester in the presence of a suitable base for example tetramethyl guanidine leads directly to a dehydroamino acid of formula 5, $R_3$=methyl and $R_4$=benzyloxy. Enantioselective reduction of 5 to the L-amino acid 6 can be effected by use of a number of reducing agents suitable for the purpose, for example, the recently described ethyl-DuPHOS rhodium reagent (Burk, M. J., Feaster, J. E.; Nugent, W. A.; Harlow, R. L. *J. Am. Chem. Soc.* 1993, 115, 10125) using essentially the literature procedure.

Reaction Scheme 1

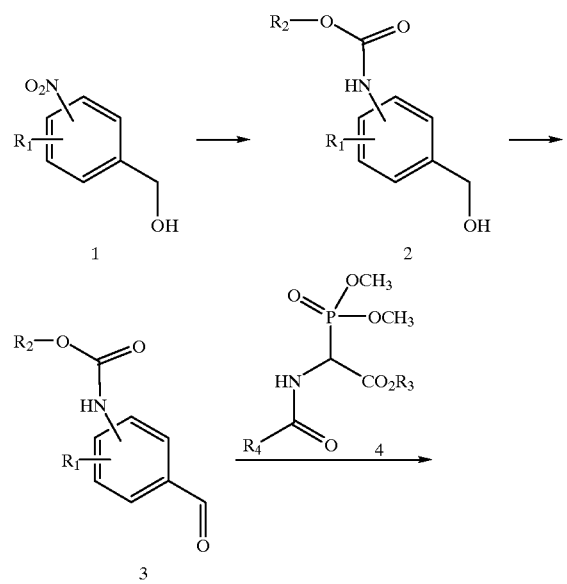

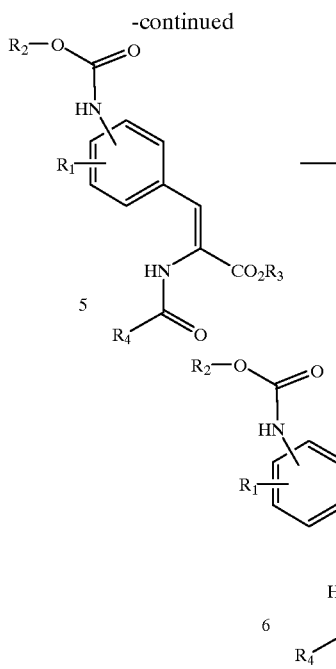

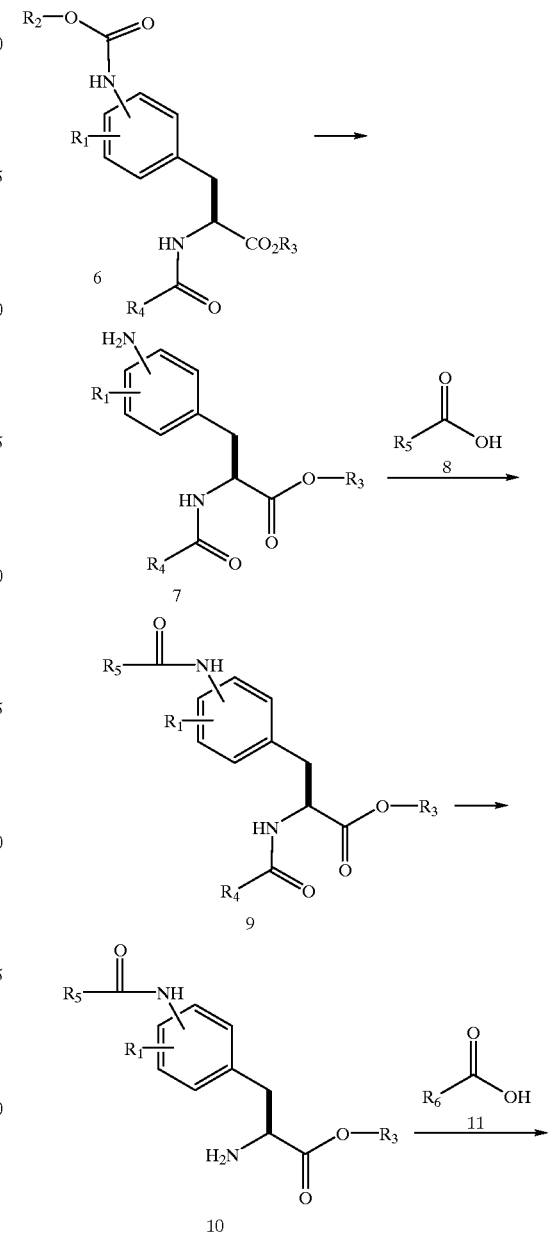

One process for the conversion of compounds of structure 6 into compounds of the invention is shown in Reaction Scheme 2. The protecting group incorporating $R_2$ can be removed under conditions dependent on the particular choice of $R_2$ as well as $R_3$ and $R_4$. The choice of these groups will be dependent on the particular target compound. A variety of common protecting groups and their use are described in "T. W. Greene and P. G. M. Wuts, Protective Groups in Organic Synthesis, $2^{nd}$ edition, Wiley Interscience, New York, 1991". For example when $R_2$ is a tert-butyl group and $R_3$ is lower alkyl and $R_4$ is either a benzyloxy group or represents a portion of one of the acyl groups of the compounds of the invention, for example ortho-substituted aryl, treatment with trifluoroacetic acid either neat or in dichloromethane solution in the presence of suitable scavengers, for example, triethylsilane or anisol leads to a compound of formula 7. This compound can be coupled with a carboxylic acid of formula 8 using standard peptide coupling conditions, for example HBTU in the presence of DIPEA in a polar, aprotic solvent such as DMF at a temperature between 0° C. and room temperature to give a compound of formula 9. In the carboxylic acid of formula 8, $R_5$ may represent a substituted alkyl group, a substituted aromatic ring, or a substituted heteroaromatic ring. $R_5$ may also incorporate suitably protected reactive functionalities to permit final conversion into compounds of the invention. The choice and use of such groups will be apparent to those skilled in the art.

Depending on the choice of $R_4$ and whether an ester or acid is the final goal of the synthesis, compound 9 may be a compound of the invention or in the case that $R_4$ is a protecting group, for example, a benzyloxy group, it may be removed under appropriate conditions, for example by catalytic hydrogenation over Pd©in a suitable solvent such as a lower alcohol to give a compound of formula 10. This intermediate can be coupled with a carboxylic acid of formula 11 using standard peptide coupling conditions, for example HBTU in the presence of DIPEA in a polar, aprotic solvent such as DMF at a temperature between 0° C. and room temperature to give a compound of formula 12. In the carboxylic acid of formula 11, $R_6$ may represent a portion of a compound of the invention, for example ortho-substituted aryl or hetereoaryl. These compounds are known compounds or can be prepared by known methods. $R_6$ may also incorporate suitably protected reactive functionalities to permit final conversion into compounds of the invention. The choice and use of such groups will be apparent to those skilled in the art. If the acid 13 is the target compound, conversion of a compound of formula 12 can be effected using standard hydrolysis conditions appropriate for the particular choice of $R_3$ and any functional groups present as part of $R_5$ and $R_6$. In the case where $R_3$ is lower alkyl, treatment with an alkali metal hydroxide, for example lithium hydroxide in aqueous THF is generally effective.

Reaction Scheme 2

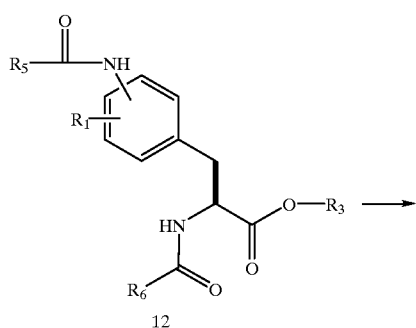

12

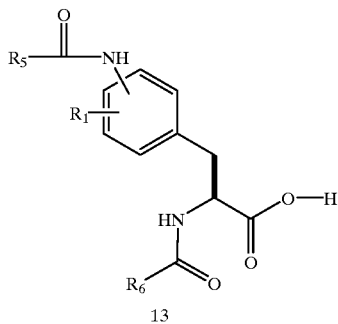

13

Reaction Scheme 3

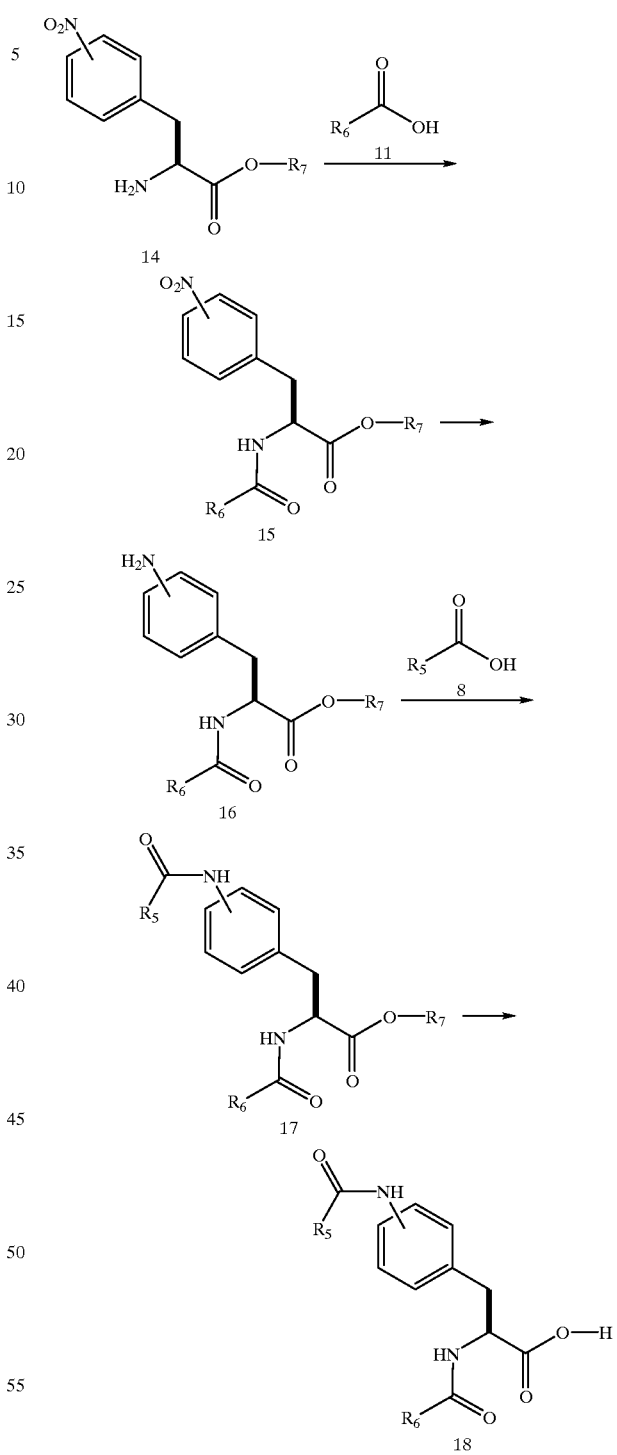

In reaction Scheme 3, a compound of formula 14 in which $R_7$ is a lower alkyl group which may serve as a protecting group or a group suitable for use in a prodrug for example methyl, ethyl, tert-butyl or the like or represents a connection to a solid phase resin, for example a Wang resin, is coupled with a carboxylic acid of formula 11 using standard peptide coupling conditions, for example HBTU in the presence of DIPEA in a polar, aprotic solvent such as DMF at a temperature between 0° C. and room temperature to give a compound of formula 15. Reduction of the nitro group of 15 can be effected by catalytic hydrogenation for example using Pd©  as a catalyst or by treatment with a standard reducing agent, for example $SnCl_2$. The resulting compound of structure 16 is useful as a key intermediate for several series of compounds. In the instance highlighted in Scheme 3, it can be coupled with an acid of formula 8 using standard peptide coupling conditions, for example HBTU in the presence of DIPEA in a polar, aprotic solvent such as DMF at a temperature between 0° C. and room temperature to give a compound of formula 17. Compound 17 may be a compound of the invention depending on the nature of $R_7$ or may be converted to a compound of the invention by an appropriate hydrolysis procedure, for example in the case where $R_7$ is lower alkyl, by hydrolysis by treatment with excess alkali metal hydroxide, such as lithium hydroxide in aqueous alcohol. When $R_7$ represents a resin suitable for solid phase synthesis, appropriate hydrolysis conditions will depend on the choice of resin. In the case of Wang resin, treatment with trifluoroacetic acid in the presence of appropriate scavengers will lead to an acid of formula 18.

In a method particularly well suited for solid phase synthesis, an N'-Alloc-amino-N$^\alpha$-Fmoc protected phenylalanine derivative of formula 19 can be coupled to a resin suitable for solid phase synthesis, for example, a Wang resin using standard coupling procedures, for example, by forming a mixed anhydride with 2,6-dichlorobenzoyl chloride and carrying out the coupling reaction in a polar, aprotic solvent such as N-methyl pyrrolidinone to give a compound of structure 20 in which $R_{7'}$ represents the resin. The Alloc group may be removed by standard methods, for example by treatment with a reducing agent such as $nBu_3SnH$ in the presence of a catalyst which is a source of $Pd^0$, for instance, $Pd(Ph_3P)_2Cl_2$ to give an amine derivative of structure 21. This compound can be coupled with a carboxylic acid of formula 8 using standard peptide coupling conditions, for example HBTU in the presence of DIPEA in a polar, aprotic solvent such as DMF at a temperature between 0° C. and room temperature to give a compound of formula 22. The Fmoc protecting group may be removed from 22 using standard base treatment well known to those practicing peptide chemistry, for example with piperidine in DMF, to afford an amine of formula 23. The resulting compound 23 can be coupled with a carboxylic acid of formula 11 using standard peptide coupling conditions, for example HBTU in the presence of DIPEA in a polar, aprotic solvent such as DMF at a temperature between 0° C. and room temperature to give a compound of formula 24. Finally the compound of structure 24 can be cleaved from the resin under conditions dependent on the particular choice of resin. For example, in the case of a Wang resin, acid treatment with trifluoroacetic acid in dichloromethae in the presence of scavengers as necessary will afford a compound of formula 18.

Depending on the particular synthetic target, the order of removal of the protecting groups from 19 may be altered so that the Fmoc group is first removed, coupling of the resulting amine with an acid of formula 11 is carried out followed by removal of the Alloc group and coupling of the product with an acid of formula 8 and cleavage from the resin. Also the choice of protecting groups can be modified to reflect the reactivities of the resin or choice of $R_7$ and the nature of any functional groups incorporated into $R_5$ and $R_6$.

Reaction Scheme 4

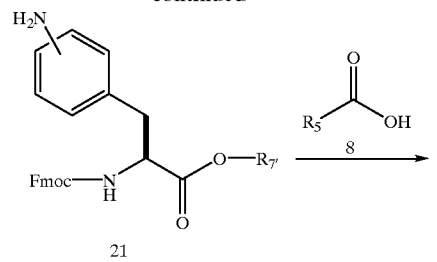

21

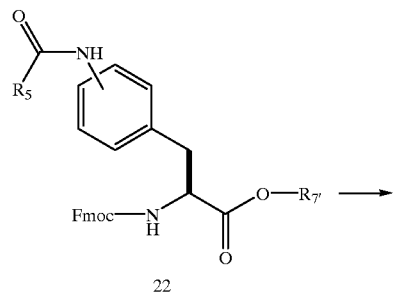

22

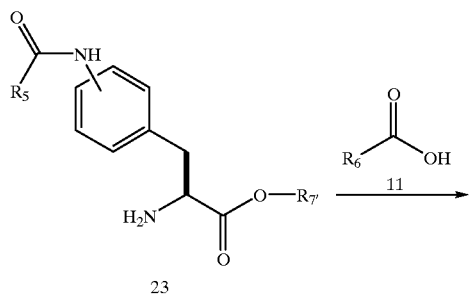

23

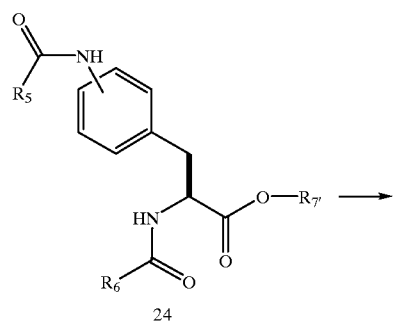

24

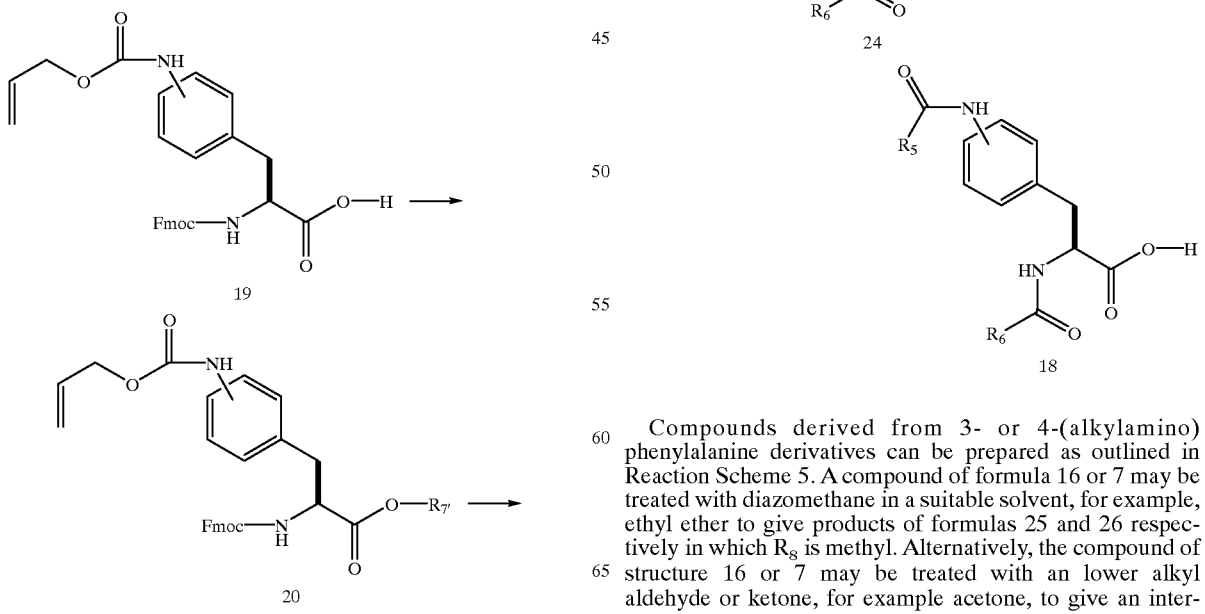

18

Compounds derived from 3- or 4-(alkylamino) phenylalanine derivatives can be prepared as outlined in Reaction Scheme 5. A compound of formula 16 or 7 may be treated with diazomethane in a suitable solvent, for example, ethyl ether to give products of formulas 25 and 26 respectively in which $R_8$ is methyl. Alternatively, the compound of structure 16 or 7 may be treated with an lower alkyl aldehyde or ketone, for example acetone, to give an intermediate Schiff's base which is in turn subjected to catalytic hydrogenation or reduction with sodium cyanoborohydride in the presence of an organic acid, for example acetic acid to give a compound of formula 25 or 26 in which $R_8$ is lower alkyl other than methyl. Conversion of compounds 25 or 26 to prodrug esters 27 or 28 or to the corresponding acids 29 or 30 respectively can be carried out as described above in Reaction Schemes 2 and 3.

Reaction Scheme 5

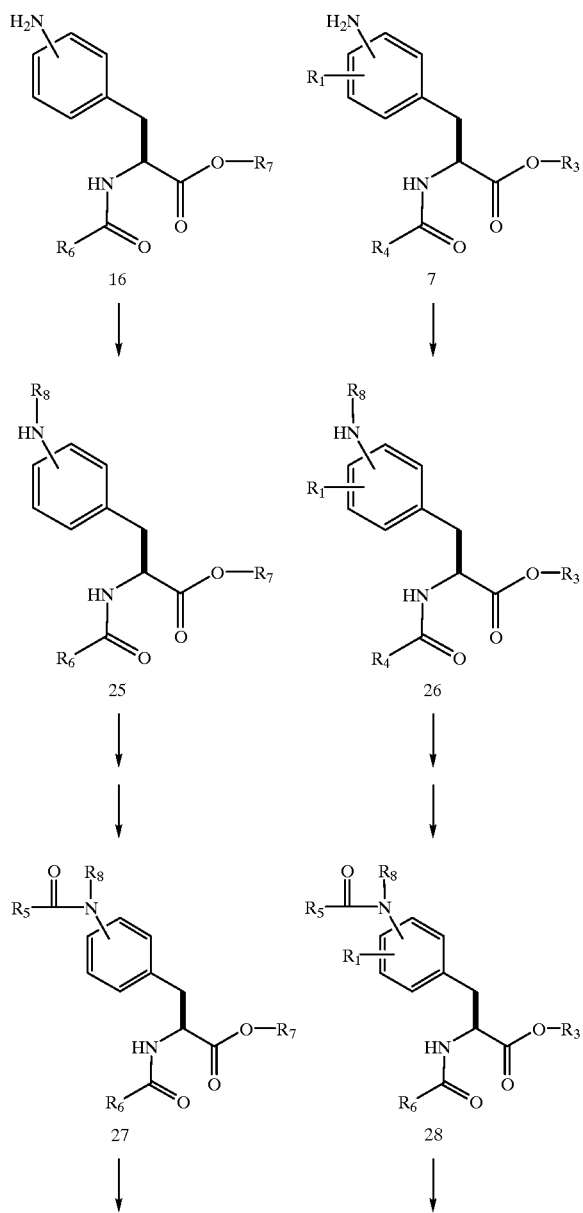

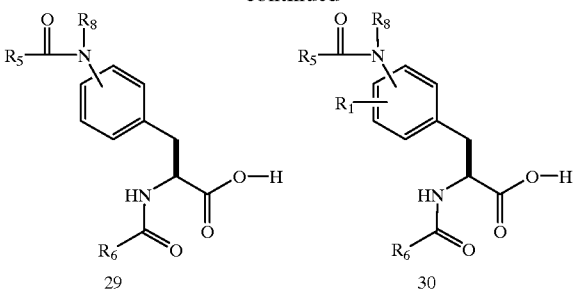

For the preparation of 3- or 4-sulfonylamnino phenylalanine derivatives, compounds of formula 7, 16, 25 or 26 may be reacted with a sulfonyl chloride of formula 31, in which $R_9$ is a substituted aryl or heteroaryl moiety, in an inert solvent, for example dichloromethane in the presence of a non-nucleophilic base, for example triethylamine or pyridine at about 0° C. to room temperature to give compounds of structure 32 or 33 respectively as illustrated in Reaction Scheme 6 for compounds 7 and 26. These can be further converted to compounds of formulas 34 and 35 if desired using the general methods described above in Reaction Schemes 2 and 3.

For the preparation of compounds derived from 3- or 4-aminomethylphenylalanine, the procedure shown in Reaction Scheme 7 may be employed. A 3- or 4-hydroxymethyl benzoate of formula 36 in which $R_{10}$ is lower alkyl, which are known compounds, or can be prepared by known methods, is treated with a silylating agent in which $R_{11}$–$R_{13}$ are lower alkyl or phenyl, for example tert-butyldimethylsilyl chloride in an inert solvent, for example dimethylformamide in the presence of imidazole at about 0° C. to give a silyl protected compound of formula 37. Reduction of 37 may be carried out using a variety of suitable reducing agents, for example, lithium aluminum hydride in an inert solvent such as ether or tetrahydrofuran at a temperature of about 0° C. followed by an aqueous workup to give an intermediate alcohol which can be oxidized by any of several oxidizing agents suitable for oxidizing benzyl alcohols to the corresponding aldehydes, for example activated manganese dioxide, to give an aldehyde of formula 38. Monosilyl protected diols are alternatively available from 3- or 4-hydroxymethylbenzylalcohols by monosilylation and separation of the side products. Alternatively, an ester of formula 37 may be reduced directly to an aldehyde of formula 38 using diisobutylaluminum hydride at low temperature, for example at −78° C.

Reaction of 38 to give a dehydroamino acid of formula 39 can be effected by treatment with a Wittig reagent of formula 4 in which $R_3$ is lower alkyl and $R_4$ is an alkoxy group, for example benzyloxy- or tert-butoxy- or represents a portion of one of the acyl groups of the compounds of the invention, for example ortho-substituted aryl or hetereoaryl. For example treatment of 38 with (±)-N-(benzyloxycarbonyl)-α-phosphonoglycine trimethyl ester in the presence of a suitable base for example tetramethyl guanidine leads directly to a dehydroamino acid of formula 39. $R_3$=methyl and $R_4$=benzyloxy. Enantioselective reduction of 39 to the L-amino acid 40 can be effected by use of one of a number of reducing agents suitable for the purpose, for example, the recently described ethyl-DuPHOS rhodium reagent. It will be readily apparent to those skilled in the art that the optimal procedure for the further conversion of 40 into compounds of the invention will depend on the choices of $R_4$ and $R_3$. For the case wherein $R_3$ is lower alkyl and $R_4$ is benzyloxy, conversion to an amine of formula 41 can be conveniently effected by catalytic transfer hydrogenation of 40 over Pd©  in a suitable solvent, for example, methanol in the presence of ammonium formate as the reducing agent. Acylation of 41 with a carboxylic acid of formula 11 can be carried as described above in Reaction Scheme 2 to give a compound of formula 42. Conditions for removal of the silyl protecting group will depend on the particular choice of $R_{11}$–$R_{13}$. In the case of $R_{11}$, $R_{12}$=methyl and $R_{13}$=tert-butyl, this group is readily removed by treatment with a strong acid, for example hydrochloric acid in an appropriate solvent for the choice of $R_3$, for example where $R_3$ is methyl, methanol.

The resulting benzylic alcohol of formula 43 can be converted to an amine of formula 45 using procedures well established for similar transformations. For example, the alcohol of formula 43 can be converted to a leaving group, for example a mesylate by treatment with methane sulfonyl chloride in the presence of a proton acceptor, for example pyridine, followed by displacement with an alkali metal azide, for example sodium azide in a polar aprotic solvent such as dimethylformamide. Alternatively, the transformation from 43 to an azide of formula 44 can be carried out directly by treatment with diphenyl phosphorazidate as described in: Thompson, A. S.; Humphrey, G R.; DeMarco, A. M.; Mathre, D. J.; Grabowski, E. J. J. *J. Org. Chem.* 1993, 58, 5886–5888. Reduction of the azide 44 to an amine of formula 45 can be carried out by a number of means suitable for the conversion of azides to amines, for example by treatment with a phosphine, for example triphenyl phosphine in an inert solvent such as dichloromethane or THF followed by an aqueous workup or by catalytic hydrogenation over an appropriate catalyst, for example Pd© in a solvent suitable for catalytic hydrogenations such as a lower alkanol or tetrahydrofuran. The resulting amine of formula 45 can be converted into the corresponding compounds of the invention using the procedures applicable to free amines described in the other reaction schemes. For example, coupling of 45 with a carboxylic acid of formula 8 under the conditions described in Reaction Scheme 2 leads to an amide of formula 46 which may be further converted to an acid of formula 47 if desired by base catalyzed hydrolysis as described in Reaction Scheme 2.

Reaction Scheme 6

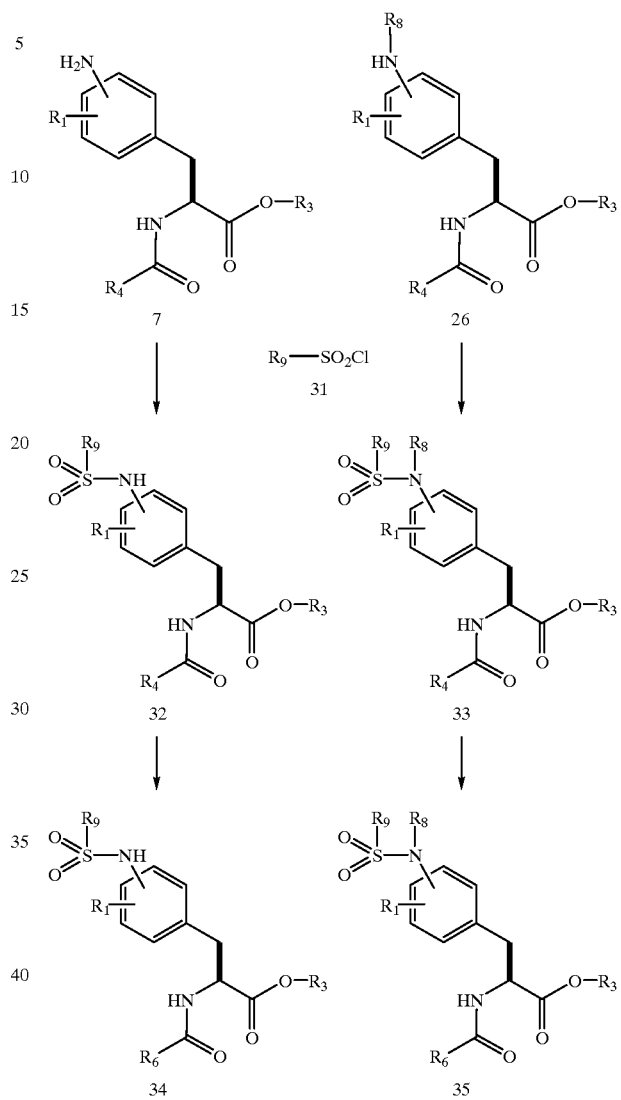

Reaction Scheme 7

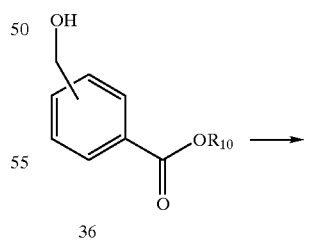

-continued
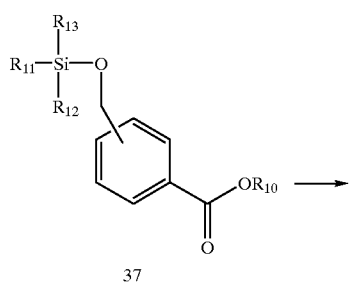
37
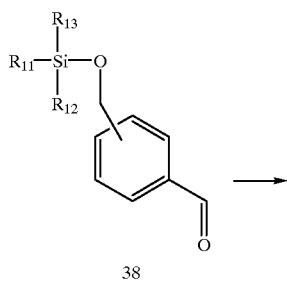
38
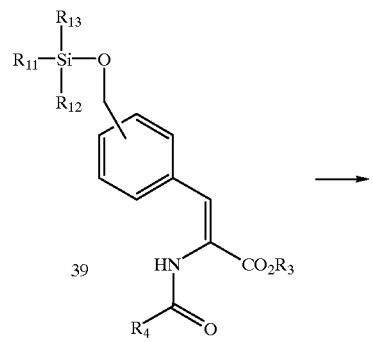
39
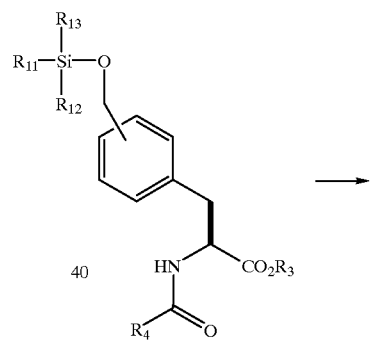
40
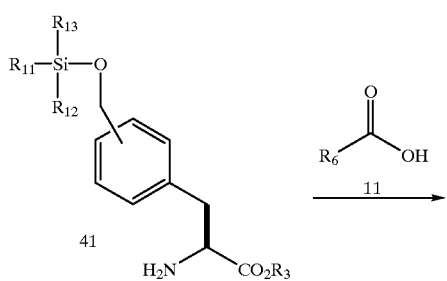 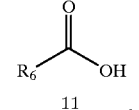
41
-continued
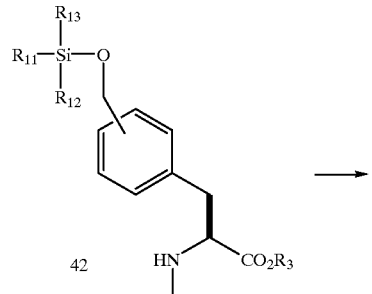
42
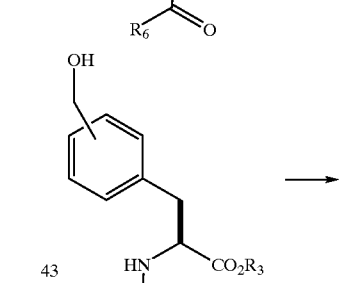
43
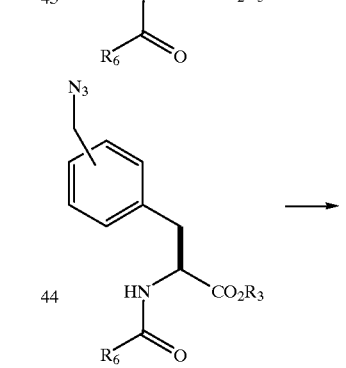
44
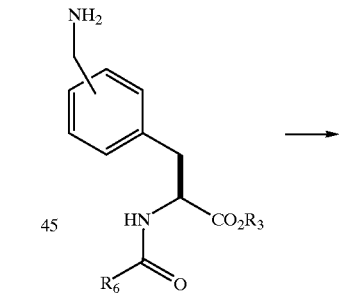
45
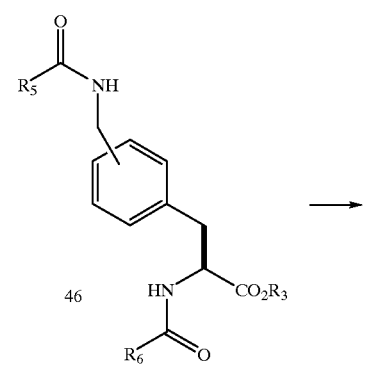
46

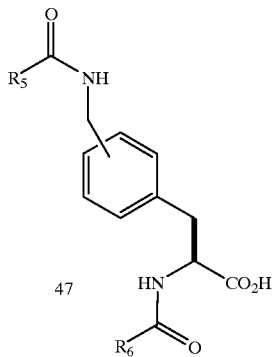

For the synthesis of urea derivatives, a compound of formula 26 can be treated with an isocyanate of formula 49, wherein $R_{14}$ is substituted aryl, substituted heteroaryl or substituted lower alkyl with potentially reactive substituents protected as appropriate using conventional protecting group strategies, in a suitable inert solvent, for example dichloromethane, to give a urea of formula 50. More generally, a compound of formula 26 can be treated with a phosgene equivalent, for example, triphosgene in an inert solvent such as dichloromethane in the presence of a non-nucleophilic proton acceptor, for example diisopropylethylamine, to give an intermediate of formula 48. Subsequent treatment of a compound of formula 48 with an amine of formula 51 in which $R_{15}$ and $R_{16}$ are independently hydrogen, substituted lower alkyl, substituted aryl, substituted heteroaryl or taken together form a substituted 5, 6 or 7 membered ring leads to a compound of formula 52. Further conversion, if necessary, of 50 or 51 to compounds of the invention can be carried out as described in Reaction Scheme 5.

Reaction Scheme 8

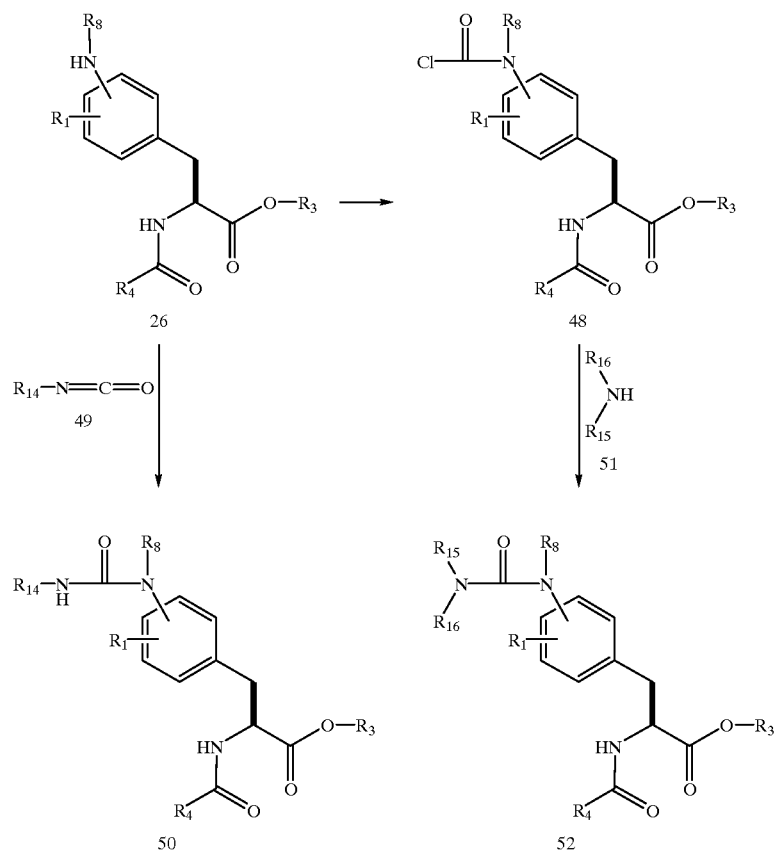

For the synthesis of imides, an aminophenylalanine derivative of structure 53 in which $R_1$ is H or lower alkyl, $R_6$ is as previously defined and $R_{7''}$ is H or a readily cleavable group such as substituted benzyl, tert-butyl, allyl, or the like, or in the event that a prodrug ester is desired as the final product, is that ester group, for example ethyl, is employed. Compounds of formula 53 can be readily obtained from intermediates described above in Reaction Scheme 2. Reaction of a compound of formula 53 with a cyclic anhydride of formula 54 in an inert solvent, for example dichloromethane leads to a ring opened intermediate of formula 55. The structure implied by 54 includes bicyclic molecules which may incorporate fused aromatic or heteroaromatic rings. In place of 54, it is also possible to use dicarboxylate acids which are capable of forming cyclic imides. In the latter case, a condensing agent must be employed in the first step, for example carbonyl dimidazole. Treatment of the compound of formula 55 with a reagent such as carbonyl diimidazole capable of effecting cyclodehydration leads to an imide of formula 56. Further manipulation of functional groups which were present on the an hydride of formula 54 and modification of $R_{7''}$ may be carried out on compound 56 as desired to obtain further analogs using standard chemistry which is compatible with the presence of the imide functionality.

For the synthesis of compounds of the invention in which $R_1$ is halogen, preferably chloro, the appropriate halogen atom can be inserted at various points during the course of the synthesis depending on the nature of the additional functionality in the molecule. For example a compound of formula 6 in which $R_1$ is hydrogen can be treated with a mild chlorinating agent, for example, N-chlorosuccinimide in the presence of a proton acceptor, for example, sodium acetate to give the corresponding compound of formula 6 in which $R_1$ is chloro. In the case where 6 is derived from 3-amino-L-phenylalanine, a mixture of regioisomers may ensue which may be separated at a convenient point in the overall synthesis. Other intermediates described in the above schemes may be more suitable starting materials for halogenation for a particular target molecule. The particular merits of individual candidate starting materials will be apparent to those skilled in the art.

Reaction Scheme 9

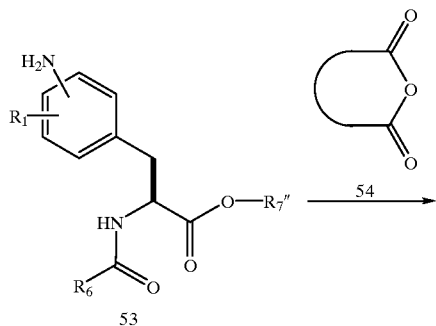

53

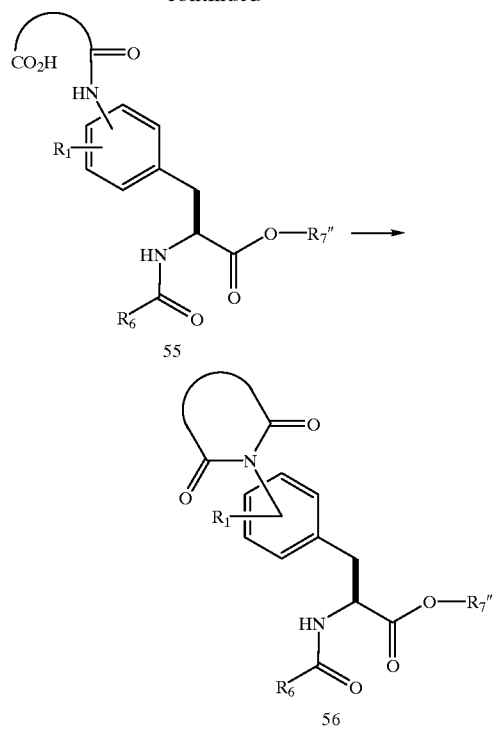

55

56

For the synthesis of the thiazolidinones of formula 62 described in reaction scheme 10, an aminophenylalanine derivative of structure 16, in which $R_6$ and $R_7$ are as previously defined may be employed. Reaction of 16 with an α-mercapto carboxylic acid of formula 59 in which $R_{20}$ can be hydrogen, lower alkyl or aryl, for example α-mercapto acetic acid, and an aldehyde of formula 60 in which $R_{21}$ can be alkyl, hydroxyalkyl or a substituted aryl group, for example benzaldehyde, in an appropriate solvent such as benzene, THF or a lower alcohol, for example methanol, in the presence of a water scavenger such as 4 Å molecular sieves at 60 to 80° C. provides compound of formula 61. Compound 61 may be a compound of the invention depending on the nature of $R_7$ or may be converted to a compound of the invention by an appropriate hydrolysis procedure, for example in the case where $R_7$ is lower alkyl, by treatment with excess alkali metal hydroxide, such as sodium hydroxide in aqueous alcohol. When $R_7$ represents a resin suitable for solid phase synthesis, the appropriate hydrolysis conditions will depend on the choice of resin. In the case of Wang resin, treatment with trifluoroacetic acid in the presence of appropriate scavengers will lead to an acid of formula 62. The sequence may be initiated with related anilines, for example a compound of formula 7 in which $R_1$ is lower alkyl or halogen to give the corresponding thiazolidinones.

Reaction Scheme 10

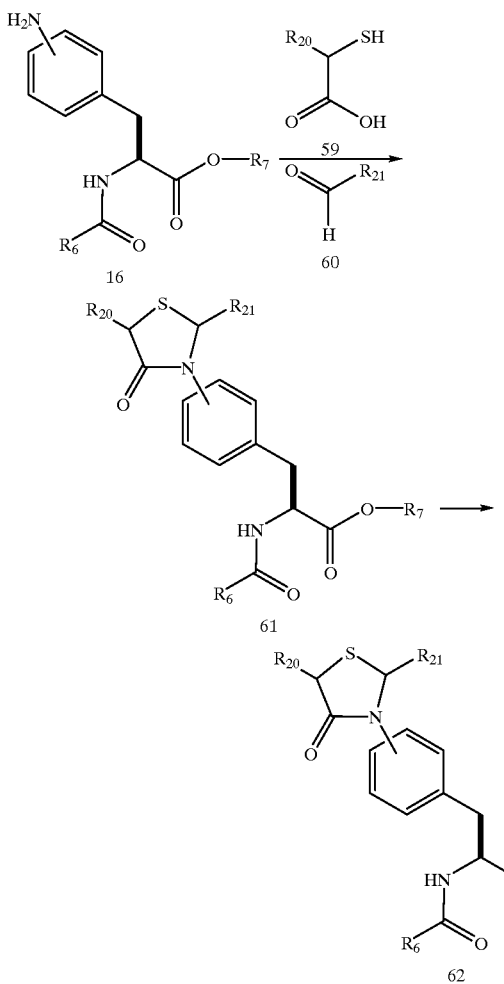

in which the $R_{21}$ is as defined above, in the presence of a water scavenger such as 4 Å molecular sieves at 60 to 80° C. in an appropriate solvent, for example THF, provides a compound of formula 66. Compound 66 may be a compound of the invention depending on the nature of $R_7$ or may be converted to a compound of the invention by an appropriate hydrolysis procedure, for example in the case where $R_7$ is lower alkyl, by hydrolysis by treatment with an alkali metal hydroxide, such as sodium hydroxide in aqueous alcohol to give a carboxylic acid of formula 67.

Reaction Scheme 11

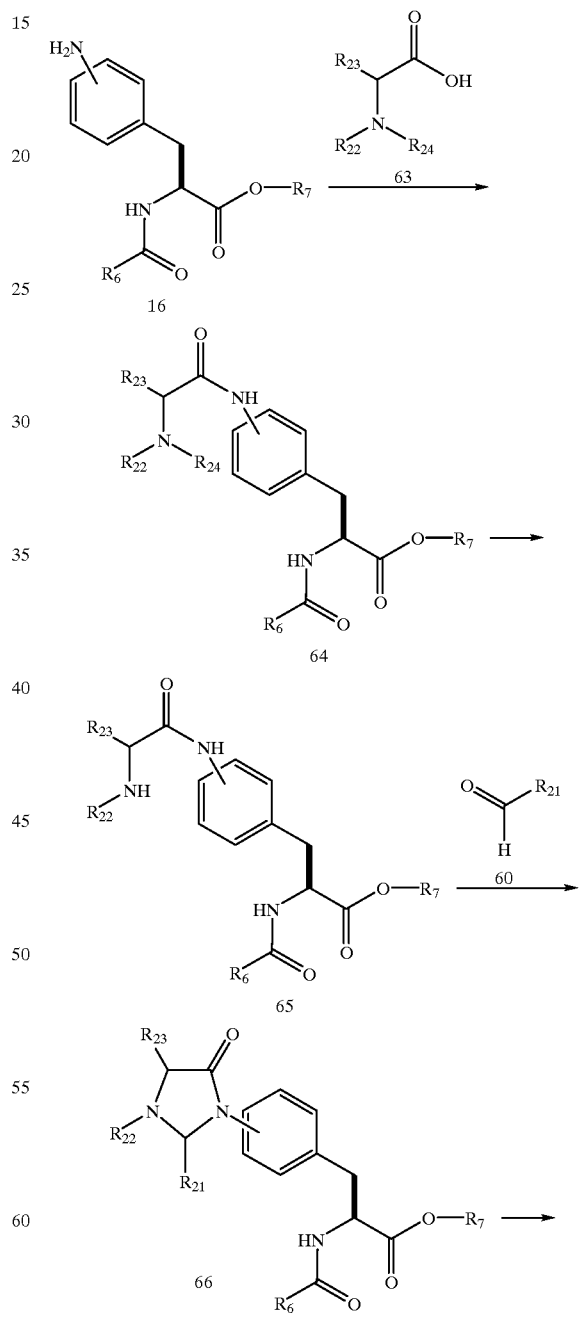

For the synthesis of imidazolidinones of formula 67 shown in reaction scheme 11, an aminophenylalanine derivative of structure 16 in which $R_6$ and $R_7$ are as previously defined may be employed. Compound 16 can be readily obtained through the synthesis described in reaction scheme 3. This compound can be coupled with a N-protected α-amino acid of formula 63, in which $R_{22}$ can be a lower alkyl or an aryl group, $R_{23}$ can be a natural or unnatural D- or L-α-amino acid side chain or $R_{22}$ and $R_{23}$ together can form a ring, for example a proline or pipicolinic acid ring and $R_{24}$ may be a standard amine protecting group suitable for the particular selection of $R_6$, $R_7$, $R_{22}$, and $R_{23}$ for example tert-butoxycarbonyl. The coupling reaction can be effected using standard peptide coupling conditions, for example HBTU in the presence of DIPEA in a polar, aprotic solvent such as DMF at a temperature between 0° C. and room temperature to give a compound of formula 64. Depending on the nature of protecting group $R_{24}$, an appropriate deprotection method is employed to give a compound of formula 65. In the event that the protecting group $R_{24}$ is a Boc group, the deprotection can be carried out by the reaction of 64 with HCl in dioxane at room temperature. Reaction of compound 65 with an aldehyde of formula 60,

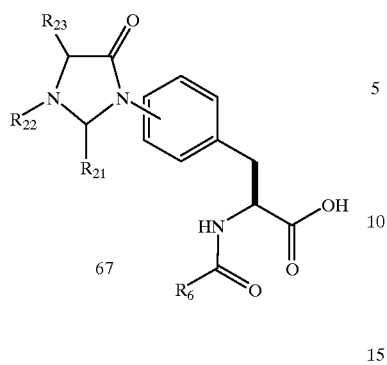

67

For the synthesis of imidazolidinones of formula 68 described in reaction scheme 12, an aminophenylalanine derivative of structure 16 in which $R_6$ and $R_7$ are as previously defined is employed. Compound 16 can be readily obtained through the synthesis described in reaction scheme 3 in the case of $R_7$ is lower alkyl. This compound can be coupled with a N-protected α-amino acid of formula 69, in which $R_{25}$ can be a natural or unnatural, D- or L-α-amino acid side chain and $R_{26}$ is a nitrogen protecting group of the type conventionally used in peptide chemistry for example, a Fmoc group, using standard peptide coupling conditions, for example HBTU in the presence of DIPEA in a polar, aprotic solvent such as DMF at a temperature between 0° C. and room temperature to give a compound of formula 70. Depending on the nature of protecting group $R_{26}$, an appropriate deprotection method is employed to give compound of formula 71. In the case of the protecting group $R_{26}$ is Fmoc group, it may be removed from 70 using standard base treatment well known to those practicing peptide chemistry, for example with piperidine in DMF, to afford an amine of formula 71. The compound 71 can then react with an aldehyde 60, in which $R_{21}$ is as previously defined, in the presence of a water scavenger such as 4 Å molecular sieves in an appropriate solvent such as dichloromethane or THF at 25–60° C. to give an imine of formula 72. The imine 72 may then be treated with an acylating agent such as the acyl chloride of formula 74 in which $R_{27}$ can be an alkyl or aryl group in the presence of a base such DIPEA or DBU in an appropriate solvent such as dichloromethane or THF at 25–60° C. to give an acyl imidazolidinone of formula 73. Alternatively, other reactive acylating group such as acid anhydrides or mixed anhydrides may be employed in this reaction. Compound 73 may be a compound of the invention, or depending on the nature of $R_7$ may be converted to a compound of the invention by an appropriate hydrolysis procedure, for example in the case where $R_7$ is lower alkyl, by hydrolysis by treatment with an alkali metal hydroxide, for example sodium hydroxide in aqueous alcohol to give, after acidification, a carboxylic acid of formula 68. The sequence may be initiated with related anilines, for example a compound of formula 7 in which $R_1$ is lower alkyl or halogen to give the corresponding 3-acyl imidazolidinones.

Reaction Scheme 12

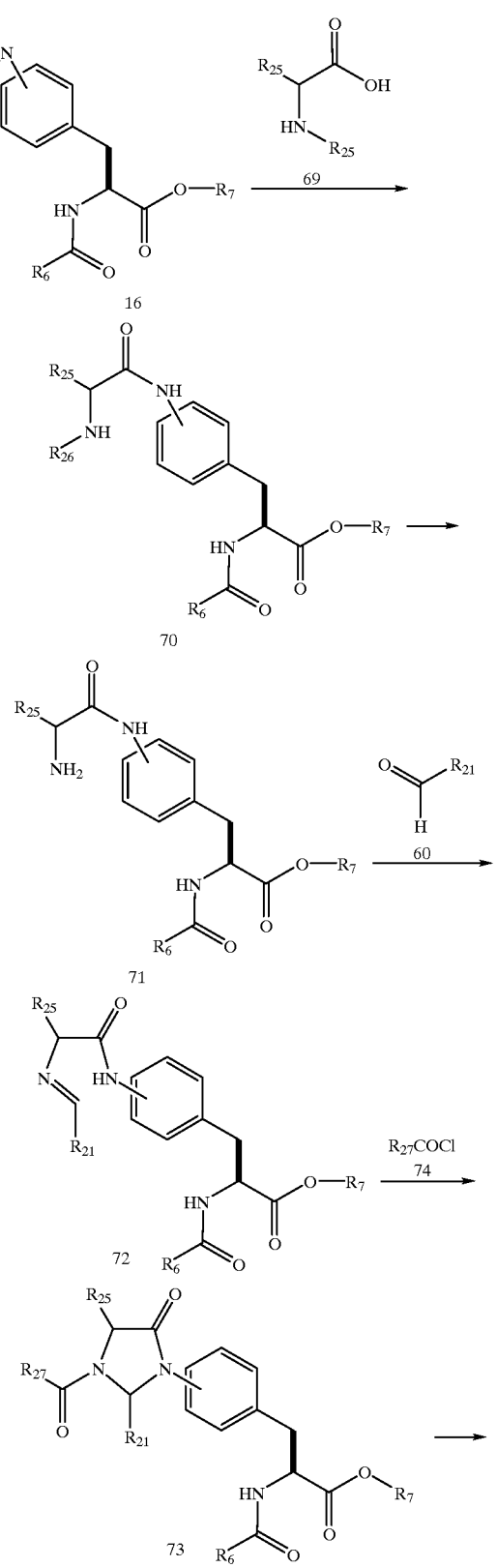

-continued

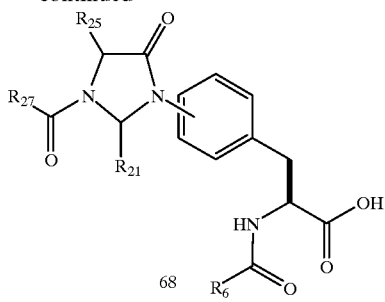

Ortho-substituted benzoic acid derivatives which are not commercially available can be prepared by conventional means. For example ortho-substituted aryl iodides or triflates may be carbonylated in the presence of carbon monoxide and a suitable palladium catalyst. The preparation of such iodide or triflate intermediates is dependent on the particular substitution pattern desired and they may be obtained by direct iodination or diazotization of an aniline followed by treatment with a source of iodide for example, potassium iodide. Triflates may be derived from the corresponding phenols by conventional means such as treatment with trifluoromethane sulfonic anhydride in the presence of a base such as triethylamine or diisopropylethylamine in an inert solvent. Other means of obtaining ortho-substituted benzoic acids involves treatment of an 2-methoxyphenyloxazoline derivative such as 75 with an alkyl Grignard reagent followed by hydrolysis of the oxazoline ring following the general procedure described by Meyers, A. I., Gabel, R., Mihelick, E. D, J. Org. Chem. 1978, 43, 1372–1379., to give an acid of formula 76. 2- or 2,6-Disubstituted benzonitriles also serve as convenient precursors to the corresponsing benzoic acids. In the case of highly hindered nitrites, for example 2-chloro-6-methylbenzonitrile, conventional hydrolysis under acidic or basic conditions is difficult and better results are obtained by DIBAL reduction to the corresponding benzaldehyde followed by oxidation using a chromium oxidizing reagent.

Reaction Scheme 13

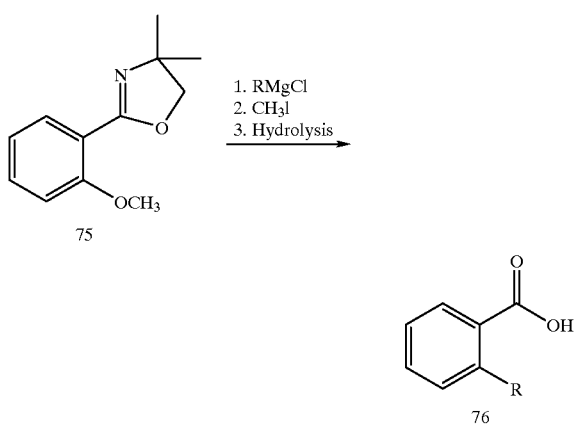

General

Melting points were taken on a Thomas-Hoover apparatus and are uncorrected. Optical rotations were determined with a Perkin-Elmer model 241 polarimeter. $^1$H-NMR spectra were recorded with Varian XL-200 and Unityplus 400 MHz spectrometers, using tetramethylsilane (TMS) as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230–400 mesh silica gel for flash chromatography; columns were run under a 0–5 psi head of nitrogen to assist flow. Thin layer chromatograms were run on glass thin layer plates coated with silica gel as supplied by E. Merck (E. Merck # 1.05719) and were visualized by viewing under 254 run UV light in a view box, by exposure to $I_2$ vapor, or by spaying with either phosphomolybdic acid (PMA) in aqueous ethanol, or after exposure to $Cl_2$, with a 4,4'-tetramethyldiaminodiphenylmethane reagent prepared according to E. Von Arx, M. Faupel and M Brugger, J. Chromatography, 1976, 120, 224–228.

Reversed phase high pressure liquid chromatography (RP-HPLC) was carried out using either a Waters Delta Prep 4000 employing a 3×30 cm. Waters Delta Pak 15 µM C-18 column at a flow of 40 mL/min employing a gradient of acetonitrile:water (each containing 0.75% TFA) typically from 5 to 95% acetonitrile over 35–40 min or a Rainin HPLC employing a 41.4×300 mm, 8 µM. Dynamax™ C-18 column at a flow of 49 mL/min and a similar gradient of acetonitrile:water as noted above. HPLC conditions are typically described in the format (5-95-35-214); this refers to a linear gradient of from 5% to 95% acetonitrile in water over 35 min while monitoring the effluent with a UV detector at a wavelenght of 214 nM.

Methylene chloride(dichloromethane), 2-propanol, DMF, THF, toluene, hexane, ether, and methanol, were Fisher reagent grade and were used without additional purification except as noted, acetonitrile was Fisher hplc grade and was used as is.

Definitions

THF is tetrahydrofuran,
DMF is N,N-dimethylformamide,
HOBT is 1-hydroxybenzotriazole,
BOP is [(benzotriazole-1-yl)oxy]tris-(dimethylamino) phosphonium hexafluorophosphate,
HATU is O-(7-azabenzotriazol-1-yl)-1,1,3,3-tetramethyluronium hexafluorophosphate
HBTU is O-benzotriazole-N,N,N',N',-tetramethyluronium hexafluorophosphate,
DIPEA is diisopropylethylamine,
DMAP is 4-(N,N-dimethylamino)pyridine
DPPA is diphenylphosphoryl azide
DPPP is 1,3-bis(diphenylphosphino)propane
DBU is 1,8-diazabicyclo[5.4.0]undec-7-ene
NaH is sodium hydride
brine is saturated aqueous sodium chloride solution
TLC is thin layer chromatography
LDA is lithium diisopropylamide
BOP-Cl is bis(2-oxo-3-oxazolidinyl)phosphinic chloride
NMP is N-methyl pyrrolidinone

EXAMPLES

Example 1

Synthesis of 4-[[(2,6-dichlorophenyl)carbonyl]amino]-N-[(1,1-dimethylethoxy)carbonyl]-L-phenylalanine methyl ester

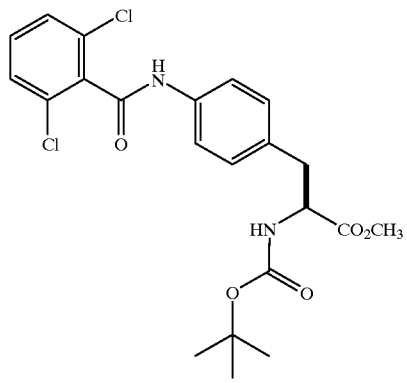

To a solution of 4-amino-N-[(1,1-dimethylethoxy) carbonyl]-L-phenylalanine methyl ester 2.6 g, 8.6 mmol) in dichloromethane (20 mL) were added diisopropylethylamine (2.3 mL, 13 mmol) followed by 2,6-dichlorobenzoyl chloride (1.99 g, 9.5 mmol) at room temperature. The mixture was stirred for 15 hr at which time a white precipitate formed. The mixture was diluted with 30 mL of dichloromethane and 50 mL of water. The layers were separated and the aqueous layer was extracted with dichloromethane (2×50 mL). The combined extracts were washed with brine and dried over anhydrous magnesium sulfate. Filtration and concentration of the solvent gave 4.03 g (quant) of 4-[(2,6-dichlorophenylcarbonyl)amino]-N-[(1,1-dimethylethoxy) carbonyl]-L-phenylalanine methyl ester as a white solid: mp 148–151° C.

Example 2

Synthesis of 4-[[(2,6-dichlorophenyl)carbonyl]amino]-L-phenylalanine methyl ester hydrochloride salt

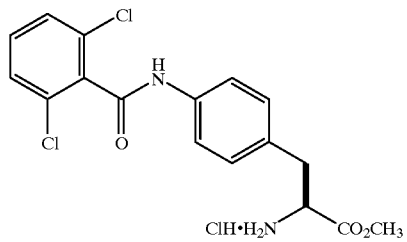

4-[[(2,6-Dichlorophenyl)carbonyl]amino]-N-[(1,1-dimethylethoxy)carbonyl]-L-phenylalanine methyl ester (1.86 g, 4.0 mmol) was treated with 10 mL of 4 N hydrochloric acid in dioxane at room temperature. After 5 minutes, the solid went into solution and the mixture was stirred for 1 hr and 25 mL of ethyl ether was added to precipitate the product. The solids were collected by filtration and were washed with hexane. The resulting hydroscopic and gummy solids were dissolved in 50 mL of methanol and concentrated. After drying under high vacuum, 4-[[(2,6-dichlorophenyl)carbonyl]amino]-L-phenylalanine methyl ester hydrochloride salt (1.64 g, 97%) was obtained as a light yellow solid, mp 158–161° C.

Example 3

Synthesis of N-(2-chloro-6-methylbenzoyl)-4-[(2,6-dichlorophenyl)carbonyl]amino]-L-phenylalanine methyl ester

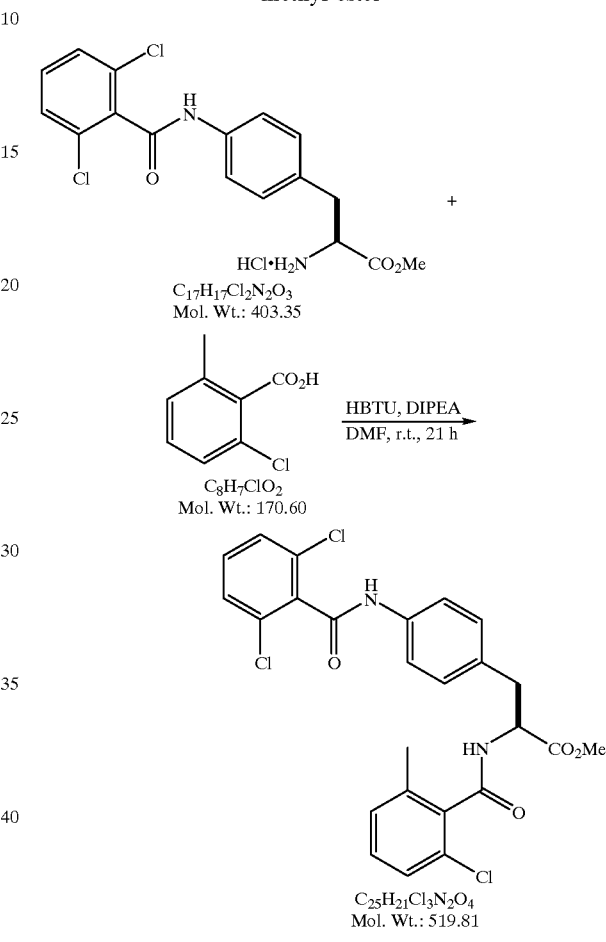

A solution of 4-[[(2,6-dichlorophenyl)carbonyl]amino]-L-phenylalanine methyl ester hydrochloride (1.23 g, 3.05 mmol), 2-chloro-6-methylbenzoic acid (0.50 g, 2.93 mmol), HBTU (1.16 g, 3.05 mmol) and DIPEA (1.33 mL, 7.6 mmol) in DMF (12 mL) was stirred 15 hr at room temperature. The mixture was diluted with ethyl acetate (250 mL) and was washed with 0.5 N HCl (2×80 mL), sat. sodium bicarbonate (2×80 mL) and brine (2×80 mL) and was dried ($Na_2SO_4$). The solution was filtered and concentrated to a yellow gum which was crystallized from ethyl acetate-hexane to give N-(2-chloro-6-methylbenzoyl)-4-[(2,6-dichlorophenyl) carbonyl]amino]-L-phenylalanine methyl ester (0.75 g), suitable for use in the next step. The mother liquors were concentrated and purified by silica gel chromatography eluting with 1:1 ethyl acetate:hexane to give an additional 0.625 g.

Examples 4 to 12

The compounds shown in below were prepared from 4-[[(2,6-dichlorophenyl)carbonyl]amino]-L-phenylalanine methyl ester hydrochloride and the appropriate benzoic acid derivatives according to the method described in example 3.

| Example | R | Yield | HRMS Obs mass | HRMS Calc mass |
|---|---|---|---|---|
| 4 | (2-F, 3-CF₃, 6-methyl phenyl) | 96 | 557.0657 | 557.0658 |
| 5 | (4-CH₃O, 2-Cl, 6-methyl phenyl) | 85 | 525.0596 | 525.0594 |
| 6 | (2,3-diCl, 6-methyl phenyl) | 84 | 539.0090 | 539.0099 |
| 7 | (2-Cl, 3-CH₃, 6-methyl phenyl) | 86 | 519.0633 | 519.0645 |
| 8 | (4-Br, 2-Cl, 6-methyl phenyl) | 89 | 582.9581 | 582.9599 |
| 9 | (3-CH₃, 4-Cl, 6-methyl phenyl) | 83 | 519.0633 | 519.0645 |
| 10 | (3-CH₃O, 4-Br, 6-methyl phenyl) | 98 | 579.0071 | 579.0089 |
| 11 | (2-SCH₃, 6-methyl phenyl) | 99 | 517.0742 | 517.0755 |

| Example | R | Yield | HRMS Obs mass | HRMS Calc mass |
|---|---|---|---|---|
| 12 | (2-NHCH₃, 6-methyl phenyl) | 80 | 500.1144 | 500.1144 |

Example 13

Synthesis of N-(2-chloro-6-methylbenzoyl)-4-[(2,6-dichlorophenyl)carbonyl]amino]-L-phenylalanine

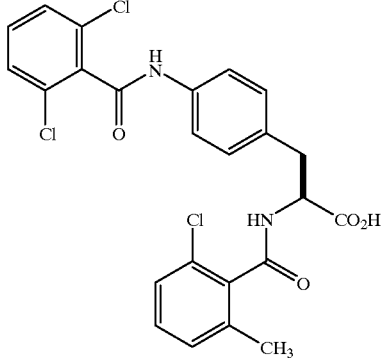

$C_{24}H_{19}Cl_3N_2O_4$
Mol. Wt.: 505.78

A solution of N-(2-chloro-6-methylbenzoyl)-4-[(2,6-dichlorophenyl)carbonyl]amino]-L-phenylalanine methyl ester (1.31 g, 2,6 mmol) in ethanol (45 mL) and 1.0 N sodium hydroxide 45 mL, 45 mmol) was stirred over night at room temperature to give a clear solution. The mixture was neutralized with 1 N hydrochloric acid to precipitate 1.28 g of a white solid. The mother liquor was extracted with ethyl acetate (2×50 mL) and the combined extracts were washed with sat. brine, dried ($Na_2SO_4$) and evaporated to give 0.56 g. Recrystallization of the first crop from ethyl acetate afforded N-(2-chloro-6-methylbenzoyl)-4-[(2,6-dichlorophenyl)carbonyl]amino]-L-phenylalanine (0.77 g). Recrystallization of the second crop from ethyl acetate afforded an additional 0.20 g. FAB HRMS: obs. mass 505.0483. Calcd mass, 505.0488 (M+H).

Example 14

Synthesis of N-(2-chloro-6-methylbenzoyl)-4-[(2,6-dichlorophenyl)carbonyl]amino]-L-phenylalanine sodium salt

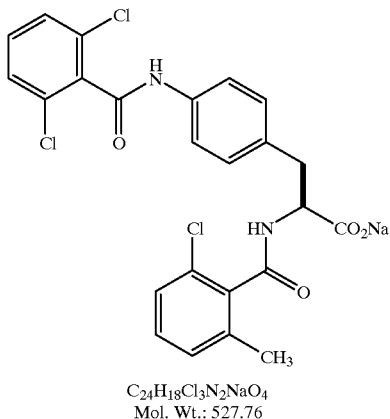

C$_{24}$H$_{18}$Cl$_3$N$_2$NaO$_4$
Mol. Wt.: 527.76

A solution of N-(2-chloro-6-methylbenzoyl)-4-[(2,6-dichlorophenyl)carbonyl]amino]-L-phenylalanine (0.15 g) in 1.0 N NaOH (0.3 mL) was applied to a 2×20 cm open column of C-18 reversed phase silica gel (40–63 μM, RP Silica Gel60, as supplied by EM Separations, Cat. 10167) eluting with water, then with 40–50% methanol in water to give N-(2-chloro-6-methylbenzoyl)-4-[(2,6-dichlorophenyl)carbonyl]amino]-L-phenylalanine sodium salt (147 mg) as an amorphous white solid after lyophilization.

Examples 15–30

The compounds shown below were prepared from the corresponding methyl esters using the method described in example 13.

| Example | Starting Material from Example | R | Yield % | HRMS Obs mass | HRMS Calc mass |
|---|---|---|---|---|---|
| 15 | 161 | 1-naphthylmethyl | 76[1] | 507.0868 | 507.0878 |
| 16 | 4 | 2-fluoro-6-(trifluoromethyl)phenyl | 98 | 543.0497 | 543.0501 |
| 17 | 163 | 2-(2-methylpropan-2-yl)phenyl | 79[1] | 513.1354 | 513.1348 |

-continued

| Example | Starting Material from Example | R | Yield % | HRMS Obs mass | HRMS Calc mass |
|---|---|---|---|---|---|
| 18 | 165 | 2,6-diisopropyl-phenyl (with CH₃) | 8¹ | 541.1665 | 541.1661 |
| 19 | 5 | 3-chloro-4-methoxyphenyl | 86² | 543.0254 | 543.0257 |
| 20 | 6 | 2,3-dichlorophenyl | 99 | 524.9939 | 524.9942 |
| 21 | 7 | 2-chloro-3-methylphenyl | 87 | 505.0482 | 505.0488 |
| 22 | 8 | 4-bromo-2-chlorophenyl | 58 | 568.9428 | 568.9437 |
| 23 | 9 | 4-chloro-3-methylphenyl | 99 | 505.0486 | 505.0488 |
| 24 | 10 | 4-bromo-3-methoxyphenyl | 90 | 564.9921 | 564.9932 |
| 25 | 11 | 2-(methylthio)phenyl | 82² | 525.0409 | 525.0418 |

-continued

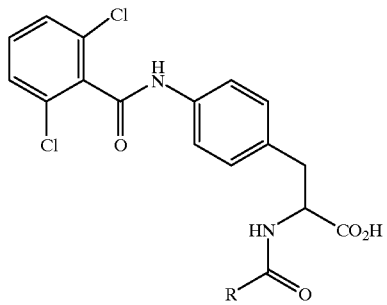

| Example | Starting Material from Example | R | Yield % | HRMS Obs mass | HRMS Calc mass |
|---|---|---|---|---|---|
| 26 | 166 | 2-methoxyphenyl (o-OCH₃-C₆H₄-) | 99[1] | 487.0839 | 487.0827 |
| 27 | 12 | 2-(methylamino)phenyl (o-NHCH₃-C₆H₄-) | 86[2] | 508.0814 | 508.0807 |
| 28 | 173 | 2-(methylsulfonyl)phenyl (o-SO₂CH₃-C₆H₄-) | 99[1] | 535.0497 | 535.0497 |

1. Yield is the for two steps following the procedure described in examples 3 and 4.
2. Isolated as the sodium salt as described in example 14.

Example 29

Synthesis of 4-[[(2,6-dichlorophenyl)carbonyl]amino]-N-[[2-(methylthio)phenyl]carbonyl]-L-phenylalanine methyl ester

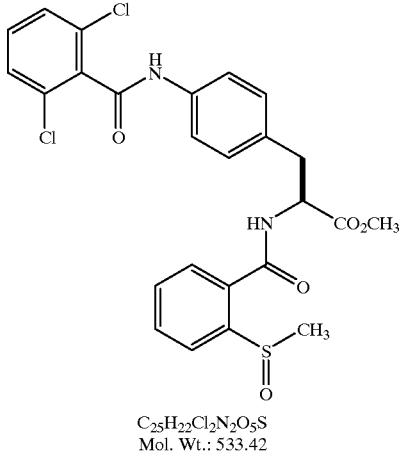

$C_{25}H_{22}Cl_2N_2O_5S$
Mol. Wt.: 533.42

A solution of 4-[(2,6-dichlorophenyl)carbonyl]amino]-N-[[2-(methylthio)phenyl]carbonyl]-L-phenylalanine methyl ester (0.25 g, 0.48 mmol) and oxone (147 mg, 0.24 mmol) in ethyl acetate (12 mL) and water (6 mL) was stirred at room temperature for 2 hr and a second portion of oxone (147 mg, 0.24 mmol) was added. The mixture was stirred over night at which time TLC (20:1 dichloromethane:methanol) suggested the presence of starting material and sulfone in addition to two sulfoxides. The layers were separated, the aqueous layer was extracted with ethyl acetate and the combined extracts were washed with sat. brine and were dried ($Na_2SO_4$). The residue after concentration was chromatographed on silica gel eluting with 20:1 dichloromethane:methanol to give 4-[[(2,6-dichlorophenyl)carbonyl]amino]-N-[[2-(methylsulfinyl)phenyl]carbonyl]-L-phenylalanine methyl ester (218 mg) as a mixture of diastereomers.

Example 30

Synthesis of 4-[[(2,6-dichlorophenyl)carbonyl]
amino]-N-[[2-(methylsulfinyl)phenyl]carbonyl]-L-
phenylalanine

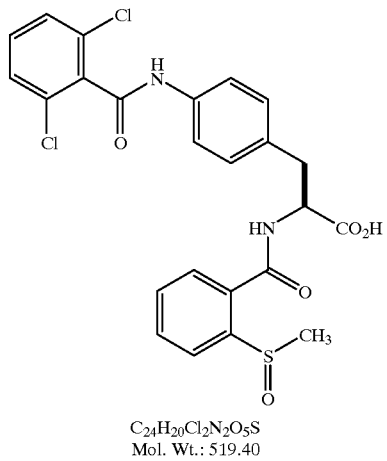

$C_{24}H_{20}Cl_2N_2O_5S$
Mol. Wt.: 519.40

Hydrolysis was carried out as described in example 13. Starting with 4-[(2,6-dichlorophenyl)carbonyl]amino]-N-[[2-(methylsulfinyl)phenyl]carbonyl]-L-phenylalanine methyl ester (214 mg, 0.41 mmol) and isolation of the product by RP HPLC, eluting with acetonitrile:water followed by lyophylization gave the more polar diastereomer 4-[[(2,6-dichlorophenyl)carbonyl]amino]-[[(N-(2-methylsulfinyl)phenyl]carbonyl]-L-phenylalanine (63.6 mg) as an amorphous solid. HR MS: Obs. mass. 541.0385. Calcd. mass. 541.0368 (M+Na) followed by the less polar diastereomer (74.2 mg). HR MS: Obs. mass, 541.0351. Calcd. mass. 541.0368 (M+Na).

Example 31

Synthesis of 4-[[(2,6-dichlorophenyl)carbonyl]
amino]-N-[[(2-phenylmethyl)phenyl]carbonyl]-L-
phenylalanine

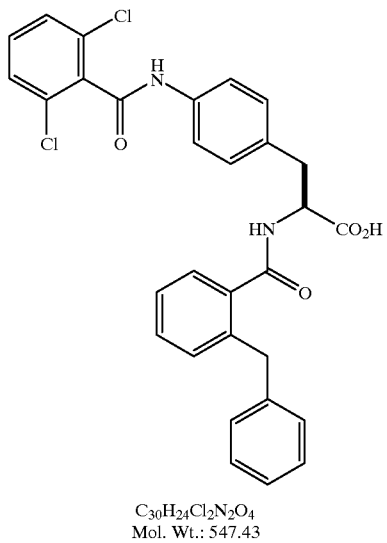

$C_{30}H_{24}Cl_2N_2O_4$
Mol. Wt.: 547.43 a. A solution of 4-[[(2-propenyloxy)carbonyl]amino]-L-phenylalanine methyl ester (935 mg, 3.54 mmol), HOAT (658 mg, 5.31 mmol), 2-benzylbenzoic acid (1.13 g, 5.31 mmol) and DCC (1.09 g, 5.31 mmol) in DMF (20 mL) was stirred over night at room temperature. The mixture was diluted with water and extracted with ethyl acetate. The combined extracts were washed with water and sat. brine, dried ($Na_2SO_4$), filtered and evaporated. The residue was recrystallized from ethyl acetate containing small amounts of dichloromethane and methanol to give 4-[[(2-propenyloxy)carbonyl]amino]-N-[[(2-phenylmethyl)phenyl]carbonyl]-L-phenylalanine (1.21 g, 74%) suitable for use in the next step.

b. Argon was passed through a solution of 4-[[(2-propenyloxy)carbonyl]amino]-N-[[(2-phenylmethyl)phenyl]carbonyl]-L-phenylalanine methyl ester (1.21 g, 2.63 mmol) and tetrakis(triphenlphosphine)palladium (61 mg, 0.053 mmol) in 45 mL of dichloromethane for 5 min and tributyltin hydride (800 μL, 2.9 mmol) was added. After 1.5 hr at room temperature, the mixture was diluted with dichloromethane (50 mL) and was washed with sat. $NaHCO_3$ and brine, dried ($Na_2SO_4$) and concentrated. The residue was dissolved in dichloromethane and ether and hexane were added to precipitate 99 mg of a white solid. The filtrate was concentrated and the residue was recrystallized from dichloromethane to give 4-amino-N-[[(2-phenylmethyl)phenyl]carbonyl]-L-phenylalanine methyl ester (594 mg).

c. A mixture of 4-amino-N-[[(2-phenylmethyl)phenyl]carbonyl]-L-phenylalanine methyl ester (200 mg, 0.52 mmol), 2,6-dichlorobenzoyl chloride (131 mg, 0.62 mmol) and triethylamine (108 μL, 0.78 mmol) in 5 mL of dichloromethane was stirred 6 hr at room temperature. The mixture was diluted with dichloromethane (10 mL) and washed with water and sat. brine. The organic layer was dried ($Na_2SO_4$) and the residue was chromatographed on silica gel, eluting with 20–60% ethyl acetate in hexane to afford 4-[[(2,6-dichlorophenyl)carbonyl]amino]-N-[[(2-phenylmethyl)phenyl]carbonyl]-L-phenylalanine methyl ester (195 mg) as an off white solid.

d. A solution of 4-[[(2,6-dichlorophenyl)carbonyl]amino]-N-[[(2-phenylmethyl)phenyl]carbonyl]-L-phenylalanine methyl ester (195 mg, 1.4 mmol) and lithium hydroxide (33.5 mg, 1.4 mmol) in THF:methanol:water (6 mL, 3:1:1) was stirred over night at room temperature and was concentrated. The residue was triturated with 1 N aqueous HCl for 10 min and the solids were collected by centrifugation, washing with water and ether to give 4-[[(2,6-dichlorophenyl)carbonyl]amino]-N-[[(2-phenylmethyl)phenyl]carbonyl]-L-phenylalanine (165 mg) as a white powder which was 97% pure by hplc analysis. FAB MS 569 (M+Na)(1 Cl), 547 (M+H)(1 Cl).

Example 32

Synthesis of 4-[[(2,6-dichlorophenyl)carbonyl]amino]-N-[[2-chloro-4-[[[(3-hydroxyphenyl)methyl]amino]carbonyl]phenyl]carbonyl]-L-phenylalanine

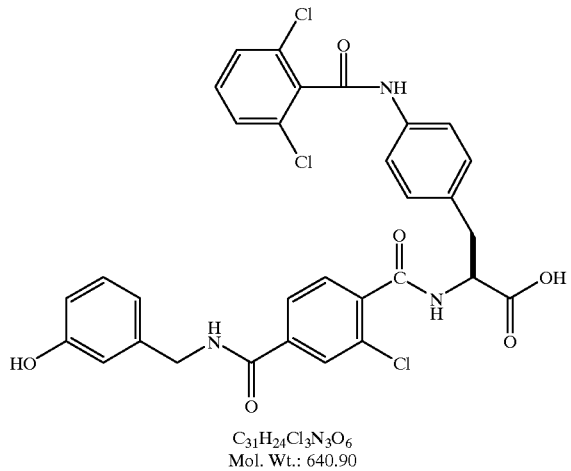

C₃₁H₂₄Cl₃N₃O₆
Mol. Wt.: 640.90

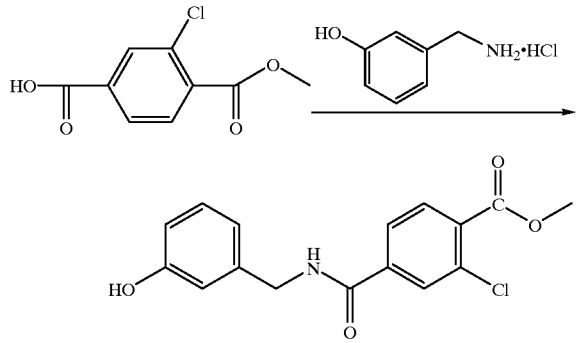

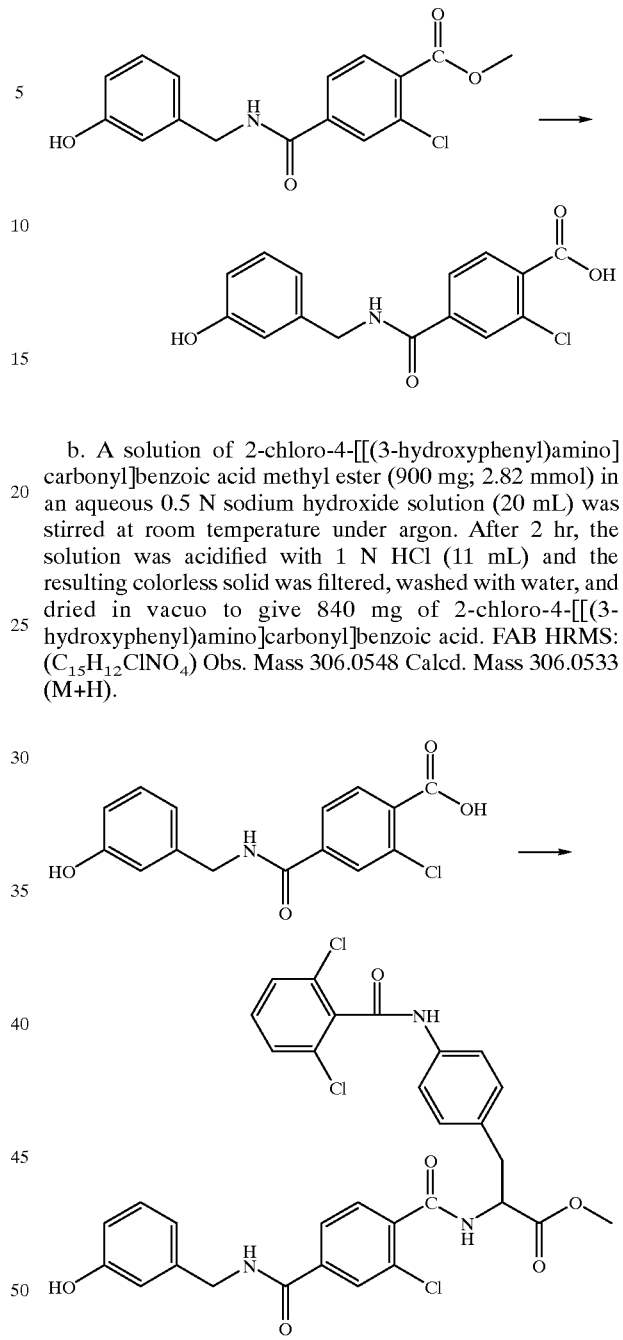

a. In an inert atmosphere, a solution of 3-chloro-4-methoxycarbonylbenzoic acid (1.13 g; 5.27 mmol), 3-hydroxybenzylamine hydrochloride (0.85 g; 5.35 mmol) and HBTU (2.08 g; 5.485 mmol) in dimethylformamide (15 mL) was stirred while DIPEA (3.54 mL; 26.33 mmol) was added. The reaction mixture was stirred overnight at room temperature, then the volatiles were removed in vacuo. The amber oily residue was partitioned between ethyl acetate (50 mL) and 0.5 N HCl (30 mL) and the organic extract was washed in turn with brine (30 mL), saturated NaHCO₃ solution (30 mL) and brine (30 mL). The aqueous layers were backwashed in turn with ethyl acetate (30 mL). Evaporation of the combined, dried (MgSO₄) orgzanic layers afforded 1.7 g of crude product. The material was chromatoaraphed (silica gel: 50 g) and eluted with ethyl acetate-hexane (2:3) to give the amide as an colorless oil (1.3 g). Crystallization from ether-hexane furnished 1.12 g of 2-chloro-4-[[(3-hydroxyphenyl)amino]carbonyl]benzoic acid methyl ester as a colorless solid. FAB HRMS: (C₁₆H₁₄ClNO₄) Obs. Mass 320.0681 Calcd. Mass 320.0689 (M+H).

b. A solution of 2-chloro-4-[[(3-hydroxyphenyl)amino]carbonyl]benzoic acid methyl ester (900 mg; 2.82 mmol) in an aqueous 0.5 N sodium hydroxide solution (20 mL) was stirred at room temperature under argon. After 2 hr, the solution was acidified with 1 N HCl (11 mL) and the resulting colorless solid was filtered, washed with water, and dried in vacuo to give 840 mg of 2-chloro-4-[[(3-hydroxyphenyl)amino]carbonyl]benzoic acid. FAB HRMS: (C₁₅H₁₂ClNO₄) Obs. Mass 306.0548 Calcd. Mass 306.0533 (M+H).

c. In an argon atmosphere, to a stirred solution of 2-chloro-4-[[(3-hydroxyphenyl)amino]carbonyl]benzoic acid (45 mg; 0.1472 mmol), 4-(2,6-dichlorobenzoylamino)-L-phenylalanine methyl ester (60 mg; 0.1488 mmol) and HBTU (59 mg; 0.16 mmol) in dimethylformamide (3 mL) was added DIPEA (0.102 mL; 0.585 mmol). The reaction mixture was stirred for 17 hr at room temperature, then was concentrated to dryness in vacuo and the residue was partitioned between dichloromethane (25 mL) and 0.5 N HCl (10 mL). The organic layer was washed with water and the aqueous layers were backwashed in turn with dichloromethane. The combined dichloromethane extracts were dried (Na₂SO₄) and evaporated to give 80 mg of crude material that was crystallized from methanol-ethyl acetate to provide 38 mg of N-[[2-chloro-4-[[(3-hydroxyphenyl)amino]carbonyl]phenyl]carbonyl]-4-[[(2,6-dichlorophenyl)carbonyl]amino]-L-phenylalanine methyl ester. mp 230–232° C. FAB HRMS: ($C_{32}H_{26}Cl_3N_3O_6$) Obs. Mass 654.0952 Calcd. Mass 654.0965 (M+H).

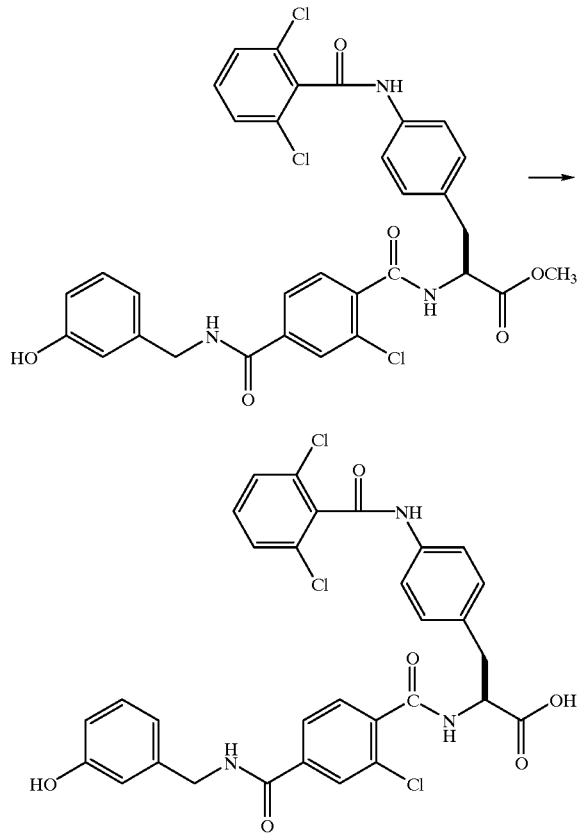

d. A solution of N-[[2-chloro-4-[[(3-hydroxyphenyl)amino]carbonyl]phenyl]carbonyl]-4-[[(2,6-dichlorophenyl)carbonyl]amino]-L-phenylalanine methyl ester (35 mg; 0.053 mmol) in methanol (0.35 mL) and tetrahydrofuran (0.35 mL) was treated with an aqueous 1N lithium hydroxide solution (0.16 mL) and the mixture was stirred at room temperature under argon for 90 minutes. The solution was concentrated under reduced pressure, then was diluted with water (5 mL) and extracted with diethyl ether (2×5 mL). The separated aqueous layer was acidified with 1 N HCl (0.18 mL) and the resulting colorless solid was filtered off, washed with water, and dried to give 29 mg of N-[[2-chloro-4-[[(3-hydroxyphenyl)amino]carbonyl]phenyl]carbonyl]-4-[[(2,6-dichlorophenyl)carbonyl]amino]-L-phenylalanine. FAB HRMS: ($C_{31}H_{24}Cl_3N_3O_6$) Obs. Mass 640.0821 Calcd. Mass 640.0809 (M+H).

Example 33
Synthesis of 4-[[(2,6-dichlorophenyl)carbonyl]amino]-N-[[2-chloro-4-[5-[[(3-hydroxyphenyl)methyl]amino]-1H-tetrazol-1-yl]phenyl]carbonyl]-L-phenylalanine

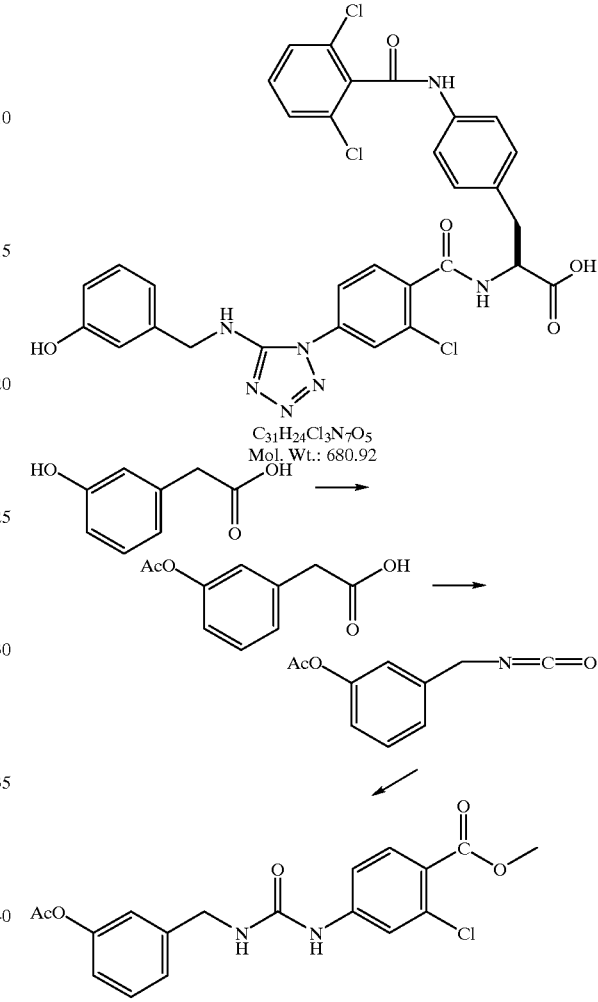

a. A stirred suspension of 3-hydroxyphenylacetic acid (10.2 g; 67 mmol) in acetic anhydride (100 mL; 1.06 mol) under anhydrous conditions was treated with pyridine (0.5 mL). In the mildly exothermic reaction, the solids dissolved within several minutes and the mixture was maintained at 40° C. for five hours. The reaction was concentrated in vacuo to about half volume, then water (30 g) in the form of ice chips was added at such a rate that the temperature remained <45° C. When the exotherm had subsided, a second portion of water (200 mL) was added slowly and the mixture was stirred for another 30 minutes. The precipitated solid was filtered, washed with water and dried to constant weight in vacuo over $P_2O_5$ to give 3-acetoxyphenylacetic acid (11.7 g) which was used without further purification.

In an inert atmosphere, a solution of the above 3-acetoxyphenylacetic acid (1.942 g; 10 mmol), diphenylphosphoryl azide (2.8 g; 10.17 mmol) and DIPEA (1.92 mL; 11 mmol) in benzene (25 mL) was stirred at room temperature for 1 hr, then the reaction temperature was slowly raised to 70° C. Evolution of gas began to be evident as the reaction temperature reached approximately 55° C. and became much more vigorous as the reaction temperature approached 70° C. Within 30 minutes at that temperature gas evolution had stopped and the reaction solution containing the formed 3-acetoxybenzylisocyanate was cooled to 40° C. Another portion of DIPEA (3.84 mL; 22 mmol) was added, followed by 4-amino-2-chlorobenzoic acid methyl ester hydrochloride salt (2.95 g; 13.3 mmol) and the brownish purple solution was stirred and heated at reflux under argon overnight. The reaction mixture was cooled, diluted with benzene (50 mL) and washed in turn with 1N HCl (50 mL) and dilute brine. The aqueous layers were re-extracted with benzene, then the combined, dried (MgSO$_4$) organic extracts were evaporated and the crude residue was purified by HPLC (silica gel; ethyl acetate-hexane-2:3). Evaporation of the appropriate fractions provided 3.24 g of the solid urea which was then crystallized from dichloromethane-ethyl acetate to give 4-[3-(3-acetoxybenzyl)ureido]-2-chlorobenzoic acid methyl ester (2.71 g) as a colorless solid. mp 113–114° C. FAB HRMS: ($C_{18}H_{17}ClN_2O_5$) Obs. Mass 377.0898 Calcd. Mass 377.0905 (M+H).

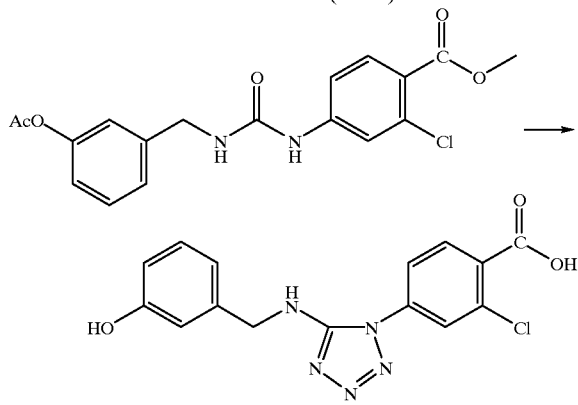

b. In a dry argon atmosphere, a solution of triphenylphosphine (1.684 g; 6.42 mmol), diethyl azodicarboxylate (1.13 g; 6.42 mmol) and 4-[3-(3-acetoxybenzyl)ureido]-2-chlorobenzoic acid methyl ester (1.21 g; 3.21 mmol) in dry THF (30 mL) was treated with trimethylsilyl azide (0.86 mL; 6.48 mmol) and was stirred at room temperature for 24 hr. Examination of the reaction mixture by TLC suggested the presence of considerable starting material, so additional amounts of triphenylphosphine (0.842 g; 3.21 mmol), diethyl azodicarboxylate (0.565 g; 3.21 mmol) and trimethylsilyl azide (0.43 mL; 3.21 mmol) were added. The reaction was stirred at room temperature for an additional 40 hr. After the solvents were removed under reduced pressure, the residue was taken up in dichloromethane (100 mL) and washed with water (2×50 mL). The aqueous extracts were backwashed in turn with dichloromethane (50 mL) and the combined, dried (MgSO$_4$) extracts were evaporated in vacuo. From a previous experiment it had been established that the reaction yielded a complex, difficultly separable, mixture of several products, some deacetylated and/or de-esterified. Accordingly, in this experiment, the residue was dissolved in a mixture of methanol (30 mL) and 1N lithium hydroxide (15 mL) and the mixture was stirred at room temperature for 2 hr to complete the hydrolyses of both the ester and phenolic acetate groups. Most of the volatiles were removed under reduced pressure then the basic solution was diluted with water (20 mL) and washed with dichloromethane (2×30 mL). The aqueous layer was then acidified with 1N HCl (16 mL) and extracted with ethyl acetate (2×50 mL). The dried (MgSO$_4$) ethyl acetate extracts were evaporated and the residual solid (810 mg), approximately a 4:1 mixture of the desired aminotetrazole and its positional isomer, was crystallized from ether to furnish 560 mg of 2-chloro-4-[5-[(3-hydroxyphenyl)amino]tetrazol-1-yl]benzoic acid as a colorless solid. FAB HRMS: ($C_{15}H_{12}ClN_5O_3$) Obs. Mass 345.0624 Calcd. Mass 345.0629 (M+H).

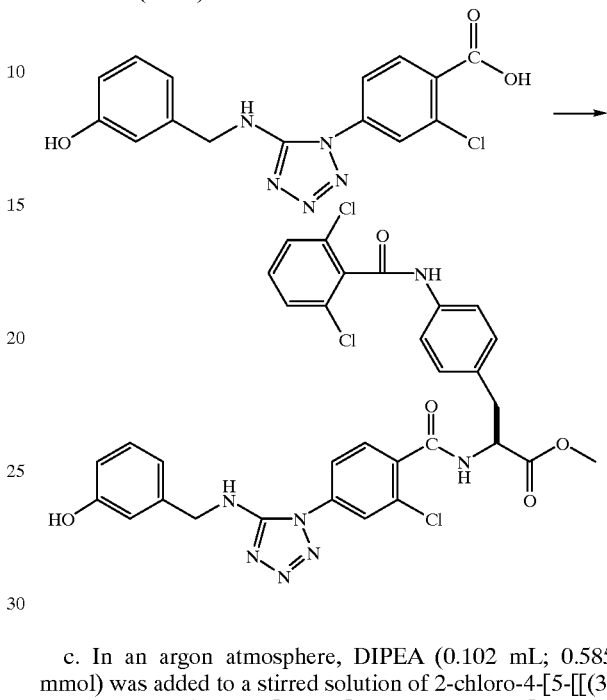

c. In an argon atmosphere, DIPEA (0.102 mL; 0.585 mmol) was added to a stirred solution of 2-chloro-4-[5-[[(3-hydroxyphenyl)methyl]amino]-1H-tetrazol-1-yl]benzoic acid (51 mg; 0.15 mmol), 4-[[(2,6-dichlorophenyl)carbonyl]amino]-L-phenylalanine methyl ester (60 mg; 0.15 mmol) and HBTU (59 mg; 0.1555 mmol) in dimethylformamide (3 mL). The reaction mixture was stirred for 17 hr at room temperature, then was concentrated under reduced pressure. The residual oil was taken up in dichloromethane (25 mL) and washed in turn with 0.5 N HCl (10 mL) and water (10 mL). The aqueous layers were backwashed in turn with dichloromethane. The combined organic layers were dried (Na$_2$SO$_4$) and evaporated to give 85 mg of crude product. This material was crystallized from dichloromethane-diethyl ether to furnish 79 mg of 4-[[(2,6-dichlorophenyl)carbonyl]amino]-N-[[2-chloro-4-[5-[[(3-hydroxyphenyl)methyl]amino]-1H-tetrazol-1-yl]phenyl]carbonyl]-L-phenylalanine methyl ester as a colorless solid, mp 155–158° C. FAB HRMS: ($C_{32}H_{26}Cl_3N_7O_5$) Obs. Mass 694.1158 Calcd. Mass 694.1139 (M+H).

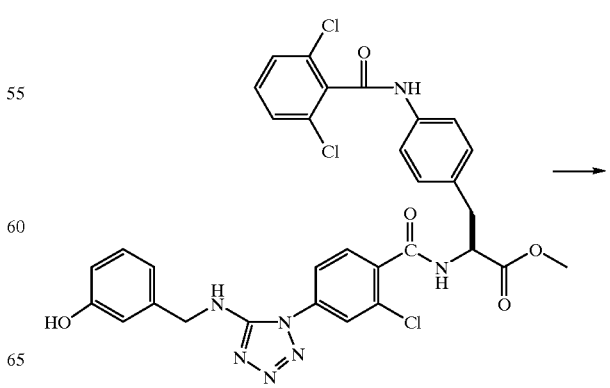

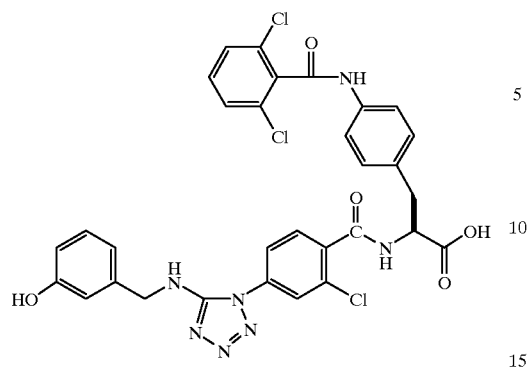

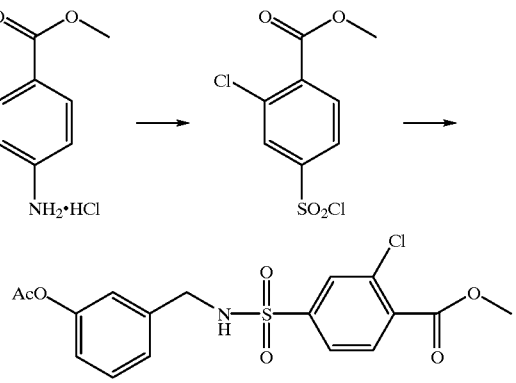

d. An aqueous 1N lithium hydroxide solution (0.33 mL) was added to a solution of 4-[[(2,6-dichlorophenyl) carbonyl]amino]-N-[[2-chloro-4-[5-[[(3-hydroxyphenyl) methyl]amino]-1 H-tetrazol-1-yl]phenyl]carbonyl]-L-phenylalanine methyl ester (75 mg; 0.108 mmol) in methanol (0.66 mL) and THF (0.66 mL) and the mixture was stirred at room temperature for 90 min. After the solvents were stripped under reduced pressure, the residue was dissolved in water (20 mL) and extracted with diethyl ether (3×5 mL). The aqueous layer was filtered through Celite, then acidified with 1 N HCl (0.35 mL). The resulting colorless solid was filtered off, washed with water, and dried in vacuo to give 57 mg of 4-[[(2,6-dichlorophenyl)carbonyl] amino]-N-[[2-chloro-4-[5-[[(3-hydroxyphenyl)methyl] amino]-1H-tetrazol-1-yl]phenyl]carbonyl]-L-phenylalanine. FAB HRMS: ($C_{31}H_{24}Cl_3N_7O_5$) Obs. Mass 680.0981 Calcd. Mass 680.0983 (M+H).

Example 34

Synthesis of 4-[[(2,6-dichlorophenyl)carbonyl] amino]-N-[[2-chloro-4-[[[(3-hydroxyphenyl)methyl] amino]sulfonyl]phenyl]carbonyl]-L-phenylalanine

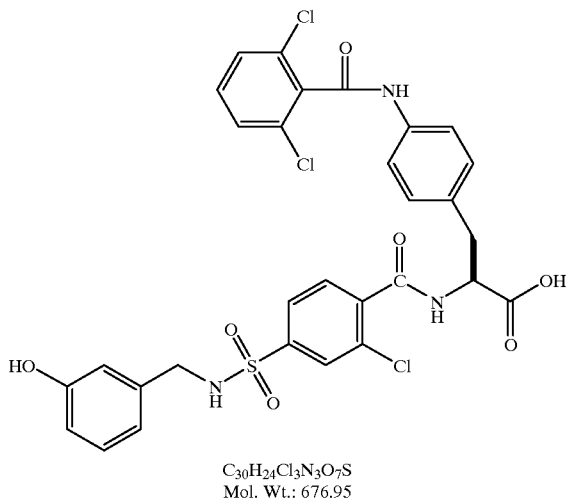

$C_{30}H_{24}Cl_3N_3O_7S$
Mol. Wt.: 676.95 a. At room temperature, a stirred solution of 4-amino-2-chlorobenzoic acid methyl ester hydrochloride (1.11 g; 5 mmol) in conc. HCl (10 mL) was treated in one portion with $NaNO_2$ (0.42 g; 6.09 mmol) in water (3 mL). After 15 minutes, the resulting suspension was added over 2 minutes to a rapidly stirred, saturated solution of $SO_2$ in acetic acid (15 mL) containing $CuCl_2$ (0.15 g) in water (1 mL). There was an immediate vigorous evolution of gas that subsided after 10 minutes, whereupon the reaction mixture was diluted with ice water (200 mL). The resulting purplish solid was filtered off, washed with water, then was dissolved in dichloromethane. The dried ($Na_2SO_4$) solution was evaporated in vacuo and the residual material was chromatographed over silica gel (50 g). The appropriate fractions, eluted with 30–40% diethyl ether in hexane, were concentrated to dryness under reduced pressure to yield 1.1 g of 3-chloro-4-methoxycarbonylbenzenesulfonyl chloride as a colorless solid.

The above 3-chloro-4-methoxycarbonylbenzenesulfonyl chloride (0.14 g; 0.52 mmol) in dichloromethane (0.5 mL) was added in one portion to a stirred solution of 3-acetoxybenzylamine hydrochloride (0.105 g; 0.52 mmol) and triethylamine (0.2 mL; 1.42 mmol) in dichloromethane (0.2 mL). The reaction was allowed to proceed for 90 minutes at ambient temperature, then was diluted with dichloromethane (20 mL) and washed sequentially with 0.5 N HCl (10 mL), brine (10 mL), saturated $NaHCO_3$ solution (10 mL) and brine (10 mL). The aqueous layers were backwashed in turn with dichloromethane (10 mL). The combined, dried ($Na_2SO_4$) organic layers were concentrated to afford 0.2 g of an oil that was chromatographed (silica gel; 15 g). The product was eluted from the column with diethyl ether-hexane (4:1) and diethyl ether to give, after evaporation of the appropriate fractions, 165 mg of 4-[(3-acetoxybenzylamino)sulfonyl]-2-chlorobenzoic acid methyl ester as a colorless solid. FAB HRMS: ($C_{17}H_{16}ClNO_6S$) Obs. Mass 398.0469 Calcd. Mass 398.0465 (M+H).

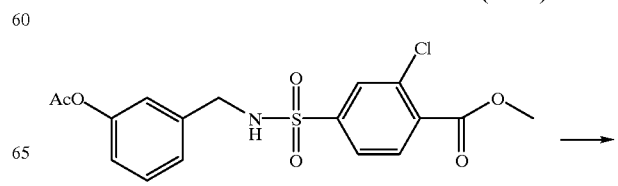

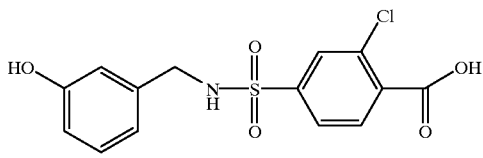

b. A stirred solution of 4-[(3-acetoxybenzylamino)sulfonyl]-2-chlorobenzoic acid methyl ester (163 mg; 0.41 mmol) in methanol (3 mL) and tetrahydrofuran (3 mL) was treated at room temperature with an aqueous 1 N lithium hydroxide solution (1.65 mL). After 2 hr the volatiles were removed under reduced pressure and the residual material was dissolved in water (15 mL) and the solution filtered through Celite. The filtrate was acidified with 1 N HCl (2 mL) and extracted with ethyl acetate (3×10 mL). After the extracts were backwashed in turn with brine, they were combined, dried ($Na_2SO_4$) and evaporated in vacuo to furnish 140 mg of 2-chloro-4-[(3)-hydroxybenzylamino)sulfonyl]benzoic acid. A small sample of the product was crystallized from ethyl acetate-hexane to give a colorless solid, mp 167–169° C. FAB LRMS: ($C_{14}H_{12}ClNO_5S$) Obs. Mass 342 Calcd. Mass 342 (M+H).

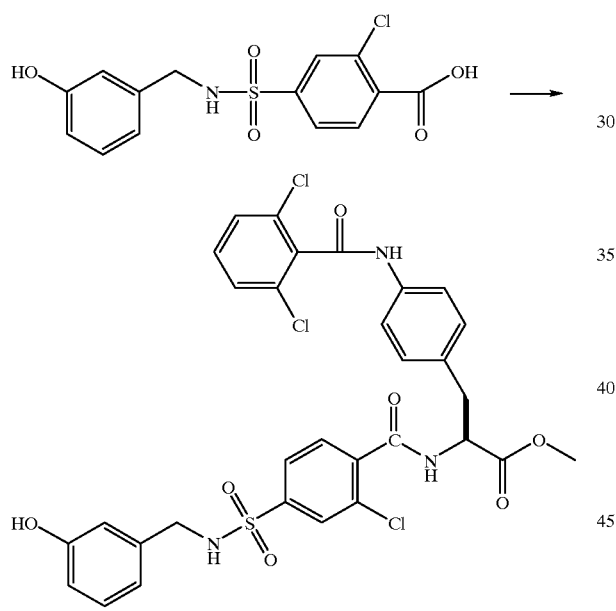

c. A solution of 2-chloro-4-[(3-hydroxybenzylamino)sulfonyl]benzoic acid (50 mg; 0.146 mmol), 4-[[(2,6-dichlorophenyl)carbonyl]amino]-L-phenylalanine methyl ester (60 mg; 0.1486 mmol), HBTU (5 mg; 0.15 mmol) and DIPEA (0.102 mL; 0.585 mmol) in dimethylformamide (3 mL) was stirred for 17 hr under argon at room temperature, then was concentrated to dryness under reduced pressure. The residue was partitioned between dichloromethane (25 mL) and 0.5 N HCl (25 mL). The separated aqueous phase was re-extracted with dichloromethane (10 mL), then the organic extacts were washed in turn with water (2×25 mL). The combined dichloromethane layers were dried ($Na_2SO_4$) and evaporated to give 90 mg of the crude product as a dark oil. Chromatography of the oil over silica gel (9 g; 4:1 ethyl acetate-hexane) yielded 55 mg of 4-[[(2,6-dichlorophenyl)carbonyl]amino]-N-[[2-chloro-4-[[[(3-hydroxyphenyl)methyl]amino]sulfonyl]phenyl]carbonyl]-L-phenylalanine methyl ester, as a colorless solid. FAB HRMS: ($C_{31}H_{26}Cl_3N_3O_7S$) Obs. Mass 690.0639 Calcd. Mass 690.0635 (M+H).

d. An aqueous 1N lithium hydroxide solution (0.25 mL) was added to a solution of 4-[[(2,6-dichlorophenyl)carbonyl]amino]-N-[[2-chloro-4-[[[(3-hydroxyphenyl)methyl]amino]sulfonyl]phenyl]carbonyl]-L-phenylalanine methyl ester (51 mg; 0.0738 mmol) in methanol (0.5 mL) and tetrahydrofuran (0.35 mL). After the reaction was stirred at room temperature for 90 minutes, the solvents were removed under reduced pressure. The crude product in the minimum amount of methanol was then applied to a column of silica eel (5 g) made up in a mixture of chloroform, methanol, acetic acid and water (15:3:1:0.6). The column was eluted with the same solvent mixture and the appropriate fractions were combined and evaporated. The residue was lyophilized from deionized water to give 36 mg of 4-[[(2,6-dichlorophenyl)carbonyl]amino]-N-[[2-chloro-4-[[[(3-hydroxyphenyl)methyl]amino]sulfonyl]phenyl]carbonyl]-L-phenylalanine as an off white solid. FAB HRMS: ($C_{30}H_{24}Cl_3N_3O_7S$) Obs. Mass 676.0482 Calcd. Mass 676.0479 (M+H).

Example 35

Coupling of N-[(9H-fluoren-9-ylmethoxy)carbonyl]-4-[[(2-propenyloxy)carbonyl]amino]-L-phenylalanine to Wang resin

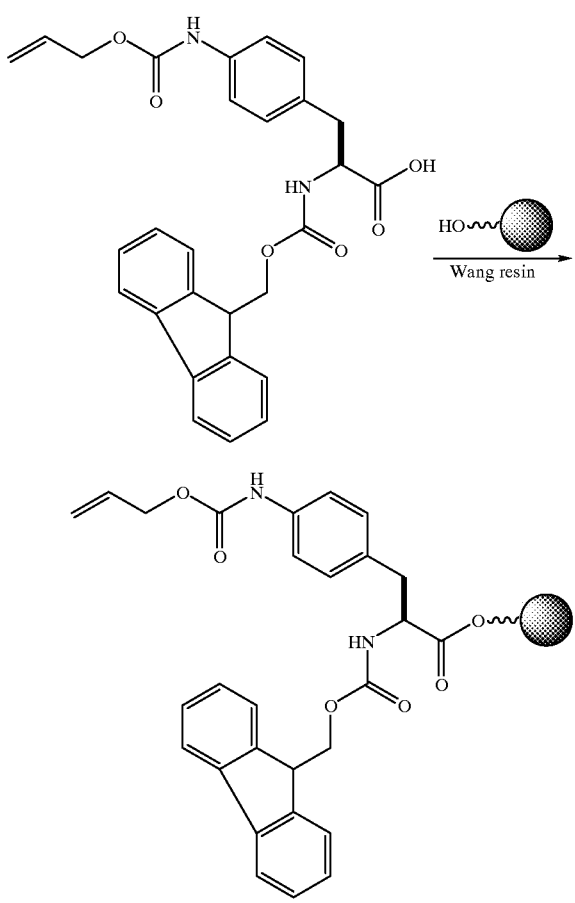

A 250 mL cylindrical glass vessel equipped with a coarse glass frit was charged with 10 g of Wang resin, (loading factor: 1.15 mmol/g, 300 mesh). The resin was washed with dichloromethane (2×100 mL), methanol (2×100 mL) and dimethylformamide (2×100 mL). To the swollen resin was added N-[(9H-fluoren-9-ylmethoxy)carbonyl]-4-[[(2-propenyloxy carbonyl]amino]-L-phenylalanine (11.2 g, 23 mmol) and 2,6-dichlorobenzoyl chloride (8.06 mL, 57.5 mmol) in N-methylpyrrolidone (70 mL) and the mixture was agitated for 30) minutes. Pyridine (6.45 mL, 80.5 mmol) was added and the resulting mixture was agitated for 24 hours. The substitution was found at 0.75 mmol of N-[(9H-fluoren-9-ylmethoxy)carbonyl]-4-[[(2-propenyloxy)carbonyl]amino]-L-phenylalanine per gram of resin by quantitative UV measurement of the Fmoc present on the resin.

Example 36

Synthesis of 4-amino-N-[(9H-fluoren-9-ylmethoxy)carbonyl]-L-phenylalanine on Wang resin

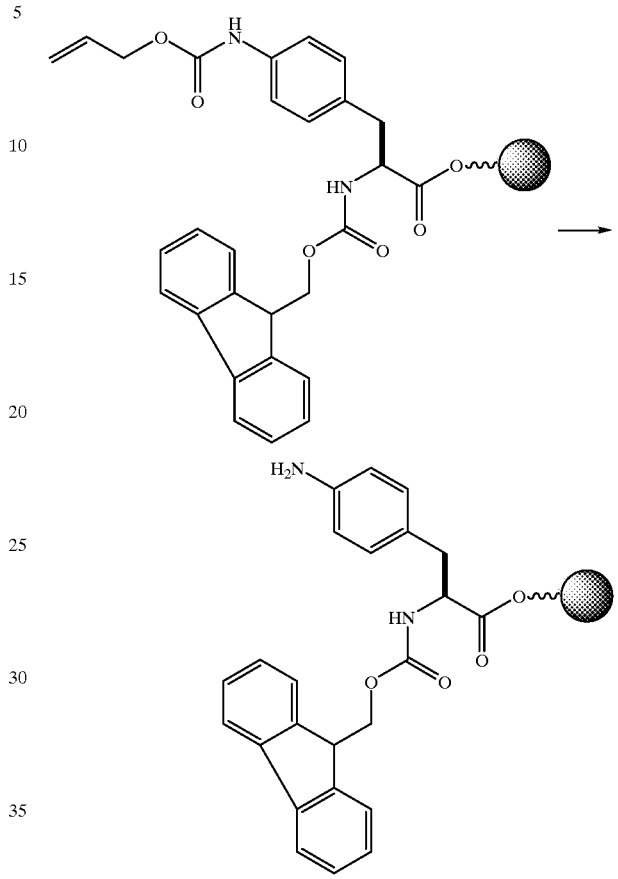

A 500 mL cylindrical glass vessel equipped with a coarse glass frit was charged with 10 g of N-[(9H-fluoren-9-ylmethoxy)carbonyl]-4-[[(2-propenyloxy)carbonyl]amino]-L-phenylalanine substituted Wang resin (10 g) obtained from Example 35 and a solution prepared from Pd(Ph$_3$P)$_2$Cl$_2$ (1.6 g, 2.3 mmol) and acetic acid (5 mL, 83 mmol) in dry dichloromethane (150 mL). The resulting mixture was agitated for 30 minutes followed by the addition of tri-n-butyl tin hydride (20 mL, 74.3 mmol). The resulting mixture was agitated for 1 hour. To the mixture was added tri-n-butyl tin hydride (10 mL, 37 mmol). Agitation was continued for 1 hour and the mixture was filtered. To the resulting resin was added a solution prepared from Pd(Ph$_3$P)$_2$Cl$_2$ (1.6 g, 2.3 mmol) and acetic acid (5 mL, 83 mmol) in dried dichloromethane (150 mL). The mixture was agitated for 30 minutes followed by the addition of tri-n-butyl tin hydride (20 mL, 74.3 mmol). The resulting mixture was agitated 1 hour. To the mixture was added additional tri-n-butyl tin hydride (10 mL, 37.15 mmol). Agitation continued for 1 hour. After the second deprotection cycle, the mixture was washed with dichloromethane (2×100 mL), methanol (2×100 mL) and dimethylformamide (2×100 mL) to give 4-amino-N-[(9H-fluoren-9-ylmethoxy)carbonyl]-L-phenylalanine on Wang resin suitable for use in subsequent steps.

Example 37

Synthesis of 4-[[(4-quinolinyl)carbonyl]amino]-L-phenylalanine on Wang resin

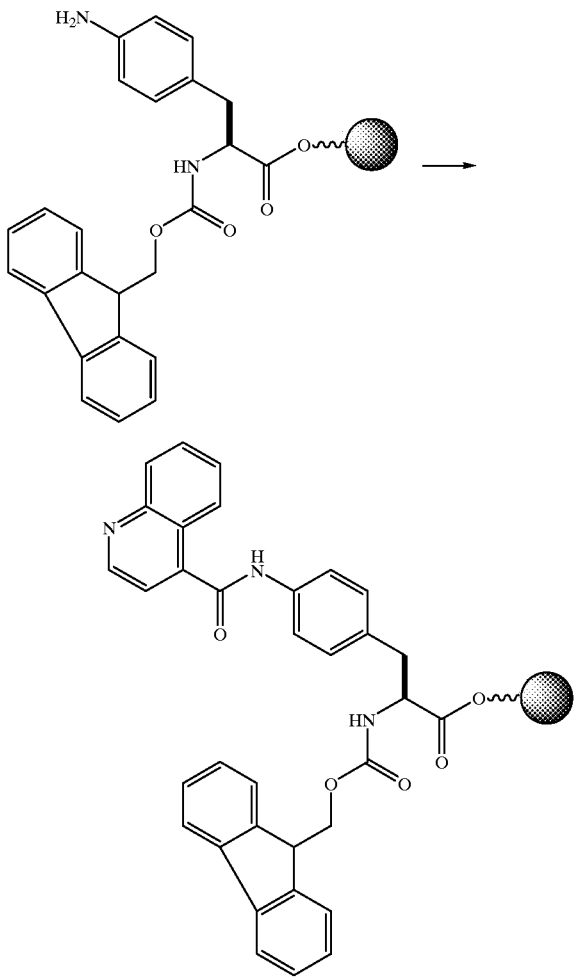

A 250 mL cylindrical glass vessel equipped with a coarse glass frit was charged with 4-amino-N-[(9H-fluoren-9-ylmethoxy)carbonyl]-L-phenylalanine on Wang resin (10 g) obtained in Example 36 and a solution prepared from quinoline-4-carboxylic acid (5.2 g, 30 mmol), BOP (13.75 g, 30 mmol) and diisopropylethylamine (6.8 mL) in 70 mL of NMP. The slurry was agitated for 4 hours. The mixture was filtered and washed with dichloromethane (2×100 mL), methanol (2×100 mL) and dimethylformamide (2×100 mL). To the washed resin was added a solution of 25% piperidine in NMP (80 mL), the mixture was agitated at room temperature for 20 minutes and filtered. The process was repeated and the resulting slurry was filtered and washed with dichloromethane (2×100 mL), methanol (2×100 mL) and dimethylformamide (2×100 mL). Filtration afforded 4-[[(4-quinolinyl)carbonyl]amino]-L-phenylalanine on Wang resin suitable for use in the next step.

Example 38

Synthesis of N-[(2,6-dimethylphenyl)carbonyl]-4-[[(4-quinolinyl)carbonyl]amino]-L-phenylalanine

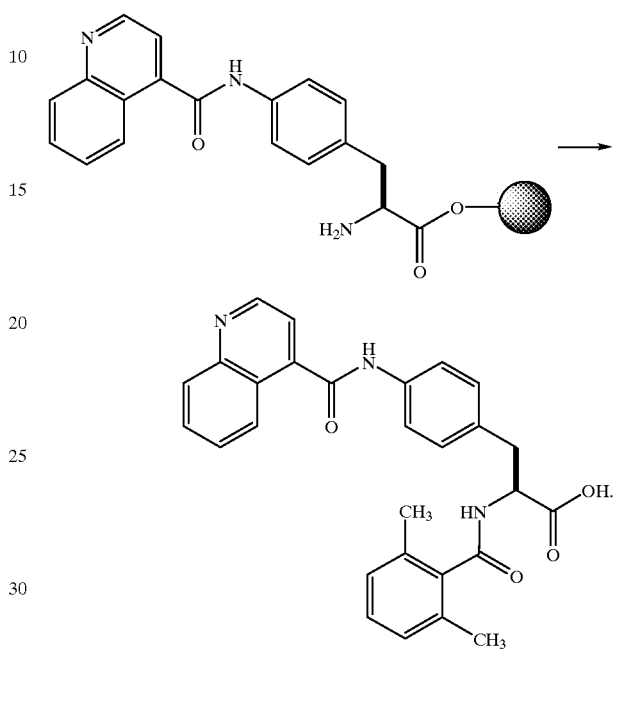

4-[[(4-Quinolinyl)carbonyl]amino]-L-phenylalanine on Wang resin (300 mg, 0.20 mmol) was washed with dichloromethane (2×10 mL), methanol (2×10 mL) and dimethylformamide (2× 10 mL). To the resin was added a solution prepared from 2,6-dimethylbenzoic acid (150 mg, 1.0 mmol), BOP (450 mg, 1.02 mmol) and diisopropylethylamine (0.23 mL) in 4 mL of N-methylpyrrolidone at room temperature. The resulting mixture was agitated for 2 hr. The reaction mixture was then filtered and washed with dichloromethane (2×10 mL), methanol (2×10 mL) and dichloromethane (2×10 mL). Cleavage was effected by treatment with 90% trifluoroacetic acid (TFA) in dichloromethane for 5 minutes. The mixture was filtered and the TFA was removed under high vaccum. Addition of ether (25 mL) effected precipitation of N-[(2,6-dimethylphenyl)carbonyl]-4-[[(4-quinolinyl)carbonyl)amino]-L-phenylalanine (0.16 g).

Examples 39–49

Using the procedure described in Example 38, the compounds shown below were prepared starting from 4-[[(4-quinolinyl)carbonyl]amino]-L-phenylalanine and the appropriate benzoic acid derivates.

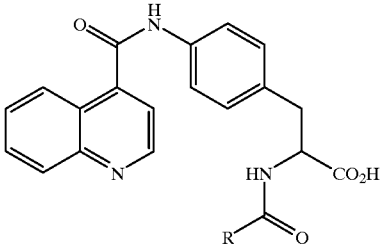
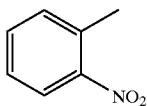
| Example | R | MW |
|---|---|---|
| 39 | 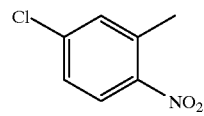 | 484.467 |
| 40 | 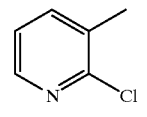 | 518.912 |
| 41 | 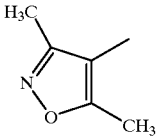 | 474.902 |
| 42 | 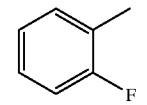 | 458.473 |
| 43 | 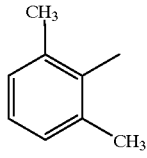 | 457.460 |
| 44 | 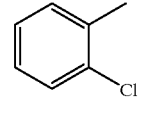 | 487.93 |
| 45 | 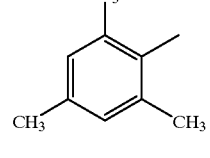 | 473.91 |
| 46 | 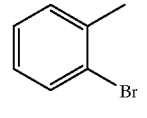 | 481.55 |
| 47 | 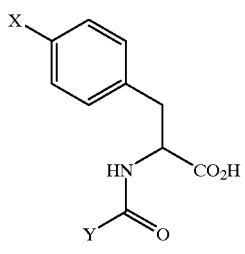 | 518.366 |
-continued
| Example | R | MW |
|---|---|---|
| 48 | 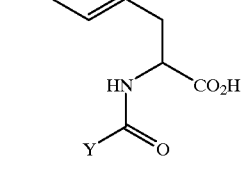 | 563.36 |
| 49 | 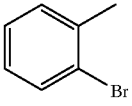 | 475.45 |
Examples 50 to 61
Using the method described in examples 37 to 38, the following compounds were prepared from 4-amino-N-[(9H-fluoren-9-ylmethoxy)carbonyl]-L-phenylalanine on Wang resin and the appropriate carboxylic acids:
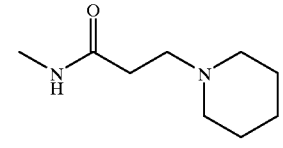
| Example | Y | X |
|---|---|---|
| 50 | 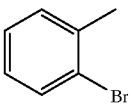 | 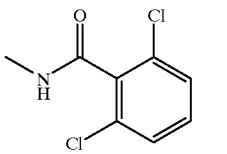 |
| 51 | | |

-continued
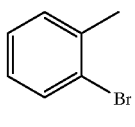
| Example | Y | X |
|---|---|---|
| 52 | 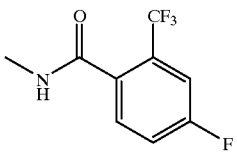 | 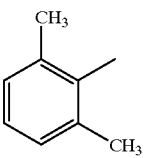 |
| 53 | 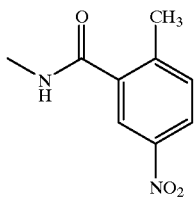 | 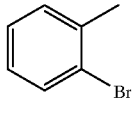 |
| 54 | 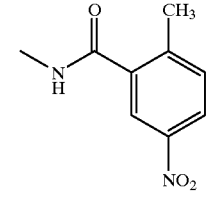 | 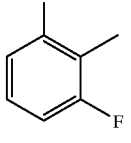 |
| 55 | 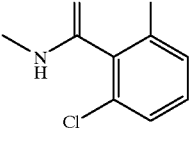 | 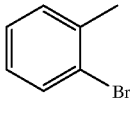 |
| 56 | 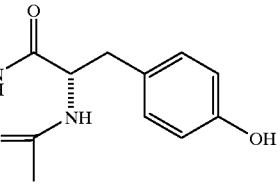 | 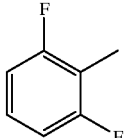 |
-continued
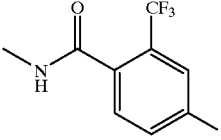
| Example | Y | X |
|---|---|---|
| 57 | 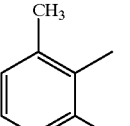 | 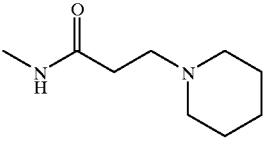 |
| 58 | 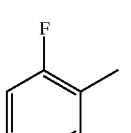 | 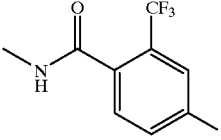 |
| 59 | 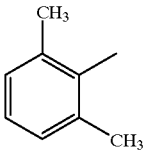 | 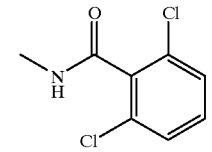 |
| 60 | 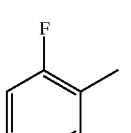 | 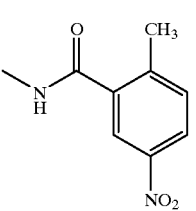 |
| 61 | | |

Example 62

Synthesis of N-[(2,6-dimethylphenyl)carbonyl]-4-[[[(2,4,6-trimethylphenyl)sulfonyl]amino]]-L-phenylalanine

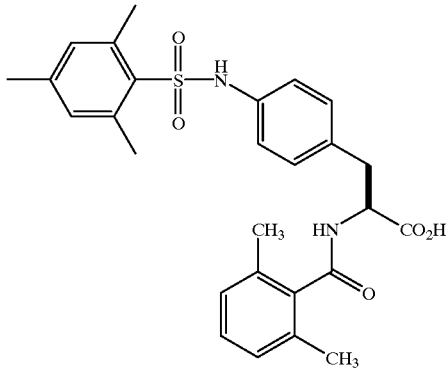

Wang resin loaded with 4-amino-N-[(9H-fluoren-9-ylmethoxy)carbonyl]-L-phenylalanine (3.0 g, 2.28 mmol) in pyridine (15 mL) was cooled to 0° C. and 2,4,6-benzenesulfonyl chloride (2.49 g, 11.4 mmol) was added and the mixture was agitated over night at room temperature. The mixture was filtered and the resin was washed with methanol and dichloromethane. The coupling procedure was repeated. To the washed resin was added a solution of 25% piperidine in N-methylpyrrolidone (10 mL), the mixture was agitated at room temperature for 20 minutes and filtered. The process was repeated and the resulting slurry was filtered and washed with dichloromethane (2×10 mL), methanol (2×10 mL) and dimethylformamide (2×10 mL). Filtration afforded 4-[[(2,4,6-trimethylphenyl)sulfonyl]amino]-L-phenylalanine on Wang resin suitable for use in the next step.

A sample of the above resin (0.3 g, 0.28 mmol) was suspended in N-methylpyrrolidinone (3 mL) and treated with 2,6-dimethylbenzoic acid (171 mg, 1.14 mmol), BOP (0.50 g, 1.14 mmol) and DIPEA (0.26 mL, 1.4 mmol). The mixture was stirred at room temperature for 3 hr, was filtered, and washed with dichloromethane (2×10 mL), methanol (2×10 mL) and dichloromethane (2×10 mL). Cleavage was effected with 90% trifluoroacetic acid (TFA) in dichloromethane for 5 minutes. The mixture was filtered and the TFA was removed under high vacuum. Addition of ether (25 mL) effected precipitation of N-[(2,6-dimethylphenyl)carbonyl]-4-[[(2,4,6-trimethylphenyl)sulfonyl]amino]]-L-phenylalanine.

Example 63

N-(2-Bromobenzoyl)-4-[[(2,4,6-trimethylphenyl)sulfonyl]amino]-L-phenylalanine was prepared from 4-[[(2,4,6-trimethylphenylsulfonyl]amino]-L-phenylalanine on Wang resin and 2-bromobenzoic acid using the general method described in example 62.

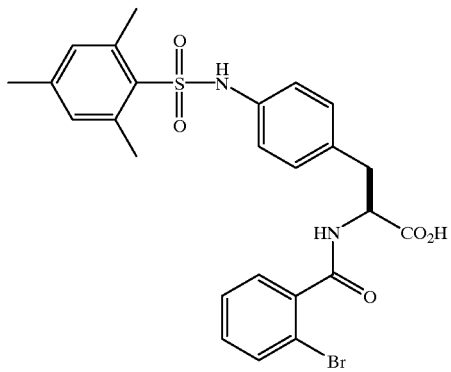

Example 64

Synthesis of 4-[[[(4-cyano-4-phenyl-1-piperidinyl)carbonyl]amino]-N-(2,6-dimethylphenyl)carbonyl]-L-phenylalanine

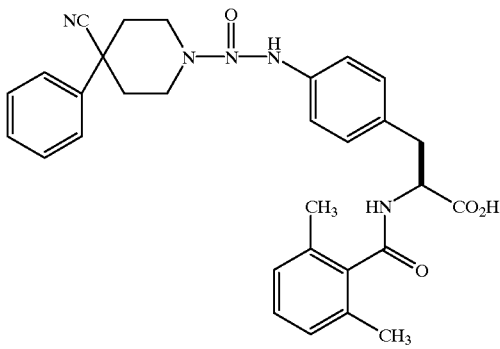

4-Amino-N-[(9H-fluoren-9-ylmethoxy)carbonyl]-L-phenylalanine on Wang resin (3.0 g, 2.04 mmol) was placed in a vessel fitted with a glass frit and was suspended in dichloromethane (50 mL) and DIPEA (0.98 mL, 5.6 mmol). The mixture was shaken for 15 min and triphosgene (1.1 g, 3.7 mmol) was added in one portion. The mixture was agitated for 2 hr at room temperature. The mixture was then filtered and washed with dichloromethane (3×25 mL). The resin was suspended in dichloromethane (50 mL) and DIPEA (1.0 mL, 5.6 mmol) and 4-cyano-4-phenylpiperidine hydrochloride (2.73 g, 12.2 mmol) was added. The resulting mixture was agitated for 4 hr. The reaction mixture was then filtered and washed with dichloromethane (2× 50 mL), methanol (2×50 mL), dimethylformamide (2×50 mL) and methanol (2×10 mL). Cleavage of the Fmoc group was effected by treatment with 25% piperidine in N-methylpyrrolidinone (2×15 min).

The above resin (0.3 g, 0.20 mmol), 2,6-dimethylbenzoic acid (0.15 g, 1 mmol) was suspended in N-methylpyrrolidinone (3 mL) and treated with BOP-Cl (0.26 g, 1.0 mmol) and DIPEA (0.23 mL, 1.3 mmol). The mixture was stirred at room temperature for 3 hr and was filtered. The reaction mixture was then filtered and washed with dichloromethane (2×10 mL), methanol (2×10 mL) and dichloromethane (2×10 mL). Cleavage was effected with 90% trifluoroacetic acid (TFA) in dichloromethane for 3 minutes. The mixture was filtered and the TFA was removed under high vacuum. Addition of ether (25 mL) effected precipitation of 4-[[[(4-cyano-4-phenyl-1-piperidinyl)carbonyl]amino]-N-[(2,6-dimethylphenyl)carbonyl]-L-phenylalanine.

Examples 65–66

Using the procedure described in Example 64, the following compounds were prepared:

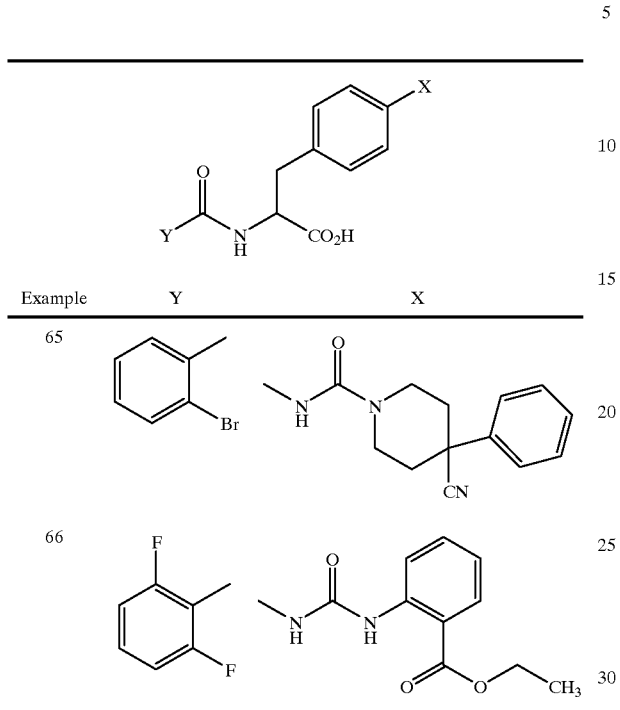

| Example | Y | X |
|---|---|---|
| 65 | | |
| 66 | | |

Example 67

Synthesis of N-(2-chloro-6-methylbenzoyl)-4-nitro-L-phenyl alanine methyl ester

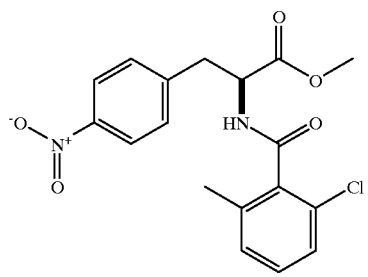

To a solution of 4-nitro-L-phenylalanine methyl ester hydrochloride (1.527 g, 5.86 mmol), 2-chloro-6-methylbenzoic acid (1.0 g, 5.86 mmol) and DIPEA (3.2 mL, 2.3 g, 18 mmol) in DMF (10 mL) was added HBTU (2.22 g, 5.86 mmol) at room temperature. After 4 hr at room temperature, the reaction mixture was diltuted with ethyl acetate (200 mL) and the organic layer was washed with water (20 mL), 1N HCl, NaHCO₃ and brine (2×30 mL for each solvent) and dried over NaSO₄. After removal of the solvent, the residue was purified by chromatography on silica gel eluting with ethyl acetate:hexane (1:2), to give N-(2-chloro-6-methylbenzoyl)-4-nitro-L-phenyl alanine methyl ester (1.71 g, 4.50 mmol, 77.6%). mp, 123–4° C. Analysis ($C_{18}H_{17}ClN_2O_5$) calcd.: C, 57.38, H, 4.55, N, 7.43. Found: C, 57.11, H, 4.58, N, 7.27.

Example 68

Synthesis of 4-amino-N-[(2-chloro-6-methylphenyl)carbonyl]-L-phenylalanine methyl ester

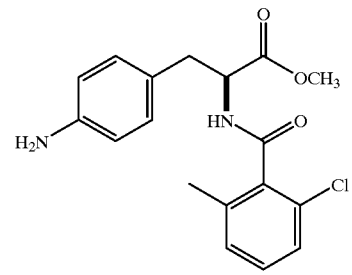

N-[(2-Chloro-6-methylphenyl)carbonyl]-4-nitro-L-phenylalanine methyl ester (1.51 g, 4.0 mmol) and SnCl₂.H₂O (4.5 g, 20 mmol) were suspended in 30 mL of ethanol. The suspension was stirred at a bath temperature of 97° C. for 1 hr. After it was cooled to room temperature, the solvent was evaporated and the residue was dissolved in 15 mL of water. The aqueous solution was then made alkaline by addition of solid K₂CO₃ to pH>10 and was extracted with ethyl acetate (3×100 mL). The combined extracts were dried over K₂CO₃ and were concentrated to give 4-amino-N-(2-chloro-6-methylbenzoyl)-L-phenylalanine methyl ester as a light yellow foam (1.37 g).

Example 69

Synthesis of (S)-N-(2-chloro-6-methylbenzoyl)-4-[[[[1-(1.1-dimethylethoxy)carbonyl]-2-piperidinyl]carbonyl]amino]-L-phenylalanine methyl ester

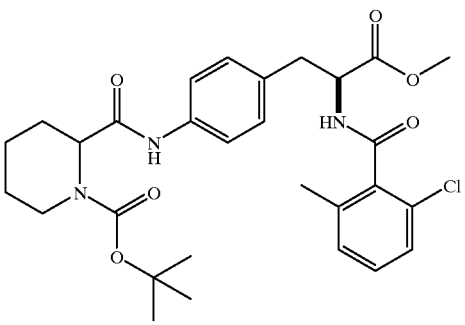

A solution of 4-amino-N-[(2-chloro-6-methylphenyl)carbonyl]-L-phenylalanine methyl ester (347 mg, 1.0 mmol) in DMF (2.0 mL) was treated with (S)-piperidine-1,2-dicarboxylic acid 1-(1,1-dimethylethyl ester (347 mg, 1.0 mmol), HBTU (380 mg, 1.0 mmol) and DIPEA (0.54 mL, 3.0. mmol) at room temperature for 6 hr. The reaction mixture was diluted to 6 mL with water and the white precipitate was collected by filtration and was washed with water (2×2 mL). After drying under vacuum, the light yellow powder was recrystillized from ethyl acetate-hexane to give (S)-N-(2-chloro-6-methylbenzoyl)-4-[[[[1-(1,1-dimethylethoxy)carbonyl]-2-piperidinyl]carbonyl]amino]-L-phenylalanine methyl ester (507 mg, 0.82 mmol. 82%) as a white solid. mp: 87–91° C. HRMS: calcd. 558.2371. Obs. 558.2359 (M+H).

Example 70

Synthesis of (S)-N-(2-chloro-6-methylbenzoyl)-4-[[(2-piperidinyl)carbonyl]amino]-L-phenylalanine methyl ester hydrochloride

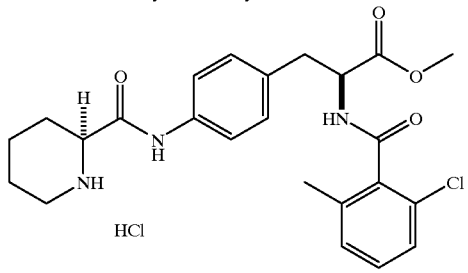

HCl

A solution of (S)-N-(2-chloro-6-methylbenzoyl)-4-[[[[1-(1,1-dimethylethoxy)carbonyl]-2-piperidinyl]carbonyl]amino]-L-phenylalanine methyl ester (475 mg, 0.85 mmol) in 2 mL of dicloromethane was treated with 4N HCl in dioxane (2 mL). The solution was stirred at room temperature for 4 hr and the solvent was then removed under vacuum. The residue was then treated with 50 mL of ether and the light yellow precipitate was collected and was dried under vacuum to give (S)-N-(2-chloro-6-methylbenzoyl)-4-[[(2-piperidinyl)carbonyl]amino]-L-phenylalanine methyl ester hydrochloride (440 mg, 0.89 mmol, >100%) as a light yellow powder. ES MS: 458 (100%) (M+H). NMR (DMSO-$d_6$, δ, ppm): 10.26 (s, 1H), 9.30 (bd, 1H), 9.00 (d, 1H, J=9 Hz), 8.80 (bt, 1H), 7.65 (d, 2H, J =7.8 Hz), 7.24 (m, 5H), 4.70 (m, 1H), 3.90 (m, 1H), 3.67 (s, 3H), 3.32 (m, 2H), 3.05 (m, 2H), 2.25 (m, 1H), 2.05 (s, 3H), 1.70 (m, 5H).

Example 71

Synthesis of N-[(2-chloro-6-methylphenyl)carbonyl]-4-[(8aS)-hexahydro-3-(4-hydroxyphenyl)-1-oxoimidazo[1,5-a]pyridin-2-yl]-L-phenylalanine

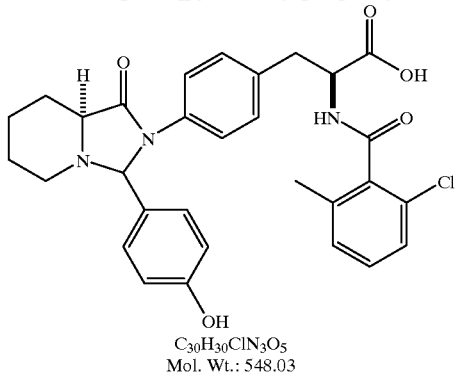

$C_{30}H_{30}ClN_3O_5$
Mol. Wt.: 548.03

(S)-N-(2-chloro-6-methylbenzoyl)-4-[[(2-piperidinyl)carbonyl]amino]-L-phenylalanine methyl ester hydrochloride (100 mg, 0.2 mmol), DIPEA (0.10 mL, 0.54 mmol) and 4-hydroxybenzaldehyde (30 mg, 0.25 mmol) was added to a suspension of activated 3 Å molecular sieves (100 mg) in THF (1.5 mL). The resulting mixture was stirred room temperature overnight and at 60° C. for 3 hr. After it was cooled to room temperature, the mixture was transferred onto a silica gel column and eluted with ethyl acetate:hexane (2:1) to give N-[(2-chloro-6-methylphenyl)carbonyl]]-4-[(8aS)-hexahydro-3-(4-hydroxyphenyl)-1-oxoimidazo[1.5-a]pyridin-2-yl]-L-phenylalanine methyl ester (17.5 mg, 0.031 mmol) as a foam. The methyl ester (17.5 mg, 0.031 mmol) was hydrolyzed with 1N NaOH (0.1 mL, 0.1 mmol) in 0.5 mL of ethanol at room temperature for 6 hr. The reaction mixture was acidified to pH<2 with TFA and was purified on RP-HPLC to give N-[(2-chloro-6-methylphenyl)carbonyl]-4-[(8aS)-hexahydro-3-(4-hydroxyphenyl)-1-oxoimidazo[1.5-a]pyridin-2-yl]-L-phenylalanine (8.3 mg, 0.015 mmol), in 7.5% yield. HRMS: calcd. 548.1952. Obs. 548.1938 (M+H).

Example 72–74

Using the procedure described in example 71, the compounds shown below were prepared.

| Example | R | Calc Mass (M + H) | Obs. Mass (M + H) |
|---|---|---|---|
| 72 | (hexahydro-3-(4-hydroxyphenyl)-1-oxoimidazo[1,5-a]pyridin-2-yl) | 548.1952 | 548.1938 |
| 73 | (hexahydro-3-(2-naphthyl)-1-oxoimidazo[1,5-a]pyridin-2-yl) | | |
| 74 | (4-isobutyl-1,3-dimethyl-2-(4-hydroxyphenyl)-5-oxoimidazolidin-yl) | 608.1904 | 608.1910 |

Example 75

Synthesis of N-(2-chloro-6-methylbenzoyl)-4-[[(2R)-2-amino-4-methyl-1-oxopentyl]amino]-L-phenylalanine methyl ester

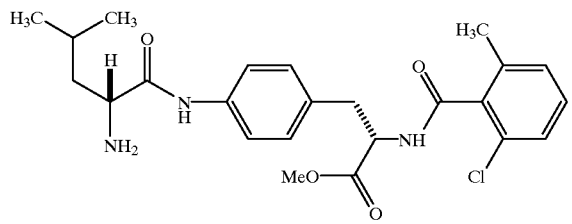

A solution of 4-amino-N-[(2-chloro-6-methylphenyl)carbonyl]-L-phenylalanine methyl ester (561 mg, 1.61 mmol), prepared using procedure described in Example 68. in DMF (4.5 mL) was treated with N-Boc-D-leucine (393.2 mg, 1.7 mmol), HBTU (644.3 mg, 1.7 mmol) and DIPEA (0.62 mL, 3.50 mmol) at room temperature for 6 hr. The reaction mixture was diluted to 30 mL with water and the white precipitate was collected by filtration and was washed with water (2×2 mL). After drying under vacuum, the light yellow powder was recrystallized from ethyl acetate-hexane to give N-(2-chloro-6-methylbenzoyl)-4-[[(2R)-2-[(1,1dimethylethoxy)carbonyl]amino-4-methyl-1-oxopentyl]amino]-L-phenylalanine methyl ester (920 mg) as a white solid. MS 560 (M+H, 1 Cl). This solid was dissolved in 4 N HCl in dioxane (5 mL). The solution was stirred at room temperature overnight. After dilution with ether, the white suspension was allowed to stand at −5° C. for 1 hr. The white solid was collected by filtration and was dried under vacuum for 5 hr. The above solid was then dissolved in 20 mL of water and the solution was treated with sodium bicarbonate followed by K2CO3 to PH >9. The mixture was then extracted with dichloromethane (2×25 mL) and was dried over sodium sulfate. After removal of solvent, the residue was then dried under vacuum at 50° C. overnight to give white solid (520 mg, 1.1 mmol) in 70% overall yield. HRMS: Obs. 460.1997, Calc. 460.2003 (M+H).

Examples 76–77

4-[(2S,4R)-3-acetyl-2-phenyl-4-(2-methylpropyl)-5-oxo-imidazolidin-1-yl]-N-(2-chloro-6-methylbenzoyl)-L-phenylalanine and 4-[(2R,4R)-3-acetyl-2-phenyl-4-(2-methylpropyl)-5-oxo-imidazolidin-1-yl]-N-(2-chloro-6-methylbenzoyl)-L-phenylalanine Example 76

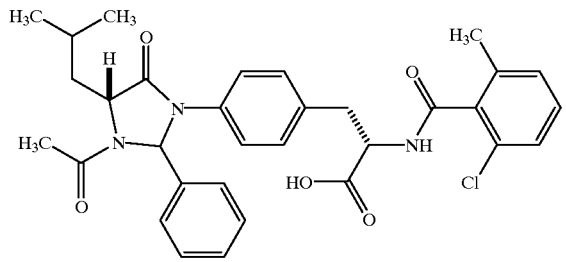

Example 77

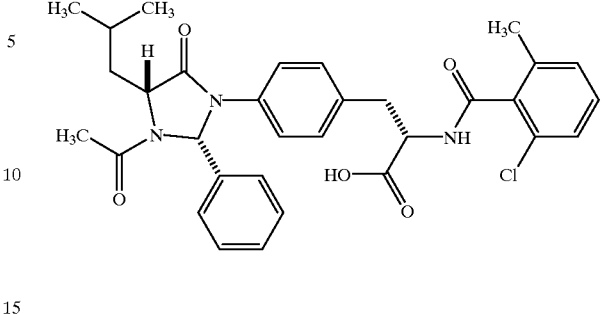

(S)-N-(2-chloro-6-methylbenzoyl)-4-[((2R)-2-amino-4-methyl-1-oxopentyl)amino]-L-phenylalanine methyl ester (100 mg, 0.2 mmol) was dissolved in mixture of THF/CH(OMe)3 (1/1, 1.0 mL). To the solution was then added benzaldehyde (21.2 mg, 0.2 mmol) and the solution was stirred at room temperature. After 24 hr, the reaction mixture was heated to 95° C., acetic anhydride (0.1 mL, 1.0 mmol) was introduced via a syringe and the solution was stirred at 110° C. for 3 hr. After evaporation of solvent, the residue was diluted with ethyl acetate and was washed twice with saturated sodium bicarbonate solution. After removal of the solvent, the residue was dissolved in 3 mL of mixed solvent (THF/ethanol/H2O=2/2/1) and was treated with 1N sodium hydroxide (0.2 mL, 0.2 mmol). After 4 hr at room temperature, the reaction was quenched with 0.5 mL of acetic acid and the crude product was purified on RP-HPLC (C18.5-95-35-214) to give the trans isomer. 4-[(2S,4R)-3-acetyl-2-phenyl-4-(2-methylpropyl)-5-oxoimidazolidin-1-yl]-N-(2-chloro-6-methylbenzoyl)-L-phenylalanine (27 mg, 46 μmol). HRMS (M+H): obs. 576.2251, calc. 576.2265. The corresponding cis-isomer, 4-[(2R,4R)-3-acetyl-2-phenyl-4-(2-methylpropyl)-5-oxoimidazolidin-1-yl]-N-(2-chloro-6-methylbenazoyl)-L-phenylalanine (50.1 mg, 86 μmol) HRMS (M+H). calc. 576.2265, obs.576.2250.

Example 78

Synthesis of N-[(2-chloro-6-methylphenyl)carbonyl]-4-[(S)-hexahydro-1,3-dioxoimidazo[1,5-a]pyridin-2-yl)]-L-phenylalanine See other copies of name in example

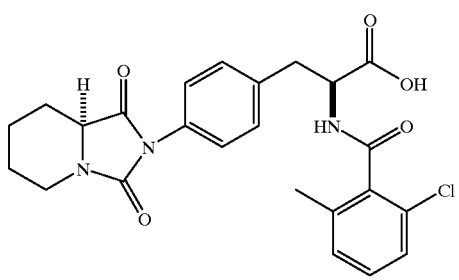

To a solution of N-(2-chloro-6-methylbenzoyl)-4-[[(S)-(2-piperidinyl)carbonyl]amino]-L-phenylalanine methyl ester hydrochloride (50 mg, 0.1 mmol) and DIPEA (0.020 mL, 0.1 mmol) in 0.2 mL of dichloromethane was added carbonyldiimidazole (16.2 mg, 0.1 mmol) at room temperature. The solution was then stirred at this temperature for 6 hr. The reaction mixture was diluted with ethyl acetate to 5 mL and the organic layer was washed with 1N HCl, sat. NaHCO3 and brine (2×1 mL for each solvent) and was dried over Na$_2$SO$_4$. The solvent was then removed under vacuum to give a light yellow solid (53.4 mg, 0.11 mmol). The above solid was then dissolved in ethanol (1 mL) and was stirred with 1N NaOH (0.1 mL, 0.1 mmol) at room temperature for 6 hr. The reaction mixture was acidified to pH<2 with TFA and was purified on RP-HPLC to give N-[(2-chloro-6-methylphenyl)carbonyl]-4-[(S)-hexahydro-1,3-dioxoimidazo[1,5-a]pyridin-2-yl)]-L-phenylalanine (27.0 mg, 0.057 mmol) in 57% overall yield. HRMS: obs. 470.1465. calcd. 470.1483 (M+H).

Examples 79–84

Using procedures described in Examples 69, 70 and 78, the following compounds were prepared from 4-amino-N-[(2-chloro-6-methylphenyl)carbonyl]-L-phenylalanine methyl ester and the appropriate amino acid derivatives:

| Example | R | IC50 nM | HRMS (H + H) Calcd. | HRMS (M + H) Obs. |
|---|---|---|---|---|
| 79 | | 0.53 | 444.1326 | 444.1320 |
| 80 | | 0.24 | 472.1639 | 472.1643 |
| 81 | | 0.49 | 472.1639 | 472.1643 |
| 82 | | 0.56 | 486.1795 | 486.1818 |
| 83 | | 0.72 | 518.1482 | 518.1469 |
| 84 | | 0.73 | 520.1639 | 520.1629 |

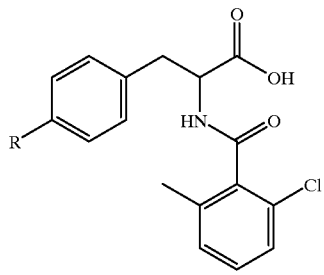

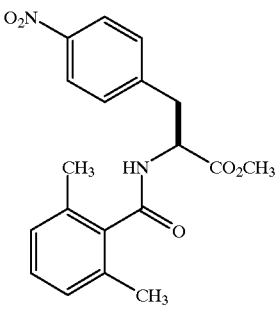

Example 85

Synthesis of 4-nitro-N-[(2,6-dimethylphenyl)carbonyl]-L-phenylalanine methyl ester A solution of 4-nitrophenylalanine methyl ester (5.21 g, 20 mmol) in 20 mL of dichloromethane and of DIPEA (15 mL) was treated with 2,6-dimethylbenzoyl chloride. After 4 hr, the mixture was concentrated, the residue was taken up in ethyl acetate (200 mL) and washed with 1 N HCl (50 mL), sat. NaHCO$_3$ (50 mL) and sat. brine (30 mL), and was dried (MgSO$_4$). Filtration and concentration gave 8.0 g of a solid which was purified by HPLC (Waters Prep 500-dual silica gel cartridges; 1:1 ethyl acetate-hexane) to give 4-nitro-N-[(2,6-dimethylphenyl)carbonyl]-L-phenylalanine methyl ester (5.26 g, 74%).

Example 86

4-Amino-N-[(2,6-dimethylphenyl)carbonyl]-L-phenylalanine methyl ester was prepared using the procedure described in example 68; from 4-nitro-N-[(2,6-dimethylphenyl)carbonyl]-L-phenylalanine methyl ester (5.2 g, 14.6 mmol) there was obtained 4-amino-N-[(2,6dimethylphenyl)carbonyl]-L-phenylalanine methyl ester (4.6 g, 97%) as a light yellow glass.

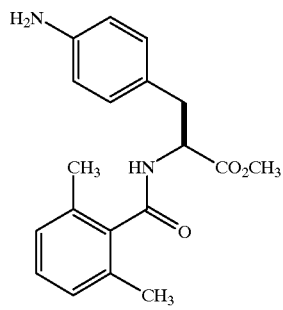

Example 87

Synthesis of 4-[[(4-carboxy-3-pyridinyl)carbonyl]amino]-N-[(2,6-dimethylphenyl)carbonyl]-L-phenylalanine and 4-[[(3-carboxy-4-pyridinyl)carbonyl]amino]-N-[(2,6-dimethylphenylkcarbonyl]-L-phenylalanine

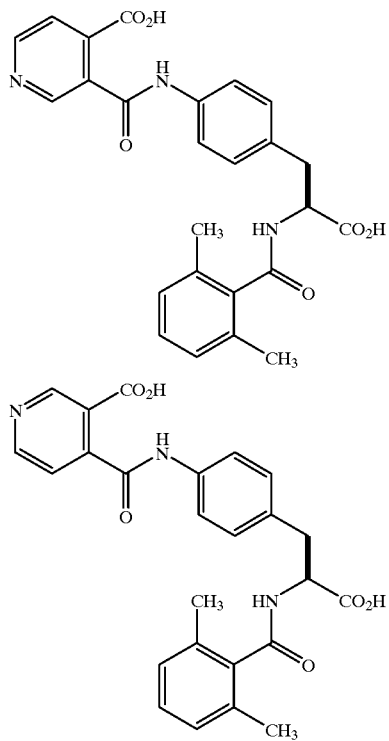

A solution of 4-amino-N-[(2,6-dimethylphenyl)carbonyl]-L-phenylalanine methyl ester (530 mg, 1.162 mmol) and 3,4-pyridinedicarboxylic acid anhydride in dichloromethane (30 mL) was allowed to stir over night and the precipitate was collected. The solids were dissolved in THF (100 mL), filtered and concentrated to give 1.1 g of a mixture of isomeric carboxylic acids. This material was dissolved in ethanol (50 mL) and treated with 1 N NaOH (15 mL, 15 mmol) and stirred for 2.5 hr. The mixture was acidified with excess acetic acid and was purified in 3 batches on the Rainin RP-HPLC to give 0.60 g of a white solid as a mixture of isomeric dicarboxylic acids.

Example 88

Synthesis of 4-(2,3-dihydro-1,3-dioxo-1H-pyrrolo[3,4-c]pyridin-2-yl)-N-(2,6-dimethylbenzoyl)-L-phenylalanine

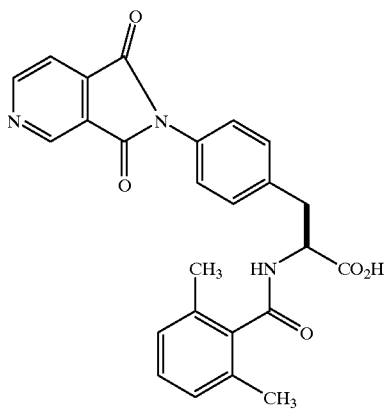

A solution of the mixture of acids from example 87 (272 mg, 0.59 mmol) in DMF (10 mL) was treated with carbonyl diimidazole (385 mg, 2.4 mmol) and was allowed to stir over night. The mixture was filtered and purified directly by HPLC on the Rainin instrument to afford, after lyophization of the product fraction, 4-(2,3-dihydro-1,3-dioxo-1H-pyrrolo[3,4-c]pyridin-2-yl)-N-(2,6-dimethylbenzoyl)-L-phenylalanine (108 mg, 41%), FAB HRMS: obs., 444.1548. Calcd., 444.1 559 (M+H).

Example 89

Synthesis of N-[(2,6-dimethylphenyl)carbonyl]-4-[(R,S)-2,3,5,6,7,7a-hexahydro-1,3-dioxo-1H-pyrrolo[3,4-c]pyridin-2-yl]-L-phenylalanine

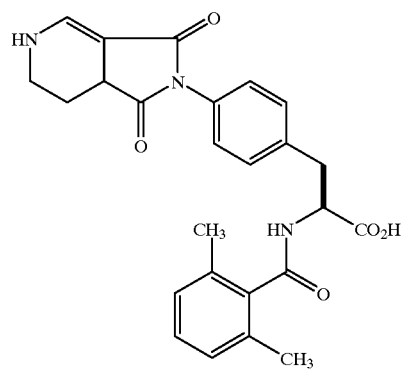

A solution of 4-(2,3-dihydro-1,3-dioxo-1H-pyrrolo[3,4-c]pyridin-2-yl)-N-(2,6-dimethylbenzoyl)-L-phenylalanine (108 mg, 0.24 mmol) in ethanol:THF (25 mL, 1:1) was hydrogenated over 10% Pd/C (20 mg) for 4 hr. The mixture was filtered, concentrated and purified by RP-HPLC on a Rainin HPLC. The first product to elute was lyophilized to give N-[(2,6-dimethylphenyl)carbonyl]-4-[(R,S)-2,3,5,6,7,7a-hexahydro-1,3-dioxo-1H-pyrrolo[3,4-c]pyridin-2-yl]-L-phenylalanine (29 mg, 27%), FAB HRMS: obs., 448.1862. Calcd., 448.1873) (M+H). The second product to elute was lyophilized to give recovered starting material (47 mg, 43%).

Examples 90–96

The compounds shown below were prepared using the methods described in example 13 by hydrolysis of 4-[[(2,6-dichlorophenyl)carbonyl]amino]-N-aroyl-L-phenylalanine methyl ester derivatives

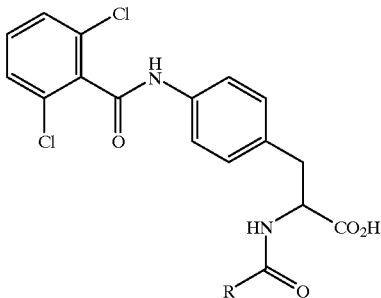

| Example | Starting Material | R | IC50 nM | IC50 Ramos nM | HRMS Calcd | HRMS Obs |
|---|---|---|---|---|---|---|
| 90 | Example 174 | (2,3-dimethyl-isopropylphenyl) | 1.2 | 23 | 513.1348 | 513.1363 |
| 91 | Example 175 | (2-bromo-3-methylphenyl) | 0.20 | 9.3 | 548.9983 | 548.9969 |
| 92 | Example 176 | (2,3-dimethyl-ethylphenyl) | 0.3 | 10 | 499.1191 | 499.1193 |
| 93 | Example 162 | (2,3-dimethylphenyl-acetyl) | 1.6 | 49 | 533.0438 | 533.0460 |

-continued

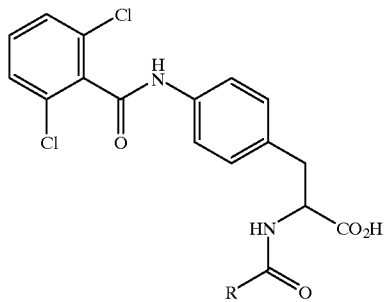

| Example | Starting Material | R | IC50 nM | IC50 Ramos nM | HRMS Calcd | HRMS Obs |
|---|---|---|---|---|---|---|
| 94 | Example 167 | ![structure] | 0.25 | 9.5 | 569.0107 | 569.0109 |
| 95 | Example 172 | ![structure] | 0.46 | 33 | 529.0100 | 529.0097 |

Example 96

N-(2-Chloro-6-methylbenzoyl)-[(R)-2,5-dioxo-3-methyl-4-(1-methylethyl)-1-imidazolininyl]-L-phenylalanine methyl ester was prepared from 4-amino-N-(2-chloro-6-methylbenzoyl)-L-phenylalanine methyl ester and N-[(1,1-dimethylethoxy)carbonyl]-N-methyl-D-valine using the procedure described in examples 69, 70 and 78.

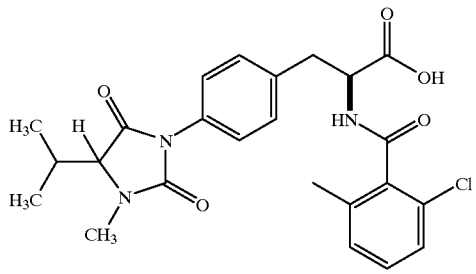

Example 97–102

Using procedures described in the Examples 75, 76 and 77 the following compounds were prepared from 4-amino-N-(2-chloro-6-methylbenzoyl)-L-phenylalanine methyl ester and the appropriate Boc-protected amino acids.

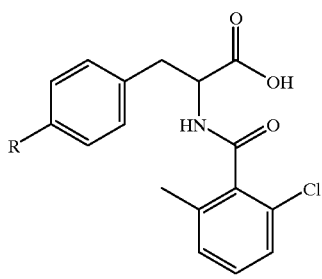
| Example | R | HRMS (M + H) calc. | HRMS (M + H) obs | IC50 (nM) |
|---|---|---|---|---|
| 97 | | 592.2214 | 592.2200 | 0.44 |
| 98 | | 592.2214 | 592.2210 | 2.35 |
| 99 | | 576.2265 | 576.2240 | 0.58 |
| 100 | | 576.2265 | 576.2252 | 10.0 |

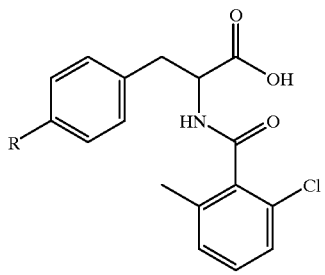

| Example | R | HRMS (M + H) calc. | HRMS (M + H) obs | IC50 (nM) |
|---|---|---|---|---|
| 101 | ![R group with H3C, CH3, H, N, H3C, O, N—] | 500.1953 | 500.1940 | 9.90 |
| 102 | ![R group with H3C, CH3, H, N, H3C, O, N—, CH3, H3C, CH3] | 556.2578 | 556.2582 | 41 |

Example 103

Preparation of 2-bromo-6-methylbenzoic acid

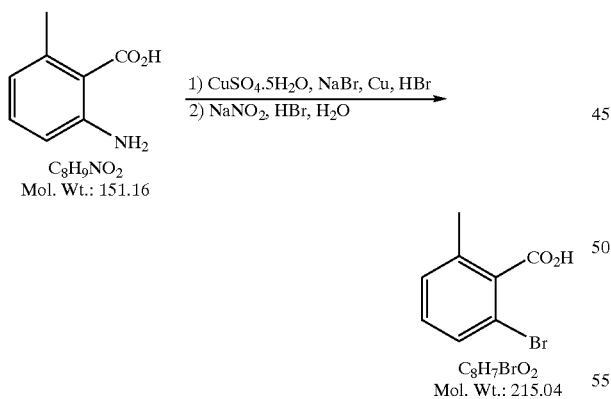

Cuprous bromide was prepared by heating a deep purple solution of $CuSO_4 \cdot 5H_2O$ (33 mmol, 8.25 g) and NaBr (66 mmol, 6.75 g) in HBr (33 mL, 48%) and adding Cu powder (66 mmol, 4.2 g) in portions until the purple solution became a colorless solution. This solution was then added in portions to a hot solution (ca.90° C.) of 2-amino-6-methylbenzoic acid (33 mmol, 5 g) in $H_2O$ (80 mL) and HBr (11.5 mL). This was followed by the dropwise addition of a solution of $NaNO_2$ (99 mmol, 6.85 g) in $H_2O$ (20 mL) to this stirred heated solution over a period of 25 min. The dark-brownish mixture was heated at ca.90° C. for 1 hr and then was heated at reflux for another 30 min before it was cooled to room temperature and stirred for 2 hr. Then, the mixture was poured into ice (~500 g), 5% NaOH solution was added until pH 14 was reached and the resulting dark suspension was filtered through celite. The yellow filtrate was acidified with conc. HCl to pH 1. Extractive work-up ($Et_2O$, 3×150 mL) gave a dark residue which was dissolved in $Et_2O$ (100 mL), charcoal was added and the resulting solution was heated to reflux. Filtration and concentration gave a material which was recrystalized from $Et_2O$/petrolium ether in hexane (100 mL) to afford the 2-bromo-6-methylbenzoic acid (3.5 g, 49%, HR MS: Obs. mass. 213.9633. Calcd. mass. 213.9629, M+) as a crystalline light pink solid; mp 104–106° C.

Example 104

Preparation of 2-ethyl-6-methylbenzoic acid

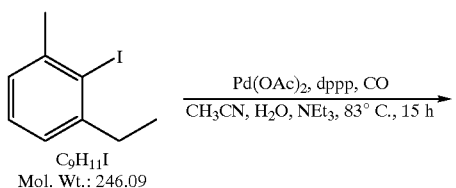

-continued

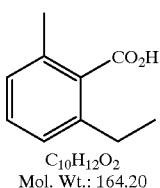

C₁₀H₁₂O₂
Mol. Wt.: 164.20

A 250 mL pressure bottle was charged with 2-ethyl-6-methyliodobenzene (30.07 mmol, 7.4 g), Pd(OAc)₂ (1.43 mmol, 334 mg) and dppp (1.43 mmol, 620 mg). The flask was closed with a septum and evacuated three times with argon. Then, acetonitrile (96 mL), triethylamine (189 mmol, 19.0 g, 26.25 mL) and water (19.1 mL) were added successively by the aid of syringe. Then, the rubber septum was replaced with teflon lined cap connected to a carbon monoxide source. The flask was now pressurized with carbon monoxide (40 psi) and the excess pressure was released. This process was repeated three times and finally the mixture was stirred for 5 min under 40 psi carbon monoxide pressure. The flask was then disconnected from the carbon monoxide cylinder and immersed in a preheated oil bath (83–85° C.). The reaction mixture turned black in 1 hr and was stirred for another 14 hr at this temperature. Then, the reaction mixture was cooled to room temperature and the pressure was released. The resulting mixture was diluted with ether (200 mL) and 1.0N NaOH (20 mL). The formed acid was extracted into water (2×100 mL). The combined water extracts were neutralized with 1.0N HCl and the acid was extracted into dichloromethane (3×100 mL). The combined dichloromethane extracts were washed with brine solution and dried over MgSO₄. Filtration of the drying agent and removal of solvent under vacuum gave 3.58 g (72.5%) of a viscous brown oil which slowly solidfied overnight. HR MS: Obs. mass. 164.0833. Calcd. mass. 164.0837 (M+).

Example 105

Preparation of 2-Chloro-6-acetylbenzoic acid
a). Preparation of 1-acetyl-3-chloro-2-[[(trifluoromethyl)sulfonyl]oxy]benzene.

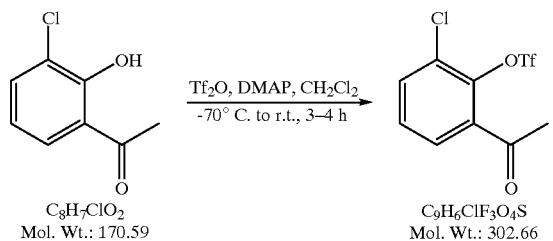

To a solution of 1-acetyl-6-chlorophenol (2.9 mmol, 0.5 g) in dichloromethane (33 mL) was added 4-(N,N-dimethylamino)pyridine (6.54 mmol, 0.8 g) at −70° C. followed by triflic anhydride (4.33 mmol, 1.22 g, 0.73 mL) at −70° C. After addition, the suspension was stirred for 30 min at this temperature and then warmed to room temperature and stirred for another 3 hr, at which time TLC of the reaction mixture indicated the absence of starting material. The mixture was diluted with H₂O (50 mL) and the two layers were separated. The aqueous layer was extracted with dichloromethane (50 mL). The combined dichloromethane extracts were washed with brine solution and were dried over MgSO₄. Filtration of the drying agent and removal of solvent under vacuum gave an yellow oil which was purified by silica gel column chromatography to obtain 0.76 g (86%) of a colorless oil. HR MS: Obs. mass, 301.9617. Calcd. mass, 301.9627 (M+).

b). Preparation of 1-acetyl-3-chlorobenzoic acid.

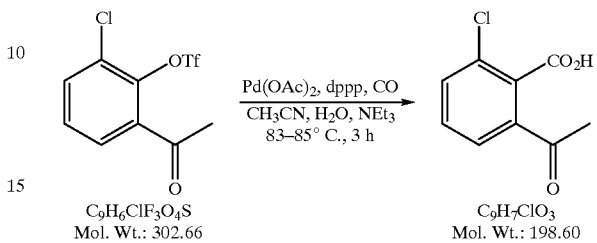

A 100 mL pressure bottle was charged with 1-acetyl-3-chloro-2-[[(trifluoromethyl)sulfonyl]oxy]benzene (2.41 mmol, 0.73 g), Pd(OAc)₂ (0.2 mmol, 47 mg) and dppp (0.2 mmol, 87 mg). Then, the flask was closed with a septum and evacuated three times with argon. Then, acetonitrile (96 mL), triethylamine (188.7 mmol, 19.0 g, 26.25 mL) and water (19.1 mL) were added successively by the aid of syringe. Then, the rubber septum was replaced with teflon lined cap connected to a carbon monoxide source. The flask was now pressurized with carbon monoxide (40 psi) and the excess pressure was released. This process was repeated three times and finally the mixture was stirred for 5 min under 40 psi carbon monoxide pressure. The flask was then disconnected from the carbon monoxide cylinder and immersed in a preheated oil bath (83–85° C.) and stirred for 3 hr. The reaction mixture was cooled to room temperature and the pressure was released and the mixture was diluted with ether (200 mL) and 1.0N NaOH (20 mL). The acid was extracted into water (2×100 mL). The combined water extracts were neutralized with 1.0N HCl and again the acid was extracted into dichloromethane (3×100 mL). The combined dichloromethane extracts were washed with brine solution and dried over MgSO₄. Filtration of the drying agent and removal of solvent under vacuum gave a crude residue which was recrystallized from dichloromethane (~10 mL) and hexane (~8 mL) and storage in the refrigerator overnight. The precipitated solid was collected by filtration and dried under high vacuum to afford 330 mg (69%) of a colorless solid: mp 128–129° C. HR MS: Obs. mass, 198.0090. Calcd. mass, 198.0084 (M+).

Example 106

Preparation of 2-iso-propyl-6-methylbenzoic acid
a). Preparation of 2-(1-methylethyl)-6-methyliodobenzene

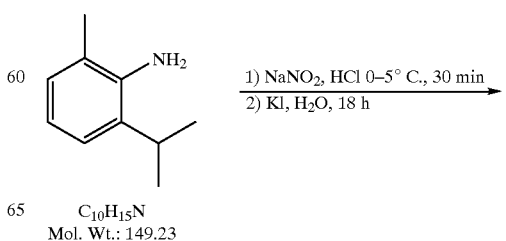

C₁₀H₁₅N
Mol. Wt.: 149.23

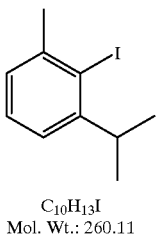

C$_{10}$H$_{13}$I
Mol. Wt.: 260.11

To a suspension of 2-(1-methylethyl)-6-methylaniline (15.57 mmol, 14.9 g), in conc. HCl (50 mL) and 30 g of ice, was added dropwise a solution of NaNO$_2$ (110 mmol, 8 g) in H$_2$O (35 mL) at −5° C. to 5° C. for 30 min. After addition, the red colored solution was stirred for another 30 min. Then, a solution of KI (200 mmol, 33.2 g) in H$_2$O (50 mL) was added dropwise over 20 min at 0–5° C. After the addition, the mixture was allowed to warm to room temperature during which time, an exothermic reaction with gas evolution occurred. The resulting red colored solution was stirred for 18 h. Then, the mixture was extracted with ethyl acetate (3×100 mL). The combined extracts were washed with sodium thiosulfate solution (200 mL), brine solution and dried over MgSO$_4$. Filtration of the drying agent and concentration of the solvent under vacuum gave a colored compound which was purified by a silica gel column chromatography to obtain pure 2-(1-methylethyl)-6-methyliodobenzene (17.8 g. 68%) of an yellow oil. HR MS: Obs. mass. 260.0063. Calcd. mass. 260.0067 (M+).

b) Preparation of 2-(1-methylethyl)-6-methylbenzoic acid.

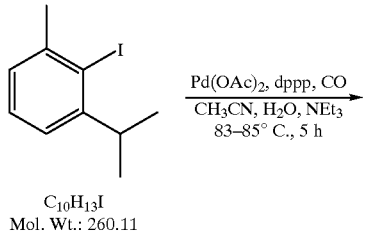

C$_{10}$H$_{13}$I
Mol. Wt.: 260.11

C$_{11}$H$_{14}$O$_2$
Mol. Wt.: 178.23

A 250 mL pressure bottle was charged with 2-(1-methylethyl)-6-methyliodobenzene (25.2 mmol, 6.55 g), Pd(OAc)$_2$ (1.2 mmol, 280 mg) and dppp (1.2 mmol, 520 mg). Then, the flask was closed with a septumn and evacuated three times with argon. Then, acetonitrile (96 mL), triethylamine (188.7 mmol, 19.0 g, 26.25 mL) and water (19.1 mL) were added successively by the aid of syringe. Then, the rubber septum was replaced with teflon lined cap connected to a carbon monoxide source. The flask was now pressurized with carbon monoxide (40 psi) and the excess pressure was released. This process was repeated three times and finally the mixture was stirred for 5 min under 40 psi carbon monoxide pressure. The flask was then disconnected from the carbon monoxide cylinder and immersed in a preheated oil bath (83–85° C.). The reaction mixture turned black in 1 hr and was stirred for another 4 hr at this temperature. Then, the reaction mixture was cooled to room temperature, the pressure was released and the mixture was diluted with ether (200 mL) and 1.0N NaOH (10 mL). The acid was extracted into water (2×100 mL). The combined water extracts were neutralized with 1.0N HCl and the acid was extracted into ethyl acetate (2×100 mL). The combined organic extracts were washed with brine solution and dried over MgSO$_4$. Filtration of the drying agent and removal of solvent under vacuum gave 2.8 g (62%) of a viscous yellow oil. HR MS: Obs. mass, 178.0996. Calcd. mass, 178.0994 (M+).

Example 107

N-(2-chloro-6-methylbenzoyl)-4-[(2,4-dimethyl-3-pyridinyl)carbonyl]amino]-L-phenylalanine

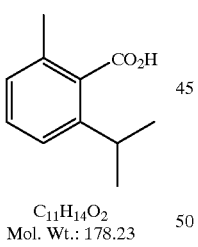

TFA a. Preparation of [[(2,4-dimethyl-3-pyridyl)carbonyl]amino]-L-phenylalanine methyl ester hydrochloride.

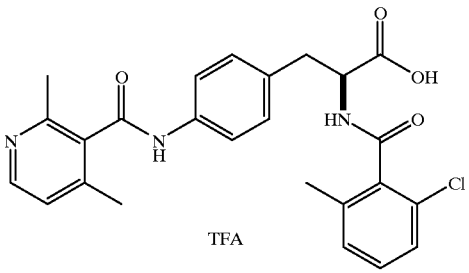

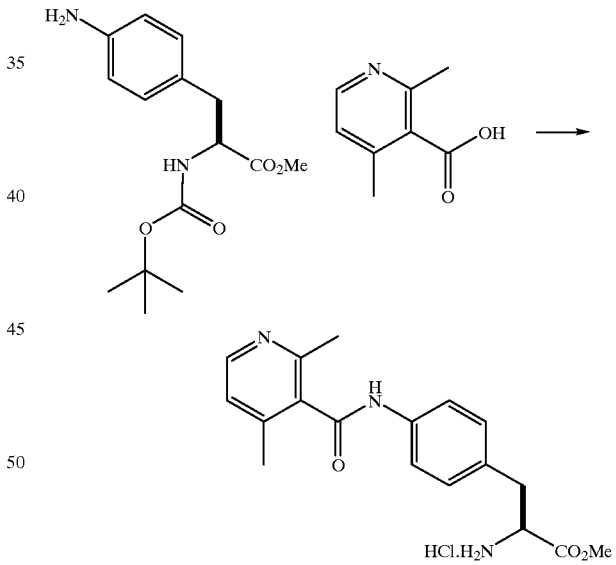

To a solution of 4-amino-N-[(1,1-dimethylethoxyl)carbonyl]-L-phenylalanine methyl ester (1.4 g, 4.8 mmol) in DMF (12 mL) were added 2,4-dimethyl-3-pyridinecarboxylic acid hydrocloride (919 mg, 4.9 mmol), HBTU (1900 mg, 5 mmol) and diisopropylethylamine (2.7 mL, 15 mmol) at room temperature. The mixture was stirred for 15 hr and was diluted with 10 mL of ethyl acetate and 10 mL of water. The layers were separated and the aqueous layer was extracted with ethyl acetate (2×20 mL). The combined extracts were washed with brine and dried over anhydrous magnesium sulfate. Filtration and concentration of the solvent gave a crude product which was purified on silica gel eluting with ethyl acetate:hexane (2:1 to 4:1) to give of 4-[(2,4-dimethyl-3-pyridyl)carbonyl)amino]-N-[(1,1-dimethylethoxyl)carbonyl]-L-phenylalanine methyl ester (226 mg). This compound (220 mg) was treated with 6 mL of 4 N hydrochloric acid in dioxane at room temperature. After 5 minutes, the solid went into solution and the mixture was stirred for 18 hr and was concentrated to give white solid (210 mg). This intermediate was used in the next step synthesis without further purification.

b. Preparation of N-(2-chloro-6-methylbenzoyl)-4-[(2,4-dimethyl-3-pyridyl)carbonyl]amino]-L-phenylalanine.

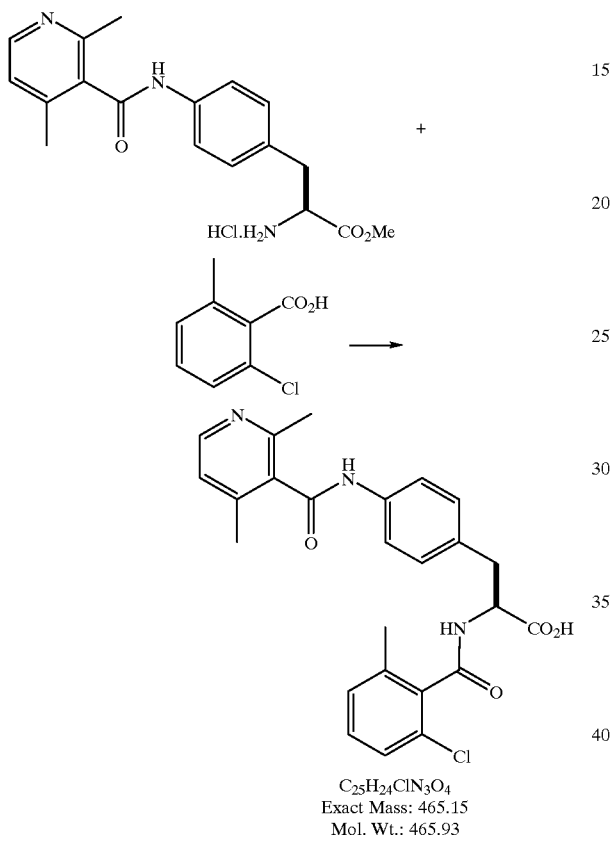

A solution of 4-[(2,4-dimethyl-3-pyridyl)carbonyl]amino]-L-phenylalanine methyl ester hydrochloride (50 mg, 0.125 mmol), 2-chloro-6-methylbenzoic acid (34 mg, 0.2 mmol), HBTU (76 mg, 0.2 mmol) and DIPEA (0.071 mL, 0.4 mmol) in DMF (0.5 mL) was stirred 15 hr at room temperature. The mixture was diluted with ethyl acetate (10 mL) and was washed with 0.5 N HCl (2×8 mL), sat. sodium bicarbonate (2×8 mL) and brine (2×8 mL) and was dried (Na₂SO₄). The solution was filtered and concentrated to a yellow gum which was hydrolyzed by treatment with 1N NaOH (0.5 mL) in MeOH (3 mL) at rt for 4 hrs. The reaction mixture was then acidified with acetic acid and purified by HPLC using conditions described in Example 76–77 to give a white solid (23.3 mg). MS (M+H): 466 (1 Cl).

Example 108

N-(2-Bromo-5-methoxybenzoyl)-4-[(2,4-dimethyl-3-pyridinyl)carbonyl]amino]-L-phenylalanine was prepared from 4-[(2,4-dimethyl-3-pyridyl)carbonyl]amino]-L-phenylalanine methyl ester hydrochloride and 2-bromo-5-methoxybenzoic acid using the general method described in example 107. MS (M+H) 526 (1 Br).

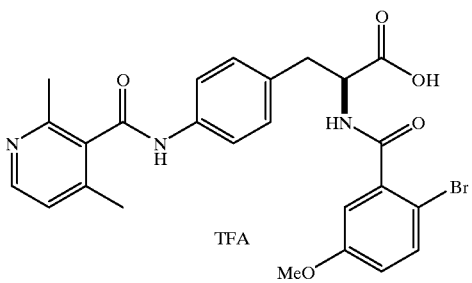

Example 109

Preparation of 4-[[(2-chloro-5-cyanophenyl)carbonyl]amino]-L-phenylalanine methyl ester

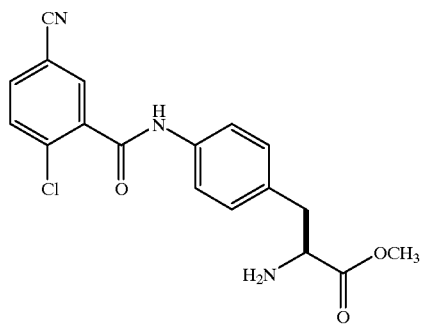

a). Preparation of 4-[(2-chloro-5-bromophenylcarbonyl)amino]-N-[(1,1-dimethylethoxy)carbonyl]-L-phenylalanine methyl ester.

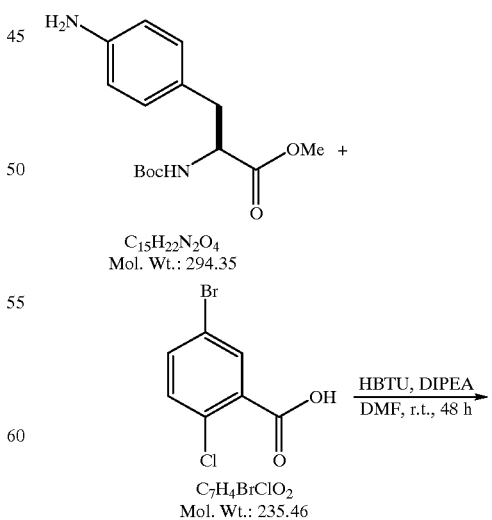

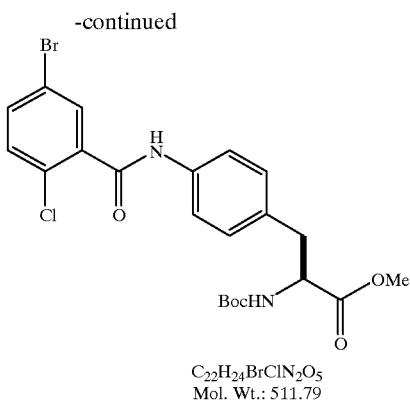

C₂₂H₂₄BrClN₂O₅
Mol. Wt.: 511.79

To a mixture of 4-amino-N-[(1,1-dimethyethoxy)carbonyl]-L-phenylalanine methyl ester (20 mmol, 5.88 g), 2-chloro-5-bromobenzoic acid (22 mmol, 5.18 g) and HBTU (22 mmol, 8.34 g) in DMF (70 mL) was added diisopropylethylamine (50 mmol, 8.7 mL) at room temperature. The suspension was stirred for 48 hr at which time TLC analysis of the mixture indicated the absence of starting material. The mixture was diluted with water (100 mL) and the solids were collected by filtration and washed with water (150 mL). After air drying, the crude product was purified by silica gel column chromatography to obtain 1.02 g (10%) of a white solid: mp 158–161° C. HR MS: Obs. mass, 533.0442. Calcd. mass, 533.0455 (M+Na).

b). Preparation of 4-[[(2-chloro-5-cyanophenyl)carbonyl]amino]-N-[(1,1-dimethylethoxy)carbonyl]-L-phenylalanine methyl ester.

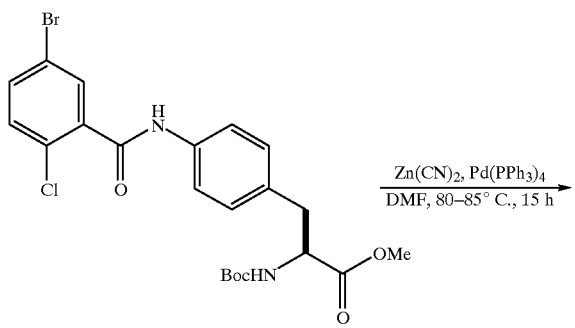

To a mixture of 4-[(2-chloro-5-bromophenylcarbonyl)amino]-N-[(1,1-dimethylethoxy)carbonl]-L-phenylalanine methyl ester (2 mmol, 1.02 g), zinc cyanide (1.3 mmol, 152 mg) and Pd(PPh₃)₄ (0.2 mmol, 231 mg) was added distilled and deoxygenated DMF (8 mL) at room temperature. The suspension was heated to 80–85° C. and stirred for 15 hr at which time TLC analysis of the mixture indicated the absence of starting material. The reaction mixture was cooled to room temperature and diluted with ethyl acetate (70 mL) and was washed with 20% aqueous ammonium hydroxide (50 mL), brine solution (50 mL) and was dried over anhydrous magnesium sulfate. Filtration of the drying agent and concentration of the solvent gave a crude product which was purified by silica gel column chromatography to obtain 555 mg (61%) of a white solid: mp 185–187° C. HR MS: Obs. mass, 480.1301. Calcd. mass, 480.1302 (M+Na).

c. Preparation of 4-[(2-chloro-5-cyanophenylcarbonyl)amino]-L-phenylalanine methyl ester TFA salt.

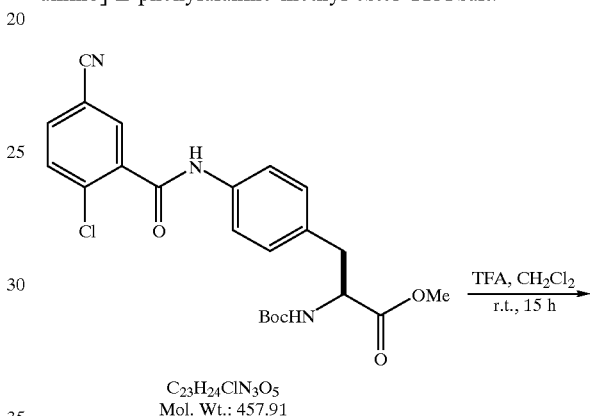

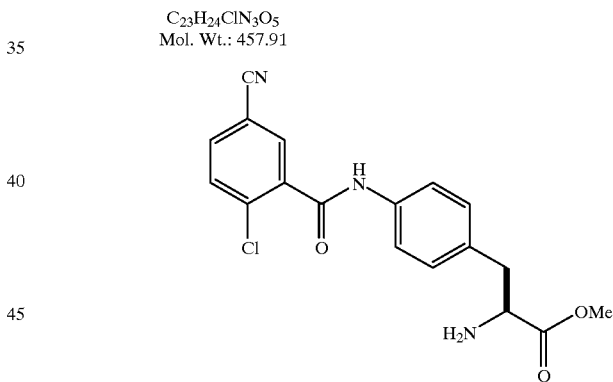

To a solution of 4-[(2-chloro-5-cyanophenylcarbonyl)amino]-N-[(1,1-dimethylethoxy)carbonyl]-L-phenylalanine methyl ester (1.2 mmol, 0.55 g) in dichloromethane (12 mL) was added trifluoroacetic acid (3 mL) at room temperature. The reaction mixture was stirred for 15 hr at room temperature at which time TLC analysis of the mixture indicated the absence of starting material. The solvent was removed under vacuum and the residue was azeotrophed with toluene (2×10 mL) and dried under high vacuum to afford 0.43 g (100%) of an yellow solid. HR MS: Obs. mass, 358.0963. Calcd. mass, 358.0959 (M+H).

Example 110

Preparation of 4-[[(2-chloro-5-cyanophenyl)carbonyl]amino]-N-[1-(2)-chloro-6-methylphenyl)carbonyl]-L-phenylalanine

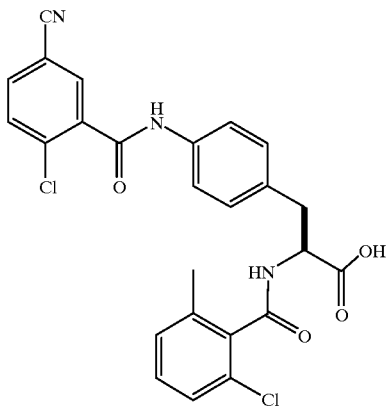

a) Preparation of 4-[(2-chloro-5-cyanophenylcarbonyl)amino]-N-[1-(2-chloro-6-methylphenyl)carbonyl]-L-phenylalanine methyl ester.

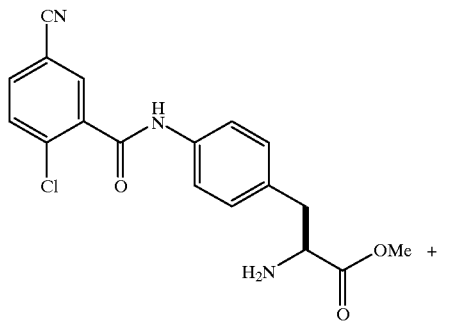

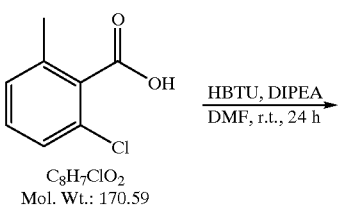

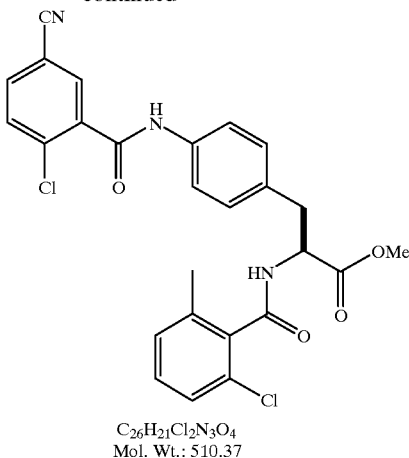

C$_{26}$H$_{21}$Cl$_2$N$_3$O$_4$
Mol. Wt.: 510.37

Using the procedure described in example 3, 4-[(2-chloro-5-cyanophenylcarbonyl)amino]-N-[1-(2-chloro-6-methylphenyl)carbonyl]-L-phenylalanine methyl ester was prepared in 61% overall yield as a white solid. HR MS: Obs. mass, 510.1003, Calcd. mass, 510.0988, M+H.

b) Preparation of 4-[(2-chloro-5-cyanophenylcarbonyl)amino]-N-[1-(2-chloro-6-methylphenyl)carbonyl]-L-phenylalanine.

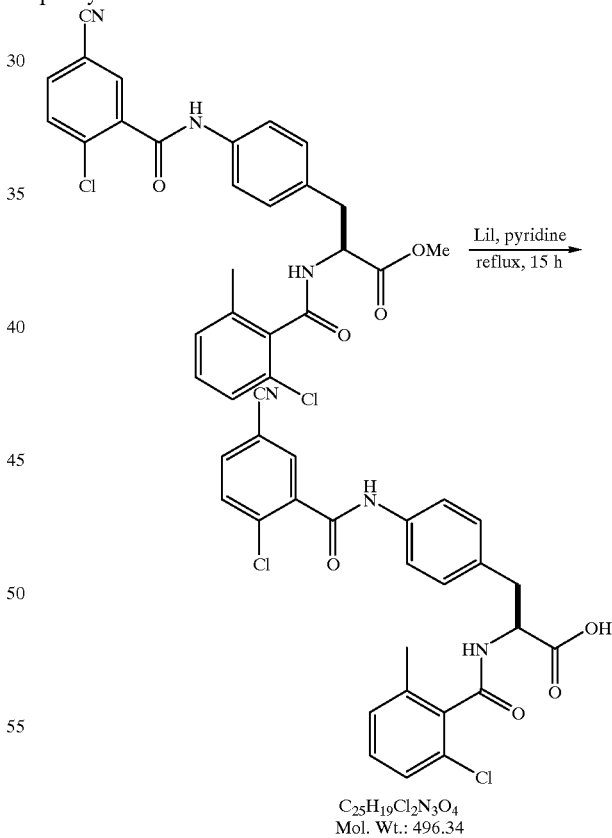

To a mixture of 4-[(2-chloro-5-cyanophenylcarbonyl)amino]-N-[1-(2-chloro-6-methylphenyl)carbonyl]-L-phenylalanine methyl ester (0.146 mmol, 75 mg) and lithium iodide (1.5 mmol, 200 mg) was added pyridine (3 mL) at room temperature. The solution was refluxed for 15 h at which time TLC analysis of the mixture indicated the absence of starting material. Then, it was cooled to room temperature and was diluted with water (15 mL). The pyridine was removed under reduced pressure on a rotary evaporator and the residue was extracted with ether (2×15 mL) to remove any neutral impurities. The aqueous layer was acidified with 1N HCl and the precipitated white solid was collected by filtration and was washed with 20 mL of water and 20 mL of hexane. After air-drying, the crude product was dissolved in ethyl acetate-hexane and stored in the refrigerator overnight. Only traces solid was formed and the solvent was decanted and removed under vacuum to give 55 mg (76%) of as a white solid. HR MS: Obs. mass, 496.0850. Calcd. mass, 496.0831 (M+H).

Example 111

Preparation of 4-[(2-chloro-6-methylphenylcarbonyl)amino]-N-[(1,1-dimethylethoxy)carbonyl]-L-phenylalanine methyl ester

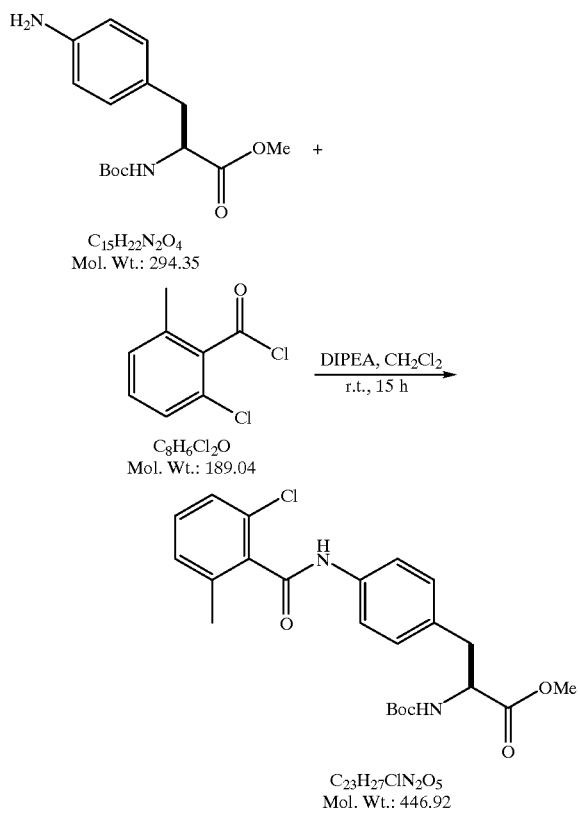

Using the procedure described in example 1, 4-[(2-chloro-6-methylphenylcarbonyl)amino]-N-[(1,1-dimethylethoxy)carbonyl]-L-phenylalanine methyl ester was prepared from 4-amino-N-[(1,1-dimethylethoxy)carbonyl]-L-phenylalanine methyl ester and 2-chloro-6-methylbenzoyl chloride in 83% overall yield as a white solid, mp 154–157° C. HR MS: Obs. mass, 469.1513. Calcd. mass, 469.1507 (M+Na).

Example 112

Preparation of 4-[(2-chloro-6-methylphenylcarbonyl)amino]-L-phenylalanine methyl ester hydrochloride salt

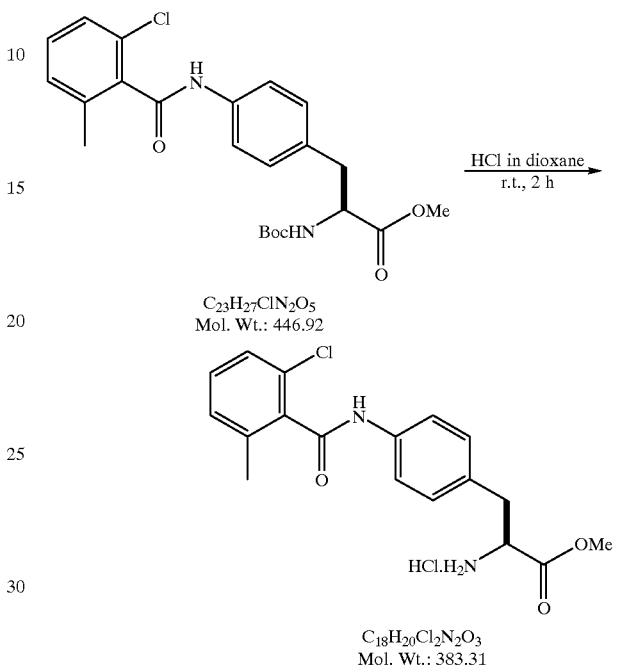

Using the procedure described in example 2, 4-[(2-chloro-6-methylphenylcarbonyl)amino]-L-phenylalanine methyl ester hydrochloride salt was prepared in 99% overall yield as a white solid:. HR MS: Obs. mass, 347.1165. Calcd. mass, 347.1162 (M+H).

Example 113

4-[(2-Chloro-6-methylphenylcarbonyl)amino]-N-[1-(2-methyl-6-ethylphenyl]carbonyl]-L-phenylalanine methyl ester was prepared using the procedure described in example 3 to give a 70% overall yield of a white solid. HR MS: Obs. mass, 515.1690. Calcd. mass, 515.1714 (M+Na).

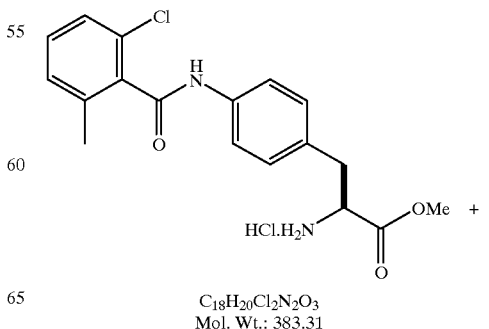

-continued

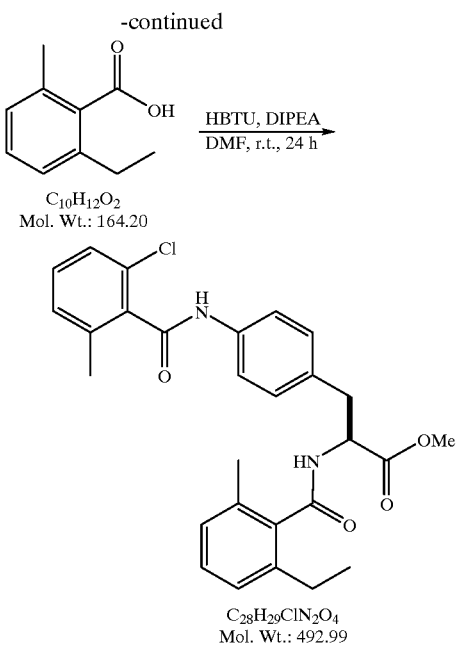

Example 114

N-[1-(2-Chloro-6-methylphenyl)carbonyl]-4-[[(2,6-difluorophenyl)carbonyl]amino]-L-phenylalanine was prepared from 4-amino-N-[(2-chloro-6 -methylphenyl)carbonyl]-L-phenylalanine methyl ester and 2,6-difluorobenzoic acid using the procedures described in examples 109 and 13. HR MS Obs. mass 473).1094. Calcd. mass 473.1079 (M+H).

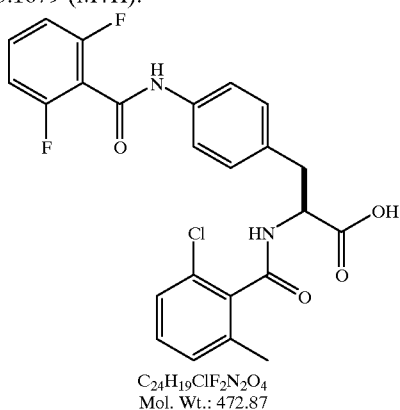

Example 115

N-[1-(2-Chloro-6-methylphenyl)carbonyl]-4-[[(2,3,4,5,6-pentafluorophenyl)carbonyl]amino]-L-phenylalanine was prepared from 4-amino-N-[(2-chloro-6-methylphenyl)carbonyl]-L-phenylalanine methyl ester and pentafluorobenzoic acid using the procedure described in examples 109 and 13. HR MS Obs. mass, 527.0798. Calcd. mass 527.0797 (M+H).

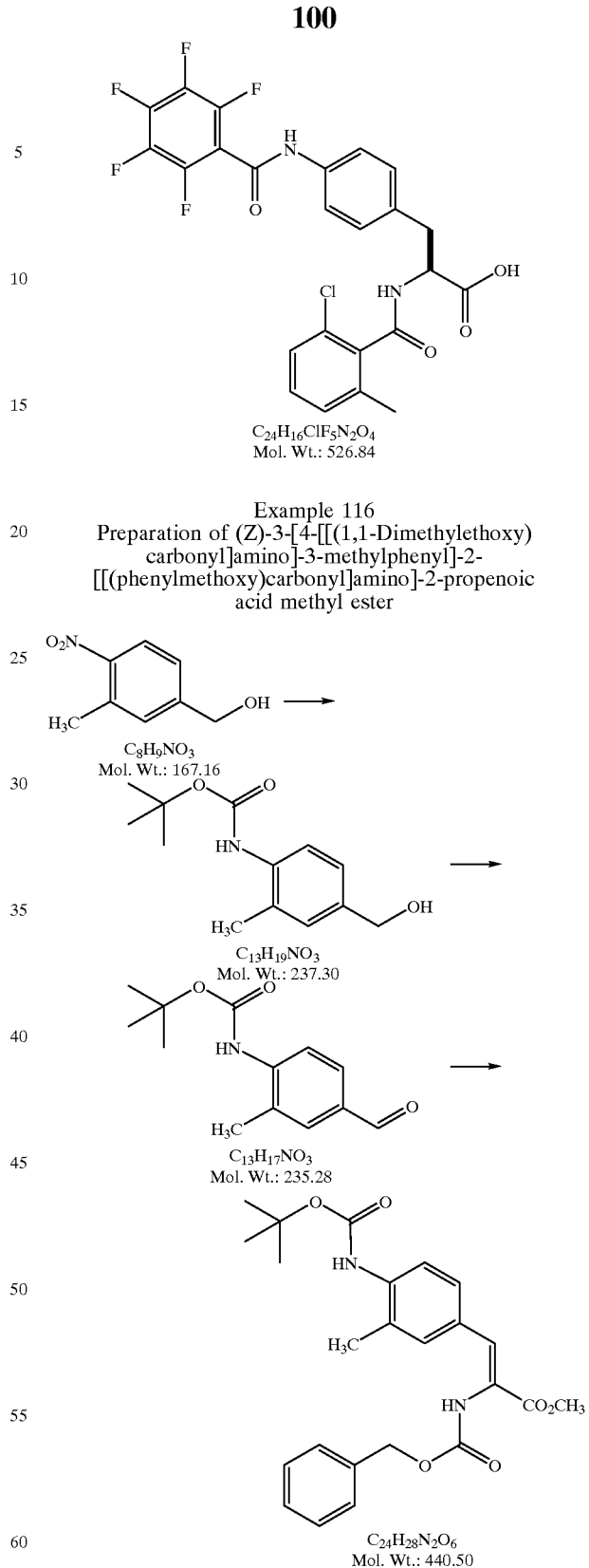

Example 116

Preparation of (Z)-3-[4-[[(1,1-Dimethylethoxy)carbonyl]amino]-3-methylphenyl]-2-[[(phenylmethoxy)carbonyl]amino]-2-propenoic acid methyl ester a. Preparation of 4-[[(1,1-Dimethylethoxy)carbonyl]amino]-3-methylbenzyl alcohol.

A solution of 3-methyl-4-nitrobenzyl alcohol (7.0 g, 42 mmol) in ethyl acetate (175 mL) and Boc anhydride (9.1 g, 42.7 mmol) was hydrogenated over 10% palladium on carbon (0.33 g) for 2 hr. The reaction mixture was filtered and the filtrate was concentrated. The residue was recrystallized from ether-hexane to give a white crystalline solid (6.73 g, (68%), mp 73–74° C. Anal. (C13H19NO3):. C, 65.80; H, 8.07; N, 5.90. Fd. C, 65.74; H, 7.80; N, 5.80.

b. Preparation of 4-[[(1,1-Dimethylethoxy)carbonyl]amino]-3-methylbenzaldehyde.

A solution of 4-[[(1,1-dimethylethoxy)carbonyl]amino]-3-methylbenzyl alcohol (7.2 g, 30.4 mmol) in dichloromethane (60 mL) was treated with manganese dioxide (4×7 g) at two hr intervals and the mixture was stirred at room temperature for 18 hr. The mixture was filtered through a pad of Celite washing with dichloromethane and the filtrate was concentrated. The residue was recrystallized from ether-hexane to give a white crystalline solid (6.3 g, 87%), mp 109–111° C. Anal. (C13H17NO3): Calcd. C, 66.36; H, 7.28; N, 5.95. Fd. C, 66.14; H. 7.14; N, 5.85.

c. Preparation of (Z)-3-[4-[[(1,1-Dimethylethoxy)carbonyl]amino]-3-methylphenyl]-2-[[(phenylmethoxy)carbonyl]amino]-2-propenoic acid methyl ester.

A solution of N-[(phenylmethoxy)carbonyl]-2-phosphonoglycine trimethyl ester (11.9 g, 36 mmol) in dichloromethane (60 mL) was treated with tetramethlguanidine (4.5 mL, 36 mmol). After 1 hr, the mixture was cooled to an internal temperature of −30° C. and was treated with a solution of 4-[[(1,1-dimethylethoxy)carbonyl]amino]-3-methylbenzaldehyde (7.02 g, 29.8 mmol) in dichloromethane (25 mL) at such a rate that there was no temperature rise. The reaction mixture was stirred at −30° C. for 30 min and was allowed to warm to room temperature over night. The mixture was diluted with ether (150 mL) and was washed successively with 0.5 N Hcl (2×50 mL) and Sat. NaHCO3 (1×50 mL) and was dried over MgSO$_4$. The solution was concentrated and the residue was purified by chromatography on a Biotage Kilo Prep HPLC using a silica gel cartridge and eluting with ethyl acetate:hexane (1:2). Fractions containing the Z-isomer were combined and concentrated, finally under high vacuum to give as a colorless glass (11.48 g, 86%). Anal. (C24H28N2O6): Calcd. C. 65.44; H, 6.41; N, 6.36. Fd. C. 64.81; H, 6.43; N, 6.04. HR MS: Obs. mass, 440.1933. Calcd. mass, 440.1947 (M+H).

Example 117

Preparation of 4 -[[(1,1-dimethylethoxy)carbonyl]amino]-3-methyl-N-[[(phenylmethoxy)carbonyl]-L-phenylalanine methyl ester

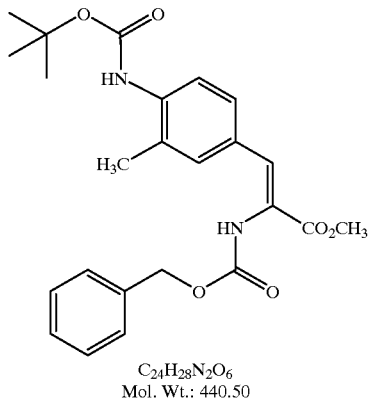

C$_{24}$H$_{28}$N$_2$O$_6$
Mol. Wt.: 440.50

-continued

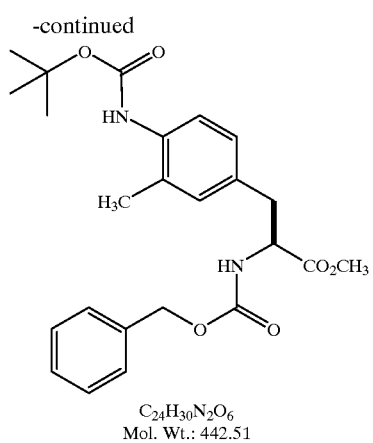

C$_{24}$H$_{30}$N$_2$O$_6$
Mol. Wt.: 442.51

A solution of (Z)-3-[4-[[(1,1-dimethylethoxy)carbonyl]amino]-3-methylphenyl)-2-[[(phenylmethoxy)carbonyl]amino]-2-propenoic acid methyl ester (10 g, 22.7 mmol) in methanol (50 mL) and THF (20 mL) was placed in a pressure bottle and a stream of Ar was passed through the mixture over night. (+)-1,2-Bis((2S,5S)-2,5-dimethylphospholano)benzene(cyclooctadiene)rhodium trifluoromethane sulfonate (100 mg, 0.15 mmol) was added and the bottle was pressurized to 50 psi with hydrogen 3 times and the mixture was stirred over night at room temperature under 50 psi of hydrogen. The pressure was released and the solution was concentrated. The residue was treated with activated charcoal and recrystallized from ethyl acetate-hexane to give 6.72 g (67%), mp 120–121° C. [α]$_{589}$–5.9° (c=1%, methanol). HR MS (C24H30N2O6): Obs. Mass 442.2113. Calcd. Mass 442.2104 (M+).

Example 118

Preparation of 4-[[(1,1-dimethylethoxy)carbonyl]amino]-3-methyl-N-[[(2-chloro-6-methylphenyl)carbonyl]-L-phenylalanine methyl ester

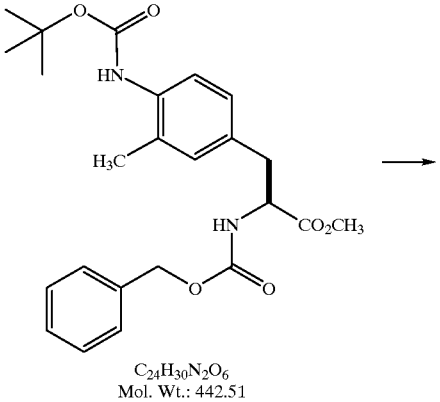

C$_{24}$H$_{30}$N$_2$O$_6$
Mol. Wt.: 442.51

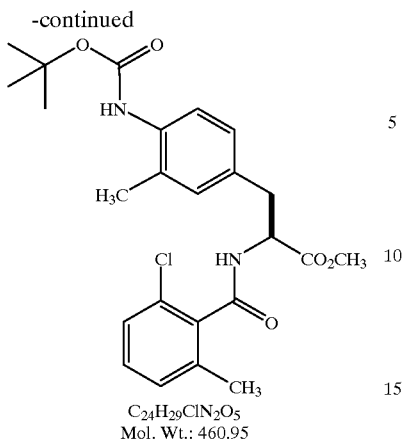

C24H29ClN2O5
Mol. Wt.: 460.95

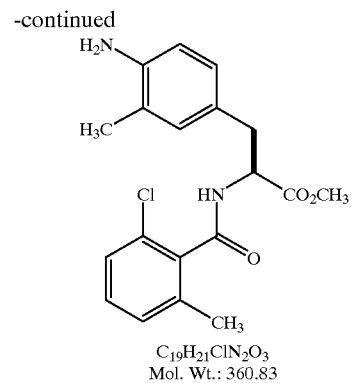

C19H21ClN2O3
Mol. Wt.: 360.83 a. A solution of 4-[[(1,1-dimethylethoxy)carbonyl] amino]-3-methyl-N-[[(phenylmethoxy)carbonyl]-L-phenylalanine methyl ester (3.0 g, 6.8 mmol) in ethanol (40 mL) and cyclohexene (14 mL, 140 mmol) was treated with 10% palladium on carbon (1.5 g) and the mixture was heated to reflux for 20 min and allowed to cool. The mixture was filtered through a pad of celite washing with ethanol and the filtrate was concentrated to give 4-[[(1,1-dimethylethoxy) carbonyl]amino]-3-methyl-L-phenylalanine methyl ester (2.24 g) as a light yellow oil. HR MS (C16H24N2O4): Obs. Mass 309.1819. Calcd. Mass 309.1815 (M+H).

b. A solution of 4-[[(1,1-dimethylethoxy)carbonyl] amino]-3-methyl-L-phenylalanine methyl ester (1.0 g, 3.24 mmol) and 2-chloro-6-methylbenzoic acid (0.66 g, 3.86 mmol) in DMF (8 mL) was treated with HBTU (1.72 g, 4.53 mmol) and DIPEA (3 mL) 17 mmol) and the mixture was stirred over night. The solution was concentrated. The residue was dissolved in ethyl acetate (30 mL) and was washed with sat. NaHCO3 (10 mL), 0.1 N HCl (10 mL), and brine (10 mL) and was dried over Mg2SO4. The residue obtained after filtration and evaporation was purified by silica gel chromatography on 140 g of silica gel, eluting with 1:9 ethyl acetate:dichloromethane to give 1.16 g (78%) of a gum. HR MS (C24H29N2O5Cl): Obs. Mass 461.1858. Calcd. Mass 461.1844 (M+H).

Example 119

Preparation of 4-amino-3-methyl-N-[[(2-chloro-6-methylphenyl)carbonyl]-L-phenylalanine methyl ester hydrochloride salt

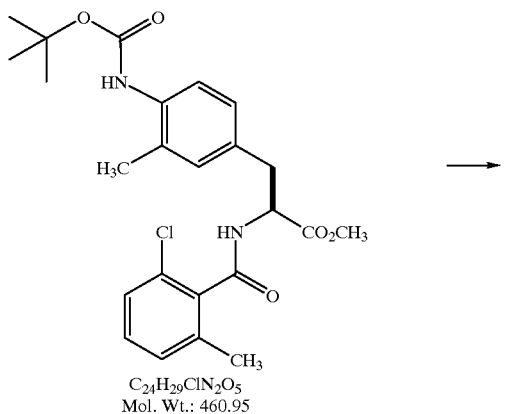

C24H29ClN2O5
Mol. Wt.: 460.95

4-[[(1,1-Dimethylethoxy)carbonyl]amino]-3-methyl-N-[[(2-chloro-6-methylphenyl)carbonyl]-L-phenylalanine methyl ester (1.1 g, 2.17 mmol)) was treated with 4 N HCl in dioxane (20 mL) for 4 hr and was concentrated to dryness. The residue was triturated with ether and filtered to give 0.83 g, 96% as a white solid. HR MS (C19H22N2O3Cl2): Obs. Mass 361.1309. Calcd. Mass 361.1320 (M+H).

Example 120

Preparation of N-[1-(2-chloro-6-methylphenyl) carbonyl]-4-[[3-(3-hydroxyphenyl))-1-oxopropyl] amino]-3-methyl-L-phenylanaline

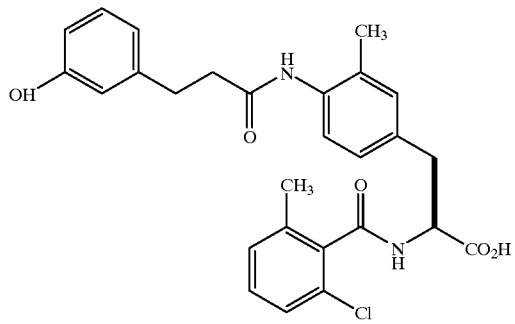

a. A solution of 4-amino-3-methyl-N-[(2-chloro-6-methylphenyl)carbonyl]-L-phenylalanine methyl ester hydrochloride salt (79.5 mg, 0.20 mmol), 3-(3-hydroxyphenyl)propanoic acid (33.2 mg, 0.20 mmol) and DIPEA (120 μL, 0.69 mmol) in dichloromethane (3 mL) was cooled to 10° C. and was treated with BOP-Cl (51 mg, 0.20 mmol). The mixture was stirred for 4 hr and was concentrated. The residue was dissolved in dichloromethane (15 mL) and was washed with 5 mL portions of 0.5 N NaCO3, 0.5 N HCl and saturated brine and was dried (MgSO4). The residue obtained after filtration and concentration was purified by chromatography on 25 g of silica gel, eluting with 7:3 ethyl acetate:hexane to give 47 mg of a colorless glass. HR MS: Obs. Mass 509.1849. Calcd. Mass 509.1844 (M+H).

b. A solution of N-[1-(2-chloro-6-methylphenyl)carbonyl] 4-[[3-(3-hydroxyphenyl))-1-oxopropyl]amino]-3-methyl-L-phenylalanine methyl ester (45 mg, 0.088 mmol) in THF (30 mL) was treated with solution of LiOH.H2O (20 mg, 0.47 mmol) in water (1.0 mL). Methanol (0.5 mL) was added for solubility and the mixture was stirred at room temperature for 18 hr. The mixture was acidified with 0.5 mL of acetic acid and was purified directly by RP-HPLC (5-95-35-214) to give, after lyopylization 34.3 mg of a white powder. HR MS (C27H27N2O5Cl): Obs. Mass 495.1697. Calcd. Mass 495.1687 (M+H).

Example 121

N-[1-(2-Chloro-6-methylphenyl)carbonyl]-4-[[2-(3-hydroxphenyl))-1-oxoethyl]amino]-3-methyl-L-phenylalanine was prepared using the general procedure described in example 120 from 4-amino-3-methyl-N-[[(2-chloro-6-methylphenyl)carbonyl]-L-phenylalanine methyl ester (79.5 mg) and 2-(3-hydroxyphenyl)acetic acid (30 mg 0.2 mmol) to give 23 mg of a colorless glass. HR MS (C26H25N2O5Cl): Obs. Mass 481.1527. Calcd. Mass 481.1530 (M+H).

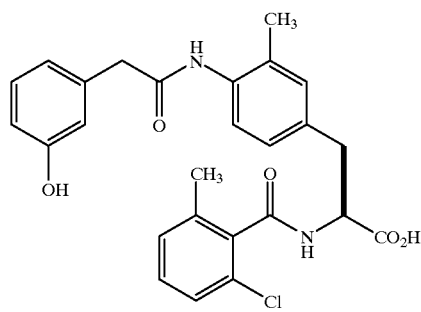

Example 122

N-[1-(2-Chloro-6-methylphenyl)carbonyl]-4-[[2-(3-nitrophenyl))-1-oxoethyl]amino]-3-methyl-L-phenylalanine was prepared from 4-amino-3-methyl-N-[[(2-chloro-6-methylphenyl)carbonyl]-L-phenylalanine methyl ester (52 mg) and 3-nitrobenzoic acid (32 mg, 0.19 mmol) using the procedure described in example 120 to give 15 mg of a white powder. HR MS (C25H22N3O6Cl): Obs. Mass 496.1288. Calcd. Mass 496.1288 (M+H).

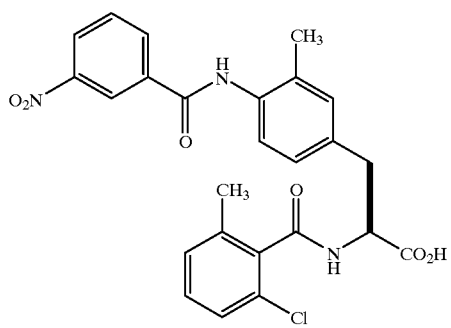

Example 123

N-[1-(2-chloro-6-methylphenyl)carbonyl]-4-[[2,6-dichlorophenyl)carbonyl]amino]-3-methyl-L-phenylalanine was prepared from 4-amino-3-methyl-N-[[(2-chloro-6-methylphenyl)carbonyl]-L-phenylalanine methyl ester (87.4 mg, 0.22 mmol) and 2,6-dichlorobenzoyl chloride using the procedures described in examples 1 and 120 to give 56 mg of a white powder. HR MS (C25H21N2O4Cl3): Obs. Mass 519.0656. Calcd. Mass 519.0645 (M+H).

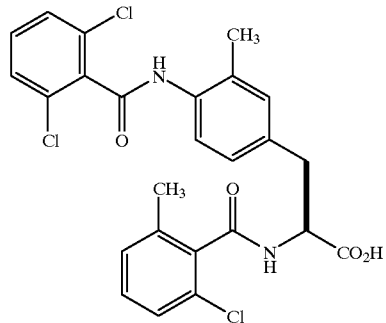

Example 124

Preparation of N-[(4-amino-2-chlorophenyl)carbonyl]-4-[[(2,6-dichlorophenyl)carbonyl]amino]-L-phenylalanine

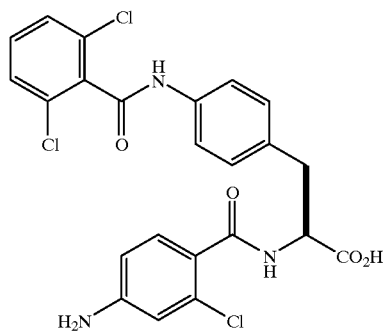

a. A solution of 4-amino-2-chlorobenzoic acid (43 mg, 0.25 mmol) and 4-[(2,6-dichlorophenyl)carbonyl]amino]-L-phenylalanine methyl ester hydrochloride (100 mg, 0.25 mmol) and HBTU (100 mg, 0.27 mmol) in DMF (3 mL) was treated with DIPEA (0.20 mL) and the mixture was stirred 2 hr at room temperature. The mixture was diluted with water and was extracted with ethyl acetate. The organic layer was washed with saturated NaHCO3 and dried MgSO4). The residue after filtration and concentration was chromatographed on 16 g of silica gel eluting with 4:1 ethyl acetate-:hexane to give N-[(4-amino-2-chlorophenyl)carbonyl]-4-[[(2,6-dichlorophenyl)carbonyl]amino]-L-phenylalanine methyl ester (66 mg, 51%) of a white foam. HR MS (C24H20Cl3N3O4): Obs. Mass 520.0589. Calcd. Mass 520.0597 (M+H).

b. A solution of N-[(4-amino-2-chlorophenyl)carbonyl]-4-[[(2,6-dichlorophenyl)carbonyl]amino]-L-phenylalanine methyl ester (66 mg, 0.126 mmol) in THF (3 mL) was treated with a solution of LiOH.H2O (20 mg, 0.48 mmol) in water (0.5 mL) and the mixture was stirred over night at room temperature. Acetic acid (0.5 mL) was added and the mixture was purified directly by RP-HPLC (5-95-35-214) to give 40 mg of a white solid. HRMS: (C23H18Cl3N3O4): Obs. Mass 506.0461. Calcd. Mass 506.0441 (M+H).

Example 125

Preparation of 4-(4-cyano-1,3-dioxo-2H-isoindol-2-yl)-N-[1-(2-chloro-6-methylphenyl)carbonyl]-L-phenylalanine a) Preparation of 4-(4-cyano-1,3-dioxo-2H-isoindol-2-yl)-N-[1-(2-chloro-6-methylphenyl)carbonyl]-L-phenylalanine methyl ester

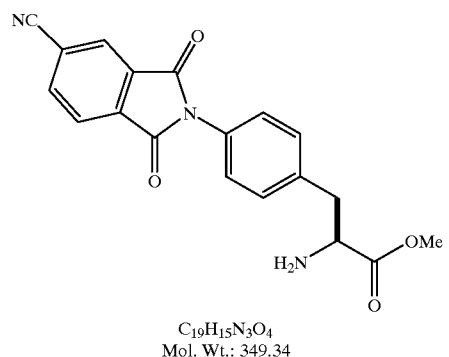

C₁₉H₁₅N₃O₄
Mol. Wt.: 349.34

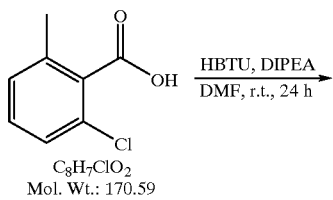

C₈H₇ClO₂
Mol. Wt.: 170.59

HBTU, DIPEA
DMF, r.t., 24 h

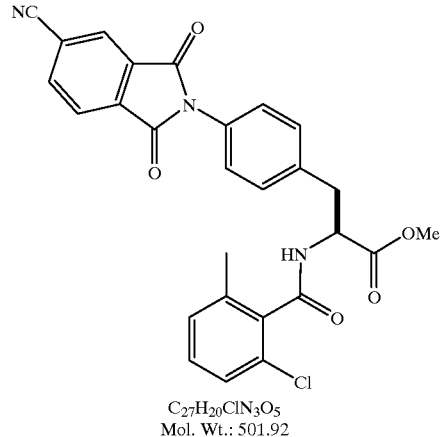

C₂₇H₂₀ClN₃O₅
Mol. Wt.: 501.92

Using the procedure described in example 3,4-(4-cyano-1,3-dioxo-2H-isoindol-2-yl)-N-[1-(2-chloro-6-methylphenyl)carbonyl]-L-phenylalanine methyl ester was prepared in 63% overall yield as a white solid: mp 200–202° C. HR MS: Obs. mass, 502.1173. Calcd. mass, 502.1169, M+H.

b) Preparation of 4-(4-cyano-1,3-dioxo-2H-isoindol-2-yl)-N-[1-(2-chloro-6-methylphenyl)carbonyl]-L-phenylalanine.

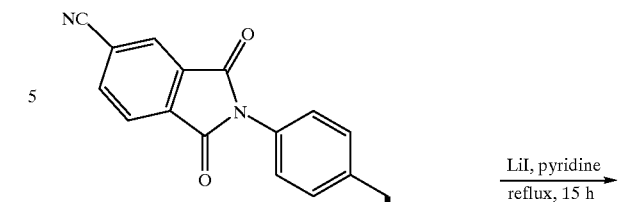

C₂₇H₂₀ClN₃O₅
Mol. Wt.: 501.92

LiI, pyridine
reflux, 15 h

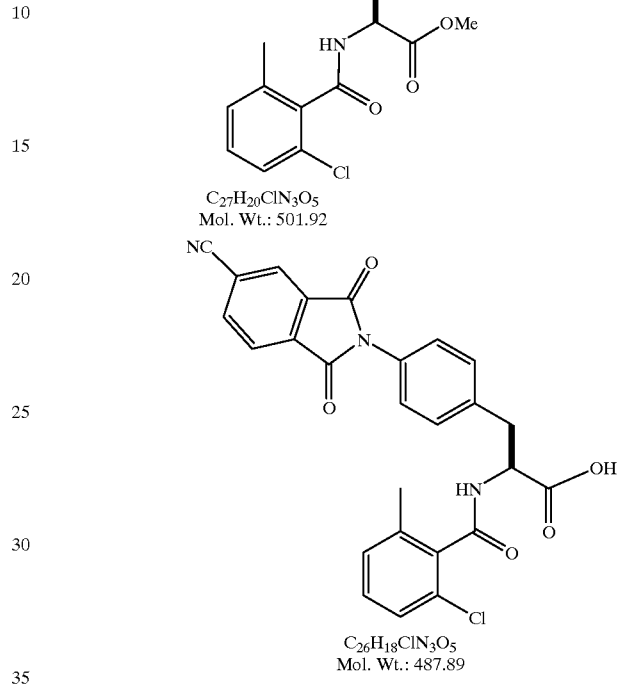

C₂₆H₁₈ClN₃O₅
Mol. Wt.: 487.89

Using the procedure described in example 110, 4-(4-cyano-1,3-dioxo-2H-isoindol-2-yl)-N-[1-(2-chloro-6-methylphenyl)carbonyl]-L-phenylalanine was prepared in 26% overall yield as a white solid: mp 170–175° C. HR MS: Obs. mass, 488.1004. Calcd. mass, 488.1013, M+H.

Example 126

Synthesis of N-(2-chloro-6-methylbenzoyl)-4-[(2,6-dichlorophenyl)carbonyl]amino]-L-phenylalanine ethyl ester

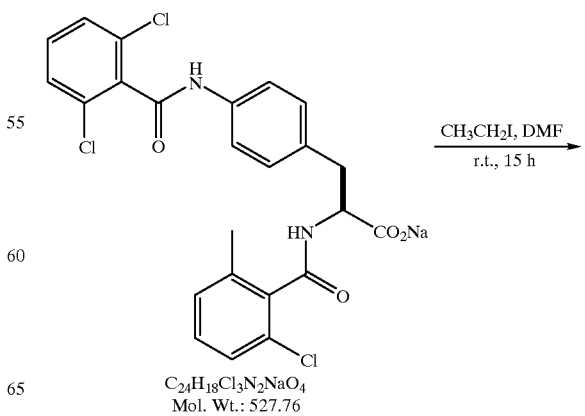

C₂₄H₁₈Cl₃N₂NaO₄
Mol. Wt.: 527.76

CH₃CH₂I, DMF
r.t., 15 h

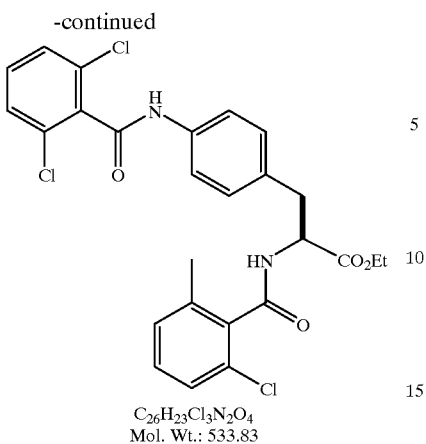

C₂₆H₂₃Cl₃N₂O₄
Mol. Wt.: 533.83

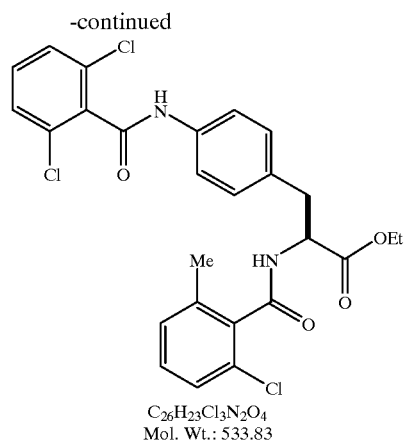

C₂₆H₂₃Cl₃N₂O₄
Mol. Wt.: 533.83

To a solution of sodium salt of N-(2-chloro-6-methylbenzoyl)-4-[(2,6-dichlorophenyl)carbonyl]amino]-L-phenylalanine (1.583 g, 3.0 mmol) in DMF (75 mL) was added excess iodoethane (3.27 g, 21 mmol) at room temperature. The resulting solution was stirred for 24 hr. TLC analysis of the mixture indicated the absence of staring material and the excess iodoethane and some DMF was removed on a rotary evaporator under vacuum. The residue was diluted with 100 mL of ethyl acetate and was washed successively with water (2×100 mL), brine solution (100 mL) and dried over MgSO₄. Filtration of the drying agent and removal of the solvent afforded a white solid which was purified by silica gel column chromatography eluting with ethyl acetate:hexane (1:1) to obtain 1.4 g (87%) of ethyl ester as a white solid. mp 230–235° C. HR MS: Obs. mass, 533.0817. Calcd. mass, 533.0801 (M+H).

To a suspension of N-(2-chloro-6-methylbenzoyl)-4-[(2,6-dichlorophenyl)carbonyl]amino]-L-phenylalanine (7.0 g, 13.84 mmol) and powdered sodium bicarbonate (5.88 g, 70 mmol) in DMF (100 mL) was added excess of iodoethane (10.91 g, 70 mmol) at room temperature. The resulting suspension was stirred for 20 h at which time TLC analysis of the mixture indicated the absence of staring material and the excess iodoethane and some DMF was removed on a rotary evaporator under vacuum. The remaining residue was diluted with 150 mL of ethyl acetate and washed successively with water (2×100 mL), brine solution (100 mL) and dried over MgSO₄. Filtration of the drying agent and removal of the solvent afforded a white solid which was crystallized from acetonitrile. The resulting crystalline solid was collected by filtration and dried under high vacuum to afford 5.58 g (77%) of N-(2-chloro-6-methylbenzoyl)-4-[(2,6-dichlorophenyl)carbonyl]amino]-L-phenylalanine ethyl ester as a white solid. mp 230–235° C.

Example 127

Synthesis of N-(2-chloro-6-methylbenzoyl)-4-[(2,6-dichlorophenyl)carbonyl]amino]-L-phenylalanine ethyl ester

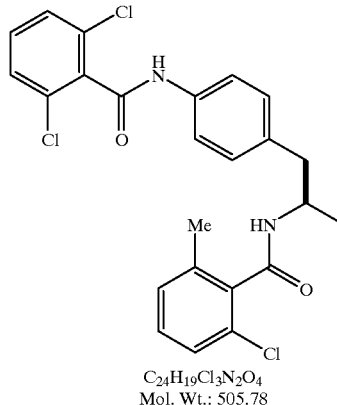

C₂₄H₁₉Cl₃N₂O₄
Mol. Wt.: 505.78

Example 128

Synthesis of of N-(2-chloro-6-methylbenzoyl)-4-[(2,6-dichlorophenyl)carbonyl]amino]-L-phenylalanine 2-morpholinoethyl ester

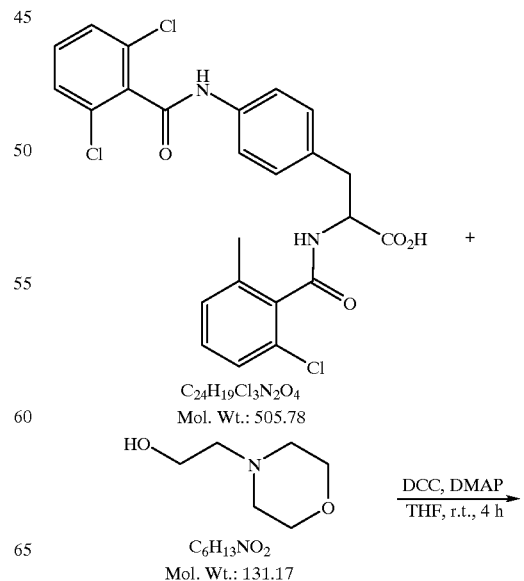

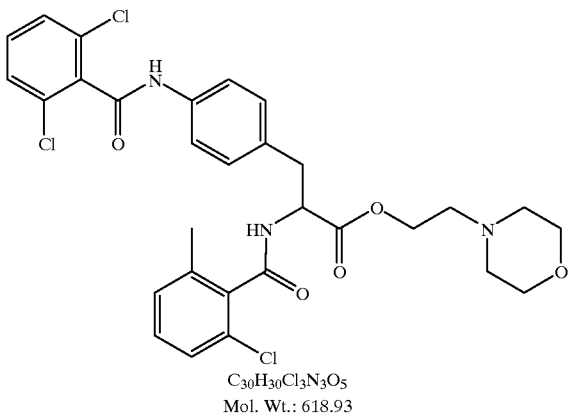

C30H30Cl3N3O5
Mol. Wt.: 618.93

To a solution of N-(2-chloro-6-methylbenzoyl)-4-[(2,6-dichlorophenyl)carbonyl]amino]-L-phenylalanine (0.505 g, 1.0 mmol) and 2-(4-morpholino)ethanol (0.262 g, 2.0 mmol) in THF (13 mL) was added dicyclohexylcarbodiimide (0.309 g, 1.5 mmol) and 4-dimethylaminopyridine (61 mg, 0.5 mmol) at room temperature. The resulting cloudy solution was stirred for 4 h at which time TLC analysis of the reaction mixture indicated the absence of acid. Then, the mixture was diluted with water (50 mL) and extracted with ethyl acetate (3×50 mL). The combined extracts were washed with water (2×100 mL) and brine solution (100 mL) and were dried over MgSO$_4$. Filtration of the drying agent and removal of the solvent gave a white solid which was purified by silica gel column chromatography using dichloromethane:methanol (15:1) as eluent to obtain 0.428 g (69%) of N-(2-chloro-6-methylbenzoyl)-4-[(2,6-dichlorophenyl)carbonyl]amino]-L-phenylalanine 2-(4-morpholino)ethyl ester as a white solid, mp 109–118° C. HR MS: Obs. mass, 618.1311. Calcd. mass, 618.1329 (M+H).

Example 129

Synthesis of of N-(2-chloro-6-methylbenzoyl)-4-[(2,6-dichlorophenyl)carbonyl]amino]-L-phenylalanine 2-(4-morpholino)ethyl ester

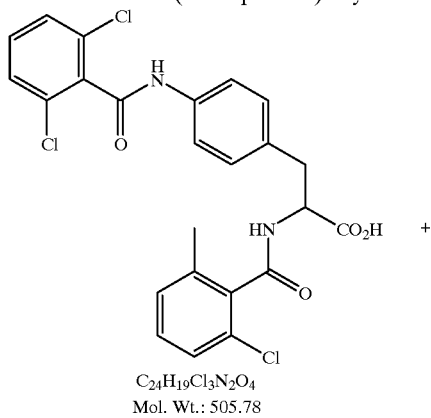

C24H19Cl3N2O4
Mol. Wt.: 505.78

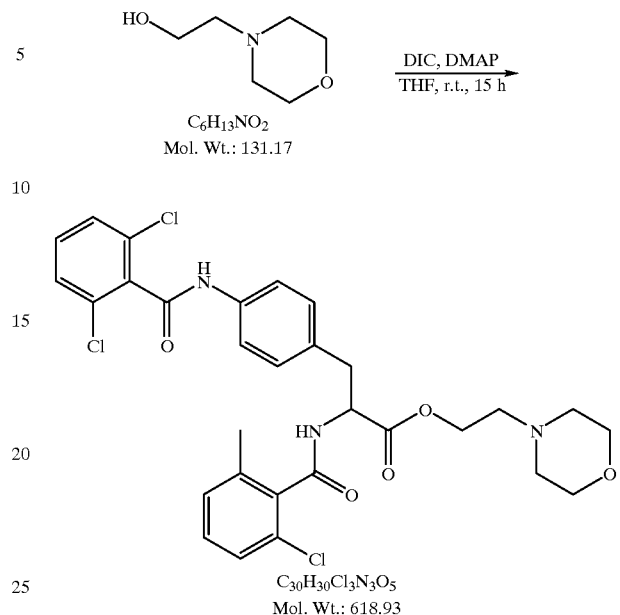

C6H13NO2
Mol. Wt.: 131.17

DIC, DMAP
THF, r.t., 15 h

C30H30Cl3N3O5
Mol. Wt.: 618.93

To a solution of N-(2-chloro-6-methylbenzoyl)-4-[(2,6-dichlorophenyl)carbonyl]amino]-L-phenylalanine (0.253 g, 0.5 mmol) and 2-(4-morpholino)ethanol (0.131 g, 1.0 mmol) in THF (5 mL) was added di-isopropylcarbodiimide (94.6 mg, 0.75 mmol) and 4-dimethylaminopyridine (30.5 mg, 0.25 mmol) at room temperature. The resulting mixture was stirred for 15 h at room temperature at which time TLC analysis of the reaction mixture indicated the absence of acid. Then, the mixture was diluted with water (50 mL) and the THF was removed under vacuum and the residue was extracted with dichloromethane (3×25 mL). The combined extracts were washed with water (2×50 mL), brine solution (50 mL) and dried over MgSO$_4$. Filtration of the drying agent and concentration of the solvent gave a white solid which was purified by silica gel column chromatography using dichloromethane and ethyl acetate (5:1 to 1:1) and pure ethyl acetate as eluent to obtain 0.2 g (65%) of a white solid, mp 109–118° C.

Example 130–132

Using the procedure described in Example 129, the following ester derivatives were prepared.

| Example | Structure | Yeild % | HRMS Calc | HRMS OBS |
|---|---|---|---|---|
| 130 | 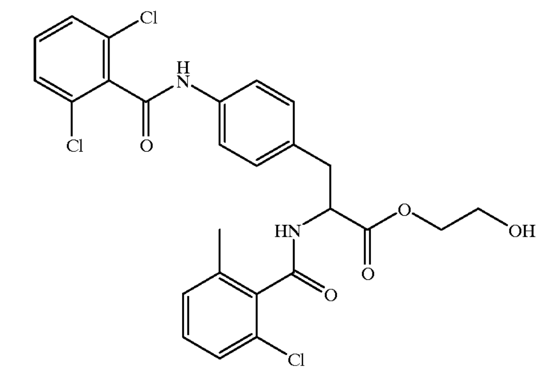 | 60 | 549.0751 | 549.0738 |
| 131 | 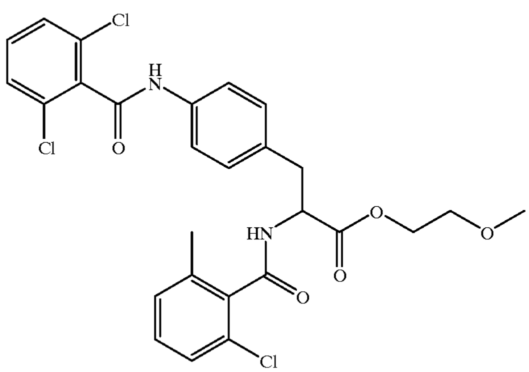 | 47 | 563.0907 | 563.0912 |
| 132 | 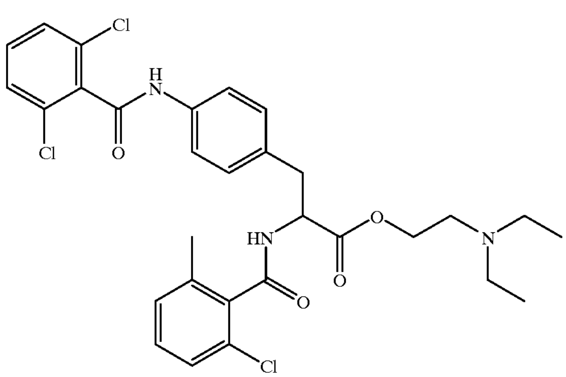 | 52 | 604.1536 | 604.1539 |

Example 133

Synthesis of N-(2-chloro-6-methylbenzoyl)-4-[(2,6-dichlorophenyl)carbonyl]amino]-L-phenylalanine 1-methyl-2-(4-morpholino)ethyl ester was prepared in 32% yield according to the procedure described in example 129. HRMS Calcd: 632.1484. Obs: 632.1486 (M+H).

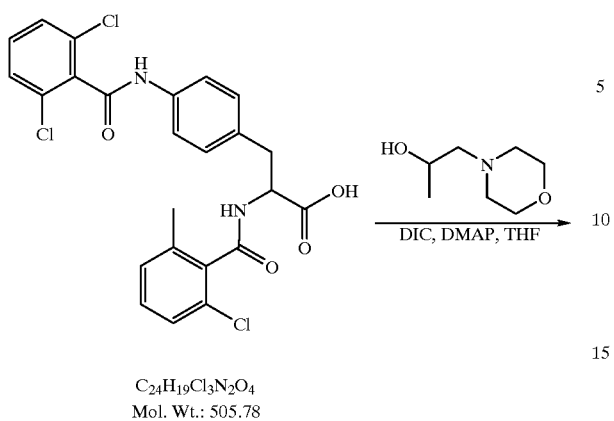

C$_{24}$H$_{19}$Cl$_3$N$_2$O$_4$
Mol. Wt.: 505.78

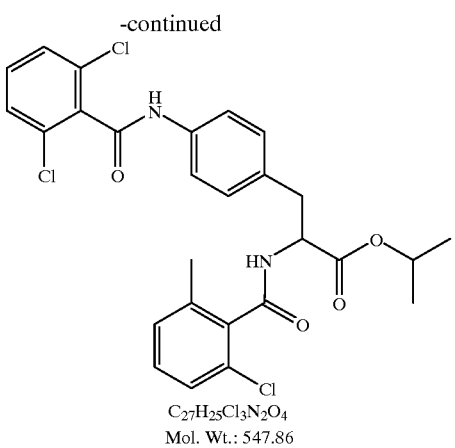

C$_{27}$H$_{25}$Cl$_3$N$_2$O$_4$
Mol. Wt.: 547.86

Example 135

N-(2-Chloro-6-methylbenzoyl)-4-[(2,6-dichlorophenyl)carbonyl]amino]-L-phenylalanine 2-methylpropyl ester was prepared by the method described in example 127. HRMS m/z Calcd, 561.1114. Obs, 561.1125 (M+H).

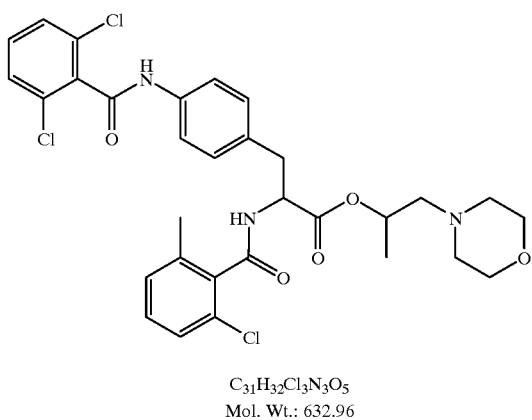

C$_{31}$H$_{32}$Cl$_3$N$_3$O$_5$
Mol. Wt.: 632.96

Example 134

N-(2-Chloro-6-methylbenzoyl)-4-[(2,6-dichlorophenyl)carbonyl]amino]-L-phenylalanine 1-methylethyl ester was prepared in 60% yield by the procedure described in example 127. HRMS m/z Calcd, 569.0778. Obs. 569.0774 (M+Na).

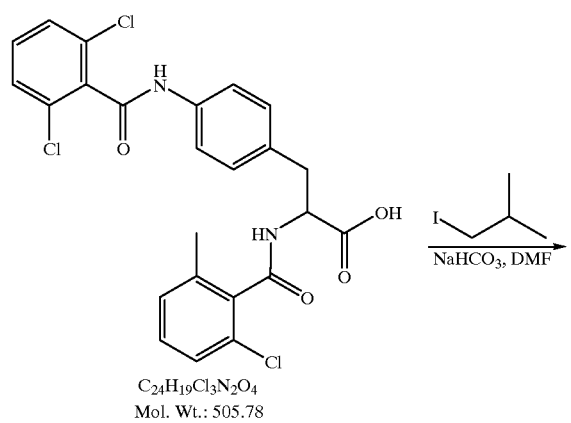

C$_{24}$H$_{19}$Cl$_3$N$_2$O$_4$
Mol. Wt.: 505.78

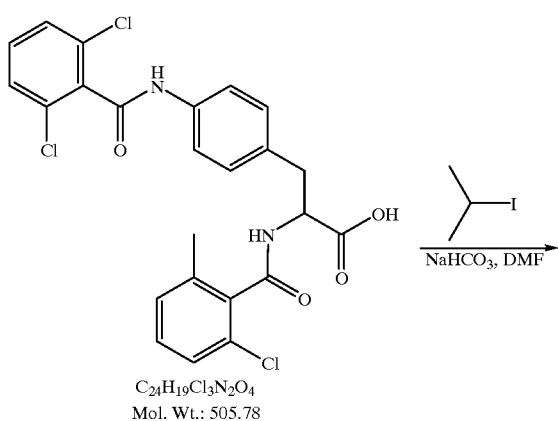

C$_{24}$H$_{19}$Cl$_3$N$_2$O$_4$
Mol. Wt.: 505.78

C$_{28}$H$_{27}$Cl$_3$N$_2$O$_4$
Mol. Wt.: 561.88

Example 136

N-(2-Chloro-6-methylbenzoyl)-4-[(2,6-dichlorophenyl)carbonyl]amino]-L-phenylalanine 1-methyl-4-piperidinyl ester was prepared in 65% by the method described in example 128. HR MS C30H30Cl3N3 O4): Obs, 602.1386.Calcd: 602.1380 (M+H).

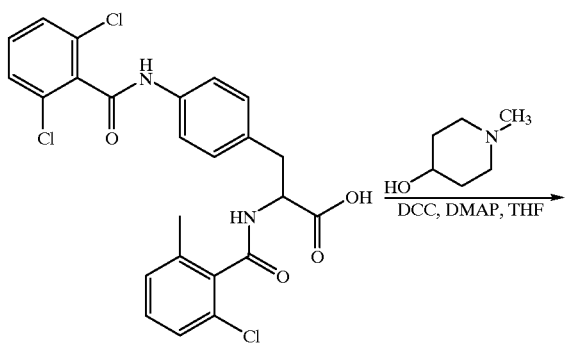

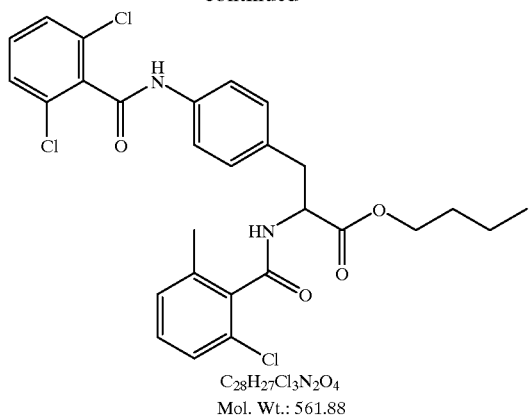

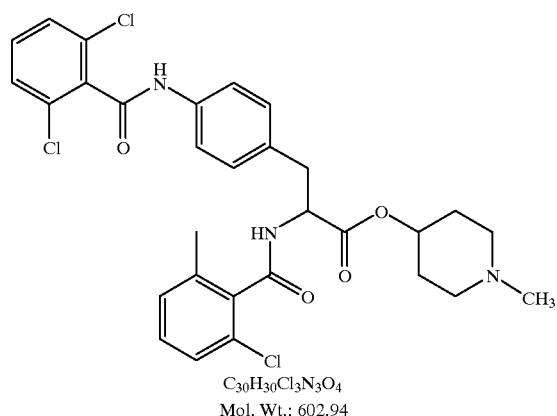

Example 137

N-(2-Chloro-6-methylbenzoyl)-4-[(2,6-dichlorophenyl)carbonyl]amino]-L-phenylalanine butyl ester was prepared in 75% yield by the procedure described in example 127. HR MS (C28H27Cl3N2O4): Obs. 561.1115. Calcd. 561.1114 (M+H).

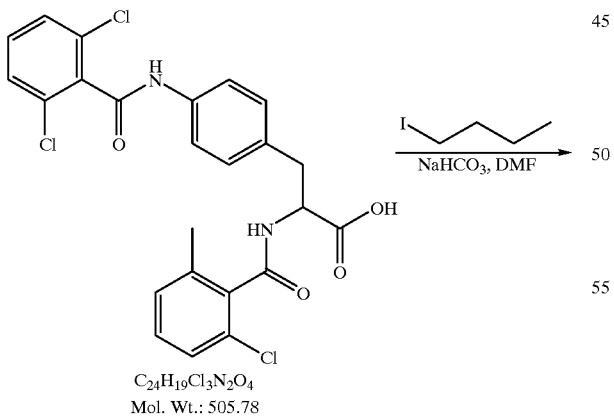

Example 138

N-(2-Chloro-6-methylbenzoyl)-4-[(2,6-dichlorophenyl)carbonyl]amino]-L-phenylalanine 2-[4-[(1,1-dimethylethoxy)carbonyl]-1-piperazinyl]ethyl ester was prepared in 78% yield from N-(2-chloro-6-methylbenzoyl)4-[(2,6-dichlorophenyl)carbonyl]amino]-L-phenylalanine and 2-[4-[(1,1-dimethylethoxy)carbonyl]-1-piperazinyl]ethanol using the procedure described in example 129. HR MS: Obs. mass, 717.1995. Calcd. mass, 717.2013 (M+).

a. A solution of 4-[[(2-propenyloxy)carbonyl]amino]-L-phenylalanine methyl ester (935 mg, 3.54 mmol), HOAT

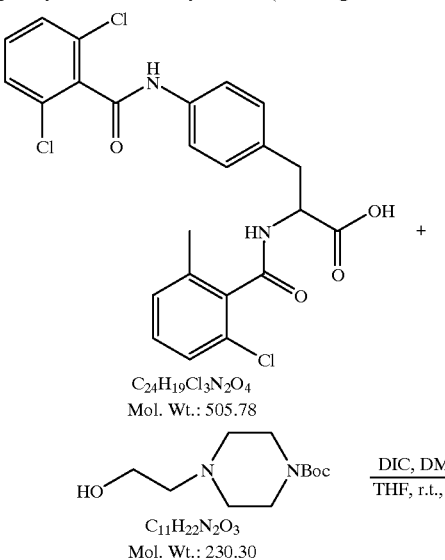

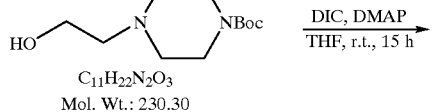

-continued

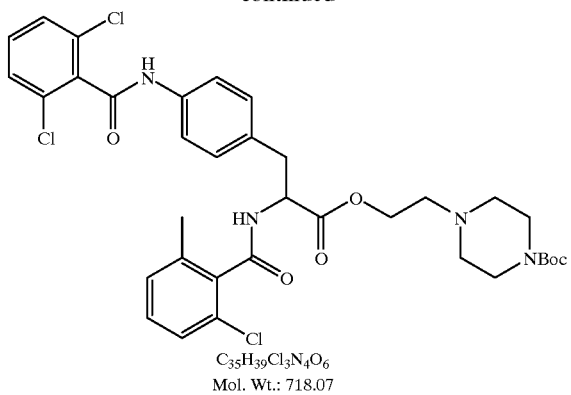

C35H39Cl3N4O6
Mol. Wt.: 718.07

Example 139

N-(2-Chloro-6-methylbenzoyl)-4-[(2,6-dichlorophenyl)carbonyl]amino]-L-phenylalanine 2-(1-piperazinyl)ethyl ester

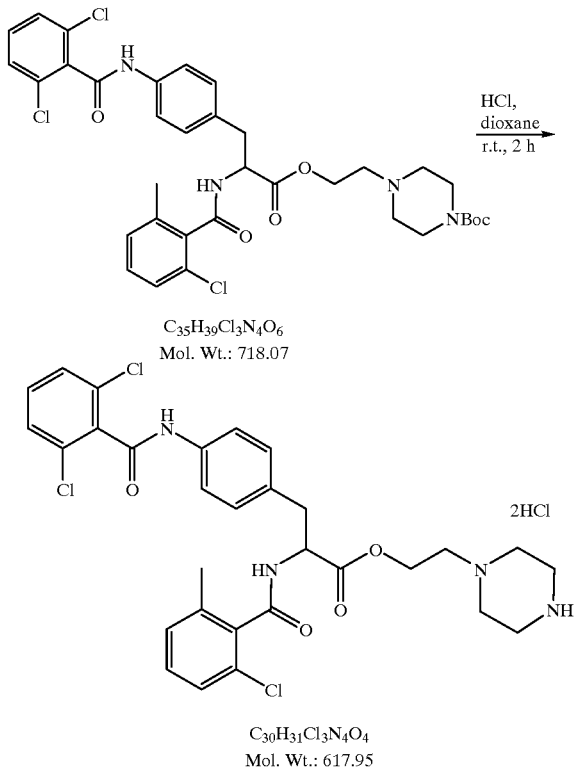

To a solution of N-(2-chloro-6-methylbenzoyl)-4-[(2,6-dichlorophenyl)carbonyl]amino]-L-phenylalanine 2-[4-[(1,1-dimethylethoxy)carbonyl]-1-piperazinyl]ethyl ester (1.0 mmol, 0.72 g) in dioxane (4 mL) was added a solution of HCl in dioxane (3.0 mmol, 0.75 mL, 4N) at room temperature. The resulting solution was stirred for 2 h at room temperature at which time TLC analysis of the reaction mixture indicated the absence of starting material. Then, the dioxane was removed under vacuum and the solid was triturated with ether (15 mL). The ether was decanted and the solid was dried under high vacuum to obtain 0.68 g (90%) as a white solid. HR MS (C30H31Cl3N4O4): Obs. mass. 617.1464. Calcd. mass. 617.1489 (M+H).

Example 140

Preparation N-(2-chloro-6-methylbenzoyl)-4-[(2,6-dichlorophenyl)carbonyl]amino]-L-phenylalanine 2-(4-methyl-1-piperazinyl)ethyl ester

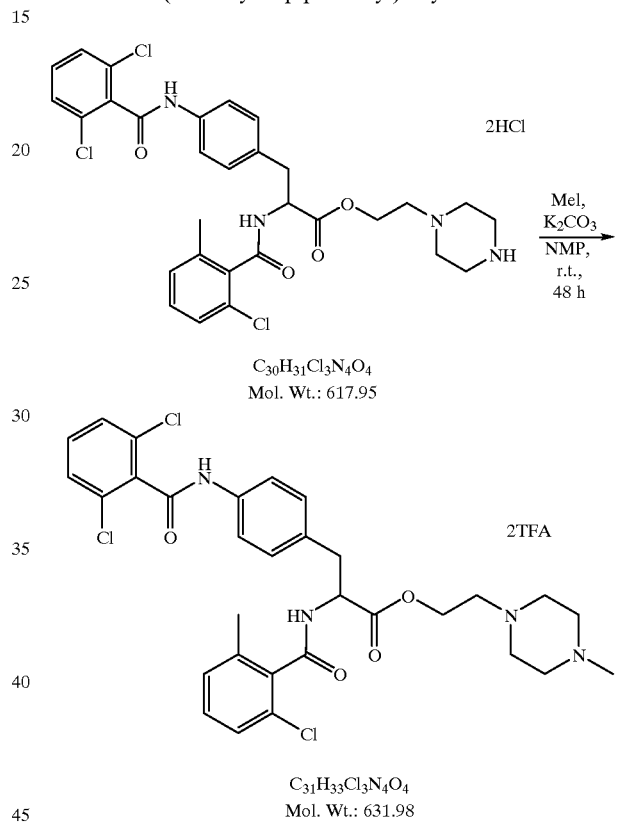

To a suspension of N-(2-Chloro-6-methylbenzoyl)-4-[(2,6-dichlorophenyl)carbonyl]amino]-L-phenylalanine 2-(1-piperazinyl)ethyl ester dihydrochloride (1.0 mmol, 0.617 g) and K2CO3 (8.0 mmol, 1.1 g) in NMP (10 mL) was added methyl iodide (3.0 mmol, 0.43 g) at room temperature. The resulting mixture was stirred for 48 h at room temperature at which time TLC analysis of the reaction mixture indicated the absence of starting material. Then, the mixture was diluted with water (100 mL) and the precipitated solid was collected by filtration and dried under high vacuum. This solid was purified by reverse phase HPLC to obtain 0.35 g (55%) of a white solid. HR MS (C31H33Cl3N4O4): Obs. mass. 631.9208. Calcd. mass. 631.9193) (M+H).

Example 141

Preparation of N-methyl-N-[1-(2-chloro-6-methylphenyl)carbonyl]-4-nitro-L-phenylalanine methyl ester

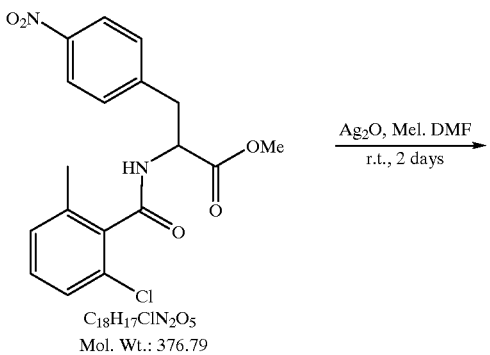

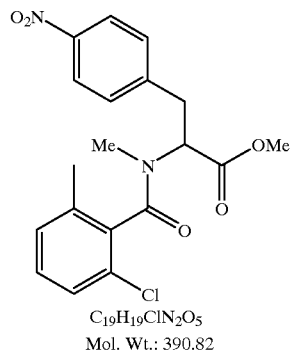

To a suspension of N-[1-(2-chloro-6-methylphenyl)carbonyl]-4-nitrophenylalanine methyl ester (0.375 mmol, 142 mg) and silver oxide (1.5 mmol, 340 mg) in DMF (2 mL) was added methyl iodide (28 mmol, 1.75 mL) at room temperature. The suspension was stirred for 2 days at room temperature, at which time TLC analysis of the mixture indicated the absence of starting material, and the solid was filtered. The solution was concentrated and diluted with ethyl acetate (30 mL) and washed with water (20 mL), brine solution (20 mL) and dried over anhydrous magnesium sulfate. Filtration of the drying agent and removal of the solvent gave 99 mg (67%) of a light brown oil. LR MS (C19H19ClN2O5): 390 (M+H).

Example 142

Preparation of 4-amino-N-methyl-N-[1-(2-chloro-6-methylphenyl)carbonyl]-L-phenylalanine methyl ester

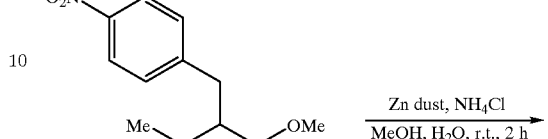

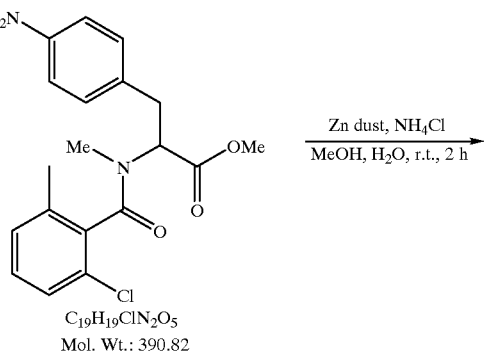

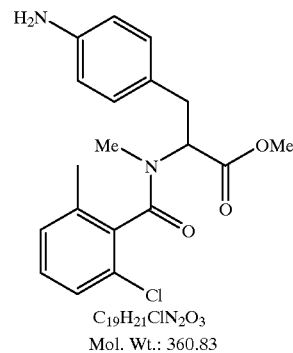

To a mixture of N-methyl-N-[1-(2-chloro-6-methylphenyl)carbonyl]-4-nitro-L-phenylalanine methyl ester (0.5 mmol, 192 mg), zinc dust (~325 mesh, 5.0 mmol, 0.33 g, 10 equiv.) and ammonium chloride (7.5 mmol, 0.4 g, 15 equiv.) was added methanol (4 mL) and water (2 mL) at room temperature. After addition of water, the reaction was exothermic. The suspension was stirred for 2 h at room temperature, at which time TLC analysis of the mixture indicated the absence of starting material, and the reaction mixture was filtered through the celite. The filter cake was washed with methanol (30 mL) and water (20 mL). The filtrate was concentrated to remove the methanol and the residue was extracted with ethyl acetate (3×20 mL). The combined extracts were washed with brine solution (30 mL) and dried over anhydrous magnesium sulfate. Filtration of the drying agent and concentration of the solvent afforded 148 mg (82%) of a yellow oil. LR MS (C19H21ClN2O3): 361 (M+H).

Example 143

Preparation of 4-[(2,6-dichlorophenylcarbonyl)amino]-N-methyl-N-[1-(2-chloro-6-methylphenyl)carbonyl]-L-phenylalanine methyl ester

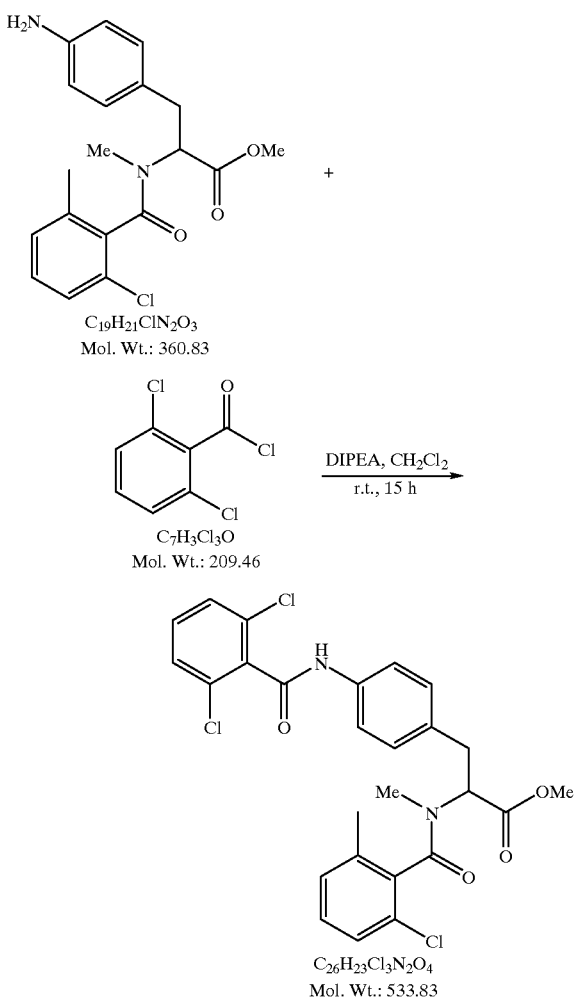

Using the procedure described in example 1, methyl 4-[[(2,6-dichlorophenyl)carbonyl]amino]-N-[1-(2-chloro-6-methylphenyl)carbonyl]-L-phenylalanine was prepared in 68% overall yield as an amorpous solid. LR MS (C26H23Cl3N2O4): 534 (M+H).

Example 144

Preparation of 4-[(2,6-dichlorophenylcarbonyl)amino]-N-methyl-N-[1-(2-chloro-6-methylphenyl)carbonyl]-L-phenylalanine

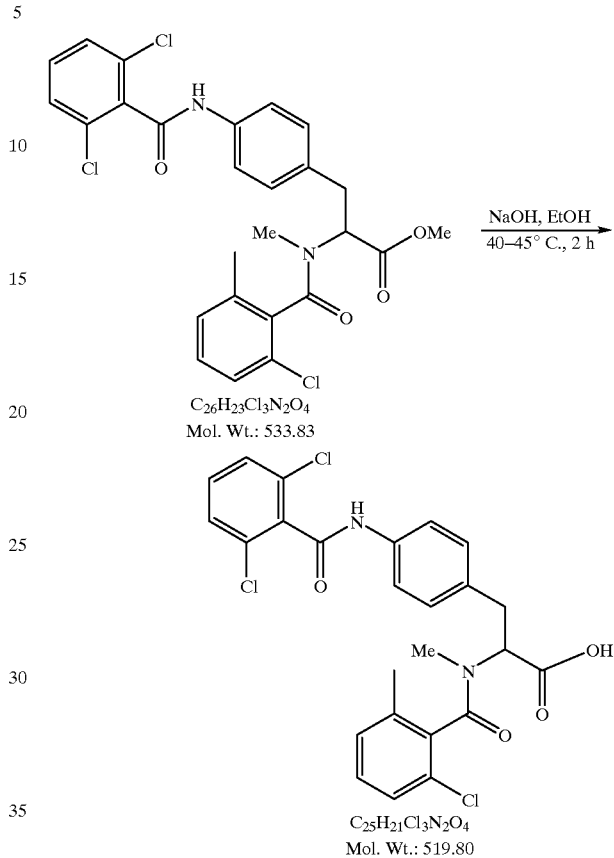

Using the procedure described in example 13, N-[1-(2-chloro-6-methylphenyl)carbonyl]-N-methyl-4-[[(2,6-dichlorophenyl)carbonyl]amino]-L-phenylalanine was prepared in 59% overall yield as a white solid. HR MS: Obs. mass. 519.0631. Calcd. mass, 519.0645 (M+H).

Example 145

Preparation of 2-chloro-6-methylbenzoic acid a. Preparation of 2-chloro-6-methylbenzaldehyde.

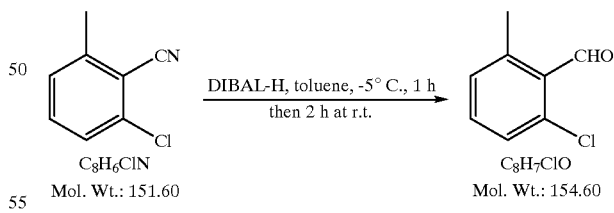

A 500 mL, three-necked, round bottomed flask equipped with a magnetic stirrer, thermometer, additional funnel, and argon inlet was charged with 75 g (494 mmol) of 2-chloro-6-methylbenzonitrile and 400 mL of toluene (stored over 4 Å molecular sieves). The mixture was cooled to −2° C. (ice+acetone) and a solution of DIBAL-H (593 mmol, 593 mL, 1.0N) in hexanes was added dropwise over a period of 30 min while maintaining the temperature below 0° C. After the addition, the reaction mixture was stirred for 1 h at 0° C. and then allowed to warm to room temperature. After 2 h at room temperature, TLC analysis indicated the absence of starting material (4:1 hexane:ether, phosphomolybdic acid spray, as analysis by UV fluorescence was misleading). The reaction mixture was poured into a ice (2000 g) and concentrated sulfuric acid (50 mL) and was stirred for overnight. The precipitated solids were collected by filtration and the filtrate was extracted with ether (2×200 mL). The combined extracts were washed with brine solution and dried over $MgSO_4$. Filtration of the drying agent and concentration of the solution gave the crude aldehyde which was combined with the above solid to afford 71.31 g (93%) of light yellow solid suitable for use in the next step.

b. Preparation of 2-chloro-6-methylbenzoic acid.

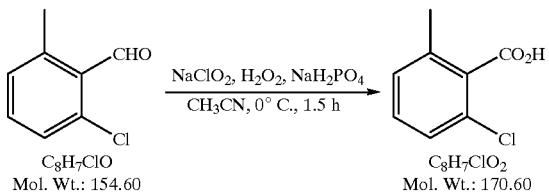

A 1000 mL, three-necked, round bottomed flask equipped with a magnetic stirrer, thermometer, additional funnel, and argon inlet was charged with 71.31 g (461 mmol, crude obtained from the above experiment) of 2-chloro-6-methylbenzaldehyde and 750 mL of acetonitrile. To this suspension, a solution of monobasic sodium phosphate (115 mmol, 15.9 g, 0.25 eq.) in water 240 mL) was added followed by hydrogen peroxide (50 mL, 30%) at room temperature. Then, a solution of sodium chlorite (73.5 g, 811 mmol, 1.76 eq.) in water (700 mL) was added dropwise at 0° C. while maintaining the temperature below 3° C. After addition, the yellow suspension was stirred for 15 h at 0° C. to room temperature at which time TLC analysis of the mixture indicated the absence of aldehyde. Then, a solution of sodium bisulfite (73 g, 701 mmol, 1.52 eq.) in water (200 mL) was added dropwise at 0° C. until the yellow color disappear (KI-paper positive). Cooling is essential to control the exothermic reaction. The solvent was removed under vacuum to afford a white solid. The solid was collected by filtration and the filtrate was extracted with ether (200 mL). The above solid also dissolved in this ether solution and was washed with 10% NaOH solution (2×200 mL). The basic aqueous solution was neutralized with 10% HCl to pH ~1. The precipitated white solid was collected by filtration and dried at air to afford 54.88 g (65%, overall in two steps) of 2-chloro-6-methyl benzoic acid as a white solid.

Example 146

Preparation of 4-[(2,6-dichlorophenyl)carbonyl]amino]-L-phenylalanine methyl ester a. Preparation of 4-nitro-N-[(1,1-dimethylethoxy)carbonyl]-L-phenylalanine methyl ester.

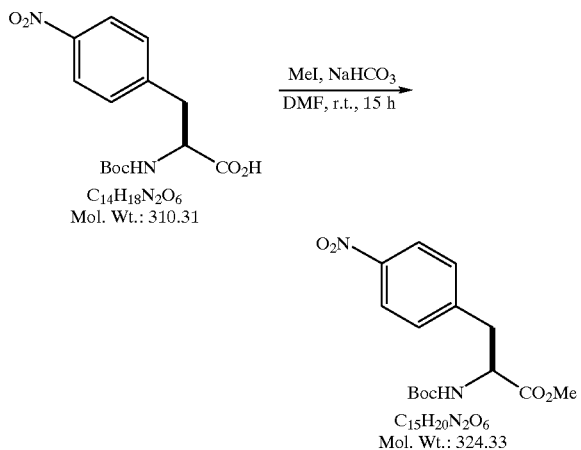

To a suspension of 4-nitro-N-[(1,1-dimethylethoxy)carbonyl]-L-phenylalanine (226.2 mmol, 70.2 g) and sodium carbonate (1.13 mmol, 95 g) in DMF (500 mL) was added methyl iodide (1.13 mmol, 70.4 mL) at room temperature. The suspension was stirred for 15 h at room temperature at this time TLC analysis of the mixture indicated the absence of starting acid and the excess methyl iodide and some DMF were removed under high vacuum. The mixture was poured into water (2 L) and stirred at room temperature as a precipitate formed slowly over weekend. The precipitated solids were collected by filtration and washed with water (2 L). After air and vacuum drying, 72 g (98%) of of 4-nitro-N-[(1,1-dimethylethoxy)carbonyl]-L-phenylalanine methyl ester was isolated as a light yellow solid. mp 95–96° C. $^1$H NMR, DMSO-$d_6$ (400 MHz) δ8.16 (d, 2H, J=20 Hz), 7.53 (d, 2H, J=20 Hz), 7.39 (d, 1H, J=22 Hz), 4.26–4.28 (m, 1H), 3.6 (s, 3H), 2.96–3.19 (m, 2H), 1.25 (s, 9H), $^{13}$C NMR, $CDCl_3$ (100 Mhz) d 172.04, 155.29, 146.27, 145.96, 130.48, 123.18, 78.36, 54.44, 51.9, 36.1, 27.99. HR MS: Obs. mass. 325.1404. Calcd. mass, 325.1400 (M+H).

b. Preparation of 4-amino-N-[(1,1-dimethylethoxy)carbonyl]-L-phenylalanine methyl ester.

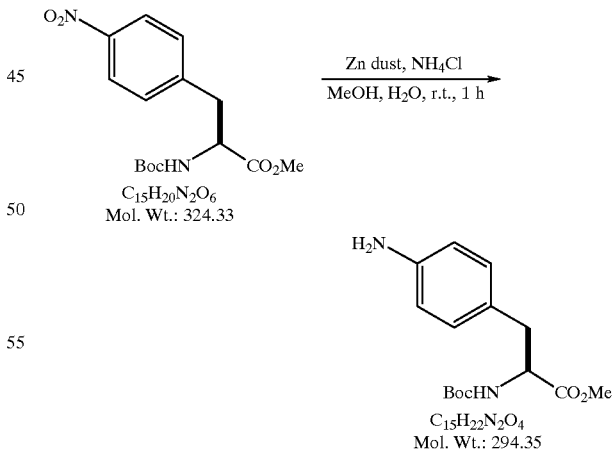

To a mixture of 4-nitro-N-[(1,1-dimethylethoxy)carbonyl]-L-phenylalanine methyl ester (222 mmol, 72 g), zinc dust (~325 mesh, 2.2 mol, 145.2 g, 10 equiv.) and ammonium chloride (3.3 mol, 178.1 g, 15 equiv.) was added methanol (1 L) and water (500 mL) at room temperature. After addition of water, the reaction mixture was exothermic and the temperature raised to 45 to 50° C. The suspension was stirred for 1 h at room temperature at which time TLC analysis of the mixture indicated the absence of starting material and the reaction mixture was filtered through the celite, washing the filtered cake with methanol (1 L) and water (500 mL). Concentration to remove the methanol and some water resulted in formation of a white solid which was collected by filtration and washed with water. After air drying, 65.5 g (quant) of a white solid, mp 86–89° C. was obtained. $^1$H NMR, DMSO-$d_6$ (400 MHz) δ6.9 (d, 2H, J=20 Hz), 6.62 (d, 2H, J=20 Hz), 7.39 (d, 1H, J=22 Hz), 4.26–4.28 (m, 1H), 3.68 (s, 3H), 2.96–3.19 (m, 2H), 1.25 (s, 9H). HR MS: Obs. mass, 284.1614. Calcd. mass, 294.1621).

c. Preparation of 4-[(2,6-dichlorophenylcarbonyl]amino]-N-[(1,1-dimethylethoxy)carbonyl]-L-phenylalanine methyl ester.

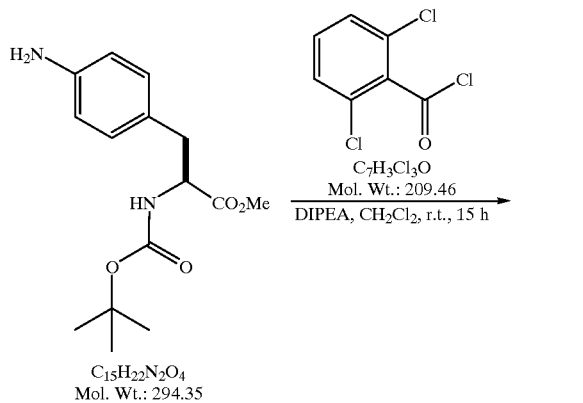

To a solution of 4-amino-N-[(1,1-dimethylethoxy)carbonyl]-L-phenylalanine methyl ester (127.6 mmol, 37.57 g) and 2,6-dichlorobenzoyl chloride (140.6 mmol, 29.45 g) in dichloromethane (350 mL) was added diisopropylethylamine (192 mmol, 33.4 mL) at room temperature. The brown solution was stirred for 15 h at room temperature to afford a white suspension. At this time, TLC analysis of the mixture indicated the absence of starting material. The solids were collected by filtration and were washed with dichloromethane (150 mL) and air dried to obtain 52.75 g (88.4%) of a white solid, mp 148–151° C. $^1$H NMR, DMSO-$d_6$ (400 MHz) δ10.68 (s, 1H), 7.47–7.6 (m, 5H), 7.2–7.29 (m, 3H), 4.12–4.17 (m, 1H), 3.62 (s, 3H), 2.79–2.99 (m, 2H), 1.33 (s, 9H). $^{13}$C NMR, CDCl$_3$ (100 Mhz) d 172.49, 161.82, 155.37, 136.99, 136.36, 131.28, 131.16, 129.48, 128.19, 119.31, 78.27, 55.3, 51.76, 35.9, 27.77. HR MS: Obs. mass, 466.1069. Calcd. mass, 466.1062 (M+H).

d. Preparation of 4-[(2,6-Dichlorophenylcarbonyl)amino]-L-phenylalanine methyl ester hydrochloride salt.

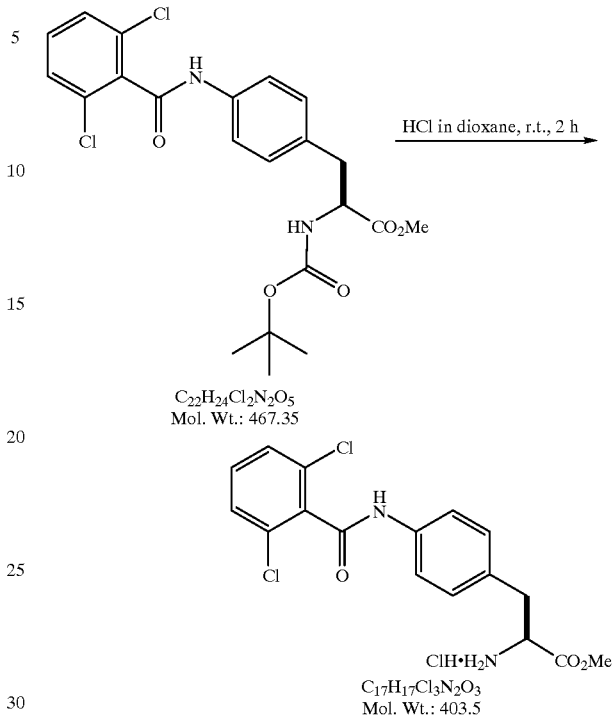

4-[(2,6-Dichlorophenylcarbonyl)amino]-N-[(1,1-dimethylethoxy)carbonyl]-L-phenylalanine methyl ester (92.97 mmol, 43.45 g) in dioxane (90 mL) was treated with 166 mL of 4 N hydrochlonic acid in dioxane at room temperature. After 5 minutes, the solids went into solution and the mixture was stirred for 2 h. Some of the dioxane was removed under vacuum to afford a yellow syrup and 250 mL of ethyl ether was added. A gum was formed which was dissolved in THF (100 mL) and methanol (100 mL). The solvent was removed under vacuum to obtain 43.7 g (100%) of the hydrochloride salt as a white solid. $^1$H NMR, DMSO-$d_6$ (400 MHz) δ10.81 (s, 1H), 7.76 (d, 2H, J=22 Hz), 7.58 (d, 2H J=18 Hz), 7.51 (t, 1H, J=15 Hz), 7.24 (d, 2H, J=22 Hz),4.23–4.26 (m, 1H), 3.56 (s, 3H), 3.14–3.17 (m, 2H). $^{13}$C NMR, CDCl$_3$ (100 Mhz) d 169.03, 161.72, 137.56, 136.11, 131.19, 130.95, 129.93, 129.79, 128.06, 119.46, 53.17, 52.6, 35.13. HR MS: Obs. mass. 367.0611. Calcd. mass, 367.0616 (M+).

Example 147

Preparation of 4-[[(2,6-dichlorophenyl)carbonyl]amino]-N-[(2-chloro-6-methylphenyl)carbonyl]-L-phenylalanine methyl ester

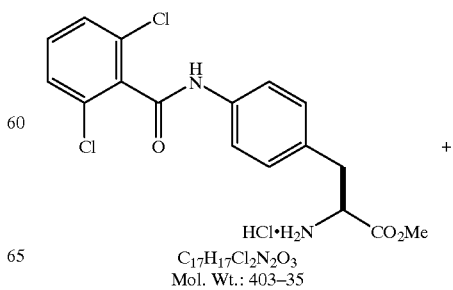

130

Example 148

Preparation of 4-[[(2,6-dichlorophenyl)carbonyl]amino]-N-[(2-chloro-6-methylphenyl)carbonyl]-L-phenylalanine

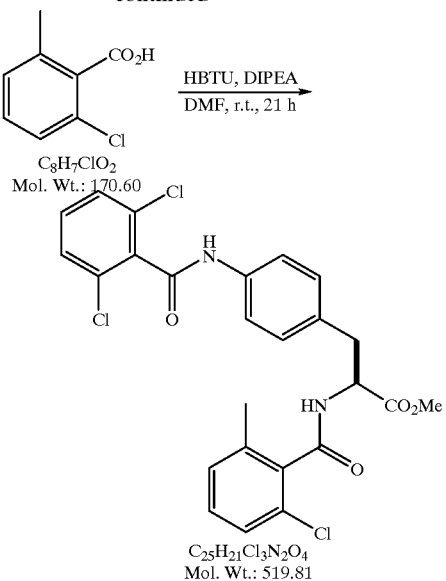

To a solution of 4-[[(2,6-dichlorophenyl)carbonyl]amino]-L-phenylalanine methyl ester hydrochloride salt (272.5 mmol, 110 g) and 2-chloro-6-methyl benzoic acid (276 mmol, 47.15 g) in DMF (600 mL) were added HBTU (276 mmol, 105 g) and diisopropylethylamine (1.24 mol, 119 mL) at room temperature. The clear solution was stirred 48 h at room temperature at which time TLC analysis of the reaction mixture indicated the absence of the starting material. The reaction mixture was poured slowly into 5 L of water which contained some ice to lower the temperature. The white precipitated solid was allowed settle and the solid was collected by filtration. The solid cake was washed with water (1 L) and hexane (1 L) and air dried to obtain 150 g of a crude product. This solid product was dissolved in hot acetonitrile (1 L) and cooled in the refrigerator. The solid was collected by filtration and washed with hexane (500 mL) and air dried to obtain 101.1 g. The mother liquor was concentrated and the residue was purified by silica gel column chromatography eluting with dichloromethane and ethyl acetate (15:1) to obtain another 17.07 g (total=118.17 g, 83%). mp 244–245° C. $^1$H NMR, DMSO-$d_6$ (400 MHz) δ10.66 (s, 1H), 8.83 (d, 1H, J=19 Hz), 7.47–7.6 (m, 5H), 7.15–7.29 (m, 5H), 4.58–4.68 (m, 1H), 3.65 (s, 3H), 3.12 (dd, 1H, J=17, 13 Hz), 2.87 (dd, 1H, J=17, 11 Hz), 2.09 (s, 3H). HR MS: Obs. mass. 518.0652. Calcd. mass, 518.0641.

To a suspension of 4-[[(2,6-dichlorophenyl)carbonyl]amino]-N-[(2-chloro-6-methylphenyl)carbonyl]-L-phenylalanine methyl ester (166 mmol, 86.2 g) in ethanol (350 mL) was added aqueous 1.0 N sodium hydroxide (250 mL) at room temperature. The mixture was heated to 40–45° C. and the resulting clear solution was stirred for 3–4 h. Then, the mixture was cooled to room temperature and the ethanol was removed on a rotary evaporator. The residue was diluted with 100 mL of water. The neutral impurities was extracted into ether (2×100 mL) and the basic aqueous layer was neutralized with 1 N HCl. The precipitated solid was collected by filtration and the solid cake was washed with water (1 L) and dried at air over weekend. The crude solid was dissolved in hot acetontile (2 L) and the resulting solution was stored in the refrigerator for 15 h. The white crystalline solids were collected by filtration and washed with cold acetonitrile (100 mL). After air drying, 79.76 g (95%) of a white solid, mp 212–215° C. was obtained. $^1$H NMR, DMSO-d$_6$ (400 MHz) δ10.66 (s, 1H), 8.85 (d, 1H, J=19 Hz), 7.47–7.6 (m, 5H), 7.15–7.29 (m, 5H), 4.58–4.68 (m, 1H), 3.12 (dd, 1H, J=17, 13 Hz), 2.87 (dd, 1H, J=17, 11 Hz), 2.09 (s, 3H). HR MS: Obs. mass, 505.0483. Calcd. mass. 505.0488 (M+).

Example 149

Preparation of 2,6-Dimethyl-4-trifluoromethyl-3-pyridinecarboxylic acid

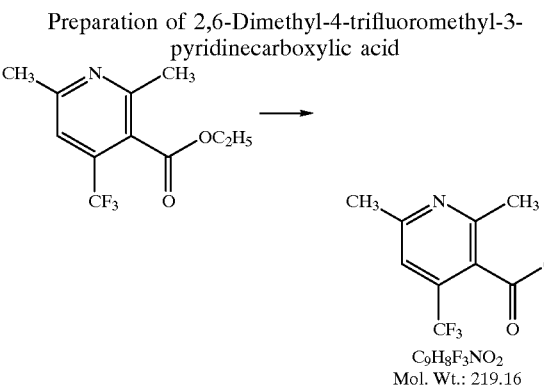

A solution of 2,6-dimethyl-4-trifluoromethyl-3-pyridinecarboxylic acid ethyl ester in 40 mL of THF and 10 mL of 1 N sodium hydroxide solution was heated to reflux for 48 h. TLC of the mixture (3:7 methanol:dichloromethane) indicated that starting material was consumed. The mixture was acidified with acetic acid (5 mL) and evaporated to dryness. The residue was triturated with THF and the solution was concentrated to give 0.7 g of material containing some THF and acetic acid as indicated by NMR. This material was combined with the product of a similar experiment and was chromatographed on 90 g of silica gel, eluting with (3:7) methanol:dichloromethane to give 1.05 g of a solid. This material was diluted with toluene (6 mL) and evaporated several times to remove most of the acetic acid to afford after drying under high vacuum, 0.9 g of a white foam. LR-ES-MS (C9H6F3NO2): 218 (M−H).

Example 150

Preparation of N-[(2-chloro-6-methylphenyl) carbonyl]-4-[(2,6-dimethyl-4-trifluoromethyl-3-pyridinyl)carbonyl]amino]-L-phenylalanine

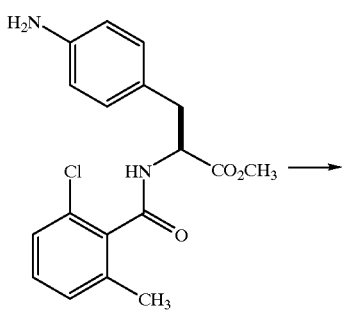

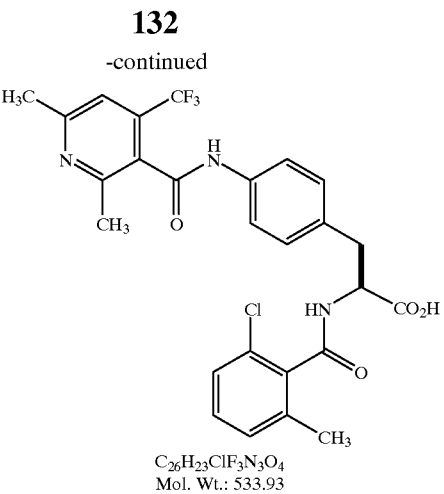

a. To a solution of 2,6-dimethyl-4-trifluoromethylpyridine carboxylic acid (102 mg, 0.6 mmol) in dichloromethane (3mL) was added a drop of DMF and oxalyl chloride (0.78 mmol, 99 mg) at 0° C. (ice bath). The solution was stirred at this temperature for 30 min, warmed to room temperature and stirred for an additional 1 h. Then, the solvent and excess oxalyl chloride was removed under vacuum and the residue was dried under high vacuum. To this 4-amino-N-[(2-chloro-6-methylphenyl)carbonyl]-L-phenylalanine methyl ester (0.5 mmol, 212 mg) was added and the mixture was dissolved in dichloromethane (5 mL). To this clear solution was added DIPEA (2.0 mmol, 0.258 g) at room temperature. The mixture was stirred for 15 h at which time TLC analysis of the mixture indicated the absence of starting material. The mixture was diluted with dichloromethane (20 mL) and water (100 mL). The two layers were separated and the organic layer was washed with saturated sodium bicarbonate solution (20 mL), brine solution (30 mL) and was dried over anhydrous magnesium sulfate. Filtration of the drying agent and removal of the solvent gave a crude product which was used directly in the next step.

Examples 151–155

The N-[(2-chloro-6-methylphenyl)carbonyl]-4-[(heteroaryl)carbonyl]amino]-L-phenylalanine derivatives listed below were prepared by treatment of equimolar amounts of 4-amino-N-[(2-chloro-6-methylphenyl) carbonyl]-L-phenylalanine methyl ester and the appropriate heteroaromatic carboxylic acids using the coupling procedure described in example 109 and the ester hydrolysis procedure described in example 13.

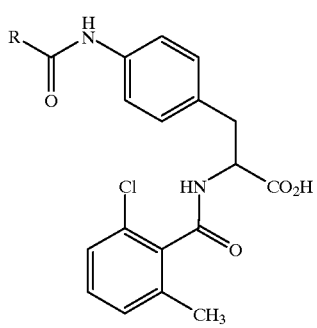

| Example | R | Yield % | Formula | LRMS (M + H) Obs | IC50 nM |
|---|---|---|---|---|---|
| 151 | (4-CF3, 5-methyl pyrimidine) | 17 | C23H18N4O4ClF3 | 507 | |
| 152 | (4,5-dimethyl-2-isopropyl thiazoline) | 38 | C25H26N3O4ClS | 500 | 967 |
| 153 | (3,4,5-trimethyl isoxazole) | 49 | C23H22N3O5Cl | 456 | 975 |
| 154 | (4,5-dimethyl-2-phenyl triazole) | 74 | C27H24N5O4Cl | 518 | 2,474 |
| 155 | (2,6-dimethyl-7-methyl pyrazolopyrimidine) | 7.5 | C26H24N5O4Cl | 506 | 644 |

Examples 156–160

The 4-[[(2,6-Dichlorophenyl)carbonyl]amino]-N-[(heteroaryl)carbonyl]-L-phenylalanine derivatives listed below were prepared by coupling of 4-[[(2,6-dichlorophenyl)carbonyl]amino]-L-phenylalanine methyl ester and the appropriate heteroaromatic carboxylic acid using the general procedure described in example 3, followed by ester hydrolysis using the general procedure described in example 13.

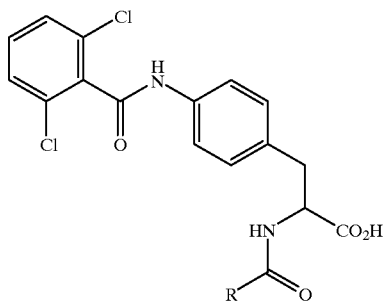

| Example | R | Yield % | Formula | LRMS (M + H) Obs | IC50 nM |
|---|---|---|---|---|---|
| 156 | 4-CF3-2,6-dimethylpyridin-3-yl | 80 | C25H20OCl2F3N3O4 | 554 | 114 |
| 157 | 2-isopropyl-4,5-dimethylthiazol-2-yl | 25 | C24H23Cl2N3O4S | 520 | |
| 158 | 3,4,5-trimethylisoxazol-4-yl | 75 | C22H19Cl2N3O5 | 476 | 946 |
| 159 | 4,5-dimethyl-2-phenyl-2H-1,2,3-triazol-4-yl | 63 | C26H21Cl2N5O4 | 538 | 988 |
| 160 | 2,6,7-trimethylpyrazolo[1,5-a]pyrimidin-3-yl | 47 | C25H21Cl2N5O4 | 526 | |

Example 161

4-[[(2,6-Dichlorophenyl)carbonyl]amino]-N-[(1-naphthyl)carbonyl]-L-phenylalanine methyl ester was prepared in 77% yield from 4-[[(2,6-dichlorophenyl)carbonyl]amino]-L-phenylalanine methyl ester and 1-naphthoic acid using the general procedure described in example 3. HR MS: Obs. mass, 521.1024. Calcd. mass. 521.1053 (M+H).

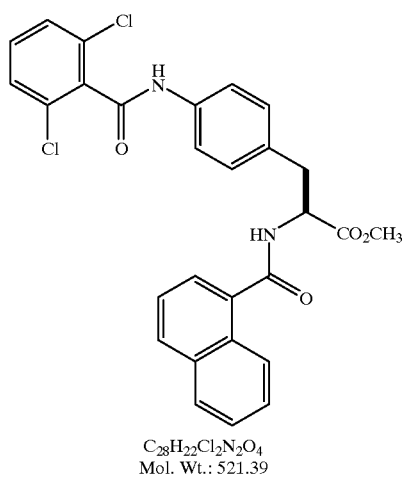

C<sub>28</sub>H<sub>22</sub>Cl<sub>2</sub>N<sub>2</sub>O<sub>4</sub>
Mol. Wt.: 521.39

Example 162

N-[(2-Acetyl-6-methylphenyl)carbonyl]-4-[[(2,6-dichlorophenyl)carbonyl]amino]-L-phenylalanine was prepared in 38% yield from 4-[[(2,6-dichlorophenyl)carbonyl]amino]-L-phenylalanine methyl ester and 2-acetyl-6-methylbenzoic acid using the general procedure described in example 3. HR MS: Obs. mass, 547.0579. Calcd. mass, 547.0594 (M+Na).

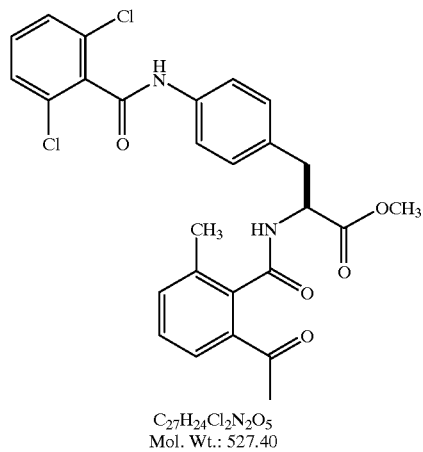

C<sub>27</sub>H<sub>24</sub>Cl<sub>2</sub>N<sub>2</sub>O<sub>5</sub>
Mol. Wt.: 527.40

Example 163

4-[[(2,6-Dichlorophenyl)carbonyl]amino]-N-[[2-(1,1-dimethylethyl)phenyl]carbonyl]-L-phenylalanine methyl ester was prepared from 4-[[(2,6-dichlorophenyl)carbonyl]amino]-L-phenylalanine methyl ester and 2-(1,1-dimethylethyl)benzoic acid using the general procedure described in example 3. HR MS: Obs. mass. 527.1523. Calcd. mass. 527.1573 (M+H).

C<sub>28</sub>H<sub>28</sub>Cl<sub>2</sub>N<sub>2</sub>O<sub>4</sub>
Mol. Wt.: 527.44

Example 164

2,6-Bis-(1-methylethyl)benzoic acid was prepared in two steps from 2,6-bis(1-methylethyl)phenol using the two step general procedure described in example 105. HR MS: Obs. mass, 206.0325. Calcd. mass, 206.0342 (M+).

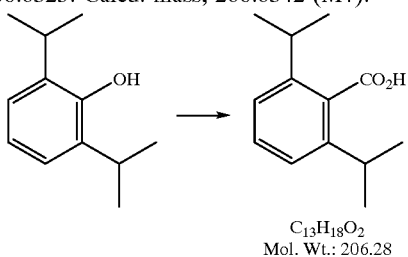

C<sub>13</sub>H<sub>18</sub>O<sub>2</sub>
Mol. Wt.: 206.28

Example 165

4-[[(2,6-Dichlorophenyl)carbonyl]amino]-N-[[2,6-bis-(1-methylethyl)phenyl]carbonyl]-L-phenylalanine methyl ester was prepared from 4-[[(2,6-dichlorophenyl)carbonyl]amino]-L-phenylalanine methyl ester and 2,6-bis-(1-methylethyl)benzoic acid using the general procedure described in example 3. LR MS: 555 (M+).

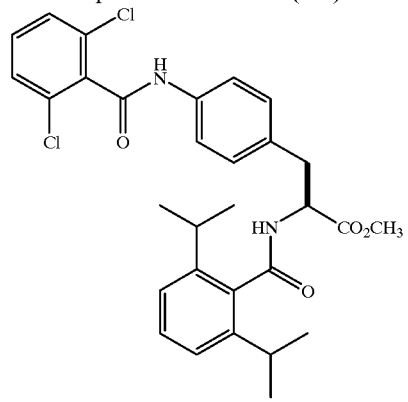

C<sub>30</sub>H<sub>32</sub>Cl<sub>2</sub>N<sub>2</sub>O<sub>4</sub>
Mol. Wt.: 555.49

Example 166

4-[[(2,6-Dichlorophenyl)carbonyl]amino]-N-[(2-methoxyphenyl)carbonyl]-L-phenylalanine methyl ester was prepared from 4-[[(2,6-dichlorophenyl)carbonyl]amino]-L-phenylalanine methyl ester and 2-methoxybenzoic acid using the general procedure described in example 3. HR MS: Obs. mass. 501.0984. Calcd. mass. 501.0984 (M+H).

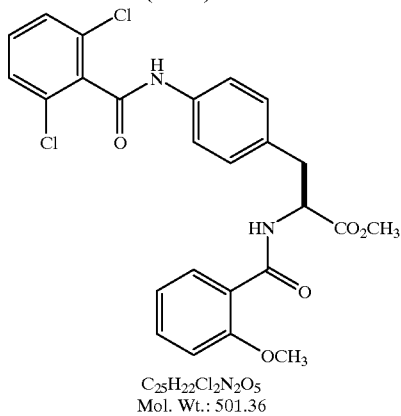

C25H22Cl2N2O5
Mol. Wt.: 501.36

Example 167

4-[[(2,6-Dichlorophenyl)carbonyl]amino]-N-[(2-chloro-4-methylsulfonylphenyl)carbonyl]-L-phenylalanine methyl ester was prepared in 73% yield from 4-[[(2,6-dichlorophenyl)carbonyl]amino]-L-phenylalanine methyl ester and 2-chloro-4-methylsulfonylbenzoic acid using the general procedure described in example 3. HR MS: Obs. mass, 583.0263. Calcd. mass, 583.0264 (M+H).

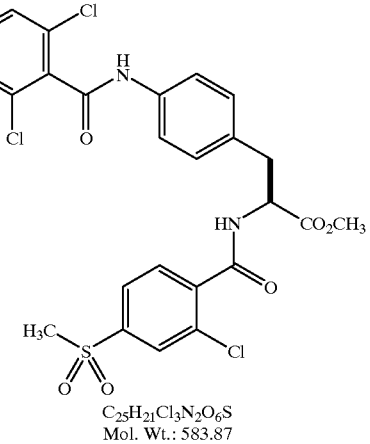

C25H21Cl3N2O6S
Mol. Wt.: 583.87

Example 168

N-[(2,6-Dichlorophenyl)carbonyl]-4-[[(2-chloro-6-methylphenyl)carbonyl]amino]-L-phenylalanine methyl ester was prepared from 4-[[(2-chloro-6-methylphenyl)carbonyl]amino]-L-phenylalanine methyl ester and 2,6-dichlorobenzoic acid using the general procedure described in example 3.

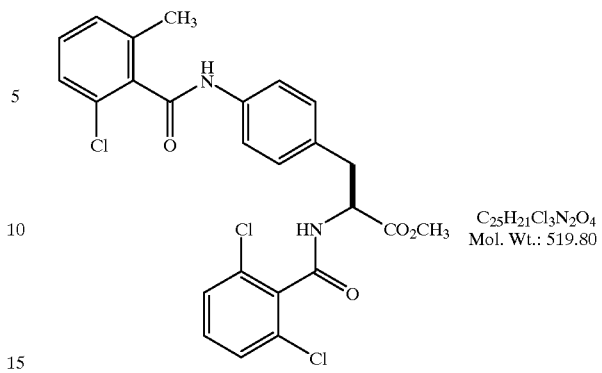

C25H21Cl3N2O4
Mol. Wt.: 519.80

Example 169

N-[(2,6-Dichlorophenyl)carbonyl]-4-[[(2-chloro-6-methylphenyl)carbonyl]amino]-L-phenylalanine was prepared by hydrolysis of N-[(2,6-dichlorophenyl)carbonyl]-4-[[(2-chloro-6-methylphenyl)carbonyl]amino]-L-phenylalanine methyl ester using the general procedure described in example 13.

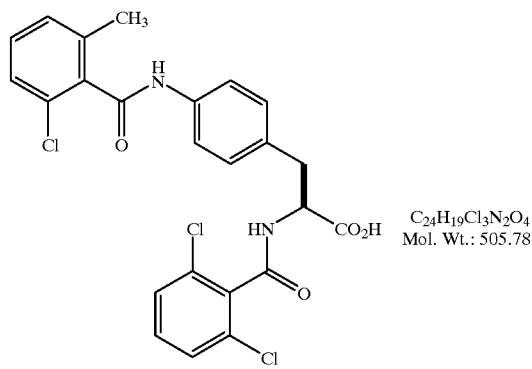

C24H19Cl3N2O4
Mol. Wt.: 505.78

Example 170

Preparation of 4-[(2S,4R)-3-Acetyl-2-phenyl-4-(phenylmethyl)-5-oxo-1-imidazolinyl]-N-[(2-chloro-6-methylphenyl)carbonyl]-L-phenylalanine and 4-[(2R,4R)-3-acetyl-2-phenyl-4-(phenylmethyl)-5-oxo-1-imidazolinyl]-N-[(2-chloro-6-methylphenyl)carbonyl]-L-phenylalanine

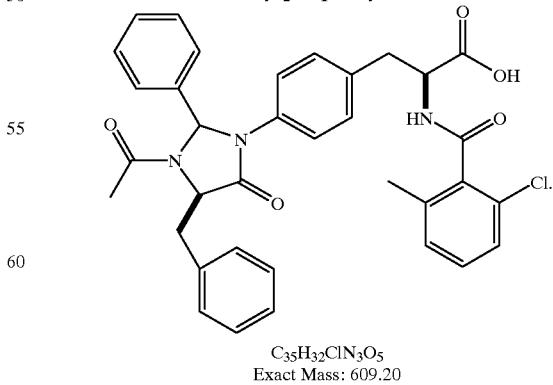

C35H32ClN3O5
Exact Mass: 609.20
Mol. Wt.: 610.10 a. Synthesis of N-[(1,1-dimethylethoxy)carbonyl]-4-[[(2R)-2-amino-1-oxo-3-phenylpropyl]amino]-L-phenylalanine methyl ester

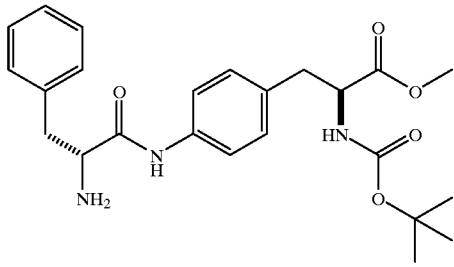

C$_{24}$H$_{31}$N$_3$O$_5$
Mol. Wt.: 441.52

To a solution of 4-amino-N-[(1,1-dimethylethoxy)carbonyl]-L-phenylalanine methyl ester (5.09 g, 17 mmol) in DMF (60 mL) was added Fmoc-D-Phenylalanine (8.70 g, 22.5 mmol), DIPEA (12 mL, 69 mmol) and HBTU (8.50 g, 22.5 mmol). The mixture was then stirred at room temperature for 4 h. The reaction mixture was diluted with water (150 mL) and the light yellow solid which precipitated was collected by filtration. This solid was then redissolved in 60 mL of acetone and the solution was treated with 100 mL of water. The solid was collected by filtration and was washed with 1N HCl, H$_2$O. After drying at 60° C. under vacuum overnight, a light yellow solid was obtained (13.2 g). A portion of this solid (2.51 g, 3.78 mmol) was dissolved in 15 mL of DMF and to the solution was added 1.5 mL of piperidine. The above solution was stirred at room temperature for 45 min. After removal of the solvent, the residue was recrystallized from ethyl acetate-hexane to give N-[(1,1-dimethylethoxy)carbonyl]-4-[[(2R)-2-amino-1-oxo-3-phenylpropyl]amino]-L-phenylalanine methyl ester (1.36 g, 3.0 mmol )in 81.5% yield. LR MS 442 (M+H).

b. Synthesis of 4-(3-acetyl-5-oxo-2-phenyl-4-phenylmethyl-1-imidazolidinyl)-N-[(1,1-dimethylethoxy)carbonyl]-L-phenylalanine methyl ester

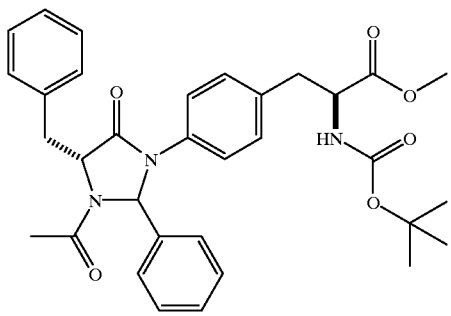

A solution of above amine (1.48, 3.35 mmol) and benzaldehyde (376 μl, 3.7 mmol) in dichloromethane (10 mL) and methyl orthoformate (10 mL) was stirred at room temperature for 3 days. The reaction flask was then warmed to 90° C. and acetic anhydride (neat, 1.8 mL) was added. The resulting mixture was stirred at 110° C. for 4 hr. The solvent was then evaporated and crude product was purified by silica gel chromatography (ethyl acetate:hexane=1:1) to give 4-(3-acetyl-5-oxo-2-phenyl-4-phenylmethyl-1-imidazolidinyl)-N-[(1,1-dimethylethoxy)carbonyl]-L-phenylalanine methyl ester diatereomer 1 (417 mg) and diastereomer 2 (1.25 g). These compounds are diastereomeric at the 2-position of the imidazolidinone ring. Both diastereomers gave LR MS (C33H37N3O6):572 (M+H).

c. Preparation of 4-[(2S,4R)-3-Acetyl-2-phenyl-4-(phenylmethyl)-5-oxo-1-imidazolinyl]-N-[(2-chloro-6-methylphenyl)carbonyl]-L-phenylalanine methyl ester.

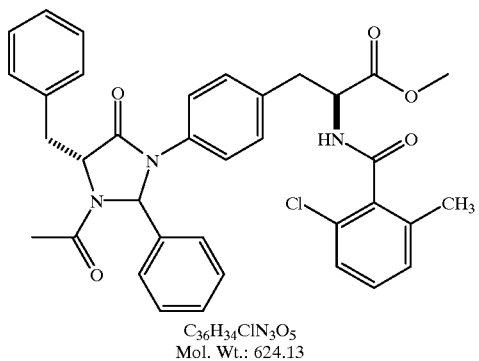

C$_{36}$H$_{34}$ClN$_3$O$_5$
Mol. Wt.: 624.13

4-(3-acetyl-5-oxo-2-phenyl-4-phenylmethyl-1-imidazolidinyl)-N-[(1,1-dimethylethoxy)carbonyl]-L-phenylalanine methyl ester (Diastereomer 1) (415 mg, 0.7 mmol) was treated with 10 mL of 4N HCl in dioxane at room temperature for 2 hr. After removal of solvent, the residue was dried overnight under vacuum. The residue (241 mg, 0.471 mmol) was dissolved in DMF (4 mL) and was treated with 2-chloro-6methylbenzoic acid (105 mg, 0.617 mmol), HBTU (234 mg, 0.617 mmol) and DIEA (246 μL, 1.42 mmol) at room temperature for 4 hr. The mixture was diluted with 30 mL of ethyl acetate, the mixture was washed with 1N HCl, water and brine (8 mL each), After it was dried over MgSO4, the solvent was removed and the residue was filtered through silica gel eluting with ethyl acetate:hexane (4:1 ) to give 4-(3-acetyl-5-oxo-2-phenyl-4-phenylmethyl-1-imidazolidinyl)-N-[(2-chloro-6-methylphenyl)carbonyl]-L-phenylalanine methyl ester diastereomer 1.

d. Preparation of 4-(3-acetyl-5-oxo-2-phenyl-4-phenylmethyl-1-imidazolidinyl)-N-[(2-chloro-6-methylphenyl)carbonyl]-L-phenylalanine diastereomer 1

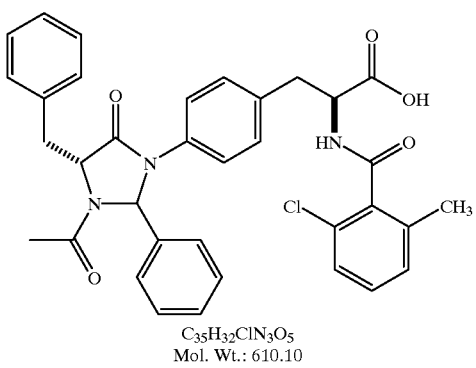

C35H32ClN3O5
Mol. Wt.: 610.10

4-(3-acetyl-5-oxo-2-phenyl-4-phenylmethyl-1-imidazolidinyl)-N-[(2-chloro-6-methylphenyl)carbonyl]-L-phenylalanine methyl ester diastereomer 1 (90 mg, 0.128 mmol) in EtOH (3 mL) was treated with NaOH (1N, 0.3 mL) at room temperature for 30 min. The resulting solution was acidified with 1 drop of HOAc and was purified by HPLC (C-18, linear gradient from 5% acetonitrile to 95% in water over 30 min) to give a white solid after lyophization. MS: obs. mass. 609.9 (M+H).

Example 171

4-[(2S,4R)-3-Acetyl-2-phenyl-4-(3-pyridinylmethyl)-5-oxo-1-imidazolinyl]-N-[(2-chloro-6-methylphenyl)carbonyl]-L-phenylalanine and 4-[(2R,4R)-3-acetyl-2-phenyl-4-(3-pyridinylmethyl)-5-oxo-1-imidazolinyl]-N-[(2-chloro-6-methylphenyl)carbonyl]-L-phenylalanine was prepared from 4-amino-N-[(2-chloro-6-methylphenyl)carbonyl]-L-phenylalanine methyl ester and Fmoc-D-3-pyridinylalanine using the general procedure described in example 170. The two diastereomers at the 2-position of the imidazoline ring were not readily separated by C-18 RP-HPLC and the compounds were assayed as a mixture. HR MS: obs. 611.2070. calc. 611.2061 (M+H).

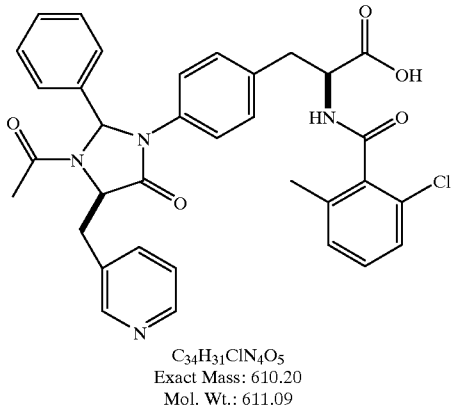

C34H31ClN4O5
Exact Mass: 610.20
Mol. Wt.: 611.09

Example 172

4-[[(2,6-Dichlorophenyl)carbonyl]amino]-N-[(2-chloro4-hydroxyphenyl)carbonyl]-L-phenylalanine methyl ester was prepared in 35% yield from 4-[[(2,6-dichlorophenyl) carbonyl]amino]-L-phenylalanine methyl ester and 2-chloro-4-hydroxybenzoic acid using the general procedure described in example 3. HR MS: Obs. mass, 521.0433. Calcd. mass, 521.0438 (M+H).

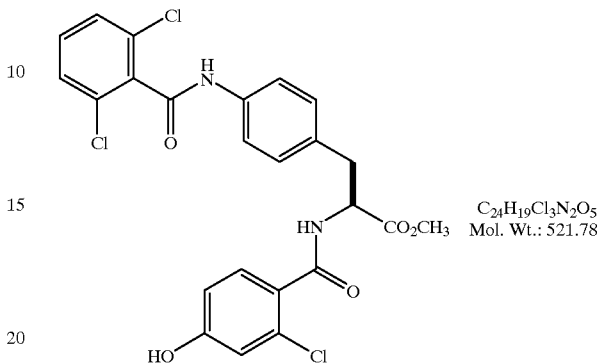

C24H19Cl3N2O5
Mol. Wt.: 521.78

Example 173

4-[[(2,6-Dichlorophenyl)carbonyl]amino]-N-[(2-methylsulfonylphenyl)carbonyl]-L-phenylalanine methyl ester was prepared in 99% yield from 4-[[(2,6-dichlorophenyl)carbonyl]amino]-L-phenylalanine methyl ester and 2-methylsulfonylbenzoic acid using the general procedure described in example, LR MS: 548 (M+).

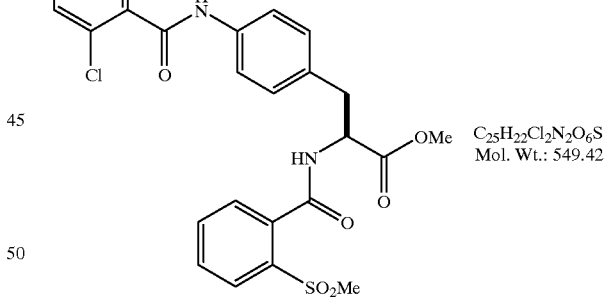

C25H22Cl2N2O6S
Mol. Wt.: 549.42

Example 174

4-[[(2,6-Dichlorophenyl)carbonyl]amino]-N-[(2-(1-methyl)ethyl-6-methylphenyl)carbonyl]-L-phenylalanine methyl ester was prepared in 35% yield from 4-[[(2,6-dichlorophenyl)carbonyl]amino]-L-phenylalanine methyl ester and 2-(1-methyl)ethyl-6-methylbenzoic acid using the general procedure described in example 3. HR MS: Obs. mass, 526.1417. Calcd. mass, 526.1426 (M+).

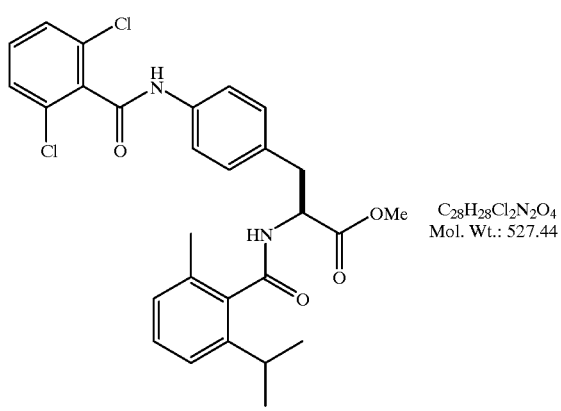

Example 175

4-[[(2,6-Dichlorophenyl)carbonyl]amino]-N-[(2-bromo-6-methylphenyl)carbonyl]-L-phenylalanine methyl ester was prepared in 64% yield from 4-[[(2,6-dichlorophenyl)carbonyl]amino]-L-phenylalanine methyl ester and 2-bromo-6-methylbenzoic acid using the general procedure described in example 3. HR MS: Obs. mass, 563.0138. Calcd. mass, 563.0140 (M+H).

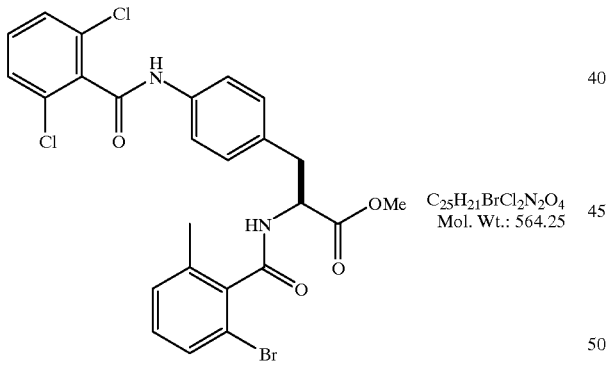

Example 176

4-[[(2,6-Dichlorophenyl)carbonyl]amino]-N-[(2-ethyl-6-methylphenyl)carbonyl]-L-phenylalanine methyl ester was prepared in 46% yield from 4-[[(2,6-dichlorophenyl)carbonyl]amino]-L-phenylalanine methyl ester and 2-ethyl-6-methylbenzoic acid using the general procedure described in example 3. HR MS: Obs. mass, 513.1359. Calcd. mass, 513.1348 (M+H).

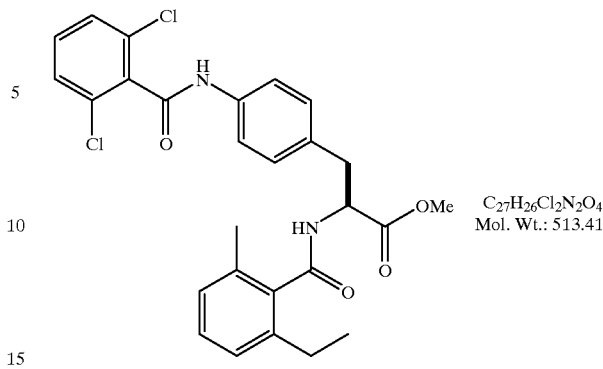

Example 177

N-[(2,6-Dichlorophenyl)carbonyl]-4-[(2,4-dimethyl-3-pyridinyl)carbonyl]amino]-L-phenylalanine was prepared from 4-[(2,4-dimethyl-3-pyridyl)carbonyl]amino]-L-phenylalanine methyl ester hydrochloride and 2,6-dichloroboenzoic acid using the general method described in example 107. MS (M+H) 486 (2Cl).

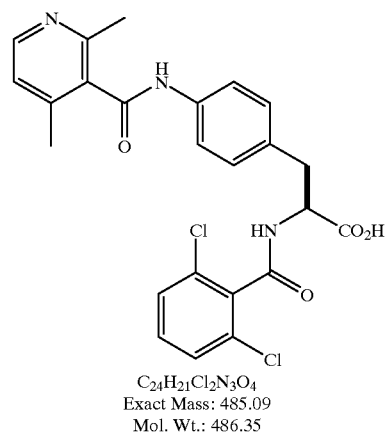

Example 178

Preparation of 4-[[(2,6-dichlorophenyl)carbonyl]amino]-N-[(2-chloro-6-methylphenyl)carbonyl]-L-phenylalanine sodium salt

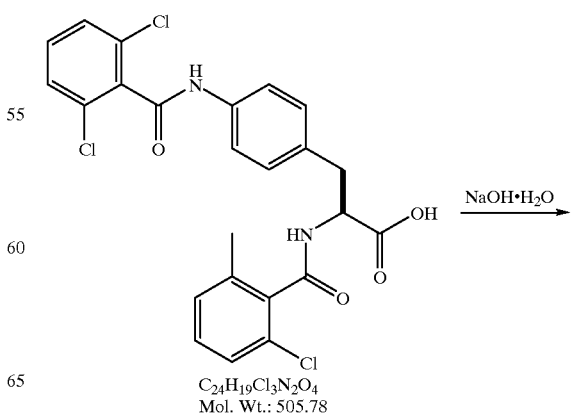

-continued

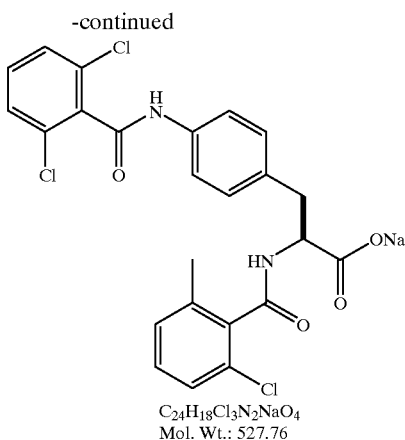

C24H18Cl3N2NaO4
Mol. Wt.: 527.76

A suspension of 4-[[(2,6-dichlorophenyl)carbonyl]amino]-N-[(2-chloro-6-methylphenyl)carbonyl]-L-phenylalanine (127.13 mmol, 64.3 g) in water (500 mL) was titrated with aqueous 1.0 N sodium hydroxide (120 mL) at room temperature until the pH of the solution became neutral. In order to effect complete dissolution, the mixture was warmed to 40–45° C. during the course of the titration. Some of the water was removed to a approximate volume of 300–350 mL under vacuum and the clear solution was lyopholized under high vacuum for 2 days to obtain 67 g (100%) as a white amorphous solid. Anal. (C24H18ClO3NaO4.0.70 H2O): Calcd. C, 54.62; H, 3.44; N, 5.31; Cl, 20.15; Na, 4.36; H2O, 2.33. Fd: C, 54.37; H, 3.49; N, 5.18; Cl, 20.11; Na, 4.25; H2O, 2.54.

Example 179

VLA-4/VCAM-1 Screening Assay

VLA-4 antagonist activity, defined as ability to compete for binding to immobilized VCAM-1, was quantitated using a solid-phase, dual antibody ELISA. VLA-4 ($\alpha4\beta1$ integrin) bound to VCAM-1 is detected by a complex of anti-integrin $\beta1$ antibody: HRP-conjugated anti-mouse IgG: chromogenic substrate (K-Blue). Initially, this entailed coating 96 well plates (Nunc Maxisorp) with recombinant human VCAM-1 (0.4 μg in 100 μl PBS), sealing each plate and then allowing the plates to stand at 4° C. for Å 18 hr. The VCAM-coated plates were subsequently blocked with 250 μl of 1% BSA/0.02% NaN₃ to reduce non-specific binding. On the day of assay, all plates are washed twice with VCAM Assay Buffer (200 μl/well of 50 mM Tris-HCl. 100 mM NaCl, 1 mM MnCl₂), 0.05% Tween 20; pH 7.4). Test compounds are dissolved in 100% DMSO and then diluted 1:20 in VCAM Assay Buffer supplemented with 1 mg/mL BSA (i.e., final DMSO=5%). A series of 1:4 dilutions are performed to achieve a concentration range of 0.005 nM–1.563 μM for each test compound. 100 μl per well of each dilution is added to the VCAM-coated plates, followed by 10 μl of Ramos cell-derived VLA-4. These plates are sequentially mixed on a platform shaker for 1 min, incubated for 2 hr at 37° C., and then washed four times with 200 μl/well VCAM Assay Buffer. 100 μl of mouse anti-human integrin $\beta1$ antibody is added to each well (0.6 μg/mL in VCAM Assay Buffer+1 mg/mL BSA) and allowed to incubate for 1 hr at 37° C. At the conclusion of this incubation period, all plates are washed four times with VCAM Assay Buffer (200 μl/well). A corresponding second antibody, HRP-conjugated goat anti-mouse IgG (100 μl per well @1:800 dilution in VCAM Assay Buffer+1 mg/mL BSA), is then added to each well, followed by a 1 hr incubation at room temperature and concluded by three washes (200 μl/well) with VCAM Assay Buffer. Color development is initiated by addition of 100 μl K-Blue per well (15 min incubation, room temp) and terminated by addition of 100 μl Red Stop Buffer per well. All plates are then read in a UV/Vis spectrophotometer at 650 nM. Results are calculated as % inhibition of total binding (i.e. VLA-4+VCAM-1 in the absence of test compound). Selected data for compounds of this invention are shown in the table below:

| Example | ELISA IC$_{50}$ nM |
|---|---|
| 13 | 0.33 |
| 15 | 5.9 |
| 16 | 0.44 |
| 17 | 1.85 |
| 18 | 11 |
| 19 | 1.87 |
| 20 | 2.2 |
| 21 | 1.4 |
| 22 | 1.6 |
| 23 | 0.48 |
| 24 | 0.25 |
| 25 | 0.42 |
| 26 | 8.6 |
| 27 | 1.9 |
| 28 | 3.3 |
| 30 | 2.0 |
| 30 | 1.6 |
| 31 | 0.51 |
| 90 | 1.2 |
| 91 | 0.20 |
| 92 | 0.42 |
| 93 | 1.6 |
| 94 | 0.25 |
| 95 | 0.46 |
| 96 | 0.47 |
| 97 | 0.44 |
| 98 | 2.35 |
| 99 | 0.58 |
| 100 | 10 |
| 101 | 9.9 |
| 102 | 41 |
| 107 | 0.79 |
| 108 | 0.63 |
| 114 | 1.14 |
| 115 | 4.5 |
| 120 | 4.5 |
| 121 | 5.8 |
| 122 | 0.67 |
| 123 | 1.7 |
| 124 | 0.63 |
| 125 | 1.7 |

Example 180

Ramos (VLA-4)/VCAM-1 Cell-Based Screening Assay Protocol

Materials

Soluble recombinant human VCAM-1 (mixture of 5- and 7-Ig domain) was purified from CHO cell culture media by immunoaffinity chromatography and maintained in a solution containing 0.1 M Tris-glycine (pH 7.5), 0.1 M NaCl, 5 mM EDTA, 1 mM PMSF, 0.02% 0.02% NaN₃ and 10 μg/mL leupeptin. Calcein-AM was purchased from Molecular Probes Inc.

Methods

VLA-4 ($\alpha4\beta1$ integrin) antagonist activity, defined as ability to compete with cell-surface VLA-4 for binding to immobilized VCAM-1, was quantitated using a Ramos-VCAM-1 cell adhesion assay. Ramos cells bearing cell-surface VLA-4, were labeled with a fluorescent dye (Calcein-AM) and allowed to bind VCAM-1 in the presence or absence of test compounds. A reduction in fluorescence intensity associated with adherent cells (% inhibition) reflected competitive inhibition of VLA-4 mediated cell adhesion by the test compound.

Initially, this entailed coating 96 well plates (Nunc Maxisorp) with recombinant human VCAM-1 (100 ng in 100 µl PBS), sealing each plate and allowing the plates to stand at 4° C. for Å 18 hr. The VCAM-coated plates were subsequently washed twice with 0.05% Tween-20 in PBS, and then blocked for 1 hr (room temperature) with 200 µl of Blocking Buffer (1% BSA/0.02% thimerosal) to reduce non-specific binding. Following the incubation with Blocking Buffer, plates were inverted, blotted and the remaining buffer aspirated. Each plate was then washed with 300 µl PBS, inverted and the remaining PBS aspirated.

Test compounds were dissolved in 100% DMSO and then diluted 1:25 in VCAM Cell Adhesion Assay Buffer (4 mM $CaCl_2$, 4 mM $MgCl_2$ in 50 mM TRIS-HCl, pH 7.5) (final DMSO=4%). A series of eight 1:4 dilutions were performed for each compound (general concentration range of 1 nM–12.500 nM). 100 µl/well of each dilution was added to the VCAM-coated plates, followed by 100 µl of Ramos cells (200,000 cells/well in 1% BSA/PBS). Plates containing test compounds and Ramos cells were allowed to incubate for 45 min at room temperature, after which 165 µl/well PBS was added. Plates were inverted to remove non-adherent cells, blotted and 300 µl/well PBS added. Plates were again inverted, blotted and the remaining buffer gently aspirated. 100 µl Lysis Buffer (0.1% SDS in 50 mM TRIS-HCl, pH 8.5) was added to each well and agitated for 2 min on a rotary shaking platform. The plates were then read for fluorescence intensity on a Cytofluor 2300 (Millipore) fluorecence measurement system (excitation=485 nm, emission=530 nm). The results are shown in the following table:

Table

| Example | Ramos IC50 nM |
|---|---|
| 13 | 15 |
| 15 | 2.600 |
| 16 | 85 |
| 19 | 351 |
| 20 | 1.630 |
| 21 | 1.270 |
| 22 | 1.320 |
| 23 | 316 |
| 24 | 20 |
| 25 | 103 |
| 90 | 23 |
| 91 | 9.3 |
| 92 | 255 |
| 93 | 49 |
| 94 | 9.5 |
| 95 | 33 |
| 107 | 20 |
| 108 | 22 |
| 115 | 678 |
| 120 | 439 |
| 121 | 515 |
| 122 | 430 |
| 123 | 316 |

-continued

| Example | Ramos IC50 nM |
|---|---|
| 124 | 985 |
| 150 | 47 |
| 152 | 967 |
| 153 | 975 |
| 154 | 2,474 |
| 155 | 644 |
| 156 | 114 |
| 158 | 946 |
| 159 | 988 |
| 169 | 30 |
| 170 | 33.5 |
| 171 | 13.5 |

Example 181

Oral Dosage Form

| Item | Ingredients | mg/tablet | | | |
|---|---|---|---|---|---|
| 1 | Compound of invention | 25 | 100 | 250 | 500 |
| 2 | Anhydrous lactose | 83 | 35 | 19 | 38 |
| 3 | Croscarmellose sodium | 6 | 8 | 16 | 32 |
| 4 | Povidone K30 | 5 | 6 | 12 | 24 |
| 5 | Magnesium stearate | 1 | 1 | 3 | 6 |
|  | Total weight (mg) | 120 | 150 | 300 | 600 |

Manufacturing Procedure

1. Mix items 1, 2, 3 in a suitable mixer for 15 minutes.
2. Granulate the powder mix from step 1 with 20% PVP K30 solution.
3. Dry the granulation in step 2 at 50° C.
4. Pass the granulation from step 3 through a suitable milling equipment.
5. Add the item 5 to the milled granulation from Step 4 and mix for 3minutes.
6. Compress the granulation from Step 5 on a suitable press.

Example 182

Aerosol Administration Formulation

| Ingrdients | Qty/mL |
|---|---|
| Compound of invention | 3–150 mg* |
| Sodium chloride | 8.0 mg |
| Phophate buffer (20 mM) pH 7.0* q.s. | 1.0 mL |

*Depending upon activity of the compound pH can be adjusted with Sodium hydroxide solution (1 N) or HCl solution (10% w/v)

Procedure

1. Dissolve the drug substance in the buffer.
2. Filter the solution through a 0.22 micron filter.

The particle size distribution after nebulizing the above solution (as measured using Malvern Mastersizer X) is in the range of 1–6 microns.

What is claimed is:
1. A compound of the formula:

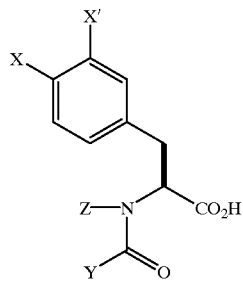

wherein:
Z is hydrogen or lower alkyl, one of X and X' is hydrogen, halogen, or lower alkyl, the other is a group of the formula:

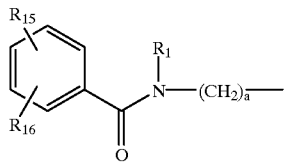

wherein:
$R_1$ is hydrogen or lower alkyl,
$R_{15}$ is halogen, nitro, lower alkyl sulfonyl, cyano, lower alkyl, OH, lower alkoxy, lower alkoxycarbonyl, carboxy, lower alkyl aminosulfonyl, perfluorolower alkyl, lower alkylthio, hydroxy lower alkyl, alkoxy lower alkyl, halo lower alkyl, alkylthio lower alkyl, alkylsulfinyl lower alkyl, alkylsufonyl lower alkyl, lower alkylsulfinyl, lower alkanoyl, aroy, aryloxy or a group of the formula $R_{17}$—C≡C—,
$R_{16}$ is hydrogen, halogen, nitro, cyano, lower alkyl, OH, perfluoro lower alkyl, or lower alkylthio,
$R_{17}$ hydrogen, aryl, heteroaryl, or lower alkyl which is unsubstituted or substituted by OH, aryl, or heteroaryl; and
a is 0 or 1;
or one of X and X' is a group of the formula:

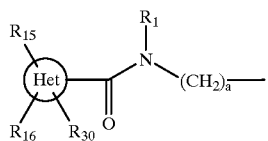

wherein
Het is a 5- or 6-membered heteroaromatic ring wherein the heteroatoms of such ring consist of 1, 2, or 3 heteroatoms selected from N, O, and S; or
Het is a 9- or 10-membered bicyclic heteroaromatic ring wherein the heteroatoms of such ring consist of 1, 2, 3 or 4 heteroatoms selected from O, S, and N,
a, $R_1$, $R_{15}$ and $R_{16}$ are as above, and
$R_{30}$ is hydrogen or lower alkyl, or is absent;

or one of X and X' is a group of the formula:

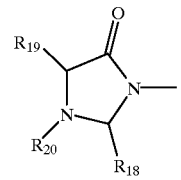

wherein:
$R_{18}$ is hydrogen, lower alkyl, aryl, heteroaryl, arylalkyl, heteroaryl alkyl,
$R_{19}$ is lower alkyl, which is unsubstituted or substituted by one or more halogen, hydroxy, lower alkoxy, aryl, hetereoaryl, alkylthio, or $R_{19}$ is aryl or heteroaryl, and
$R_{20}$ is lower alkyl or lower alkanoyl, or
$R_{19}$ and $R_{20}$ taken together are tetramethylene; and
Y is a group of the formula:

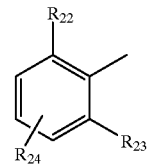

wherein:
$R_{22}$ and $R_{23}$ are independently hydrogen, lower alkyl, lower alkoxy, lower alkoxylalkyl, lower alkylamino, aryl, arylalkyl, nitro, cyano, lower alkylthio, lower alkylsulfinyl, lower alkyl sulfonyl, lower alkanoyl, halogen, or perfluoro lower alkyl and at least one of $R_{22}$ and $R_{23}$ is other than hydrogen, and
$R_{24}$ is hydrogen, hydroxy, lower alkyl, lower alkoxy, amino, aryl, nitro, cyano, lower alkyl sulfonyl, halogen, or is a group of the formula:

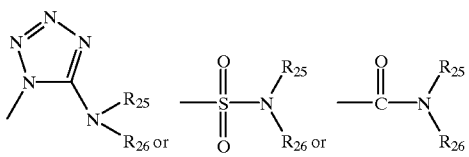

wherein
$R_{25}$ is hydrogen, lower alkyl, aryl, aryl lower alkyl, alkoxy lower alkyl and $R_{26}$ is hydrogen or lower alkyl, or
$R_{22}$ and $R_{24}$ taken together are a fused benzene ring; or
Y is a group Y-2 which is a five or six membered monocyclic heteroaromatic group wherein the heteroatoms of such group consist of 1, 2 or 3 heteroatoms selected from N, O, and S, or a 9- or 10-membered bicyclic heteroaromatic group wherein the heteroatoms of such group consist of 1, 2, 3 or 4 heteroatoms selected from O, S, and N, wherein said heteroaromatic group is bonded via a carbon atom to the amide carbonyl and one or two carbon atoms of said heteoaromatic group are substituted by lower alkyl, halogen, cyano, perfluoroalkyl, or aryl and at least one of said substituted carbon atoms is adjacent to the carbon atom bonded to the amide carbonyl;
or the pharmaceutically acceptable salts or esters thereof.

2. The compound of claim 1 wherein Y is Y-1 whereby said compound is of the formula:

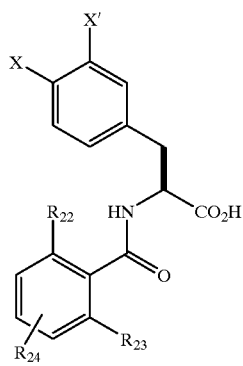

wherein X, X', $R_{22}$, $R_{23}$ and $R_{24}$ are as in claim 1.

3. The compound of claim 2 wherein:
$R_{22}$ and $R_{23}$ are independently hydrogen, lower alkyl, lower alkoxy, nitro, lower alkylthio, lower alkylamino, lower alkylsulfinyl, lower alkyl sulfonyl, lower alkanoyl, halogen, or perfluoroalkyl wherein at least one of $R_{22}$ and $R_{23}$ is not hydrogen, and
$R_{24}$ is hydrogen, hydroxy, lower alkyl, lower alkoxy, lower alkyl sulfonyl, amino, nitro, halogen or a group of the formula:

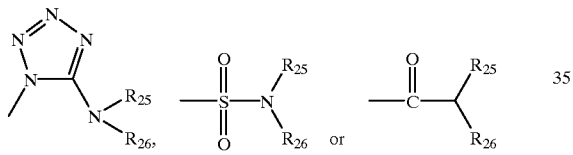

wherein $R_{25}$ is aryl lower alkyl and $R_{26}$ is hydrogen or lower alkyl, or $R_{22}$ and $R_{24}$ taken together are a fused benzene ring.

4. The compound of claim 3 wherein X' is hydrogen.

5. The compound of claim 3 wherein $R_{23}$ is nitro, lower alkoxy, lower alkylthio, lower alkylamino, lower alkylsulfinyl, lower alkyl sulfonyl, lower alkanoyl, or perfluoroalkyl.

6. The compound of claim 5 wherein $R_{22}$ and $R_{24}$ are independently hydrogen or halogen, or $R_{22}$ and $R_{24}$ taken together are a fused benzene ring.

7. The compound of claim 6 wherein X is a group of the formula:

X-7

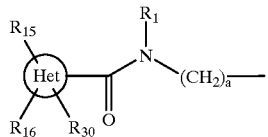

wherein
Het is a 5- or 6-membered heteroaromatic ring wherein the heteroatoms of such ring consist of 1, 2, or 3 heteroatoms selected from N, O, and S; or
Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and
$R_{30}$ is hydrogen or lower alkyl, or is absent.

8. The compound of claim 7 wherein X is a group of the formula:

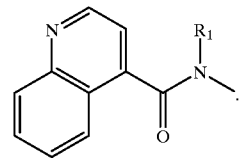

9. The compound of claim 8 wherein $R_{23}$ is nitro and $R_{22}$ is hydrogen.

10. The compound of claim 9 wherein $R_{24}$ is hydrogen or chlorine.

11. The compound of claim 10 having the formula:

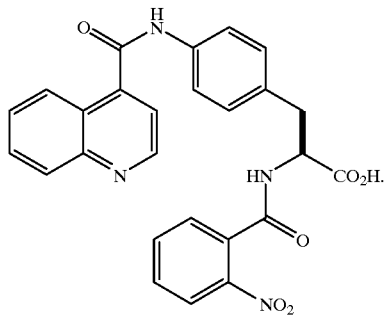

12. The compound of claim 10 having the formula:

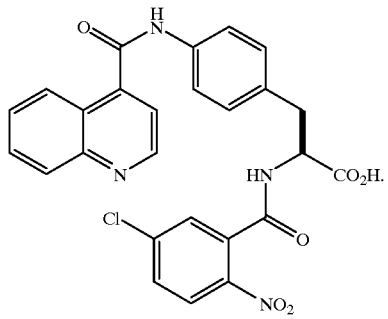

13. The compound of claim 6 wherein X is a group of the formula:

X-6

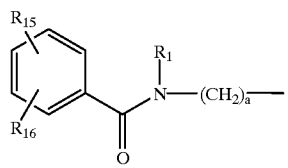

wherein a, $R_1$, $R_{15}$, and $R_{16}$ are as in claim 1.

14. The compound of claim 13 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

15. The compound of claim 14 wherein $R_{15}$ and $R_{16}$ are chloro.

16. The compound of claim 15 wherein X is a group of the formula:

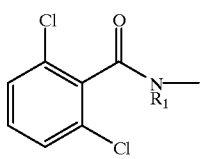

wherein $R_1$ is as in claim 1.

17. The compound of claim 16 wherein $R_{23}$ is lower alkylthio.

18. The compound of claim 17 having the formula:

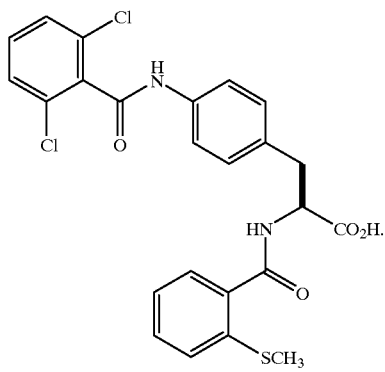

19. The compound of claim 16 wherein $R_{23}$ is lower alkoxy.

20. The compound of claim 19 having the formula:

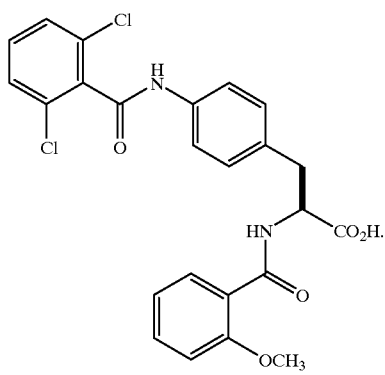

21. The compound of claim 16 wherein $R_{23}$ is lower alkylamino.

22. The compound of claim 21 having the formula:

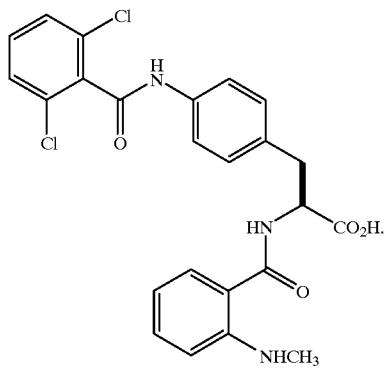

23. The compound of claim 16 wherein $R_{23}$ is perfluoroalkyl.

24. The compound of claim 23 having the formula:

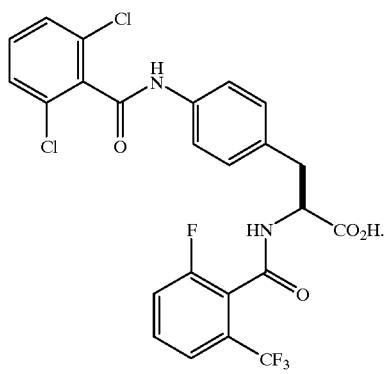

25. The compound of claim 16 wherein $R_{23}$ is lower alkylsulfinyl or lower alkyl sulfonyl.

26. The compound of claim 25 having the formula:

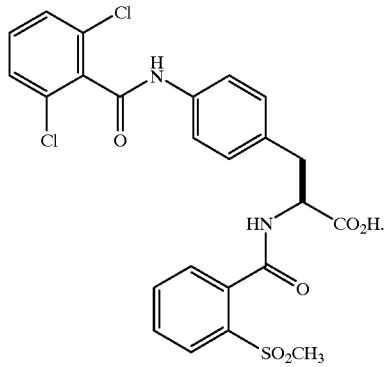

27. The compound of claim 25 having the formula:

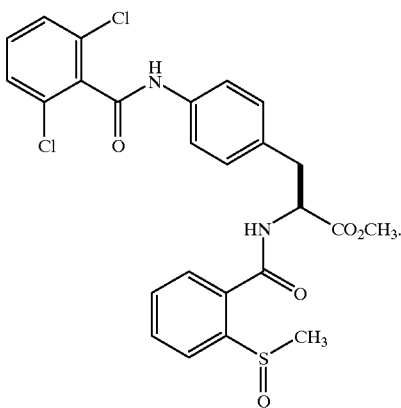

28. The compound of claim 16 wherein $R_{23}$ is hydrogen and $R_{22}$ and $R_{24}$ taken together are a fused benzene ring.

29. The compound of claim 28 having the formula:

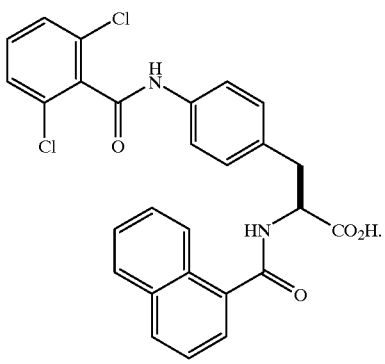

30. The compound of claim 3 wherein $R_{23}$ is lower alkyl, lower alkanoyl or halogen and $R_{22}$ is hydrogen, lower alkyl or halogen.

31. The compound of claim 30 wherein $R_{22}$ is lower alkyl, $R_{23}$ is lower alkanoyl, and $R_{24}$ is hydrogen.

32. The compound of claim 31 wherein X is a group of the formula:

X-6

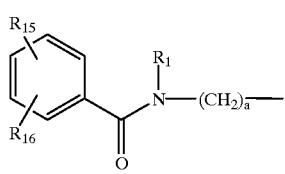

wherein a, $R_1$, $R_{15}$, and $R_{16}$ are as in claim 1.

33. The compound of claim 32 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

34. The compound of claim 33 wherein $R_{15}$ and $R_{16}$ are chloro.

35. The compound of claim 34 wherein X is a group of the formula:

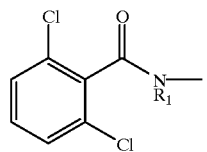

wherein $R_1$ is as in claim 1.

36. The compound of claim 35 having the formula:

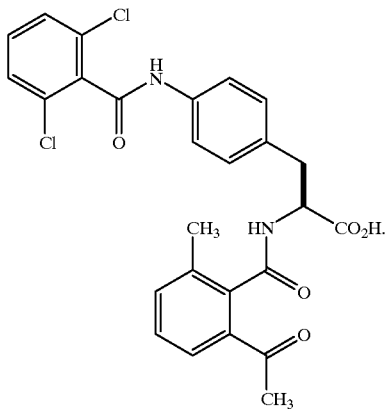

37. The compound of claim 30 wherein $R_{23}$ is lower alkyl.

38. The compound of claim 37 wherein $R_{22}$ and $R_{24}$ are both hydrogen.

39. The compound of claim 38 wherein X is a group of the formula:

X-6

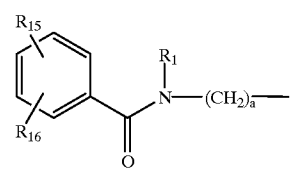

wherein a, $R_1$, $R_{15}$, and $R_{16}$ are as in claim 1.

40. The compound of claim 39 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

41. The compound of claim 40 wherein $R_{15}$ and $R_{16}$ are chloro.

42. The compound of claim 41 wherein X is a group of the formula:

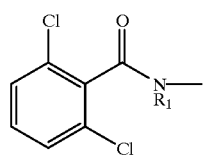

wherein $R_1$ is as in claim 1.

43. The compound of claim 42 having the formula:

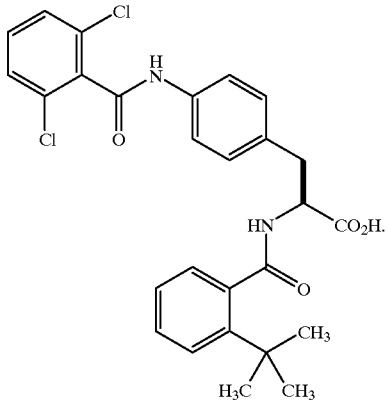

44. The compound of claim 37 wherein $R_{22}$ is lower alkyl.
45. The compound of claim 44 wherein $R_{24}$ is lower alkyl.
46. The compound of claim 45 wherein X is a group of the formula:

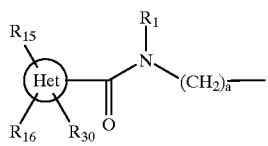
X-7 wherein
Het is a 5- or 6-membered heteroaromatic ring wherein the heteroatoms of such ring consist of 1, 2, or 3 heteroatoms selected from N, O, and S; or
Het is a 9- or 10-membered bicyclic heteroaromatic ring wherein the heteroatoms of such ring consist of 1, 2, 3 or 4 heteroatoms selected from O, S, and N,
a, $R_1$, $R_{15}$ and $R_{16}$ are as in claim 1, and
$R_{30}$ is hydrogen or lower alkyl, or is absent.

47. The compound of claim 46 wherein X is a group of the formula:

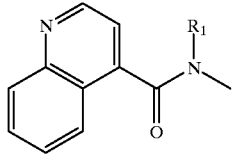

wherein $R_1$ is as in claim 1.

48. The compound of claim 47 having the formula:

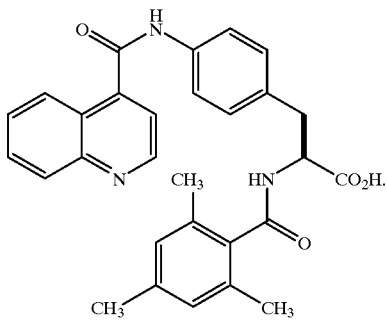

49. The compound of claim 44 wherein $R_{24}$ is hydrogen.
50. The compound of claim 49 wherein $R_{22}$ is methyl.
51. The compound of claim 50 wherein X is a group of the formula:

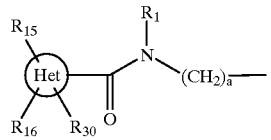
X-7 wherein
Het is a 5- or 6-membered heteroaromatic ring wherein the heteroatoms of such ring consist of 1, 2, or 3 heteroatoms selected from N, O, and S; or
Het is a 9- or 10-membered bicyclic heteroaromatic ring wherein the heteroatoms of such ring consist of 1, 2, 3 or 4 heteroatoms selected from O, S, and N,
a, $R_1$, $R_{15}$ and $R_{16}$ are as in claim 1, and
$R_{30}$ is hydrogen or lower alkyl, or is absent.

52. The compound of claim 51 wherein X is a group of the formula:

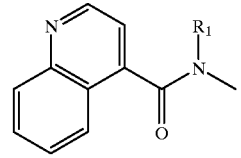

wherein $R_1$ is as in claim 1.

53. The compound of claim 52 having the formula:

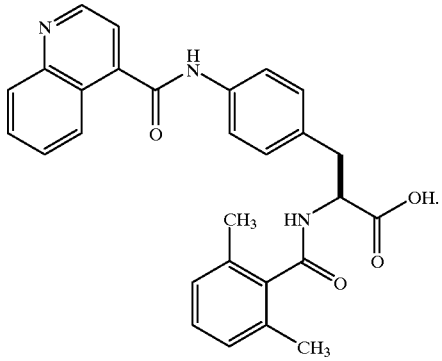

54. The compound of claim 50 wherein X is a group of the formula:

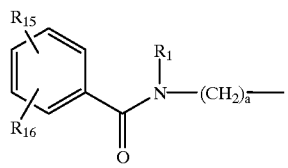
X-6 wherein a, $R_1$, $R_{15}$, and $R_{16}$ are as in claim 1.

55. The compound of claim 54 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

56. The compound of claim 55 wherein $R_{15}$ and $R_{16}$ are chloro.

57. The compound of claim 56 wherein X is a group of the formula:

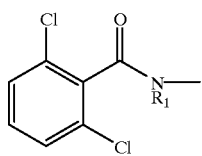

wherein $R_1$ is as in claim 1.

58. The compound of claim 57 having the formula:

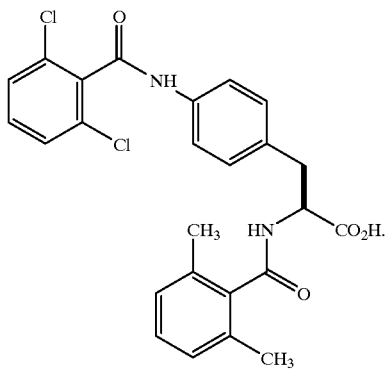

59. The compound of claim 57 having the formula:

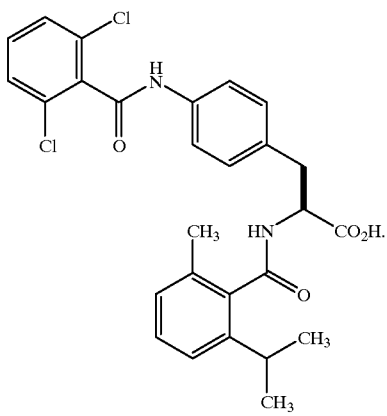

60. The compound of claim 57 having the formula:

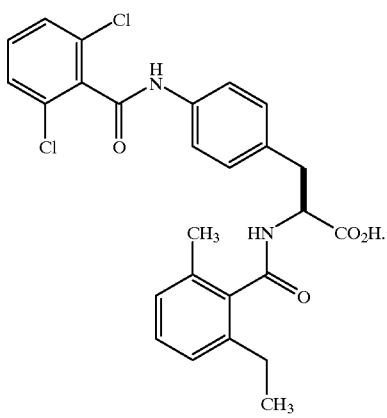

61. The compound of claim 55 wherein one of $R_{15}$ and $R_{16}$ is lower alkyl and the other is nitro.

62. The compound of claim 61 wherein X is a group of the formula:

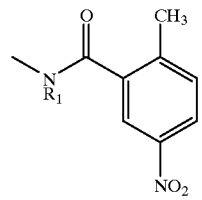

wherein $R_1$ is as in claim 1.

63. The compound of claim 62 having the formula:

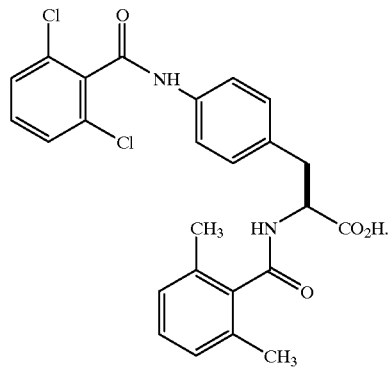

64. The compound of claim 49 wherein $R_{22}$ and $R_{23}$ are both isopropyl.

65. The compound of claim 64 wherein X is a group of the formula:

X-6

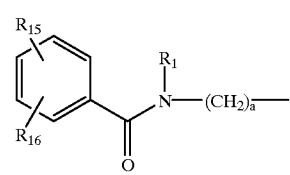

wherein a, $R_1$, $R_{15}$, and $R_{16}$ are as in claim 1.

66. The compound of claim 65 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

67. The compound of claim 66 wherein $R_{15}$ and $R_{16}$ are chloro.

68. The compound of claim 67 wherein X is a group of the formula:

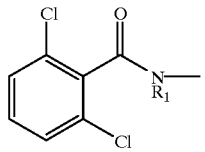

wherein $R_1$ is as in claim 1.

69. The compound of claim 68 having the formula:

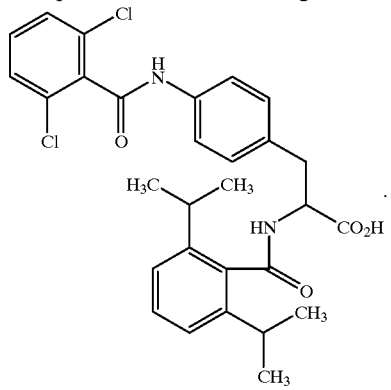

70. The compound of claim 37 wherein $R_{22}$ is halogen.
71. The compound of claim 70 wherein $R_{24}$ is hydrogen.
72. The compound of claim 71 wherein $R_{22}$ is chloro and $R_{23}$ is methyl.
73. The compound of claim 72 wherein X is a group of the formula:

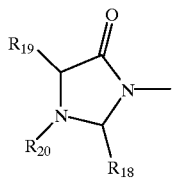

X-10 wherein $R_{18}$, $R_{19}$ and $R_{20}$ are as in claim 1.
74. The compound of claim 73 wherein $R_{18}$ is hydrogen or lower alkyl.
75. The compound of claim 74 wherein $R_{19}$ is lower alkyl which is unsubstituted or substituted by pyridyl or phenyl wherein the phenyl ring is unsubstituted or monosubstituted by lower alkoxy or halogen, and $R_{20}$ is lower alkanoyl.
76. The compound of claim 75 wherein $R_{19}$ is unsubstituted lower alkyl.
77. The compound of claim 76 having the formula:

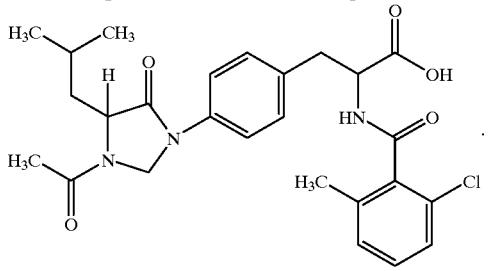

78. The compound of claim 76 having the formula:

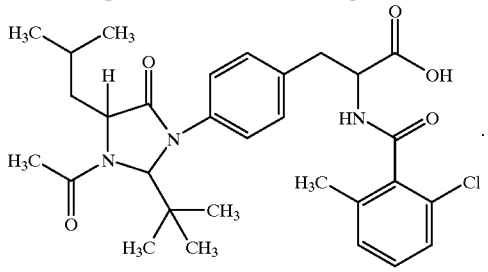

79. The compound of claim 73 wherein $R_{18}$ is aryl.
80. The compound of claim 79 wherein $R_{18}$ is naphthyl or phenyl which is unsubstituted or para-substituted by hydroxyl.
81. The compound of claim 80 wherein $R_{19}$ and $R_{20}$ are both lower alkyl.
82. The compound of claim 81 wherein $R_{20}$ is methyl.
83. The compound of claim 82 having the formula:

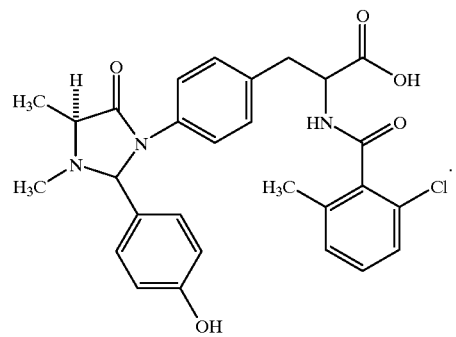

84. The compound of claim 82 having the formula:

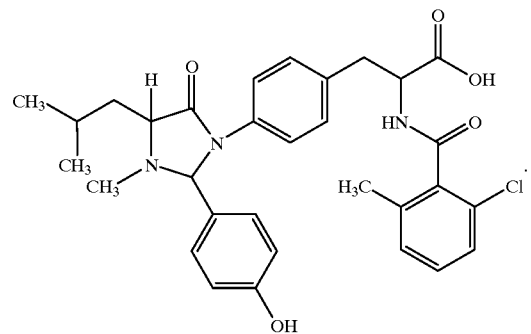

85. The compound of claim 82 having the formula:

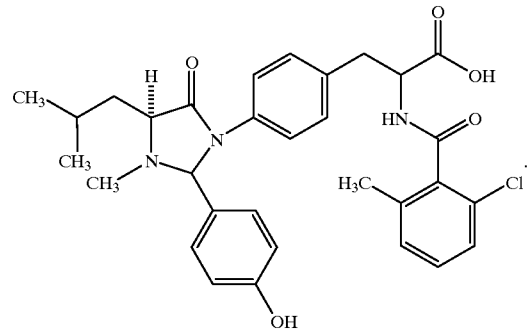

86. The compound of claim 82 having the formula:

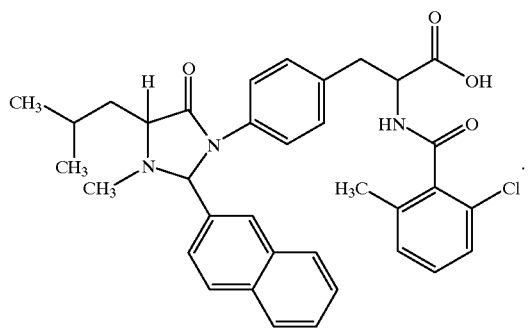

87. The compound of claim 80 wherein $R_{19}$ and $R_{20}$ taken together are tetramethylene.

88. The compound of claim 87 having the formula:

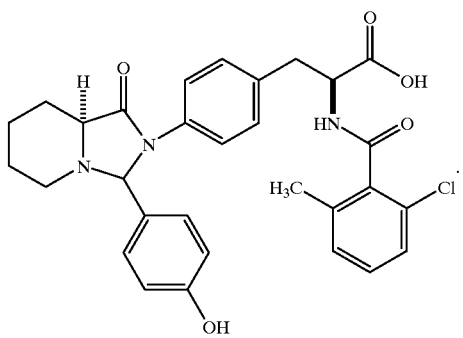

89. The compound of claim 87 having the formula:

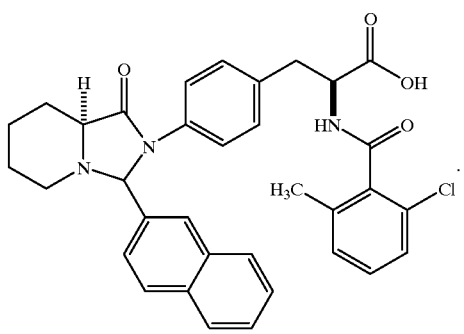

90. The compound of claim 87 having the formula:

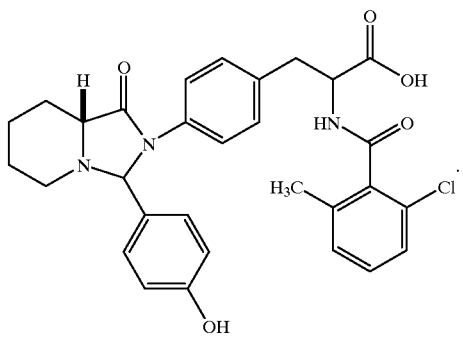

91. The compound of claim 80 wherein $R_{19}$ is lower alkyl which is unsubstituted or substituted by pyridyl or phenyl wherein the phenyl ring is unsubstituted or monosubstituted by lower alkoxy or halogen, and $R_{20}$ is lower alkanoyl.

92. The compound of claim 91 wherein $R_{19}$ is unsubstituted lower alkyl.

93. The compound of claim 92 having the formula:

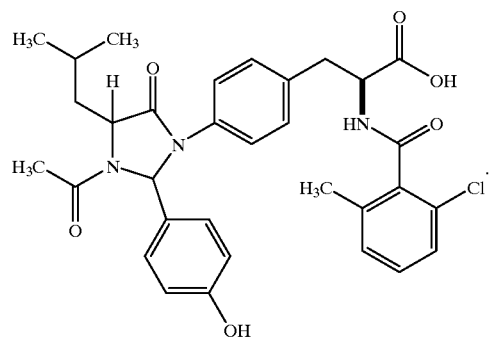

94. The compound of claim 92 having the formula:

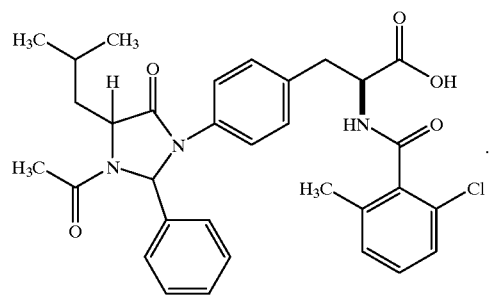

95. The compound of claim 91 wherein $R_{19}$ is phenyl lower alkyl.

96. The compound of claim 95 having the formula:

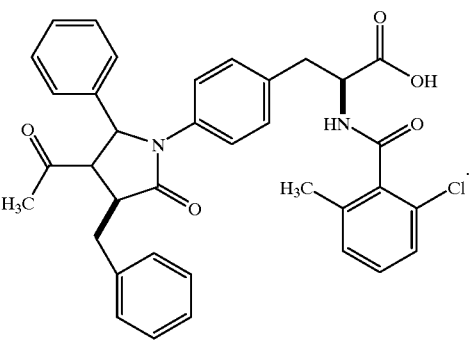

97. The compound of claim 72 wherein X is a group of the formula:

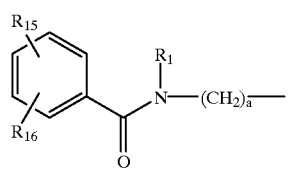

X-6 wherein a, $R_1$, $R_{15}$ and $R_{16}$ are as in claim 1.

98. The compound of claim 97 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

99. The compound of claim 98 wherein $R_{15}$ and $R_{16}$ are chloro.

100. The compound of claim 99 wherein X is a group of the formula:

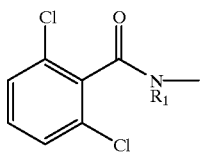

wherein $R_1$ is as in claim 1.

101. The compound of claim 100 having the formula:

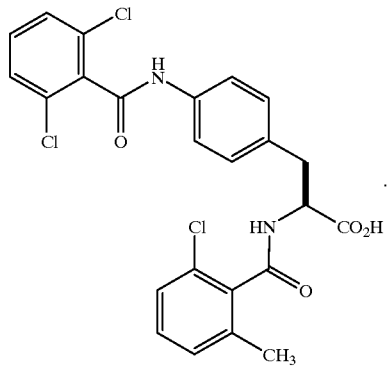

102. The compound of claim 98 wherein $R_{15}$ is nitro and $R_{16}$ is hydrogen.

103. The compound of claim 102 wherein X is a group of the formula:

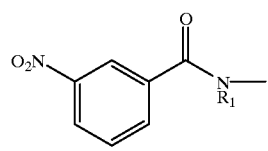

wherein $R_1$ is as in claim 1.

104. The compound of claim 103 having the formula:

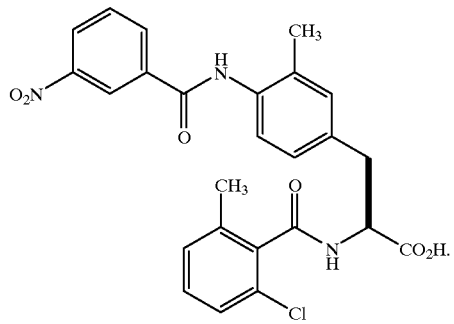

105. The compound of claim 98 wherein $R_{15}$ is halogen and $R_{16}$ is cyano.

106. The compound of claim 105 wherein X is a group of the formula:

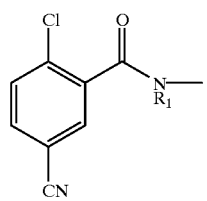

wherein $R_1$ is as in claim 1.

107. The compound of claim 106 having the formula:

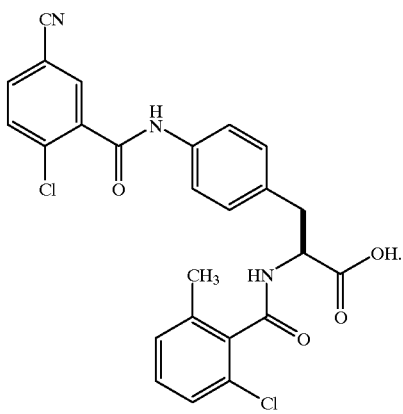

108. The compound of claim 98 wherein $R_{15}$ and $R_{16}$ are both fluoro.

109. The compound of claim 108 wherein X is a group of the formula:

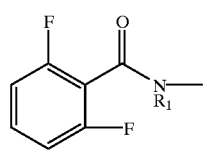

wherein $R_1$ is as in claim 1.

110. The compound of claim 109 having the formula:

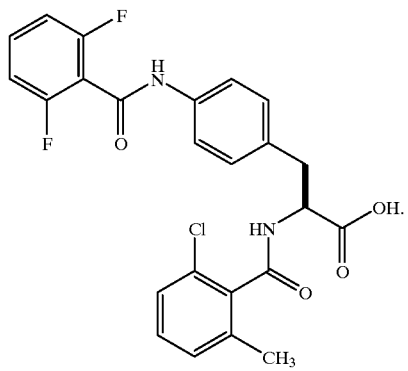

111. The compound of claim 72 wherein X is a group of the formula:

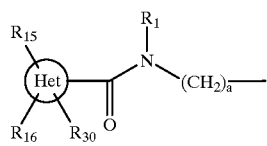

X-7 wherein

Het is a 5- or 6-membered heteroaromatic ring wherein the heteroatoms of such ring consist of 1, 2, or 3 heteroatoms selected from N, O, and S; or Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and $R_{30}$ is hydrogen or lower alkyl, or is absent.

112. The compound of claim 111 wherein Het is a 6-membered heteroaromatic ring of the formula:

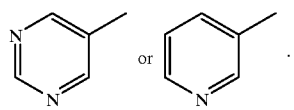

113. The compound of claim 112 having the formula:

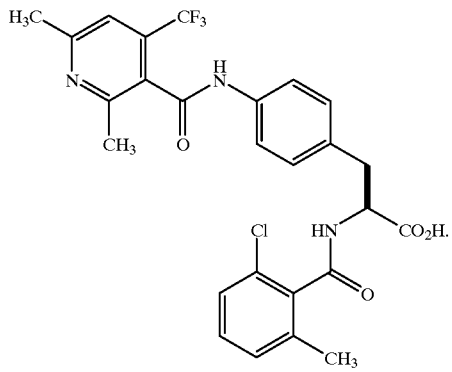

114. The compound of claim 112 having the formula:

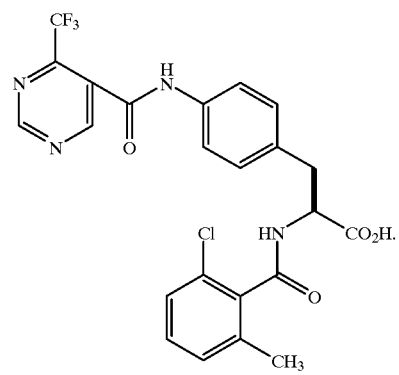

115. The compound of claim 111 wherein Het is a 5-membered heteroaromatic ring of the formula:

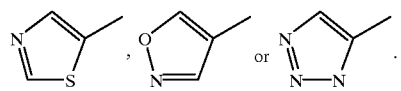

116. The compound of claim 115 having the formula:

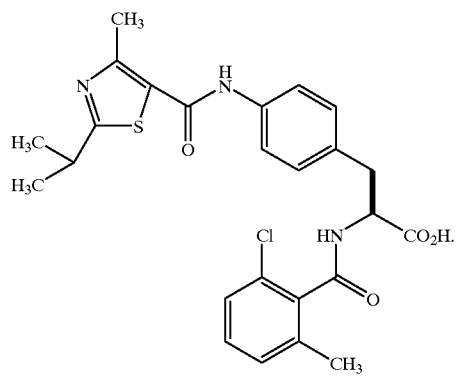

117. The compound of claim 115 having the formula:

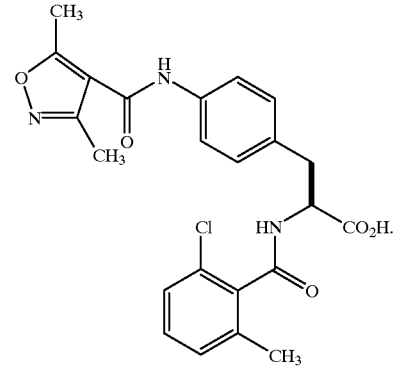

118. The compound of claim 115 having the formula:

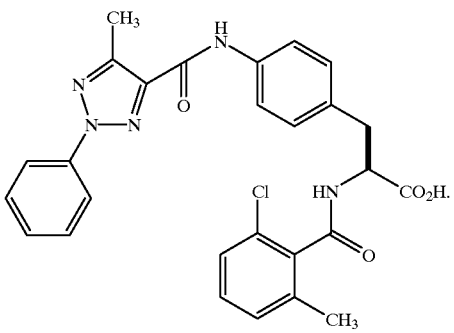

119. The compound of claim 111 wherein Het is a 9-membered hetearomatic ring of the formula:

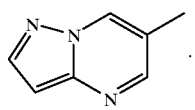

120. The compound of claim 119 having the formula:

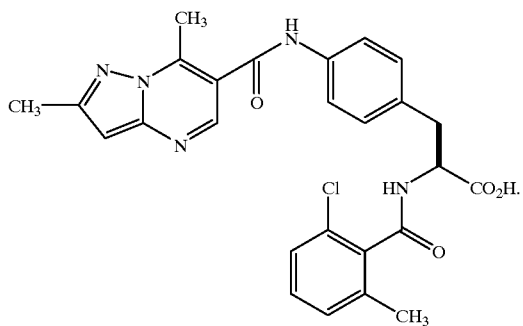

121. The compound of claim 30 wherein $R_{23}$ is halogen.

122. The compound of claim 121 wherein $R_{23}$ is bromo.

123. The compound of claim 122 wherein $R_{22}$ and $R_{24}$ are both hydrogen.

124. The compound of claim 123 wherein X is a group of the formula:

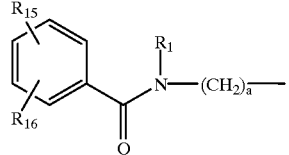

X-6 wherein a, $R_1$, $R_{15}$, and $R_{16}$ are as in claim 1.

125. The compound of claim 124 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

126. The compound of claim 125 wherein $R_{15}$ and $R_{16}$ are chloro.

127. The compound of claim 126 wherein X is a group of the formula:

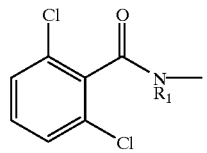

wherein $R_1$ is as in claim 1.

128. The compound of claim 127 having the formula:

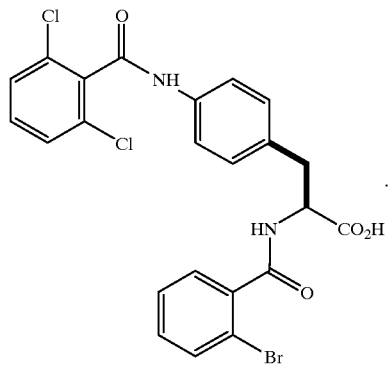

129. The compound of claim 124 wherein one of $R_{15}$ and $R_{16}$ is lower alkyl and the other is nitro.

130. The compound of claim 129 wherein X is a group of the formula:

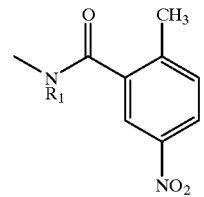

wherein $R_1$ is as in claim 1.

131. The compound of claim 130 having the formula:

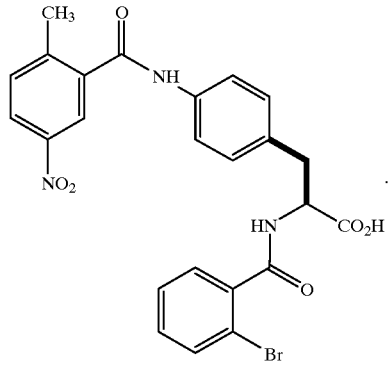

132. The compound of claim 124 wherein one of $R_{15}$ and $R_{16}$ is perfluoromethyl and the other is fluoro.

133. The compound of claim 132 wherein X is a group of the formula:

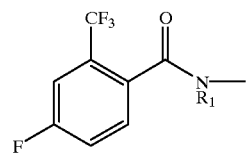

wherein $R_1$ is as in claim 1.

134. The compound of claim 133 having the formula:

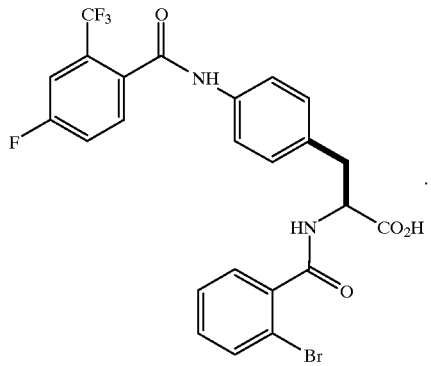

135. The compound of claim 123 wherein X is a group of the formula:

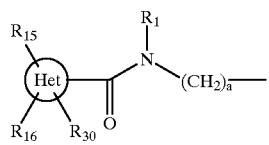

X-7 wherein

Het is a 5- or 6-membered heteroaromatic ring wherein the heteroatoms of such ring consist of 1, 2, or 3 heteroatoms selected from N, O, and S; or Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and $R_{30}$ is hydrogen or lower alkyl, or is absent.

136. The compound of claim 135 wherein X is a group of the formula:

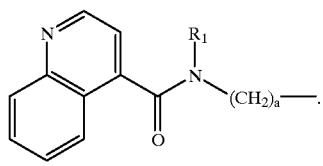

137. The compound of claim 136 wherein a is 0.

138. The compound of claim 137 of the formula:

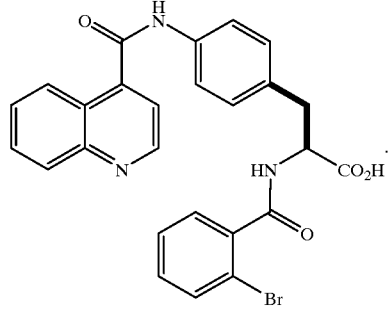

139. The compound of claim 122 wherein one of $R_{22}$ and $R_{24}$ is other than hydrogen.

140. The compound of claim 139 wherein $R_{22}$ is lower alkyl and $R_{24}$ is hydrogen.

141. The compound of claim 140 wherein X is a group of the formula:

X-6

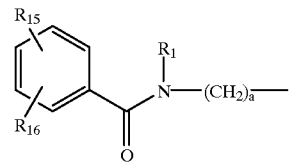

wherein a, $R_1$, $R_{15}$, and $R_{16}$ are as in claim 1.

142. The compound of claim 141 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

143. The compound of claim 142 wherein $R_{24}$ is m-nitro or m-methoxy.

144. The compound of claim 143 wherein $R_{15}$ and $R_{16}$ are chloro.

145. The compound of claim 144 wherein X is a group of the formula:

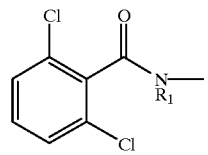

wherein $R_1$ is as in claim 1.

146. The compound of claim 145 having the formula:

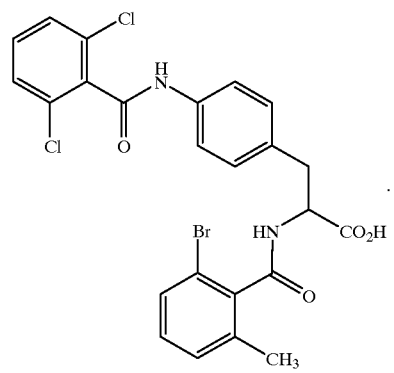

147. The compound of claim 139 wherein $R_{24}$ is halogen, lower alkyl, lower alkoxy or nitro.

148. The compound of claim 147 wherein $R_{22}$ is hydrogen.

149. The compound of claim 148 wherein X is a group of the formula:

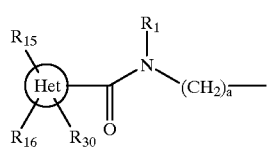

X-7 wherein

Het is a 5- or 6-membered heteroaromatic ring wherein the heteroatoms of such ring consist of 1, 2, or 3 heteroatoms selected from N, O, and S; or Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and $R_{30}$ is hydrogen or lower alkyl, or is absent.

150. The compound of claim 149 wherein $R_{24}$ is m-nitro or m-methoxy.

151. The compound of claim 150 wherein X is a group of the formula:

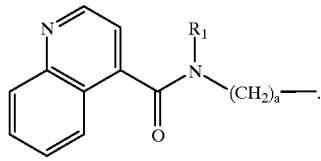

152. The compound of claim 151 wherein a is 0.

153. The compound of claim 152 having the formula:

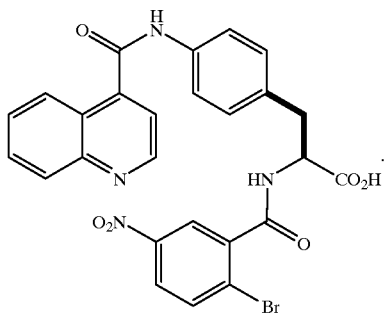

154. The compound of claim 150 wherein Het is a 6-membered heteroaromatic ring of the formula:

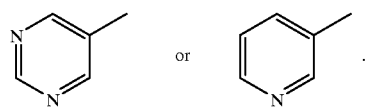

155. The compound of claim 154 having the formula:

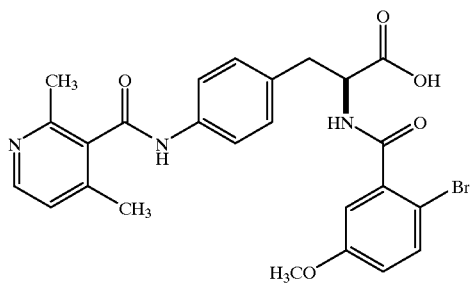

156. The compound of claim 148 wherein X is a group of the formula:

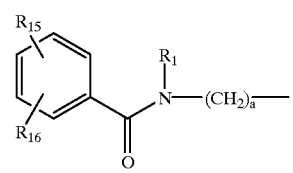

X-6 wherein a, $R_1$, $R_{15}$, and $R_{16}$ are as in claim 1.

157. The compound of claim 156 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

158. The compound of claim 157 wherein $R_{24}$ is m-nitro or m-methoxy.

159. The compound of claim 158 wherein $R_{15}$ and $R_{16}$ are chloro.

160. The compound of claim 159 wherein X is a group of the formula:

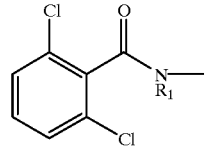

wherein $R_1$ is as in claim 1.

161. The compound of claim 160 having the formula:

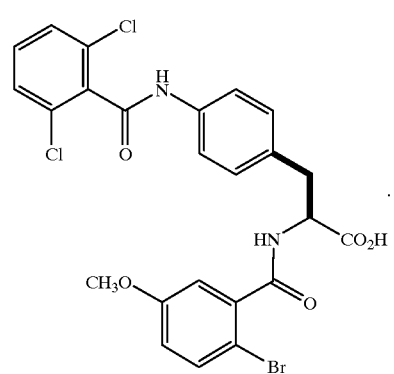

162. The compound of claim 121 wherein $R_{23}$ is fluoro.

163. The compound of claim 162 wherein $R_{22}$ and $R_{24}$ are both hydrogen.

164. The compound of claim 163 wherein X is a group of the formula:

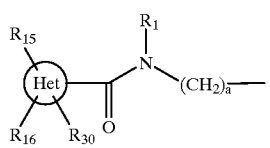

X-7 wherein
Het is a 5- or 6-membered heteroaromatic ring wherein the heteroatoms of such ring consist of 1, 2 or 3 heteroatoms selected from N, O, and S; or
Het is a 9- or 10-membered bicyclic heteroaromatic ring wherein the heteroatoms of such ring consist of 1, 2, 3 or 4 heteroatoms selected from O, S, and N,
a, $R_1$, $R_{15}$ and $R_{16}$ are as in claim 1, and
$R_{30}$ is hydrogen or lower alkyl, or is absent.

165. The compound of claim 164 wherein X is a group of the formula:

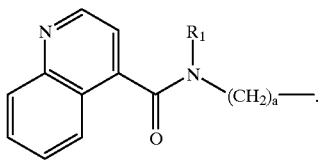

166. The compound of claim 165 wherein a is 0.
167. The compound of claim 166 having the formula:

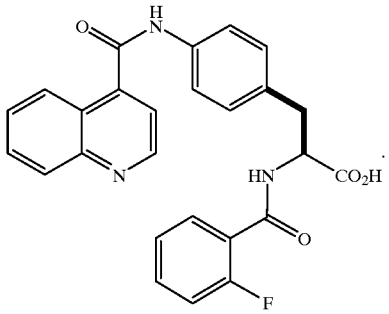

168. The compound of claim 162 wherein one of $R_{22}$ and $R_{24}$ is other than hydrogen.
169. The compound of claim 168 wherein $R_{24}$ is hydrogen.
170. The compound of claim 169 wherein $R_{22}$ is fluoro.
171. The compound of claim 170 wherein X is a group of the formula:

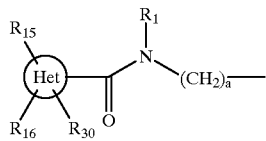

X-7 wherein
Het is a 5- or 6-membered heteroaromatic ring wherein the heteroatoms of such ring consist of 1, 2, or 3 heteroatoms selected from N, O, and S; or
Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and
$R_{30}$ is hydrogen or lower alkyl, or is absent.

172. The compound of claim 171 wherein X is a group of the formula:

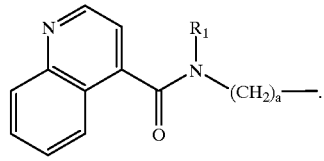

173. The compound of claim 172 wherein a is 0.
174. The compound of claim 173 having the formula:

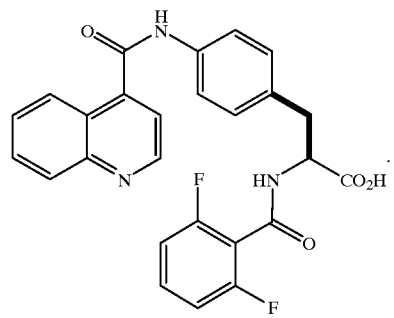

175. The compound of claim 170 wherein X is a group of the formula:

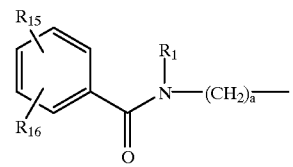

X-6 wherein a, $R_1$, $R_{15}$, and $R_{16}$ are as in claim 1.

176. The compound of claim 175 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

177. The compound of claim 176 wherein $R_{15}$ and $R_{16}$ are chloro.

178. The compound of claim 177 wherein X is a group of the formula:

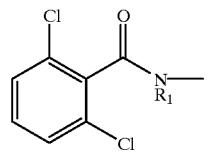

wherein $R_1$ is as in claim 1.

179. The compound of claim 178 having the formula:

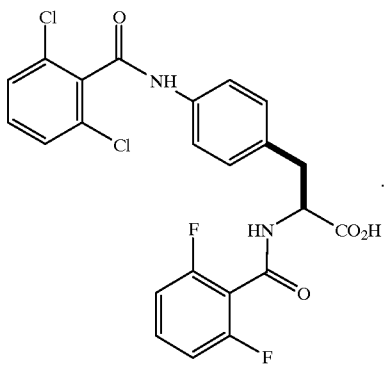

180. The compound of claim 176 wherein one of $R_{15}$ and $R_{16}$ is lower alkyl and the other is nitro.

181. The compound of claim 180 wherein X is a group of the formula:

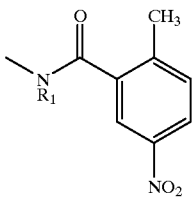

wherein $R_1$ is as in claim 1.

182. The compound of claim 181 having the formula:

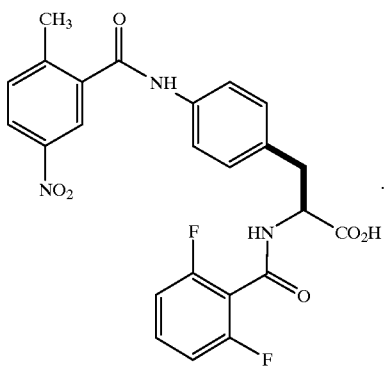

183. The compound claim 176 wherein one of $R_{15}$ and $R_{16}$ is perfluoro lower alkyl and the other is fluoro.

184. The compound of claim 183 wherein X is a group of the formula:

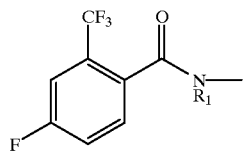

wherein $R_1$ is as in claim 1.

185. The compound of claim 184 having the formula:

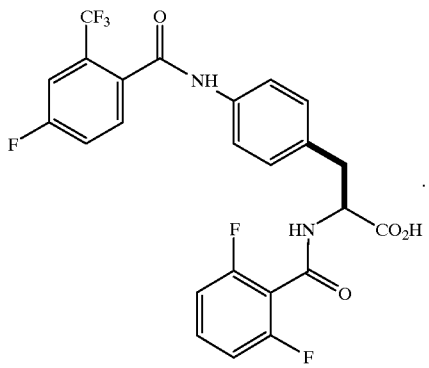

186. The compound of claim 121 wherein $R_{23}$ is chloro.

187. The compound of claim 186 wherein $R_{22}$ and $R_{24}$ are both hydrogen.

188. The compound of claim 187 wherein X is is a group of the formula:

X-7

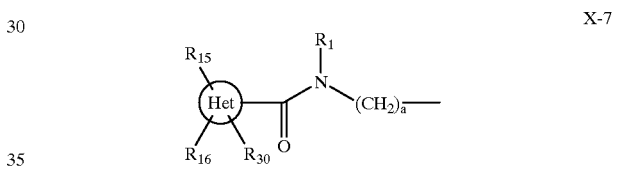

wherein

Het is a 5- or 6-membered heteroaromatic ring wherein the heteroatoms of such ring consist of 1, 2, or 3 heteroatoms selected from N, O, and S; or Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and $R_{30}$ is hydrogen or lower alkyl, or is absent.

189. The compound of claim 188 wherein X is a group of the formula:

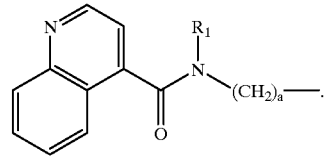

wherein $R_1$ and a are as in claim 1.

190. The compound of claim 189 wherein a is 0.

191. The compound of claim 190 having the formula:

192. The compound of claim 186 wherein $R_{22}$ is hydrogen and $R_{24}$ is halogen, amino, lower alkyl, lower alkylsulfonyl, hydroxy, lower alkoxy, or a group of the formula:

wherein $R_{25}$ is aryl lower alkyl and $R_{26}$ is hydrogen or lower alkyl.

193. The compound of claim 192 wherein $R_{24}$ is lower alkyl, lower alkylsulfonyl, hydroxy, lower alkoxy or amino.

194. The compound of claim 193 wherein X is a group of the formula:

X-6 wherein a, $R_1$, $R_{15}$, and $R_{16}$ are as in claim 1.

195. The compound of claim 194 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

196. The compound of claim 195 wherein $R_{15}$ and $R_{16}$ are chloro.

197. The compound of claim 196 wherein $R_{24}$ is methyl, methoxy, methylsulfonyl, hydroxy or amino.

198. The compound of claim 197 wherein X is a group of the formula:

wherein $R_1$ is as in claim 1.

199. The compound of claim 198 having the formula:

200. The compound of claim 198 having the formula:

201. The compound of claim 198 having the formula:

202. The compound of claim 198 having the formula:

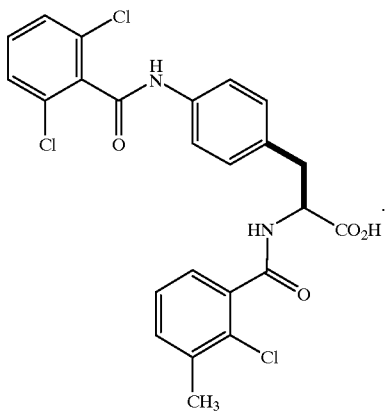

203. The compound of claim 198 having the formula:

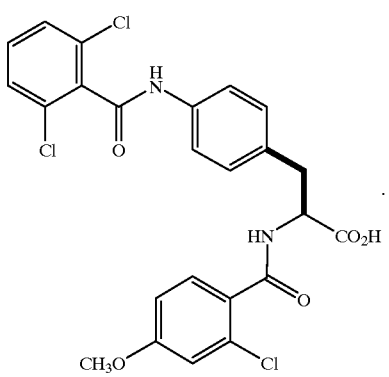

204. The compound of claim 198 having the formula:

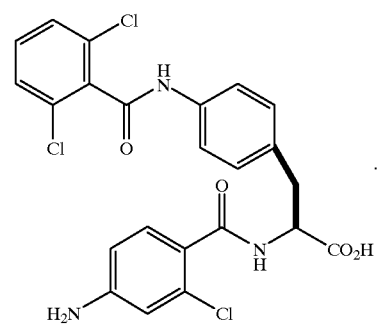

205. The compound of claim 192 wherein $R_{24}$ is halogen.
206. The compound of claim 205 wherein X is a group of the formula:

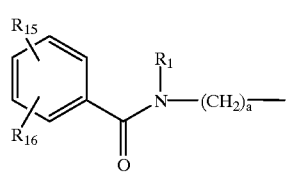

X-6 wherein a, $R_1$, $R_{15}$, and $R_{16}$ are as in claim 1.

207. The compound of claim 206 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.
208. The compound of claim 207 wherein $R_{15}$ and $R_{16}$ are chloro.
209. The compound of claim 208 wherein $R_{24}$ is bromo or chloro.
210. The compound of claim 209 wherein X is a group of the formula:

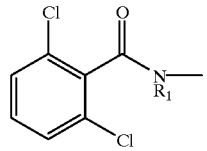

wherein $R_1$ is as in claim 1.
211. The compound of claim 210 having the formula:

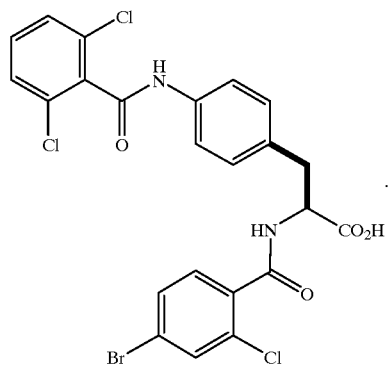

212. The compound of claim 210 having the formula:

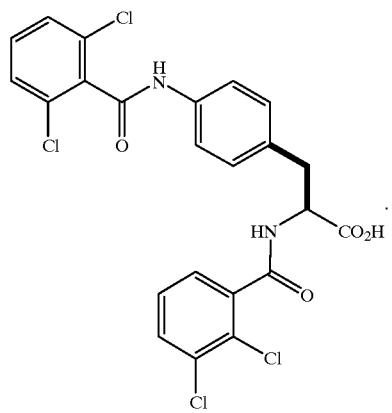

213. The compound of claim 192 wherein $R_{24}$ is a group of the formula:

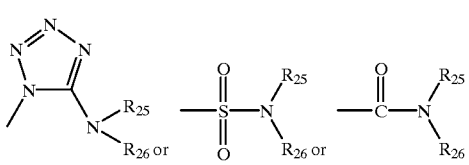

wherein $R_{25}$ is aryl lower alkyl and $R_{26}$ is hydrogen or lower alkyl.

214. The compound of claim 213 wherein X is a group of the formula:

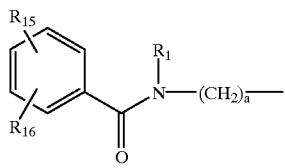

X-6 wherein a, $R_1$, $R_{15}$, and $R_{16}$ are as in claim 1.

215. The compound of claim 214 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

216. The compound of claim 215 wherein $R_{15}$ and $R_{16}$ are chloro.

217. The compound of claim 216 wherein $R_{26}$ is hydrogen.

218. The compound of claim 217 wherein $R_{25}$ is a group of the formula:

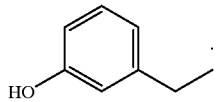

219. The compound of claim 218 wherein X is a group of the formula:

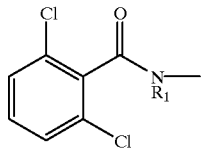

wherein $R_1$ is as in claim 1.

220. The compound of claim 219 having the formula:

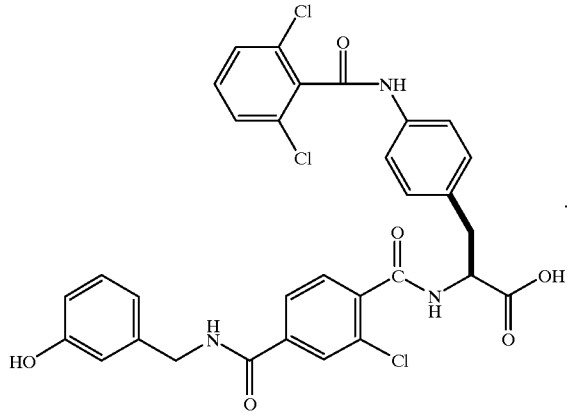

221. The compound of claim 219 having the formula:

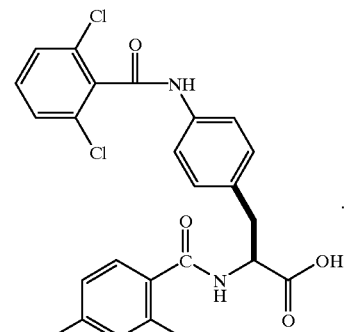

222. The compound of claim 219 having the formula:

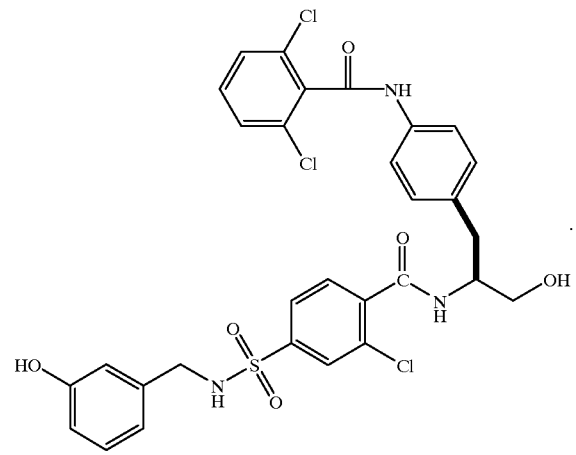

223. The compound of claim 186 wherein $R_{22}$ is halogen and $R_{24}$ is hydrogen.

224. The compound of claim 223 wherein $R_{22}$ is chloro.

225. The compound of claim 224 wherein X is a group of the formula:

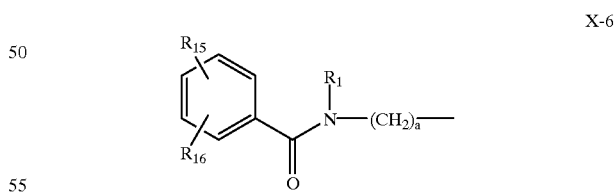

X-6 wherein a, $R_1$, $R_{15}$ and $R_{16}$ are as in claim 1.

226. The compound of claim 225 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

227. The compound of claim 226 wherein $R_{15}$ is halogen and $R_{16}$ is lower alkyl.

228. The compound of claim 227 wherein X is a group of the formula:

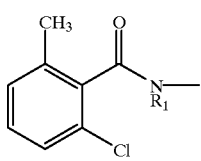

wherein R₁ is as in claim 1.

229. The compound of claim 228 having the formula:

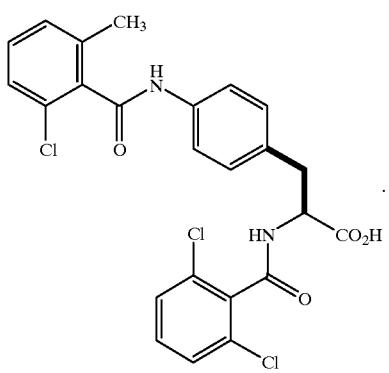

230. The compound of claim 224 wherein X is a group of the formula:

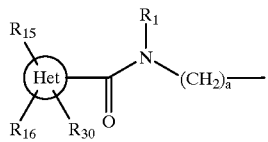

X-7 wherein

Het is a 5- or 6-membered heteroaromatic ring wherein the heteroatoms of such ring consist of 1, 2, or 3 heteroatoms selected from N, O, and S; or Het is a 9- or 10-membered bicyclic heteroaromatic ring wherein the heteroatoms of such ring consist of 1, 2, 3 or 4 heteroatoms selected from O, S, and N, a, R₁, R₁₅ and R₁₆ are as in claim 1, and R₃₀ is hydrogen or lower alkyl, or is absent.

231. The compound of claim 230 wherein Het is a 6-membered heteroaromatic ring of the formula:

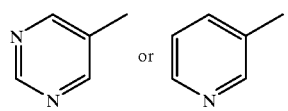

232. The compound of claim 231 having the formula:

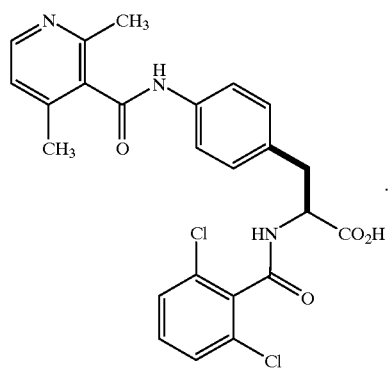

233. The compound of claim 1 wherein Y is the group Y-2.

234. The compound of claim 233 wherein the heteroaromatic group of Y-2 is a 5-membered monocyclic group of the formula:

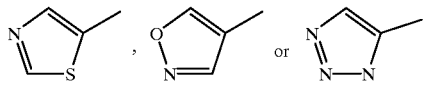

or is a 6-membered monocyclic group of the formula:

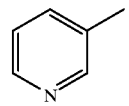

or is a 9-membered bicyclic group of the formula:

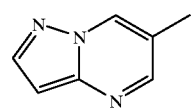

235. The compound of claim 234 wherein heteroaromatic group is a group of the formula:

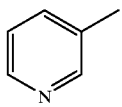

236. The compound of claim 234 wherein X is a group of the formula:

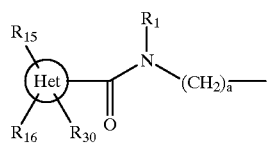

X-7 wherein

Het is a 5- or 6-membered heteroaromatic ring wherein the heteroatoms of such ring consist of 1, 2, or 3 heteroatoms selected from N, O, and S; or Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and $R_{30}$ is hydrogen or lower alkyl, or is absent.

237. The compound of claim 236 wherein X is a group of the formula:

[Structure: quinoline-4-carboxamide with N-$R_1$ and -(CH$_2$)$_a$-]

wherein $R_1$ and a are as in claim 1.

238. The compound of claim 237 wherein Y-2 is a group of the formula:

[Structure: 2-chloro-3-methylpyridine]

239. The compound of claim 238 wherein a is 0.

240. The compound of claim 239 having the formula:

[Structure]

241. The compound of claim 235 wherein X is a group of the formula:

X-6

[Structure with $R_{15}$, $R_{16}$, $R_1$, (CH$_2$)$_a$]

wherein a, $R_1$, $R_{15}$, and $R_{16}$ are as in claim 1.

242. The compound of claim 241 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

243. The compound of claim 242 wherein $R_{15}$ and $R_{16}$ are halogen.

244. The compound of claim 243 wherein X is a group of the formula:

[Structure: 2,6-dichlorobenzamide with N-$R_1$]

wherein $R_1$ is as in claim 1.

245. The compound of claim 244 wherein Y-2 is a group of the formula:

[Structure: pyridine with CF$_3$, CH$_3$ groups]

246. The compound of claim 244 having the formula:

[Structure]

247. The compound of claim 233 wherein the heteroaromatic group is a group of the formula:

[Structure: methylisoxazole]

248. The compound of claim 247 wherein X is a group of the formula:

X-7

[Structure with Het, $R_{15}$, $R_{16}$, $R_{30}$, $R_1$, (CH$_2$)$_a$]

wherein

Het is a 5- or 6-membered heteroaromatic ring wherein the heteroatoms of such ring consist of 1, 2, or 3 heteroatoms selected from N, O, and S; or Het is a 9- or 10-membered bicyclic heteroaromatic ring wherein the heteroatoms of such ring consist of 1, 2, 3 or 4 heteroatoms selected from O, S, and N, a, $R_1$, $R_{15}$ and $R_{16}$ are as in claim 1, and $R_{30}$ is hydrogen or lower alkyl, or is absent.

249. The compound of claim 248 wherein X is a group of the formula:

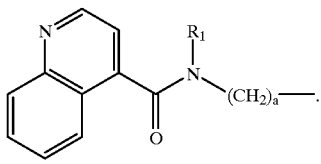

wherein $R_1$ and a are as in claim 1.

250. The compound of claim 249 wherein Y-2 is disubstituted by lower alkyl.

251. The compound of claim 250 wherein Y-2 is a group of the formula:

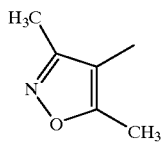

252. The compound of claim 251 wherein a is 0.

253. The compound of claim 252 having the formula:

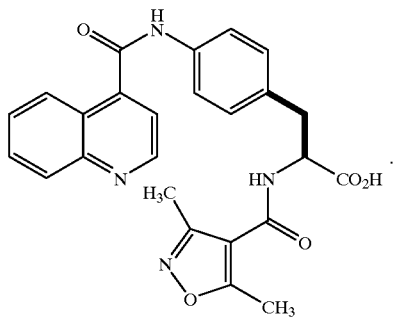

254. The compound of claim 247 wherein X is a group of the formula:

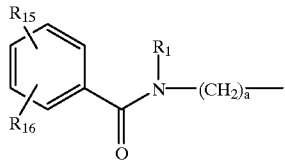

wherein a, $R_1$, $R_{15}$, and $R_{16}$ are as in claim 1.

255. The compound of claim 254 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

256. The compound of claim 255 wherein $R_{15}$ and $R_{16}$ are halogen.

257. The compound of claim 256 wherein X is a group of the formula:

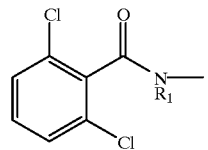

wherein $R_1$ is as in claim 1.

258. The compound of claim 257 wherein Y-2 is a group of the formula:

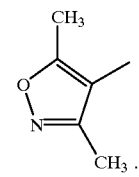

259. The compound of claim 257 having the formula:

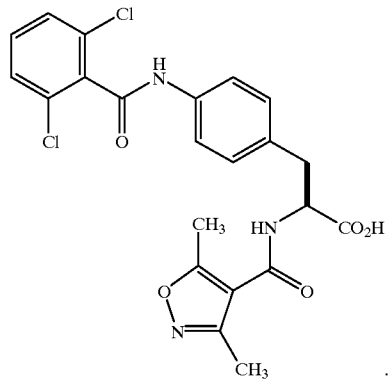

260. The compound of claim 233 wherein the heteroaromatic group is a group of the formula:

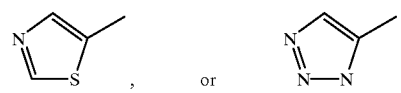

261. The compound of claim 260 wherein X is a group of the formula:

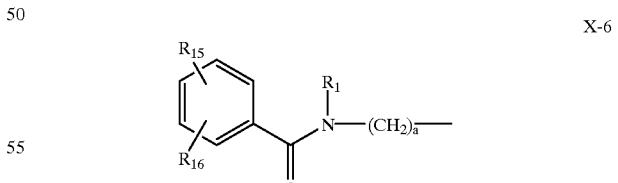

wherein a, $R_1$, $R_{15}$, and $R_{16}$ are as in claim 1.

262. The compound of claim 261 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

263. The compound of claim 262 wherein $R_{15}$ and $R_{16}$ are halogen.

264. The compound of claim 263 wherein X is a group of the formula:

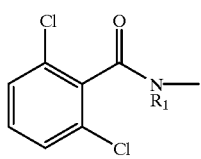

wherein R₁ is as in claim 1.

265. The compound of claim 264 wherein the heteroaromatic group is a group of the formula:

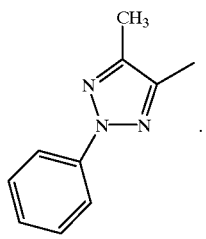

266. The compound of claim 265 having the formula:

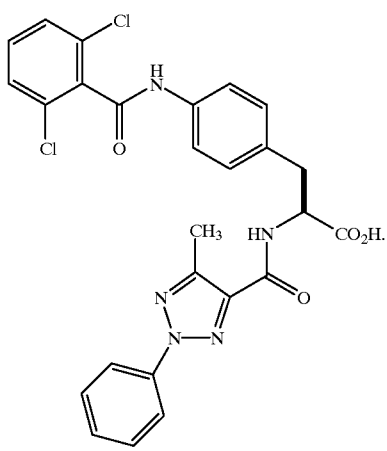

267. The compound of claim 264 wherein Y-2 is a group of the formula:

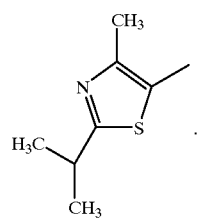

268. The compound of claim 267 having the formula:

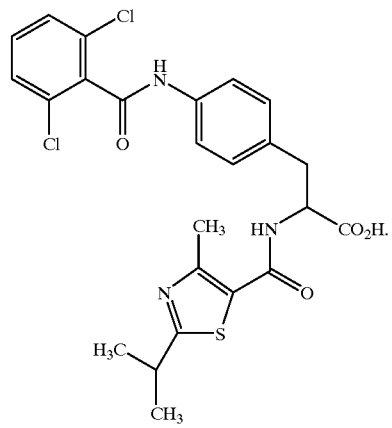

269. The compound of claim 234 wherein the heteroaromatic group is a group of the formula:

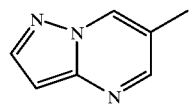

270. The compound of claim 269 wherein X is a group of the formula:

X-6

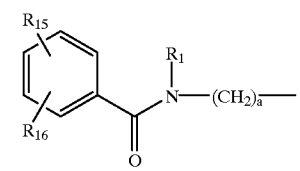

wherein a, R₁, R₁₅, and R₁₆ are as in claim 1.

271. The compound of claim 270 wherein R₁₅ and R₁₆ are independently hydrogen, halogen, nitro, cyano, perfluoro lower alkyl, or lower alkyl, or R₁₅ is phenoxy and R₁₆ is hydrogen.

272. The compound of claim 271 wherein R₁₅ and R₁₆ are halogen.

273. The compound of claim 272 wherein X is a group of the formula:

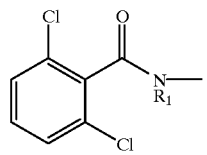

wherein R₁ is as in claim 1.

274. The compound of claim 273 wherein Y-2 is a group of the formula:

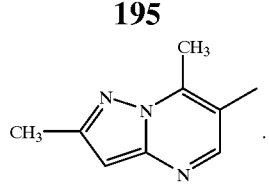

275. The compound of claim 274 having the formula:

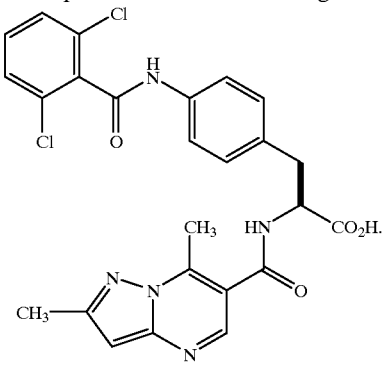

276. The compound of claim 1 which is an ester of the formula:

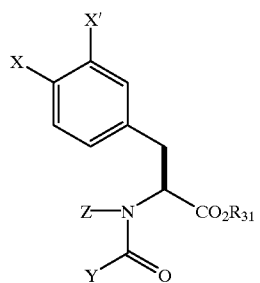

wherein:
R$_{31}$ is lower alkyl; or
R$_{31}$ a group of formula:

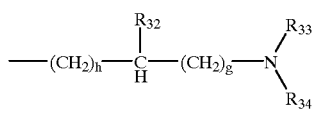

P-1 wherein:
R$_{32}$ is hydrogen or lower alkyl,
R$_{33}$ is hydrogen, lower alkyl, or aryl,
R$_{34}$ is hydrogen or lower alkyl,
h is an integer from 0 to 2,
g is an integer from 0 to 2, and
the sum of h and g is 1 to 3; or
R$_{31}$ is a group of formula:

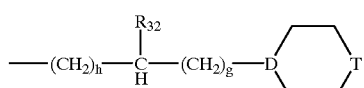

P-2 wherein:
R$_{32}$, g, and h are as above for P-1,
D is CH or N,
T is O, S, —(CH$_2$)$_j$—, a group of the formula N—R$_{35}$, or when j=0, a bond,
R$_{35}$ is hydrogen, lower alkyl, lower alkanoyl, or lower alkoxycarbonyl, and j is 0, 1 or 2
and wherein X, X' Y and Z are as in claim 1.

277. The compound of claim 276 wherein Y is Y-1 and Z is hydrogen whereby said compound is of the formula:

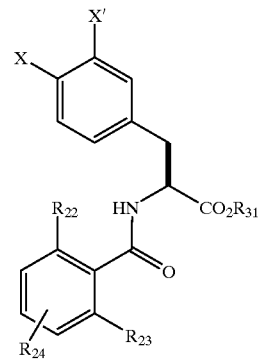

wherein X, X', R$_{22}$, R$_{23}$ and R$_{24}$ are as in claim 1.

278. The compound of claim 277 wherein R$_{22}$ and R$_{23}$ are independently hydrogen, lower alkyl, nitro, lower alkylthio, lower alkylamino, lower alkylsulfinyl, lower alkyl sulfonyl, lower alkanoyl, halogen, or perfluoroalkyl wherein at least one of R$_{22}$ and R$_{23}$ is not hydrogen, and R$_{24}$ is hydrogen, lower alkyl, lower alkoxy, amino, nitro, halogen or a group of the formula:

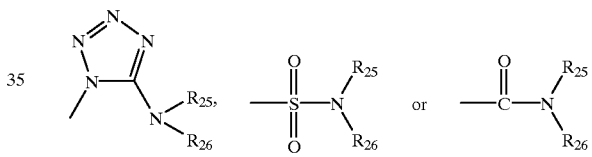

wherein

R$_{25}$ is aryl lower alkyl and R$_{26}$ is hydrogen or lower alkyl, or

R$_{22}$ and R$_{24}$ taken together are a fused benzene ring.

279. The compound of claim 278 wherein X' is hydrogen.

280. The compound of claim 279 wherein R$_{22}$ is lower alkyl, R$_{23}$ is halogen and X is a group of the formula:

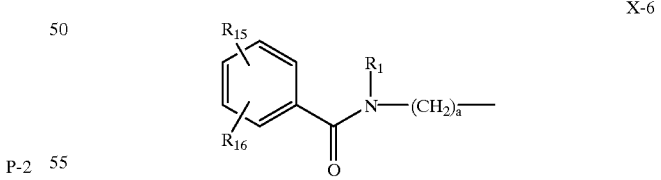

X-6 wherein a, R$_1$, R$_{15}$, and R$_{16}$ are as in claim 1.

281. The compound of claim 280 wherein R$_{15}$ and R$_{16}$ are independently hydrogen, halogen, nitro, cyano, perfluoro lower alkyl, or lower alkyl, or R$_{15}$ is phenoxy and R$_{16}$ is hydrogen.

282. The compound of claim 281 wherein R$_{15}$ and R$_{16}$ are halogen.

283. The compound of claim 282 wherein X is a group of the formula:

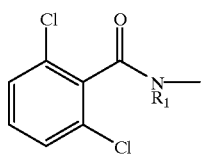

wherein R₁ is as in claim 1.

284. The compound of claim 283 wherein R₁ is hydrogen, R₂₂ is methyl, R₂₃ is chloro, and R₂₄ is hydrogen whereby said compound has the formula:

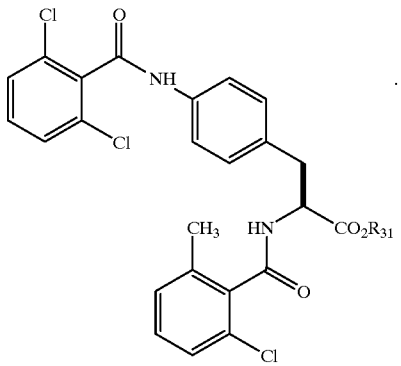

285. The compound of claim 284 wherein R₃₁ is lower alkyl.

286. The compound of claim 285 having the formula:

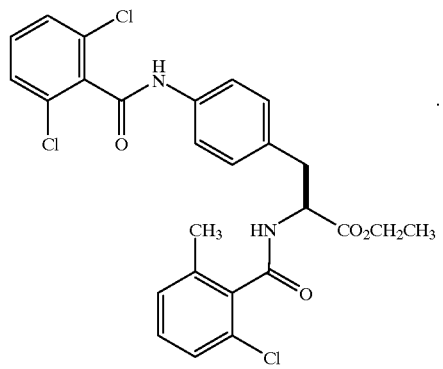

287. The compound of claim 285 having the formula:

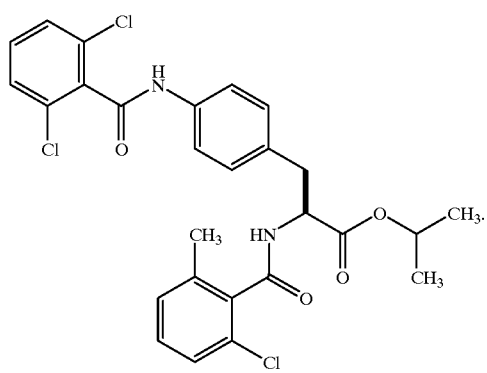

288. The compound of claim 285 having the formula:

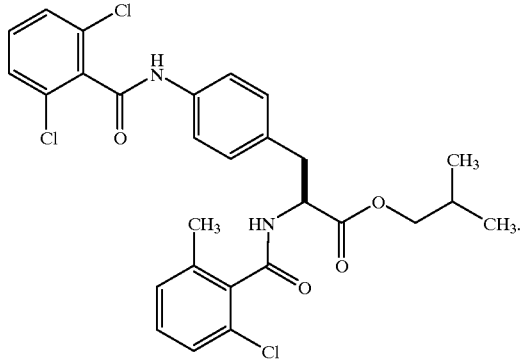

289. The compound of claim 285 having the formula:

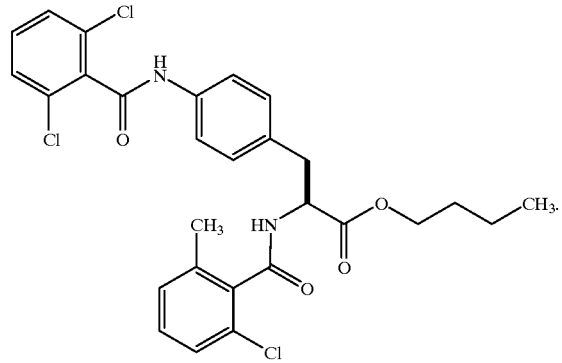

290. The compound of claim 285 having the formula:

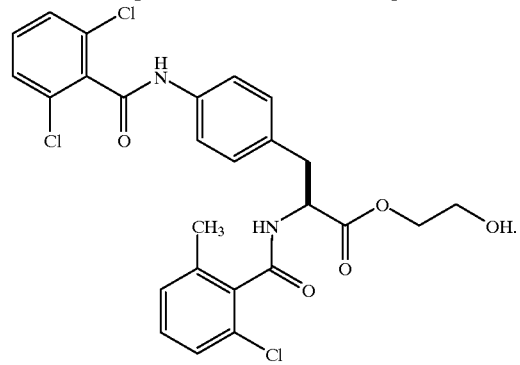

291. The compound of claim 285 having the formula:

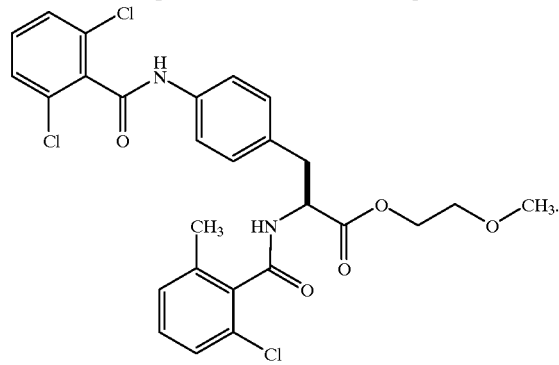

292. The compound of claim 284 wherein $R_{31}$ is the group P-1 wherein $R_{32}$ is hydrogen, h is 0, g is 1 and $R_{33}$ and $R_{34}$ are independently hydrogen or lower alkyl.

293. The compound of claim 292 having the formula:

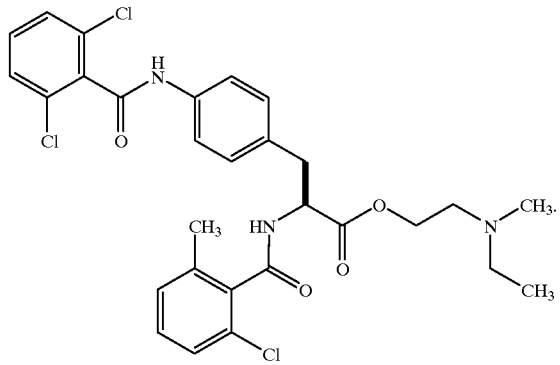

294. The compound of claim 284 wherein $R_{31}$ is the group P-2 wherein $R_{32}$ is hydrogen or methyl, h is 0, g is 0 or 1, T is O or N—$R_{35}$ wherein $R_{35}$ is hydrogen or lower alkyl.

295. The compound of claim 285 having the formula:

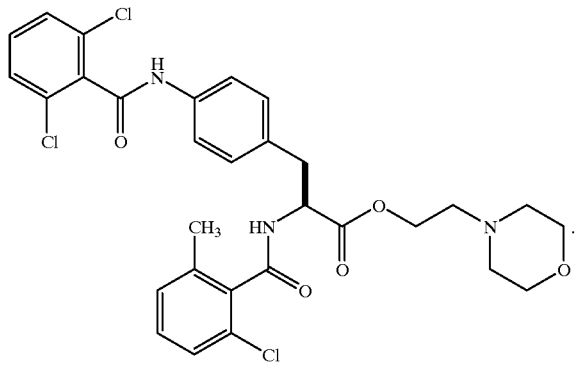

296. The compound of claim 285 having the formula:

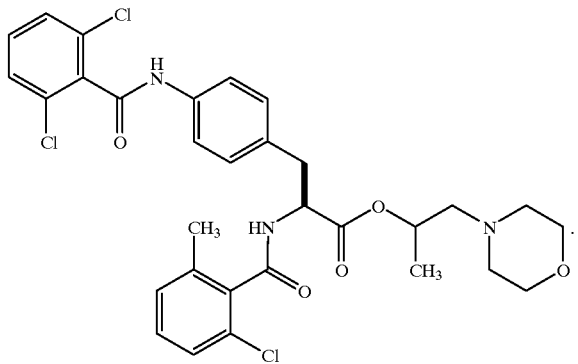

297. The compound of claim 285 having the formula:

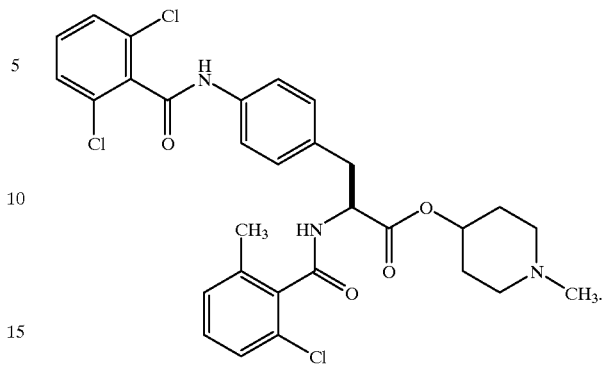

298. The compound of claim 285 having the formula:

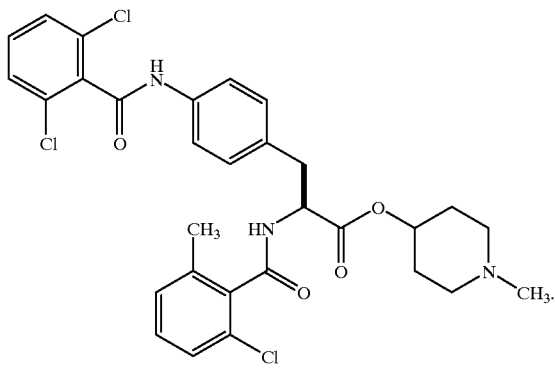

299. The compound of claim 1 wherein Z is lower alkyl.

300. The compound of claim 299 wherein Y is Y-1 whereby said compound is of the formula:

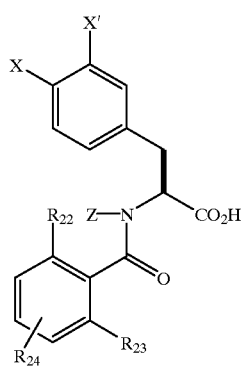

wherein X, X', $R_{22}$, $R_{23}$ and $R_{24}$ are as in claim 1.

301. The compound of claim 300 wherein $R_{22}$ and $R_{23}$ are independently hydrogen, lower alkyl, nitro, lower alkylthio, lower alkylamino, lower alkylsulfinyl, lower alkyl sulfonyl, lower alkanoyl, halogen, or perfluoroalkyl wherein at least one of $R_{22}$ and $R_{23}$ is not hydrogen, and $R_{24}$ is hydrogen, lower alkyl, lower alkoxy, amino, nitro, halogen or a group of the formula:

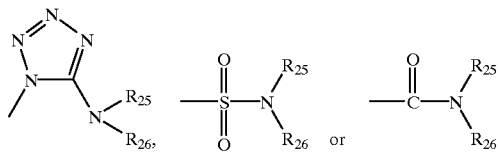

wherein R₂₅ is aryl lower alkyl and R₂₆ is hydrogen or lower alkyl, or

R₂₂ and R₂₄ taken together are a fused benzene ring.

302. The compound of claim 301 wherein X' is hydrogen.

303. The compound of claim 302 wherein R₂₂ is lower alkyl, R₂₃ is halogen and X is a group of the formula:

X-6

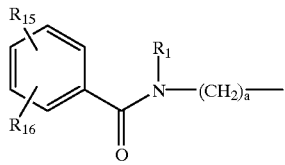

wherein a, R₁, R₁₅, and R₁₆ are as in claim 1.

304. The compound of claim 303 wherein R₁₅ and R₁₆ are independently hydrogen, halogen, nitro, cyano, perfluoro lower alkyl, or lower alkyl, or R₁₅ is phenoxy and R₁₆ is hydrogen.

305. The compound of claim 304 wherein R₁₅ and R₁₆ are halogen.

306. The compound of claim 305 wherein X is a group of the formula:

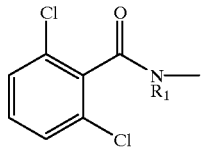

wherein R₁ is as in claim 1.

307. The compound of claim 306 wherein R₁ is hydrogen, R₂₂ is methyl, R₂₃ is chloro, and R₂₄ is hydrogen whereby said compound has the formula:

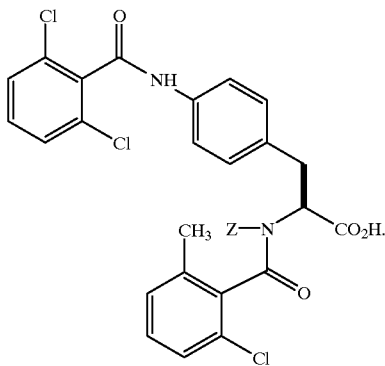

308. The compound of claim 307 having the formula:

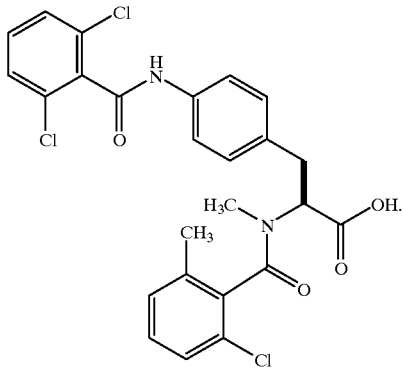

* * * * *

UNITED STATES PATENT AND TRADEMARK OFFICE
CERTIFICATE OF CORRECTION

PATENT NO. : 6,229,011 B1
DATED : May 8, 2001
INVENTOR(S) : Li Chen et al.

It is certified that error appears in the above-identified patent and that said Letters Patent is hereby corrected as shown below:

Column 153, claim 3,
Lines 32-39, replace the present formula with

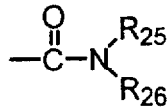

Column 166, claim 96,
Lines 50-65, replace the present formula with

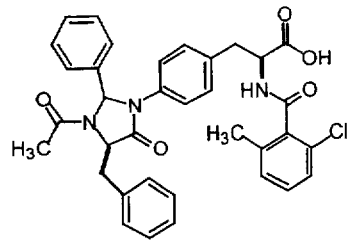

Column 186, claim 222,
Lines 22-40, replace the present formula with

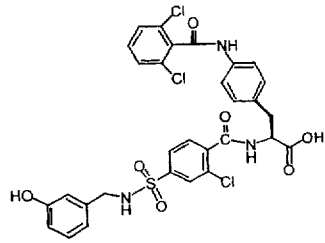

Column 199, claim 293,
Lines 7-24, replace the present formula with

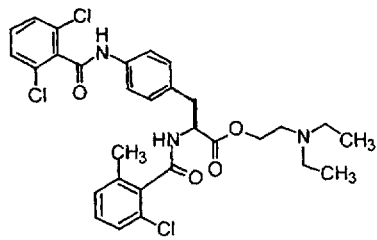

UNITED STATES PATENT AND TRADEMARK OFFICE
CERTIFICATE OF CORRECTION

PATENT NO.   : 6,229,011 B1
DATED         : May 8, 2001
INVENTOR(S)  : Li Chen et al.

It is certified that error appears in the above-identified patent and that said Letters Patent is hereby corrected as shown below:

<u>Column 200, claim 298,</u>
Lines 20-35, replace the present formula with

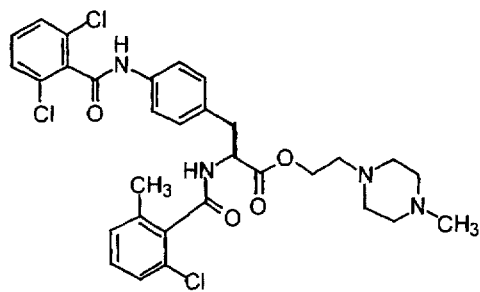

Signed and Sealed this

Ninth Day of April, 2002

*Attest:*

*Attesting Officer*

JAMES E. ROGAN
*Director of the United States Patent and Trademark Office*